(12) United States Patent
Fuge et al.

(10) Patent No.: US 8,758,816 B2
(45) Date of Patent: Jun. 24, 2014

(54) COMPOSITIONS COMPRISING AZELASTINE AND METHODS OF USE THEREOF

(75) Inventors: Dennis Fuge, Somerset, NJ (US); John Higson, Plymouth Meeting, PA (US); Bryan A. Roecklein, Somerset, NJ (US); Gul Balwani, West Windsor, NJ (US); Alexander D. D'Addio, Piscataway, NJ (US)

(73) Assignee: Meda Pharmaceuticals Inc., Somerset, NJ (US)

( * ) Notice: Subject to any disclaimer, the term of this patent is extended or adjusted under 35 U.S.C. 154(b) by 498 days.

(21) Appl. No.: 12/569,548

(22) Filed: Sep. 29, 2009

(65) Prior Publication Data

US 2010/0152147 A1   Jun. 17, 2010

Related U.S. Application Data

(63) Continuation-in-part of application No. 11/486,454, filed on Jul. 14, 2006, now abandoned, which is a continuation-in-part of application No. 11/284,109, filed on Nov. 22, 2005, now Pat. No. 8,071,073.

(60) Provisional application No. 60/630,274, filed on Nov. 24, 2004.

(51) Int. Cl.
*B65D 35/00* (2006.01)
*A61K 9/00* (2006.01)

(52) U.S. Cl.
USPC .............. 424/467; 222/92; 222/93; 222/94; 222/95; 222/206; 424/400

(58) Field of Classification Search
USPC .................................. 222/92, 93, 94, 95, 206
See application file for complete search history.

(56) References Cited

U.S. PATENT DOCUMENTS

| 158,564 | A | 1/1875 | Barnes |
|---|---|---|---|
| 2,119,643 | A | 6/1938 | Mendl |
| 2,136,940 | A | 11/1938 | Ehbrecht |
| 2,457,024 | A | 12/1948 | Arp |
| 2,822,314 | A | 2/1958 | Ferlauto et al. |
| 2,925,417 | A | 2/1960 | Elslager et al. |
| 2,995,308 | A | 8/1961 | Ashkenaz |
| 3,017,411 | A | 1/1962 | Engelbrecht et al. |
| 3,144,485 | A | 8/1964 | Benn et al. |
| 3,173,876 | A | 3/1965 | Zobrist |
| 3,267,586 | A | 8/1966 | Molstedt et al. |
| 3,541,005 | A | 11/1970 | Strathmann et al. |
| 3,541,006 | A | 11/1970 | Bixler et al. |
| 3,546,142 | A | 12/1970 | Michaels et al. |
| 3,753,988 | A | 8/1973 | Rodway et al. |
| 3,813,384 | A | 5/1974 | Vogelsang et al. |
| 3,845,052 | A | 10/1974 | Stachel et al. |
| 3,854,770 | A | 12/1974 | Grise et al. |
| 3,878,217 | A | 4/1975 | Carr et al. |
| 4,061,768 | A | 12/1977 | Gorvin |
| 4,077,407 | A | 3/1978 | Theeuwes et al. |
| 4,091,108 | A | 5/1978 | Batchelor et al. |
| 4,094,968 | A | 6/1978 | Hodson et al. |
| 4,226,848 | A | 10/1980 | Nagai et al. |
| 4,235,236 | A | 11/1980 | Theeuwes |
| 4,254,129 | A | 3/1981 | Carr et al. |
| 4,313,931 | A | 2/1982 | Walther et al. |
| 4,430,343 | A | 2/1984 | Iemura et al. |
| 4,435,440 | A | 3/1984 | Hough et al. |
| 4,449,983 | A | 5/1984 | Cortese et al. |
| 4,455,143 | A | 6/1984 | Theeuwes et al. |

(Continued)

FOREIGN PATENT DOCUMENTS

| AU | 37674/72 | 7/1973 |
|---|---|---|
| DE | 1 046 625 | 12/1958 |

(Continued)

OTHER PUBLICATIONS

Cheng et al., PNAS, vol. 23, No. 17, 6682-6687, ¶2 (Apr. 25, 2006).*

(Continued)

*Primary Examiner* — Michael G Hartley
*Assistant Examiner* — Robert Cabral
(74) *Attorney, Agent, or Firm* — Sterne, Kessler, Goldstein & Fox P.L.L.C.

(57) ABSTRACT

The present invention provides pharmaceutical compositions comprising azelastine, or a pharmaceutically acceptable salt or ester thereof including azelastine hydrochloride, and optionally one or more additional active agents. Preferred such compositions further comprise one or more pharmaceutically acceptable carriers or excipients that reduce the amount of post-nasal drip, and/or that minimize or mask the unpleasant bitter taste associated with post-nasal drip, of the compositions into the oral cavity, upon intranasal or ocular administration of the compositions. Especially effective excipients used in the compositions of the present invention are hypromellose as a viscosity modifier and sucralose as a taste-masking agent. The invention also generally relates to pharmaceutical compositions comprising one or more active pharmaceutical ingredients, such as azelastine or pharmaceutically acceptable salts or esters thereof including azelastine hydrochloride, particularly wherein the compositions are provided in unit dosage form. In certain embodiments, the invention provides such unit dosage pharmaceutical compositions comprising azelastine hydrochloride formulated for use as nasal sprays and/or ocular solutions or drops. The invention also provides methods of treating or preventing certain disorders, or symptomatic relief therefrom, by administering the compositions of the invention to a patient, e.g., for the symptomatic relief of a variety of allergic and non-allergic conditions, particularly conjunctivitis, sinusitis, rhinitis and rhinosinusitis. The compositions and methods of the present invention provide significant value in terms of patient acceptability, convenience, and compliance.

141 Claims, 10 Drawing Sheets

(56) References Cited

U.S. PATENT DOCUMENTS

| | | | |
|---|---|---|---|
| 4,495,170 A | 1/1985 | Beyts et al. | |
| 4,501,893 A | 2/1985 | Findlay et al. | |
| 4,570,630 A | 2/1986 | Elliott et al. | |
| 4,602,099 A | 7/1986 | Parker | |
| 4,621,094 A | 11/1986 | Findlay et al. | |
| 4,628,055 A | 12/1986 | Sherlock | |
| 4,704,285 A | 11/1987 | Alderman | |
| 4,704,387 A | 11/1987 | Engel et al. | |
| 4,728,509 A | 3/1988 | Shimizu et al. | |
| 4,738,984 A | 4/1988 | Parker | |
| 4,749,700 A | 6/1988 | Wenig | |
| 4,751,294 A | 6/1988 | Jackson | |
| 4,769,369 A | 9/1988 | Thomas et al. | |
| 4,795,754 A | 1/1989 | Sawaki et al. | |
| 4,810,716 A | 3/1989 | Connor et al. | |
| 4,811,731 A | 3/1989 | Newell et al. | |
| 4,829,064 A | 5/1989 | Sunshine et al. | |
| 4,829,088 A | 5/1989 | Doulakas | |
| 4,835,249 A | 5/1989 | Gallagher et al. | |
| 4,841,047 A | 6/1989 | Engel et al. | |
| 4,868,175 A | 9/1989 | Engle | |
| 4,871,733 A | 10/1989 | Sunshine et al. | |
| 4,918,182 A | 4/1990 | Jackson et al. | |
| 4,927,646 A | 5/1990 | Jenner et al. | |
| 4,971,797 A | 11/1990 | Cherukuri et al. | |
| 4,975,426 A * | 12/1990 | Sunshine et al. | 514/159 |
| 5,035,237 A | 7/1991 | Newell et al. | |
| 5,086,050 A | 2/1992 | Hettche et al. | |
| 5,110,814 A | 5/1992 | Engel et al. | |
| 5,164,194 A * | 11/1992 | Hettche | 424/489 |
| 5,223,493 A | 6/1993 | Boltralik | |
| 5,232,919 A | 8/1993 | Scheffler et al. | |
| 5,271,946 A | 12/1993 | Hettche | |
| 5,380,541 A | 1/1995 | Beyts et al. | |
| 5,384,311 A | 1/1995 | Antenucci et al. | |
| 5,420,120 A | 5/1995 | Boltralik | |
| 5,464,838 A | 11/1995 | Kutscher et al. | |
| 5,497,944 A | 3/1996 | Weston et al. | |
| 5,565,160 A * | 10/1996 | Makuuchi et al. | 264/485 |
| 5,621,005 A | 4/1997 | Gowan, Jr. | |
| 5,654,316 A | 8/1997 | Carruthers et al. | |
| 5,658,919 A | 8/1997 | Ratnaraj et al. | |
| 5,662,271 A | 9/1997 | Weston et al. | |
| 5,688,960 A | 11/1997 | Shankar | |
| 5,691,362 A | 11/1997 | McCormick et al. | |
| 5,696,267 A | 12/1997 | Reichard et al. | |
| 5,719,156 A | 2/1998 | Shue et al. | |
| 5,783,579 A | 7/1998 | McCormick | |
| 5,789,422 A | 8/1998 | Reichard et al. | |
| 5,795,894 A | 8/1998 | Shue et al. | |
| 5,798,359 A | 8/1998 | Shue et al. | |
| 5,804,587 A | 9/1998 | Cupps et al. | |
| 5,830,490 A | 11/1998 | Weinstein et al. | |
| 5,840,279 A | 11/1998 | Narodylo et al. | |
| 5,859,003 A | 1/1999 | Hettche et al. | |
| 5,881,719 A | 3/1999 | Gottenauer et al. | |
| 5,897,858 A | 4/1999 | Haslwanter et al. | |
| 5,901,882 A * | 5/1999 | Siegel | 222/131 |
| 5,941,241 A | 8/1999 | Weinstein et al. | |
| 5,947,118 A | 9/1999 | Hochrainer et al. | |
| 5,964,416 A | 10/1999 | Jaeger et al. | |
| 5,998,403 A | 12/1999 | Hettche et al. | |
| 6,017,909 A | 1/2000 | Hettche et al. | |
| 6,017,963 A | 1/2000 | Alfonos et al. | |
| 6,071,498 A | 6/2000 | Narodylo et al. | |
| 6,149,941 A | 11/2000 | Schwarz et al. | |
| 6,165,512 A | 12/2000 | Mezaache et al. | |
| 6,241,969 B1 | 6/2001 | Saidi et al. | |
| 6,245,353 B1 | 6/2001 | Tritthart et al. | |
| 6,260,549 B1 | 7/2001 | Sosiak | |
| 6,270,790 B1 | 8/2001 | Robinson et al. | |
| 6,294,153 B1 | 9/2001 | Modi | |
| 6,297,227 B1 | 10/2001 | Johnson | |
| 6,319,513 B1 | 11/2001 | Dobrozsi | |
| 6,328,034 B1 | 12/2001 | Eisele et al. | |
| 6,380,046 B1 | 4/2002 | Yamazaki | |
| 6,382,205 B1 | 5/2002 | Weinstein et al. | |
| 6,391,340 B1 | 5/2002 | Malmqvist et al. | |
| 6,402,055 B1 | 6/2002 | Jaeger et al. | |
| 6,497,373 B2 | 12/2002 | Jaeger et al. | |
| 6,552,024 B1 | 4/2003 | Chen et al. | |
| 6,576,677 B1 | 6/2003 | Ukai et al. | |
| 6,596,298 B2 | 7/2003 | Leung et al. | |
| 6,599,913 B1 | 7/2003 | Johnson et al. | |
| 6,610,271 B2 | 8/2003 | Wermeling | |
| 6,615,826 B1 | 9/2003 | Gabrio et al. | |
| 6,620,438 B2 | 9/2003 | Pairet et al. | |
| 6,641,658 B1 | 11/2003 | Dubey | |
| 6,646,121 B2 | 11/2003 | El Kabbani et al. | |
| 6,649,602 B1 | 11/2003 | Yanni | |
| 6,652,901 B2 | 11/2003 | Ishii | |
| 6,681,768 B2 | 1/2004 | Haaije de Boer et al. | |
| 6,696,042 B2 | 2/2004 | Pairet et al. | |
| 6,715,486 B2 | 4/2004 | Gieschen et al. | |
| 6,723,348 B2 | 4/2004 | Faham et al. | |
| 6,726,124 B2 | 4/2004 | Jaeger et al. | |
| 6,779,520 B2 | 8/2004 | Genova et al. | |
| 6,806,256 B2 | 10/2004 | Ulrich et al. | |
| 6,809,198 B2 | 10/2004 | El Kabbani et al. | |
| 6,911,453 B2 | 6/2005 | Hofmeister et al. | |
| 6,918,547 B2 | 7/2005 | Jaeger et al. | |
| 7,022,687 B1 | 4/2006 | Szelenyl et al. | |
| 7,135,495 B2 | 11/2006 | Torisu et al. | |
| 8,071,073 B2 | 12/2011 | Dang et al. | |
| 2001/0025040 A1 | 9/2001 | Poppe et al. | |
| 2001/0053775 A1 | 12/2001 | Seidel et al. | |
| 2002/0006440 A1* | 1/2002 | Cherukuri | 424/465 |
| 2002/0009418 A1 | 1/2002 | Steiner et al. | |
| 2002/0037297 A1 | 3/2002 | Crespo et al. | |
| 2002/0061281 A1 | 5/2002 | Osbakken et al. | |
| 2002/0076382 A1 | 6/2002 | Kaplan et al. | |
| 2002/0147201 A1 | 10/2002 | Chen et al. | |
| 2002/0187188 A1 | 12/2002 | Cherukuri | |
| 2003/0013675 A1 | 1/2003 | Yeadon et al. | |
| 2003/0032600 A1 | 2/2003 | Ulrich et al. | |
| 2003/0059511 A1 | 3/2003 | Ishii | |
| 2003/0113377 A1 | 6/2003 | Dobrozsi et al. | |
| 2003/0161879 A1 | 8/2003 | Ohmori et al. | |
| 2003/0215503 A1 | 11/2003 | Havlir et al. | |
| 2004/0053902 A1 | 3/2004 | Smith | |
| 2004/0097474 A1 | 5/2004 | Cagle et al. | |
| 2004/0105928 A1 | 6/2004 | Ishii | |
| 2004/0115133 A1 | 6/2004 | Wermeling et al. | |
| 2004/0136918 A1 | 7/2004 | Garrett et al. | |
| 2004/0141925 A1 | 7/2004 | Bosch et al. | |
| 2004/0149774 A1* | 8/2004 | Strong | 222/94 |
| 2004/0204399 A1 | 10/2004 | Osbakken et al. | |
| 2004/0208830 A1 | 10/2004 | Chaudry | |
| 2004/0235807 A1 | 11/2004 | Weinrich et al. | |
| 2004/0242624 A1 | 12/2004 | Ahari et al. | |
| 2004/0242638 A1 | 12/2004 | Yanni et al. | |
| 2004/0247648 A1 | 12/2004 | Fadden et al. | |
| 2004/0253307 A1 | 12/2004 | Hague et al. | |
| 2004/0265372 A1 | 12/2004 | Wynn et al. | |
| 2005/0059639 A1 | 3/2005 | Wei | |
| 2005/0121027 A1 | 6/2005 | Nilsson et al. | |
| 2005/0121032 A1 | 6/2005 | Nilsson et al. | |
| 2005/0123486 A1 | 6/2005 | Nilsson et al. | |
| 2005/0147672 A1 | 7/2005 | Ohmori et al. | |
| 2005/0148562 A1 | 7/2005 | Pairet et al. | |
| 2005/0153946 A1 | 7/2005 | Hirsch et al. | |
| 2005/0196355 A1 | 9/2005 | Georgiades et al. | |
| 2005/0196357 A1 | 9/2005 | Georgiades et al. | |
| 2005/0196358 A1 | 9/2005 | Georgiades et al. | |
| 2005/0266031 A1 | 12/2005 | Dickerson et al. | |
| 2005/0281772 A1 | 12/2005 | Bromley et al. | |
| 2006/0025391 A1 | 2/2006 | Lulla et al. | |
| 2006/0110331 A1 | 5/2006 | Dang et al. | |
| 2006/0263350 A1 | 11/2006 | Lane | |
| 2007/0020330 A1 | 1/2007 | Dang et al. | |
| 2007/0202050 A1* | 8/2007 | Berry et al. | 424/45 |
| 2007/0274925 A1* | 11/2007 | Chaudry | 424/45 |
| 2009/0291143 A1 | 11/2009 | Lulla et al. | |
| 2009/0318397 A1 | 12/2009 | Lulla et al. | |

(56) References Cited

U.S. PATENT DOCUMENTS

| | | | |
|---|---|---|---|
| 2010/0152147 A1 | 6/2010 | Fuge et al. | |
| 2010/0331289 A1 | 12/2010 | Lulla et al. | |
| 2012/0083479 A1 | 4/2012 | Dang et al. | |
| 2012/0149690 A1 | 6/2012 | Dang et al. | |

FOREIGN PATENT DOCUMENTS

| | | |
|---|---|---|
| DE | 2164058 | 7/1972 |
| DE | 2 114 884 | 10/1972 |
| DE | 35 30 793 A1 | 3/1986 |
| DE | 36 34 942 A1 | 5/1987 |
| DE | 1994 7234 A1 | 4/2001 |
| EP | 0 164 593 A1 | 12/1985 |
| EP | 0 164 593 B1 | 12/1985 |
| EP | 0 174 464 A2 | 3/1986 |
| EP | 0 222 191 A1 | 5/1987 |
| EP | 0 289 939 A1 | 11/1988 |
| EP | 0 316 639 A2 | 5/1989 |
| EP | 0 174 464 B1 | 1/1990 |
| EP | 0 222 191 B1 | 1/1991 |
| EP | 0 780 127 A1 | 6/1997 |
| EP | 0 903 151 A1 | 3/1999 |
| FR | 2 816 507 A1 | 5/2002 |
| GB | 1377231 | 12/1974 |
| WO | WO 97/01337 | 1/1997 |
| WO | WO 97/46243 | 12/1997 |
| WO | WO 98/48839 | 11/1998 |
| WO | WO 01/26658 A2 | 4/2001 |
| WO | WO 01/52818 A1 | 7/2001 |
| WO | WO 02/056876 A2 | 7/2002 |
| WO | WO 02/083036 A2 | 10/2002 |
| WO | WO 03/049770 A1 | 6/2003 |
| WO | WO 03/105856 A1 | 12/2003 |
| WO | WO 2004/019955 A1 | 3/2004 |
| WO | WO 2004/112771 A1 | 12/2004 |
| WO | WO 2005/027839 A2 | 3/2005 |
| WO | WO 2005/030331 A1 | 4/2005 |

OTHER PUBLICATIONS

Ansel, H.C., "Chapter 11—Ophthalmic Preparations," and "Chapter 12—Ear, Nose, and Topical Oral Formulations," in *Introduction to Pharmaceutical Dosage Forms*, Lea & Febiger, Philadelphia, PA., pp. 333-349 (1976).

Banov, C.H. and Lieberman, Phil, "Efficacy of azelastine nasal spray in the treatment of vasomotor (perennial nonallergic) rhinitis," *Ann. Allergy Asthma Immunol.* 86:28-35, American College of Allergy, Asthma, and Immunology, United States (2001).

Barkman, R., et al., "Preservatives in Eye Drops," *ACTA Ophthamologica* 47:461-475, Munksgaard, Denmark (1969).

Bende, M. and Pipkorn, U., "Topical levocabastine, a selective H1 antagonist, in seasonal allergic rhinoconjunctivitis," *Allergy* 42:512-515, Munksgaard, Denmark (1987).

Bentley, A.J. and Jackson, R.T., "Changes in the Patency of the Upper Nasal Passage Induced by Histamine and Antihistamines," *The Laryngoscope: LXXX*:1859-1870, Lippincott Wilkins & Williams, United States (1970).

Berger, W.E., et al., "Double-blind trials of azelastine nasal spray monotherapy versus combination therapy with loratadine tablets and beclomethasone nasal spray in patients with seasonal allergic rhinitis," *Ann. Allergy Asthma Immunol.* 82:535-541, American College of Allergy, Asthma, and Immunology, United States (1999).

Blue, J.A., "Current Concepts of Allergy of the Eye," *Annals of Allergy* 33:267-273, American College of Allergy and Immunology, United States (1974).

Burstein, N.L., "The Effects of Topical Drugs and Preservatives on the Tears and Corneal Epithelium in Dry Eye," *Trans. Opthalmol. Soc. U.K.* 104:402-409, The Ophthalmological Societies of the United Kingdom, United Kingdom (1985).

Busse, W.W., et al., "Corticosteroid-sparing Effect of Azelastine in the Management of Bronchial Asthma," *Am J. Respir. Crit. Care Med.* 153:122-127, American Thoracic Society, United States (1996).

Chand, N., et al., "Inhibition of Allergic Histamine Release by Azelastine and Selected Antiallergic Drugs from Rabbit Leukocytes," *Int. Arch. Allergy Appl. Immunol.* 77:451-455, Karger, Switzerland (1985).

Chand, N., et al., "Inhibition of acute lung anaphylaxis by aerosolized azelastine in guinea pigs sensitized by three different procedures," *Ann. Allergy* 58:344-349, American College of Allergists, United States (1987).

Chien, Y.W. and Chang, S., "Intranasal Drug Delivery for Systemic Medications," *Crit. Rev. Ther. Drug Carrier Syst.* 4:67-194, CRC Press, United Kingdom (1987).

Corrado, O.J., et al., "Histamine and allergen induced changes in nasal airways resistance measured by anterior rhinomanometry: reproducibility of the technique and the effect of topically administered antihistaminic and anti-allergic drugs," *Br. J. Clin. Pharmacol.* 24:283-292, Blackwell Scientific Laboratories, United Kingdom (1987).

Day, Nigel, "13: Aqueous Nasal Dosage Forms," in *Pharmaceutical Preformulation and Formulation*, Gibson, Mark, ed., CRC Press, Boca Raton, FL., pp. 491-513 (2002).

Diamantis, W., et al., "In Vivo and In Vitro $H_1$ Antagonist Properties of Azelastine," *Pharmacologist* 23:149 (198), American Society for Pharmacology and Experimental Therapeutics, Inc., United States (1981).

Diamantis, W., et al., "Inhibition of Release of SRS-A and Its Antagonism by Azelastine (A), an $H_1$ Antagonist-Antiallergic Agent," *Pharmacologist* 24:200 (574), American Society for Pharmacology and Experimental Therapeutics, Inc., United States (1982).

Dolovich, J., et al., "Control of the hypersecretion of vasomotor rhinitis by topical ipratropium bromide," *J. Allergy Clin. Immunol.* 80:274-278, Mosby, United States (1987).

Duarte, C., et al., "Treatment of Severe Seasonal Rhinoconjunctivitis by a Combination of Azelastine Nasal Spray and Eye Drops: A Double-Blind, Double-Placebo Study," *J. Investig. Allergol. Clin. Immunol.* 11:34-40, Hogrefe & Huber, United States (2001).

Duzman, E., et al., "Topically Applied Oxymetazoline: Ocular Vasoconstrictive Activity, Pharmacokinetics, and Metabolism," *Arch. Ophthalmol.* 101:1122-1126, American Medical Association, United States (1983).

*Eli Lilly & Co. v. Aradigm Corp.*, 376 P.3d 1352, United States (Fed. Cir. 2004).

Feinberg, G. and Stokes T.C., "Application of Histamine-Induced Conjuncitivitis to the Assessment of a Topical Antihistamine, Levocabastine," *Int. Arch.Allergy Appl. Immunol.* 82:537-538, Karger, Switzerland (1987).

Feinberg, S.M., "Drugs in Allergy," *Trans. Amer. Acad. of Opthalmol. & Otolaryngol.* 124:283-286, Douglas Printing Company, United States (1950).

Feinberg, S.M., "Antihistamine Therapy. Experimental and Clinical Correlation," *Annals of the New York Acadmey of Sciences* 50:1186-1201, New York Academy of Sciences, United States (1950).

File, R R. and Patton, T.F., "Topically Applied Pilocarpine: Human Pupillary Response as a Function of Drop Size," *Arch. Ophthal.* 98:112-115, American Medical Association, United States (1980).

Fräki, J.E., et al., "Contact Allergy to Various Components of Topical Preparations for Treatment of External Otitis," *Acta Otolaryngol.* 100:414-418, Taylor & Francis, United Kingdom (1985).

Gibson, M., "12: Ophthalmic Dosage Forms," in *Pharmaceutical Preformulation and Formualation*, Gibson, Mark, ed., CRC Press, Boca Raton, FL., pp. 459-489 (2002).

Giede-Tuch, C., et al., "Azelastine eye-drops in seasonal allergic conjunctivitis or rhinoconjunctivitis," *Allergy* 53:857-862, Munksgaard (1998).

Golden,, S.J. and Craig, T.J., "Efficacy and safety of azelastine nasal spray for the treatment of allergic rhinitis," *J. Am. Osteopath. Assoc.* 99:S7-S12, American Osteopathic Association, United States (1999).

Hamilton, L.H., "Effect of Topical Decongestants on Nasal Airway Resistance," *Curr. Ther. Res. Clin. Exp.* 24:261-268, Therapeutic Research Press, Inc., United States (1978).

Havas, T.E., et al., "The Effects of combined $H_1$ and $H_2$ histamine antagonists on alterations in nasal airflow resistance induced by topical histamine provocation," *J. Allergy Clin. Immunol.* 78:856-860, Mosby, United States (1986).

(56) References Cited

OTHER PUBLICATIONS

Hermens, W.A.. and Merkus, F.W.., "The Influence of Drugs on Nasal Ciliary Movement," *Pharm. Res.* 4:445-449, Plenum Publishers, United States (1987).
Horak, F., et al., "Azelastine in Pollen-Induced Allergic Rhinitis, A Pharmacodynamic Study of Onset of Action and Efficacy," *Clin. Drug Investig.* 7:34-40, Adis International Ltd., New Zealand (1994).
International Search Report for International Application No. PCT/US05/42362, United States Patent and Trademark Office, United States, mailed May 4, 2006.
Kassem, A.A., et al., "Formulation and Stabilization of Antazoline Hydrochloride Nasal Drops," *Bulletin of the Faculty of Pharmacy XV*:161-175, Cairo University Press, Egypt (1976).
Keeney, E.I., "Medical Progress: Histamine and the Antihistamine Drugs," *Calif. Med.* 72:377-389, California Medical Association, United States (1950).
Kersten, R.C., "Ophthalmic Drugs," *Prim. Care* 9:743-756, Saunders, United States (1982).
*Kimberly-Clark Corp. v. The Proctor & Gamble Distributing Co., Inc.*, 973 F.2d911, 23 U.S.P.Q.2d 1921, United States (Fed. Cir. 1992).
Kirkegaard, J., et al., "Effect of the $H_1$ Antihistamine Chlorpheniramine Maleate on Histamine-Induced Symptoms in the Human Conjuctiva," *Allergy* 37:203-208, Blackwell Munksgaard, Denmark (1982).
Kirkegaard, J., et al., "Inhibition of Histamine-Induced Nasal Symptoms by the $H_1$ Antihistamine Chlorphenitamine Maleate: Demonstration of Topical Effect," *Br. J. Dis. Chest* 77:113-121, Balliere Tindall and Cassell, United Kingdom (1983).
Kubo, N., et al., "Antimuscarinic Effects of Antihistamines: Quantitative Evaluation by Receptor-Binding Assay," *Jpn. J. Pharmacol.* 43:277-282, Japanese Pharmacological Society, Japan (1987).
Lancer, J.M., et al., "A comparison by rhinomanometry of beclomethasone and terfenadine in the treatment of seasonal rhinitis," *J. Laryngol. Otol.* 101:350-354, Headley Brothers Ltd., United Kingdom (1987).
Lam, S.W., et al., "Determination of Thimerosal in Opthalmic Solutions by Radial Compression Separation HPLC," *J. Parenter. Sci. Technol.* 35:262-265, Parenteral Drug Association, United States (1981).
Lenhard, G. et al., "Double-blind, Randomised, Placebo-controlled Study of Two Concentrations of Azelastine Eye Drops in Seasonal Allergic Conjunctivitis or Rhinoconjunctivitis," *Curr. Med. Res. Opin.* 14:21-28, LibraPharm, Ltd., United Kingdom (1997).
Lieberman, P., "Management of allergic rhinitis with a combination antihistamine/anti-inflammatory agent," *J. Allergy Clin. Immunol.* 103:S400-404, Mosby, United States (1999).
McNeely, W. and Wiseman, L.R., "Intranasal Azelastine: A Review of its Efficacy in the Management of Allergic Rhinitis," *Drugs* 56:91-114, Adis International, Ltd., New Zealand (1998).
Meltzer, E.O. and Schatz, M., "Pharmacotherapy of Rhinitis—1987 and Beyond," *Immunol. Allergy Clin. North Am.* 7:57-91, W.B. Saunders, United States (1987).
Naclerio, R.M., et al., "In Vivo Model for the Evaluation of Topical Antiallergic Medications," *Arch. Otolaryngol.* 110:25-27, American Medical Association, United States (1984).
Newsom-Smith, G., et al., "A placebo controlled study comparing the efficacy of intranasal azelastine and beclomethasone in the treatment of seasonal allergic rhinitis," *Eur. Arch. Otorhinolaryngol.* 254:236-241, Springer-Verlag, Germany (1997).
Okuda, M., et al., "Effect of E-0659 for Nasal Allergy," *Oto-Rhino-Laryngology Tokyo* 23:441-461, Tokyo, Jibinkokagaku Kyoshitsu, Tokyo Jikei Ika Daigaku, Japan (1980).
Okuda, M., et al., English language abstract for Okuda, M., et al., "Effect of E-0659 for Nasal Allergy," *Oto-Rhino-Laryngology Tokyo* 23:441-461, Tokyo, Jibinkokagaku Kyoshitsu, Tokyo Jikei Ika Daigaku, Japan (1980) (listed on accompanying PTO/SB/08B as document NPL49).
Orgel, H. A., et al., "Clinical, rhinomanometric, and cytologic evaluation of seasonal allergic rhinitis treated with beclomethasone dipropionate as aqueous nasal spray or pressurized aerosol," *J. Allergy Clin. Immunol.* 77:858-864, Mosby, United States (1986).
Pearlman, D.S., "Antihistamines: Pharmacology and Clinical Use," *Drugs* 12:258-273, ADIS Press, New Zealand (1976).
Pécoud, A., et al., "Effect of a New Selective $H_1$ Receptor Antagonist (Levocabastine) in a Nasal and Conjuctival Provocation Test," *Int. Arch. Allergy Appl. Immunol.* 82:541-543, Karger, Switzerland (1987).
Physicians' Desk Reference, 33rd ed., Huff, Barbara and Kelly, Gwynned L., eds., Medical Economics Company, Oradell, N.J., pp. 570-572, 873, 892, 1512, 1515, and 1851 (1979).
Physicians' Desk Reference, 1st ed., Huff, Barbara and Kelly, Gwynned L., eds. Medical Economics Company, Oradell, N.J., pp. 502, 503, 506, 522, 539, 553, 616, 637, 638, 646, 654, and 655 (1980).
Physicians' Desk Reference, 59th ed., Murray, Lori, ed., Thomson PDR, Montvale, N.J., pp. 1973-1975 (2005).
Pipkorn, U., et al., "A Double-Blind Evaluation of Topical Levocabastine, a New Specific $H_1$ Antagonist in Patients with Allergic Conjuctivitis," *Allergy* 40:491-496, Blackwell Munksgaard, Germany (1985).
Portmann, D., et al., English language abstract of "Acceptability of local treatment of allergic rhinitis with a combination of a corticoid (beclomethasone) and an antihistaminic (azelastine)," *Rev. Laryngol. Otol. Rhinol. (Bord.)* 121:273-9, Revue De Laryngologie, France (2000).
Reader, M.J., "Influence of Isotonic Agents on the Stability of Thimerosal in Ophthalmic Formulations," *J. Pharm. Sci.* 73:840-841, American Pharmaceutical Association, United States (1984).
Reich, I., et al., "Tonicity, Osmoticity, Osmolality and Osmolarity," in *Remington: The Science and Practice of Pharmacy, 20th edition*, Gennaro, Alfonso R., et al., eds., Lippincott Williams and Wilkins, Philadelphia, PA. pp. 246-262 (2000).
Saito, Y., "Recent Trends in Aerosol Therapy for Allergic Rhinitis," *Z. Erkr. Atmungsorgane* 166:25-29, Johann Ambrosius Barth, Germany (1986).
Secher, C., et al., "Significance of $H_1$ and $H_2$ receptors in the human nose: rationale for topical use of combined antihistamine preparations," *J. Allergy Clin. Immunol.* 70:211-218, Mosby, United States (1982).
Shin, M.-H., et al., "The effect of azelastine on the early allergic response," *Clin. Exp. All.* 22:289-295, Blackwell Scientific Publications, United Kingdom (1992).
Tasaka, K. and Akagi, M., "Anti-allergic Properties of a New Histamine Antagonist, 4-(p-Chlorobenzyl)-2-[N-Methyl-perhydroazepinyl-(4)]-1-(2H)-phthalazinone Hydrochloride (Azelastine)," *Arzneimittel Forschung: Drug Research* 29:488-493, Editio Cantor, Germany (1979).
Tatsumi, K., et al., "Studies on Metabolic Fate of a New Antiallergic Agent, Azelastine (4-(p-Chlorobenzyl)-2-[N-Methylperhydroazepinyl-(4)]-1-(2H)-Phthalazinone Hydrochloride)," *Japan. J. Pharmacol.* 30:37-48, The Japanese Pharmacological Society, Japan (1980).
Tatsumi, K., et al., "Metabolism of an Antiallergic Agent, Azelastine (4-(p-Chlorobenzyl)-2[N-Methylperhydroazepinyl-(4)]-1-(2H)-Phthalazinone Hydrochloride) in Rats and Guinea Pigs," *Hiroshima J. Med. Sci.* 33:669-678, Hiroshima University School of Medicine, Japan (1984).
Togias, A. G., et al., "Demonstration of Inhibition of Mediator Release from Human Mast Cells by Azatadine Base," *J. Am. Med. Assoc.* 255:225-229, American Medical Association, United States (1986).
van de Donk, H.J., et al., "The effects of nasal drops on the ciliary beat frequency of chicken embryo tracheas," *Rhinology* 19:215-230, International Rhinologic Society, Netherlands (1981).
van de Donk, H.J., et al., "The effects of drugs on ciliary motility: III. Local anaesthetics and anti-allergic drugs," *Int. J. Pharm.* 12:77-85, Elsevier Biomedical Press, Netherlands (1982).
Vanden Bussche, G., "Levocabastine Hydrochloride," *Drugs Future* 11:841-843, J R Prous S.A. Publishers, United States (1986).
Wang, D., et al., "Effect of Topical Applications of Budesonide and Azelastine on Nasal Symptoms, Eosinophil Count and Mediator

(56) References Cited

OTHER PUBLICATIONS

Release in Atopic Patients after Nasal Allergen Challenge during the Pollen Season," *Int. Arch. Allergy Immunol.* 114:185-192, S. Karger, Switzerland (1997).
Wasicko, M.J., et al., "Nasal and Pharyngeal Resistance after Topical Mucosal Vasoconstriction in Normal Humans," *Am. Rev. Respir. Dis.* 144:1048-1052, American Lung Association, United States (1991).
Weeke, E.R., "Epidemiology of Hay Fever and Perennial Allergic Rhinitis," *Monogr. Allergy* 21:1-20, Karger, Switzerland (1987).
Weiler, J.M., et al., "Multicenter, double-blind, multiple-dose, parallel groups efficacy and safety trial of azelastine, chlorpheniramine, and placebo in the treatment of spring allergic rhinitis," *J. Allergy Clin. Immunol.* 82:801-11, Mosby, United States (1998).
Young, T., et al., "Nasal obstruction as a risk factor for sleep-disordered breathing," *J. Allergy Clin. Immunol.* 99:S757-62, Mosby, United States (1997).
Dialog File 351, Accession No. 4564452, Derwent WPI English language abstract for EP 289939 A1 (listed on accompanying PTO/SB/08A as document FP2) (1988).
Dialog File 351, Accession No. 4782022, Derwent WPI English language abstract for EP 316639 A2 (listed on accompanying PTO/SB/08A as document FP3) (1994).
Dialog File 351, Accession No. 12914778, Derwent WPI English language abstract for FR 2 816 507 A1 (listed on accompanying PTO/SB/08A as document FP10) (2002).
Letter from Apotex to MedPointe Pharmaceuticals, "Re: Apotex Azelastine Hydrochloride Nasal Spray (hereinafter 'Apotex Azelastine product')," pp. 1-24, dated Jan. 24, 2006.
Answer of Apotex Corp. to Plaintiff's Amended Complaint, Affirmative Defenses and Couterclaims in *MedPointe Healthcare Inc.* v. *Apotex Inc. and Apotex Corp.*, C.A. 06-164 (SLR), Electronically mailed on Apr. 14, 2006.
Aberer, W. and Tappeiner, G., "Allergy to Topically-applied Antihistamines—Discrepancy Between Literature and Practice," *Wiener klin. Wochen.* 100:763-765, Springer-Verlag, Germany (1988).
Breuninger, H., "Nosedrops and Eardrops," *HNO* 19:65-68, Springer-Verlag, Germany (1971).
Chand, N., et al., "Effect of Aerosolized Azelastine on Acute Lung Anaphylaxis in Guinea Pigs (GP) Sensitized by Two Different Procedures," *Pharmacologist* 27:162, Abstract No. 76, American Society for Pharmacology and Experimental Therapeutics, United States (1985).
Chand, N., et al., "Inhibition of IgE-mediated allergic histamine release from rat peritoneal mast cells by azelastine and selected antiallergic drugs," *Agents & Actions* 16:318-322, Birkhäuser, Germany (1985).
Dolder, B.V.R. and Triemli, S., "7. Arzneiformen zur Anwendung an Auge, Ohr und Nase," in: *Pharmazeutische Technoalogie*, Sucker, H., et al., eds., Georg Thieme Verlag, Stuttgart, Germany, pp. 693-729 (1978).
Dolovich, M.B., et al., "Aerosols in diagnosis: ventilation, airway penetrance, airway reactivity, epithelial permeability and mucociliary transport," *Aerosols in Medicine Principles, Diagnosis and Therapy*, Morén, F., et al., eds., Elsevier, New York, NY, pp. 225-259 (1985).
Etter, J.C., et al., "Le contrôle des gouttes nasales: action de différentes solutions sur la muqueuse du cobaye et sur celle de l'homme," *Schweiz. Med. Wochenschr.* 94:1531-1534, EMH Swiss Medical Publishers, United States (1964).
Fickweiler, E., "Biopharmazie der Oto-Rhino-Laryngologica," *Die Pharmazie* 38:274-278, Govi-Verlag Pharmazautischer Verlag, Germany (1983).
Grumbach, P.E., et al., "Remarques sur le contrôle physiologique des gouttes nasales," *Schweiz. Med. Wochenschr.* 96:358-360, EMH Swiss Medical Publishers, United States (1966).
Lippold, B.C., ed., "I. Arzneformen zur Anwendung in der Nase," in: *Biopharmazie*, Wissenschaftliche Verlagsgesellschaft mbH, Stuttgart, Germany, pp. 142-145 (1984).

Meltzer, E.O., et al., "Efficacy of azelastine in perennial allergic rhinitis: Clinical and rhinomanometric evaluation." *J. Allergy Clin. Immunol.* 82:447-455, The C.V. Mosby Company, United States (1988).
Mirimanoff, A. and Paley, A., "Contrôle physiologique des gouttes nasales sur la muqueuse du cobaye: Effet toxique temporaire et permanent," *Pharm. Acta Helvetiae* 41:25-38, City-Druck AG, Germany (1966).
Morén, F., "Chap. 10. Aerosol dosage forms and formulations," in: *Aerosols in Medicine Principles Diagnosis and Therapy*, Morén, F., et al., eds., Elsevier, New York, NY, pp. 261-287 (1985).
Mygind, N, "Chap 1. Upper airway: structure, function and therapy," in: *Aerosols in Medicine Principles, Diagnosis and Therapy*, Morén, F., et al., eds., Elsevier, New York, NY, pp. 1-20 (1985).
Naclerio, R.M., "The effect of antihistamines on the immediate allergic response: A comparative review," *Otolaryngol. Head Neck Surg.* 108:723-730, Mosby, United States (1993).
Newman, S.P. and Clarke, S.W., "Chap. 11. Aerosols in therapy," in: *Aerosols in Medicine. Principles, Diagnosis and Therapy*, Morén, F., et al., eds., Elsevier, New York, NY, pp. 289-312 (1985).
Rafferty, P., et al., "The in vivo potency and selectivity of azelastine as an $H_1$ histamine-receptor antagonist in human airways and skin," *J. Allergy Clin. Immunol.* 82:1113-1118, The C.V. Mosby Company, United States (1988).
Schlumpf, R., "3.5.5. Sterilität und Konservierung wäßriger Augentropfen," in: Ophthalmika. Pharmakologie, Biopharmazie und Galenik der Augenarzneimittel, Dolder, R., et al., eds., Wissenschaftlicje Verlagsgesellschaft mbH, Stuttgart, Gemany, pp. 392-415 (1983).
Togias, A., et al., "The effect of a topical tricyclic antihistamine on the response of the nasal mucosa to challenge with cold, dry air and histamine," *J. Allergy Clin. Immunol.* 79:599-604, The C.V. Mosby Company, United States (1987).
"Allergische Rhinits—eine Crux medicorm," *Z. Allg. Med.* 57:1939-1940, Hippokrates Verlag GmbH, Germany (1981).
Andersen, N.H., et al., "Treatment of hay fever with sodium cromoglycate, hyposensitization, or a combination," *Allergy* 42:343-351, Munksgaard, Denmark (1987).
Asta Pharma Aktiennesellschaft, "Comparison of efficacy and tolerability of azelastine nasal spray, azelastine tablets and astemizole in the treatment of seasonal allergic rhinitis," *Asta Pharma Report*, Project No. A-05610, Asta Pharma Aktiennesellschaft, 5 pages (1990).
Asta-Werke Aktiengesellschaft Chemische Fabrik, "Löslichkeit von Azelastin und Azelastinsalzen," *Asta-Werke Report*, Report No. UB 61.83, Asta-Werke Aktiengesellschaft Chemische Fabrik, 10 pages (1983).
Chand, N., et al., "Modulation of in vitro anaphylaxis of guinea-pig isolated tracheal segments by azelastine, inhibitors of arachidonic acid metabolism and selected antiallergic drugs," *Br. J. Pharmac.* 87:443-448, The Macmillan Press Ltd., United Kingdom (1986).
Etter, J.C., et al., "Le contrôle des gouttes nasales: action de différentes solutions sur la muqueuse du cobaye et sur celle de l'homme," *Schweiz. Med. Wochenschr.* 94:1531-1534, EMH Swiss Medical Publishers, Switzerland (1964).
Fukuda, T., et al., "Influence of 1-(2-Ethoxyethyl)-2-(4-methyl-1-homopiperazinyl)benzimidazole Difumarate (KB-2413), a New Antiallergic, on Ciliary Movement," *Arzneim.-Forsch.* 34:816-818, Editio Cantor, Germany (1984).
*Handbook of Nonprescription Drugs*, 7th Ed., American Pharmaceutical Association, Washington, DC, pp. 166-169 and 428-430 (1982).
Kemp, J.P., et al., "A dose-response study of the bronchodilator action of azelastine in asthma," *J. Allerg. Clin. Immunol.* 79:893-899, The C.V. Mosby Company, United States (1987).
Kranz, O., ed., *Vademecum*, 12th Ed., Editio Cantor Aulendorf, Germany, pp. 174-181 (1981).
Magnussen, H., "The Inhibitory Effect of Azelastine and Ketotifen on Histamine-induced Bronchoconstriction in Asthmatic Patients," *Chest* 91:855-858, American College of Chest Physicians, United States (1987).
Mirimanoff, A. and Paley, A., "Contrôle physiologique des gouttes nasales sur la muqueuse du cobaye: Effet toxique temporaire et

(56) References Cited

OTHER PUBLICATIONS permanent," *Pharm. Acta Helvet.* 41:25-38, Schweizerische Apotheker-Verein, The Netherlands (1966).

Morrison, W.W., ed., "Formulary: Prescriptions for Medications to be Used by Patients," *Diseases of the Ear, Nose & Throat*, 2nd Ed., Appleton-Century-Crofts, Inc., New York, pp. 699-707 (1948).

Ollier, S., et al., "The effect of single and multiple dose therapy with azelastine on the immediate asthmatic response to allergen provocation testing," *J. Allergy Clin. Immunol.* 78:358-364, The C.V. Mosby Company, United States (1986).

Pivonka, J., et al., "Determination of Azelastine and Desmethylazelastine in Human Plasma by High-Performance Liquid Chromatography." *J. Chromat.* 420:89-98. Elsevier Science Publishers B.V., The Netherlands (1987).

Sauer P.-H., "Rhinomanometrische Kontrollen des Nasenwiderstandes," *Die Med. Welt.* 34:1319-1324, Schattauer, Germany (1983).

Schaffer, N. and Seidmon, E.E., "The Intranasal Use of Prophenpyridamine Maleate and Chlorpropenpyridamine Maleate in Allergic Rhinitis," *Ann. Allergy* 10:194-196, The American College of Allergists, United States (1952).

Su, X.Y. and Po, A.L.W., "The effect of some commercially available antihistamine and decongestant intra-nasal formulations on ciliary beat frequency," *J. Clin. Pharm. Therap.* 18:219-222, Blackwell Scientific Publications, United Kingdom (1993).

Wanner, A., "Effects of Methylxanthines on Airway Mucociliary Function," *Am. J. Med.* 79:16-21, Technical Publishing, United States (1985).

Yu, C.D., et al., "Cascade Impactor Method for the Droplet Size Characterization of a Metered-Dose Nasal Spray," *J. Pharm. Sci.* 73:344-348, The American Pharmaceutical Association, United States (1984).

German Patent Application No. 34 33 776.8, applicant Asta-Werke Aktiengesellschaft Chemische Fabrik, filed Sep. 14, 1984.

Unverified English language translation of German Patent Application No. 34 33 776.8, applicant Asta-Werke Aktiengesellschaft Chemische Fabrik, conducted on Jan. 14, 2008.

German Patent Application No. 35 39 873.6, applicant Asta-Werke Aktiengesellschaft Chemische Fabrik, filed Nov. 11, 1985.

Unverified English language translation of German Patent Application No. 35 39 873.6, applicant Asta-Werke Aktiengesellschaft Chemische Fabrik, conducted on Apr. 19, 2007.

STNEasy, Chemical Abstracts Service, Accession No. 1961:38125, unverified English language abstract of DE 1 046 625 (listed on accompanying PTO/SB/08A as document FP20) (1958).

Dialog File 351, Accession No. 498209, WPI unverified English language abstract of DE 2 114 884 (listed on accompanying PTO/SB/08A as document FP21) (1971).

Dialog File 351, Accession No. 3637108, WPI unverified English language abstract of EP 0 174 464 A2 and B1 (listed on accompanying PTO/SB/08A as documents FP23 and FP28 respectively) and of DE 35 30 793 A1 (listed on accompanying PTO/SB/08A as document FP24) (1986).

Dialog File 351, Accession No. 4037878, WPI unverified English language abstract of EP 0 222 191 A1 and B1 (listed on accompanying PTO/SB/08A as documents FP26 and FP29 respectively) and of DE 36 34 942 A1 (listed on accompanying PTO/SB/08A as document FP25) (1987).

Wilson, C.O., et al., "Recent Antihistamine Developments: The "Dual-Acting" Antihistamines," in *Wilson and Gisvold's Textbook of Organic Medicinal and Pharmaceutical Chemistry: Edition: 11*, Block, J.H., and Beale Jr., J.M., eds., Lippincott Williams & Wilkins, Baltimore, MD, p. 717 (Jan. 2004).

International Search Report for International Application No. PCT/GB03/02557, mailed on Sep. 17, 2003, European Patent Office, Rijswijk, Netherlands.

Dialog File 351, Accession No. 11047925, Derwent WIP English language abstract for DE 1994 7234 A1 (cited as document FP30) (2001).

Office Action for U.S. Appl. No. 10/518,016, Lulla, A., et al., filed Jul. 6, 2005, mailed on Jan. 23, 2009.

Office Action for U.S. Appl. No. 10/518,016, Lulla, A., et al., filed Jul. 6, 2005, mailed on Oct. 17, 2008.

Office Action for U.S. Appl. No. 11/284,109, Dang, P.G., et al., filed Nov. 22, 2005, mailed on Feb. 27, 2009.

Bielory, L., et al., "Treating the Ocular Component of Allergic Rhinoconjunctivitis and Related Eye Disorders," *Medscape Gen. Med.* 9: 15 pages, available online at http://www.medscape.com/viewarticle/560750, Medscape, United States (Aug. 2007).

Brain, J.D., et al., "Chap. 5. Mechanisms of aerosol deposition and clearance," in: *Aerosols in Medicine Principles, Diagnosis and Therapy*, Morén, F., et al., eds., Elsevier, New York, NY, pp. 123-147, 198-199, 207-209 (1985).

Chand, N., et al., "Is Airway Hyperactivity in Asthma Due to Histamine $H_2$-Receptor Deficiency?," *Med. Hypoth.* 6:1105-1112, Churchill Livingstone, United States (1980).

Chand, N., et al., "Inhibition of Calcium Ionophore (A23187)-Stimulated Histamine Release from Rat Peritoneal Mast Cells by Azelastine: Implications for Its Mode of Action," *Eur. J. Pharm.* 96:227-233, Elsevier Science Publishers B.V., Netherlands (1983).

Chand, N., et al., "Inhibition of allergic and non-allergic histamine secretion from rat peritoneal mast cells by calcium antagonists," *Br. J. Pharmac.* 83:899-902, Macmillan Press Ltd., United Kingdom (1984).

Chand, N., et al., "Inhibition of Passive Cutaneous Anaphylaxis (PCA) by Azelastine: Dissociation of Its Antiallergic Activities from Antihistaminic and Antiserotonin Properties," *Int. J. Immunopharmac.* 7:833-838, Pergamon Press, United Kingdom (1985).

Chand, N., et al., "Inhibition of Leukotriene (SRS-A)-Mediated Acute Lung Anaphylaxis by Azelastine in Guinea Pigs," *Allergy* 41:473-478, Munksgaard International Publishers, Denmark (1986).

Chien, Y.W., ed., "2. Histamine and Antihistamines" in: *Transnasal Systemic Medications*, Elsevier, Netherlands, pp. 80-81 (1985).

Cirillo, V.J., et al., "Pharmacology and Therapeutic Use of Antihistamines," *Am. J. Hosp. Pharm.* 33:1200-1207, American Society of Hospital Pharmacists, United States (1976).

Deardorff, D.I., "Chap. 83. Ophthalmic Solutions,", in: *Remington's Pharmaceutical Sciences*, 14th Ed., Hoover, J.E., et al., eds., Mack Publishing Company, Easton, PA, pp. 1545-1577 (1970).

Druce, H.M., "Allergic and Nonallergic Rhinitis," in *Allergy, Principles & Practice*, vol. II, Mosby, St. Louis, MO, pp. 1005 and 1014 (1998).

Fields, D.A.S., et al., "Inhibition by azelastine of nonallergic histamine release from rat peritoneal mast cells," *J. Allergy Clin. Immunol.* 73:400-403, The C.V. Mosby Company, United States (1984).

Fokkens, W.J., et al., "Once daily fluticasone furoate nasal spray is effective in seasonal allergic rhinitis caused by grass pollen," *Allergy* 62:1078-1084, Blackwell Munksgaard, Denmark (2007).

Gale A.E., et al., "Intranasal topical flunisolide therapy in children with seasonal allergic rhinitis," *Clin. Allergy* 10:527-533, Blackwell Scientific Publications, United Kingdom (1980).

Hill, D., et al., "Beclomethasone Dipropionate Aerosol in the Treatment of Children with Severe Perennial Rhinitis," *Med. J. Austr.* 2:603-604, Australian Medical Association, Australia (1978).

Hoover, J.E., "Chap. 78. Classification," in: *Remington's Pharmaceutical Sciences*, 14th Ed., Hoover, J.E., et al., eds., Mack Publishing Company, Easton, PA, pp. 1461-1462 (1970).

Kimura, E.T., "Effects of Chemical on Ciliated Tracheal Epithelium," *A.M.A. Arch. Otolaryngol.* 69:674-686, American Medical Association, United States (1959).

Knothe, V.J. and Aschoff, E., "Experimentelle Untersuchungen zum Effekt einiger schleimhantabschwellender Nasentropfen," *Das Deutsche Gesundheit.* 24:2384-2388, VEB Verlag Volk and Gesundheit, Germany (1969).

Lancaster, R., "Topical or Systemic Therapy?," *Prescribers' J.* 23:47-53 HMSO (1983).

Ledford, D.K., "Rhinitis," in: *Allergic Diseases, Diagnosis and Treatment*, 2nd Ed., Lieberman, P., and Anderson, J.A., eds., Humana Press, Totowa, NJ, pp. 159-182 (2000).

(56) References Cited

OTHER PUBLICATIONS

Lieberman, P., "Antihistamines," in: *Allergic Diseases, Diagnosis and Treatment*, 2nd Ed., Lieberman, P., and Anderson, J.A., eds., Humana Press, Totowa, NJ, pp. 323-335 (2000).

Pernarowski, M., "Chap. 80. Solutions, Emulsions, and Suspensions,", in: *Remington's Pharmaceutical Sciences*, 14th Ed., Hoover, J.E., et al., eds., Mack Publishing Company, Easton, PA, pp. 1478-1500 (1970).

Sciarra, J.J., "Chap. 90. Aerosols," in: *Remington's Pharmaceutical Sciences*, 14th Ed., Hoover, J.E., et al., eds., Mack Publishing Company, Easton, PA, pp. 1729-1753 (1970).

Simons, F.E , "Chap. 100. New Medications for rhinitis," in: *Asthma and Rhinitis*, Busse, W.W. and Holgate, S.T., eds., Blackwell Scientific Publications, Boston, MA, pp. 1325-1336 (1995).

Simons, F.E.R., "Antihistamines," in: *Allergy, Principles & Practice*, vol. II, Mosby, St. Louis, MO, pp. 612-637 (1998).

Swift, D.L., "Chap. 3, Aerosol characterization and generation," in: *Aerosols in Medicine, Principles, Diagnosis and Therapy*, Morén, F., et al., eds., Elsevier, New York, NY, pp. 53-76 (1985).

Swinyard, E.A. and Harvey, S.C., Chap. 64, "Histamine and Antihistamines," in: *Remington's Pharmaceutical Sciences*, 14th Ed., Hoover, J.E., et al., eds., Mack Publishing Company, Easton, PA, pp. 1142-1153 (1970).

*United States Pharmacopeia, The National Formulary*, 21st Revision, United States Pharmacopeial Convention, Inc., Rockville, MD, pp. 1329, 1333-1343, 1635, 1639, 1655, 1657-1660 (1985).

Weiler, J.M. and Meltzer, E.O., "Azelastine nasal spray as adjunctive therapy to azelastine tablets in the management of seasonal allergic rhinitis," *Ann. Allergy Asthma Immunol.* 79:327-332, American College of Allergy, Asthma & Immunology, United States (1997).

Zechal, H.-J., "Pharmacological and Toxicological Properties of Azelastine, a Novel Antiallergic Agent," *Arzeim.-Forsch./Drug Res.* 31:1184-1193, Editio Cantor, Germany (1981).

Zopf, L.C. and Blaug, S.M., "Chap. 85. Medicated Applications," in: *Remington's Pharmaceutical Sciences*, 14th Ed., Hoover, J.E., et al., eds., Mack Publishing Company, Easton, PA, pp. 1594-1625 (1970).

Ciprandi, G. et al., "Adhesion Molecules Modulation: A new target for rhinitis treatment," in: Passali, D., Ed., *Pediatric Otorhinolaryngology: An Update*, Kugler Publications, pp. 157-161 (1998).

Office Action mailed Sep. 14, 2009 in U.S. Appl. No. 11/284,109, Dang, P.G., et al., filed Nov. 22, 2005.

Office Action mailed Feb. 3, 2010 in U.S. Appl. No. 11/284,109, Dang, P.G., et al., filed Nov. 22, 2005.

Office Action mailed Apr. 28, 2010 in U.S. Appl. No. 10/518,016, Lulla, A., et al., filed Jul. 6, 2005.

Gray, H., "Anatomy of the Human Body," 20th ed., Lewis, W., ed., Lea & Febiger, Philadelphia, PA (1918), http://www.bartleby.com/107/ (cited in an Office Action dated Feb. 17, 2010, in parent U.S. Appl. No. 11/486,454, filed Jul. 14, 2006).

Allen, L., et al., "Ansel's Pharmaceutical Dosage Forms and Drug Delivery Systems," Lippincott Williams & Wilkins, 7th ed., pp. 93-98 (1999).

"Drug Facts and Comparisons," 1994 ed., Wolters Kluwer Co., pp. 2278.

The Washington Manual Allergy, Asthma and Immunology Subspecialty Consult, Lippincott Williams & Wilkins, pp. 148-149 (2003).

"Allergic Rhinitis-Prevention," WebMD Medical Reference, accessed at: http://www.webmd.com/allergies/tc/allergic-rhinitis-prevention (cited in an Office Action dated Nov. 18, 2001 in parent U.S. Appl. No. 11/486,454, filed Jul. 14, 2006).

Office Action mailed on Sep. 9, 2010 in U.S. Appl. No. 11/486,454, inventors Dang et al., filed Jul. 14, 2006.

Office Action mailed on Feb. 17, 2010 in U.S. Appl. No. 11/486,454, inventors Dang et al., filed Jul. 14, 2006.

Office Action mailed on Aug. 31, 2009 in U.S. Appl. No. 11/486,454, inventors Dang et al., filed Jul. 14, 2006.

Office Action mailed on Nov. 18, 2008 in U.S. Appl. No. 11/486,454, inventors Dang et al., filed Jul. 14, 2006.

Office Action mailed on Jan. 26, 2009 in U.S. Appl. No. 11/284,109, inventors Dang et al., filed Nov. 22, 2005.

Office Action mailed on Apr. 29, 2011 in U.S. Appl. No. 11/486,454, inventors Dang et al., filed Jul. 14, 2006.

"Combination of azelastine and steroids," inventors Lulla, A. et al., U.S. Appl. No. 12/879,515, filed Sep. 10, 2010.

Pre-Grant Opposition Brief filed Feb. 2, 2010 by Cipla Limited against Indian Patent Application No. 2092/KOLNP/2007.

Office Action mailed Apr. 29, 2011 in U.S. Appl. No. 11/486,454, inventors Dang et al., filed Jul. 14, 2006.

Office Action mailed on Jul. 21, 2011 in U.S. Appl. No. 11/284,109, inventors Dang et al., filed Nov. 22, 2005.

Office Action mailed Sep. 8, 2010 in U.S. Appl. No. 11/284,109, inventors Dang et al, filed Nov. 22, 2005.

Office Action mailed Feb. 23, 2011 in U.S. Appl. No. 11/284,109, inventors Dang et al, filed Nov. 22, 2005.

Office Action mailed Sep. 30, 2010 in U.S. Appl. No. 12/508,393, inventors Lulla et al., filed Jul. 23, 2009.

Office Action mailed Sep. 30, 2010 in U.S. Appl. No. 12/508,388, inventors Lulla et al., filed Jul. 23, 2009.

Bernstein, J.A. et al., "Double-blind, placebo-controlled trial of reformulated azelastine nasal spray in patients with seasonal allergic rhinitis," *Am. J. Rhinol. Allergy* 23: 512-517, Oceanside Publications, Inc. (2009).

Schmidt, B.M.W et al., "The New Topical Steroid Ciclesonide Is Effective in the Treatment of Allergic Rhinitis," *J. Clin. Pharm.* 39: 1062-1069, American College of Clinical Pharmacology (1999).

LaForce, C. et al., "Safety and efficacy of azelastine nasal spray (Astelin NS) for seasonal allergic rhinitis: a 4-week comparative multicenter trial," *Annals of Allergy, Asthma, and Immunology* 76: 181-188, Elsevier (1996).

Office Action mailed on Jun. 27, 2012 in U.S. Appl. No. 13/284,836, inventors Dang et al., filed Oct. 28, 2011.

Storms, W.W., "Treatment of seasonal allergic rhinitis with fluticasone propionate aqueous nasal spray: review of comparator studies," *Allergy 50* (Supplement 23): 25-29, John Wiley & Sons, Belgium (1995).

* cited by examiner

COMPOSITIONS COMPRISING AZELASTINE AND METHODS OF USE THEREOF

CROSS REFERENCE TO RELATED APPLICATIONS

The present application is a continuation-in-part of U.S. application Ser. No. 11/486,454, filed Jul. 14, 2006, now abandoned, which is a continuation-in-part of U.S. application Ser. No. 11/284,109, filed Nov. 22, 2005, now, U.S. Pat. No. 8,071,073 which claims the benefit of the filing date of U.S. Provisional Patent Application No. 60/630,274, filed Nov. 24, 2004, the disclosures of all of which are incorporated herein by reference in their entireties.

BACKGROUND OF THE INVENTION

1. Field of the Invention

The present invention is in the fields of pharmaceuticals, formulations chemistry and pharmacology. The invention generally relates to compositions comprising azelastine or pharmaceutically acceptable salts or esters thereof, including azelastine hydrochloride. In certain embodiments, the invention provides pharmaceutical compositions comprising azelastine hydrochloride formulated for use as nasal sprays and/or ocular solutions or drops, as well as dosage formulations for oral and pulmonary delivery. The invention also relates to pharmaceutical compositions comprising one or more active pharmaceutical ingredients, including antihistamines such as azelastine or pharmaceutically acceptable salts or esters thereof, for example, azelastine hydrochloride, particularly wherein the compositions are provided in unit dosage form. In certain embodiments, the invention provides such unit dosage pharmaceutical compositions comprising antihistamines such as azelastine hydrochloride formulated for use as nasal sprays and/or ocular or otic solutions or drops. The invention also relates to methods of use of such compositions in treating, alleviating or preventing symptoms associated with a variety of allergic and non-allergic conditions, particularly conjunctivitis and rhinitis.

2. Related Art

Azelastine is a second-generation H1 antagonist antihistamine which is used for its anti-allergic, anti-asthmatic and antihistamine properties. Azelastine is a phthalazinone derivative having the following structural formula:

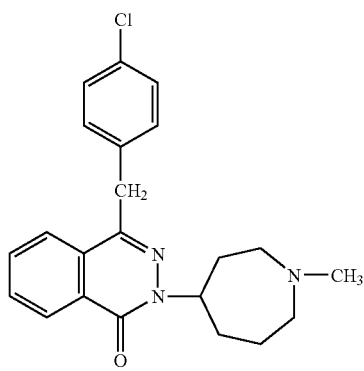

(I)

Azelastine can be produced in a variety of salt forms. The form most frequently used in pharmaceuticals is azelastine hydrochloride, which occurs as a white, almost odorless, crystalline powder with a strong bitter taste. The chemical name for azelastine hydrochloride is (±)-1-(2H)-phthalazinone, 4-[(4-chlorophenyl)methyl]-2-(hexahydro-1-methyl-1H-azepin-4-yl)-, mono-hydrochloride and its molecular formula is $C_{22}H_{24}ClN_3O \cdot HCl$. Other salt forms suitable for use in pharmaceutical compositions include azelastine embonate, which is reduced in bitterness compared to azelastine HCl (see U.S. Pat. No. 5,232,919 the disclosure of which is incorporated herein by reference), but which may also be less effective than azelastine HCl.

Research has shown that azelastine and its physiologically acceptable salt forms exhibit beneficial effects when the corresponding formulations are applied directly onto the nasal mucosa and/or the conjunctival sac of the eye (see U.S. Pat. No. 5,164,194). Elimination of symptoms or noticeable relief has thus been achieved in allergic rhinitis (seasonal and/or nonseasonal), vasomotor rhinitis and allergic conjunctivitis.

Despite its effectiveness, azelastine hydrochloride possesses a strong bitter taste. This bitter taste is so intense that it was found to be unpleasant even at a dilution of $1 \times 10^6$ (see U.S. Pat. No. 5,164,194). The bitter taste was not thought to be a problem in intranasal delivery of azelastine hydrochloride (see id.). However, subsequent clinical studies have shown that the bitter taste of azelastine hydrochloride is, indeed, an undesired element as a portion of the medication usually drips down into the pharynx after intranasal administration leading to an unpleasant and undesired taste experience by the patient. For example, MedPointe Pharmaceuticals, Inc. (Somerset, N.J.) has reported in the ASTELIN® product label insert that in clinical studies, the bitter taste adverse event occurred statistically more often in patients treated with ASTELIN® brand Nasal Spray (containing 0.10% w/v azelastine hydrochloride) versus vehicle placebo (19.7% vs. 0.6%). Likewise, the fluid formed by a combination of an ocularly administered medication, and induced tears secreted by the lachrymal glands, drains via the nasolachrymal duct into the nose and ultimately down the pharynx (see Day, N., "Ophthalmic Dosage Forms," in: *Pharmaceutical Preformulation and Formulation*, Buffalo Grove, Ill.: Interpharm Press (2002)). Such post-nasal drip caused by the ocular administration of compositions comprising azelastine hydrochloride therefore can also induce a bitter and unpleasant taste experience by the patient. Ukai et al. (U.S. Pat. No. 6,576,677) disclose the use of polyvinylpyrrolidone and/or copolyvidone to mask the taste of bitter medicaments, including azelastine.

Although the current conventional systems used for application of nasal or ocular pharmaceutical formulations have been shown to be clinically efficacious, they can suffer from relatively low efficiency levels in delivering pharmaceutical-containing solutions to the nasal mucosa or conjunctiva of a patient, thereby wasting a substantial portion of the pharmaceutical formulations and substantially increasing drug delivery costs. The low efficiency of current conventional delivery systems can also require patients to devote relatively long time periods or high volume of application of the formulations to receive an effective dose of the active pharmaceutical ingredient, which can lead to decreased patient compliance. Moreover, the use of preservatives in pharmaceutical formulations, often problematic for nasal or ocular medications due to the stinging of the nose or eye associated with the preservative, is nonetheless typically required so as to reduce or avoid bacterial contamination in multi-use conventional containers currently used for storage and application of nasal and ocular pharmaceutical formulations.

There remains a need for a therapeutically effective dose of azelastine hydrochloride, particularly for nasal, ocular, or pulmonary delivery, which possesses a more desired taste and/or has a reduced ability to drip down into the pharynx after intranasal or ocular administration, thus improving patient acceptability and compliance. Accordingly, there is also a need for new and improved methods and devices for the storage and delivery of pharmaceutical compositions, such as those comprising antihistamines including azelastine hydrochloride, particularly for nasal, ocular, otic or topical delivery, which will reduce administration costs, increase patient compliance, enhance overall effectiveness of the therapy and reduce or eliminate the need for including preservatives in the formulations.

BRIEF SUMMARY OF THE INVENTION

The present invention provides compositions, particularly stable pharmaceutical compositions, comprising azelastine and/or one or more pharmacologically acceptable salts or esters thereof, particularly azelastine hydrochloride, in unit dosage configuration. In certain embodiments, the pharmaceutical compositions comprise one or more pharmaceutically acceptable carriers or excipients, particularly one or more such carriers or excipients that are useful in formulating the composition into a form suitable for delivery to a variety of locations in or on the body, including intranasal, intraocular, intraotic and skin (topical) application. In particular embodiments, the pharmaceutical compositions comprise one or more pharmaceutically acceptable carriers or excipients, particularly one or more such carriers or excipients that are useful in formulating the composition into a form suitable for intranasal delivery, e.g., via aerosol or spray approaches, or for ophthalmic delivery, e.g., via ocular drops, or for pulmonary delivery, e.g., via a suitable device in a unit dosage configuration.

In certain additional embodiments, the invention provides pharmaceutical compositions comprising (or consisting essentially of) suitable concentrations of azelastine, or a pharmaceutically acceptable salt or ester thereof (such as azelastine hydrochloride (HCl)) to provide a therapeutically effective dose of azelastine, or a pharmaceutically acceptable salt or ester thereof, and one or more pharmaceutically acceptable carriers or excipients, wherein at least one of the pharmaceutically acceptable carriers or excipients is a taste-masking agent that masks the bitter taste associated with azelastine or its salts or esters such that the bitter taste experienced by a patient, upon administration of the pharmaceutical composition to the patient, is reduced or eliminated, thus enhancing the organoleptic acceptance of the composition when applied to the nasal, ocular, oral or pharyngeal mucosa. In preferred such embodiments, the taste-masking agent is selected from the group consisting of sucralose, thaumatin (e.g., Talin®) sucrose, saccharin (including the salt forms: sodium, calcium, etc.), fructose, dextrose, corn syrup, aspartame, acesulfame-K, xylitol, sorbitol, erythritol, ammonium glycyrrhizinate, thaumatin, neotame, mannitol, eucalyptus oil, camphor, and natural or artificial flavors or flavoring agents (for example menthol, mints, vanilla, orange, etc.), or combinations of two or more of such agents. Particularly preferred such embodiments provide such pharmaceutical compositions in which the taste-masking agent is sucralose, at a suitable concentration, for example, from about 0.001% to 1%, preferably from about 0.01% to about 0.5%, more preferably from about 0.02% to about 0.2%, or most preferably from about 0.05% to about 0.15%, of the total composition. Additional such embodiments may further comprise one or more additional flavoring agents, such as menthol, mints, vanilla, orange, etc. The compositions of the present invention preferably can be formulated for administration via any of a variety of routes, including but not limited to intranasal, ocular, oral, buccal, sublingual administration and the like.

In additional embodiments, the invention provides the intranasal or ocular pharmaceutical compositions described above, which may further comprise one or more agents that reduce or prevent postnasal drip of the compositions into the pharynx upon intranasal or ocular administration of the compositions. Certain such compositions may comprise, for example, one or more viscosity-increasing agents that increase the viscosity of the azelastine-containing composition. Suitable viscosity-increasing agents for use in accordance with this aspect of the invention include, but are not limited to, polyvinylpyrrolidones (PVP) (preferably having a molecular weight of about 10,000 to about 360,000, as well as mixtures containing one or more grades or molecular weight of PVP), cellulose derivatives (including, but not limited to, hydroxyethyl cellulose, carboxymethyl cellulose or its salts, hypromellose, and the like), carrageenan, guar gum, alginates, carbomers, polyethylene glycols, polyvinyl alcohol, xanthan gum, and the like. In certain preferred embodiments, hypromellose is used as a viscosity-increasing agent in the nasal or ocular formulations provided by the present invention.

Certain compositions of the invention may further comprise one or more additional components or agents, including one or more solvents, one or more preservatives, one or more stabilizers, one or more solubility-improving agents, one or more isotonicity agents, one or more buffers or buffering agents, one or more synthetic, semi-synthetic or natural bioadhesives, and the like.

The invention also provides methods of treating or preventing a variety of allergy-related and/or vasomotor-related conditions, or symptoms thereof, including allergic rhinitis, vasomotor rhinitis, allergic conjunctivitis and the like. According to this aspect of the invention, the compositions may be administered to the patient via any suitable mode of administration, including intranasal, ocular, oral, buccal, sublingual, pulmonary or the like. Suitably, the compositions are administered directly to the nasal mucosa (i.e., intranasally, e.g., in the form of a nasal spray or drops) or to the conjunctival sac of the eye (i.e., ocularly, e.g., in the form of ocular drops).

The present invention also provides oral dosage pharmaceutical compositions comprising (or consisting essentially of) a therapeutically effective dose of azelastine, or a pharmaceutically acceptable salt or ester thereof, at a concentration of from about 0.05% to about 5.0% by weight, or to provide about 0.5 mg to about 10 mg per dose, and one or more pharmaceutically acceptable carriers or excipients, wherein at least one of the pharmaceutically acceptable carriers or excipients is a taste masking agent, e.g., sucralose. In certain such embodiments, the amount of azelastine, or a pharmaceutically acceptable salt thereof (e.g., azelastine HCl) is in the range of about 0.05 mg to about 10 mg. Suitably the concentration of sucralose is about 0.05% to about 0.15% by weight. Exemplary forms of oral dosage compositions include, but are not limited to, liquid solutions, suspensions, tablets, capsules, chewable tablets, orally disintegrating tablets, effervescent compositions and orally dissolving/consumable films.

The present invention also provides pharmaceutical compositions comprising (or consisting essentially of) a therapeutically effective dose of azelastine, or a pharmaceutically acceptable salt or ester thereof, at a concentration of from about 0.05% to about 5.0% by weight, and one or more pharmaceutically acceptable carriers or excipients, wherein at least one of the pharmaceutically acceptable carriers or excipients is sucralose, and wherein the pharmaceutical composition further comprises one or more additional active agents. Suitable additional active agents for use in such compositions include, but are not limited to, antihistamines (such as cetirizine, fexofenadine, olopatadine, terfenadine and loratadine), steroids (such as fluoromethalone, fluticasone, mometasone, triamcinolone, betamethasone, flunisolide, budesonide, beclomethasone, budesonide, rimexolone, loteprednol (e.g., loteprednol etabonate), beloxil, prednisone and dexamethasone) or pharmaceutically acceptable salt, esters or derivatives thereof, leukotriene antagonists (such as albuterol sulfate, aminophylline, amoxicillin, ampicillin, astemizole, attenuated tubercle *bacillus*, azithromycin, bacampicillin, beclomethasone dipropionate, budesonide, bupropion hydrochloride, cefaclor, cefadroxil, cefixime, cefprozil, cefuroxime axetil, cephalexin, ciprofloxacin hydrochloride, clarithromycin, clindamycin, cloxacillin, doxycycline, erythromycin, ethambutol, fenoterol hydrobromide, fluconazole, flunisolide, fluticasone propionate, fluticasone furoate, formoterol fumarate, gatifloxacin, influenza virus vaccine, ipratropium bromide, isoniazid, isoproterenol hydrochloride, itraconazole, ketoconazole, ketotifen, levofloxacin, minocycline, montelukast, moxifloxacin, nedocromil sodium, nicotine, nystatin, ofloxacin, orciprenaline, oseltamivir, oseltamivir sulfate, oxtriphylline, penicillin, pirbuterol acetate, pivampicillin, pneumococcal conjugate vaccine, pneumococcal polysaccharide vaccine, prednisone, pyrazinamide, rifampin, salbutamol, salmeterol xinafoate, sodium cromoglycate, terbutaline sulfate, terfenadine, theophylline, triamcinolone acetonide, zafirlukast and zanamivir), decongestants (such as pseudoephedrine, phenylephedrine, phenylephrine, phenylpropanolamine, oxymetazoline, propylhexedrine, xylometazoline, epinephrine, ephedrine, desoxyephedrine, naphazoline, and tetrahydrozoline), expectorants (such as guaifenesin, sodium cromoglycate, codeine phosphate, and isoproternol hydrochloride), anti-fungal agents (such as amphotericin B, nystatin, fluconazole, ketoconazole, terbinafine, itraconazole, imidazole, triazole, ciclopirox, clotrimazole, and miconazole), non-steroidal anti-inflammatory agents (such as ibuprofen, diclofenac, aceclofenac, naproxen, etodolac, flurbiprofen, fenoprofen, ketoprofen, suprofen, fenbufen, fluprofen, tolmetin sodium, oxaprozin, zomepirac, sulindac indomethacin, piroxicam, mefenamic acid, nabumetone, meclofenamate sodium, diflunisal, flufenisal, piroxicam, ketorolac, sudoxicam and isoxicam), non-steroidal immunophilin-dependent immunosuppressants (such as cyclosporine, tacrolimus, ascomycin, pimecrolimus, rapamycin, everolimus, and other agents that inhibit calcineurin), COX-2 inhibitors (such as rofecoxib, celecoxib, valdecoxib, lumiracoxib, meloxicam, and nimesulide), anti-infective agents (such as penicillin, beta lactam antibiotics, cephalosporins, macrolides, ketolides, sulfonamides, quinolones, aminoglycosides, cefuroxime, vancomycin, amoxicillin, gentamicin and linezolid), mucolytic agents (such as acetylcysteine and dornase alpha), anticholinergic agents (such as mivacurium, atracurium, fazadinium, rocuronium, vecuronium, doxacurium, metocurine, pancuronium, pipecuronium, gallamine, hexafluoronium, suxamethonium, succinylcholine, decamethonium, atropine, scopolamine, hyoscyamine, benzatropine, trihexyphenidyl, biperiden, glycopyrrolate, ipratropium, pirenzepine, telenzepine, tiotropium, darifenacin, vedaclidine, tropicamide, cyclopentolate, dicycloverine, tolterodine, oxybutynin, homatropine, orphenadrine, diphenhydramine, hemicholinium-3, vesamicol, pralidoxime, obidoxime, oxitropium, alcuronium, dimethyltubocurarine, tubocurarine and ipratropium), mast cell stabilizers (such as cromolyn and nedcromil sodium), anti-viral agents (such as abacavir, acyclovir, adefovir, amantadine, amprenavir, arbidol, atazanavir, atripla boceprevir, cidofovir, combivir, darunavir delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, integrase inhibitor, lamivudine, lopinavir, loviride, maraviroc, moroxydine, nelfinavir, nevirapine nexavir, oseltamivir, peginterferon alfa-2a, penciclovir, peramivir, pleconaril, podophyllotoxin, raltegravir, ribavirin, rimantadine, ritonavir, saquinavir, stavudine, tenofovir, tipranavir, trifluridine, trizivir, tromantadine, truvada, valaciclovir, valganciclovir, vicriviroc, vidarabine, viramidine, zalcitabine, zanamivir and zidovudine), antiseptics (such as iodine, chlorhexidine acetate, sodium hypochlorite and calcium hydroxide), neurokinin antagonists (such as oximes, hydrazones, piperidines, piperazines, aryl alkyl amines, hydrazones, nitroalkanes, amides, is oxazolines, quinolines, isoquinolines, azanorbornanes, naphthyridines and benzodiazepines), 5-lipoxygenase inhibitors (such as zileuton, docebenone, piripost and tenidap) and triamcinolone or triamcinolone derivatives. Suitably the amount of sucralose in such compositions is about 0.05% to about 0.15% by weight. The pharmaceutical compositions can also comprise combinations of azelastine and multiple additional active agents, for example, azelastine, one or more steroids and one or more decongestants; or azelastine, one or more steroids and one or more leukotriene antagonists. Such combination compositions can also further comprise sucralose and/or other additional carriers or excipients.

In another embodiment, the present invention provides sustained release pharmaceutical compositions for oral delivery comprising (or consisting essentially of) a therapeutically effective dose of azelastine, or a pharmaceutically acceptable salt or ester thereof, and one or more pharmaceutically acceptable carriers or excipients, wherein at least one of the pharmaceutically acceptable carriers or excipients is sucralose, and wherein the azelastine, or the pharmaceutically acceptable salt or ester thereof, is: 1) coated with one or more sustained release components; 2) bound to a cation exchanger; 3) reacted with one or more osmotically active substances and coated with a semi-permeable membrane and a hole is bored into the membrane; or 4) embedded in, or is bound to, one or more substances selected from of the group consisting of digestible fats, indigestible fats, polymers and swelling agents. Suitably, the amount of azelastine in such sustained release compositions is about 0.05% to about 10.0% by weight and the amount of sucralose in such sustained release compositions is about 0.05% to about 0.15% by weight. In certain such embodiments, the amount of azelastine or salt thereof (e.g., azelastine HCl) is about 0.5 mg to about 10 mg.

In another embodiment, the present invention provides liquid pharmaceutical compositions for ocular administration, comprising (or consisting essentially of) a therapeutically effective dose of azelastine, or a pharmaceutically acceptable salt or ester thereof, and one or more pharmaceutically acceptable carriers or excipients, wherein at least one of the pharmaceutically acceptable carriers or excipients is sucralose, wherein the composition is free, or substantially free of preservatives, and wherein the composition is provided in a single unit-dose container or multi-dose container. Suitably, the amount of azelastine in such liquid, unit-dose or multi-dose pharmaceutical compositions is about 0.05% to about 0.15% by weight and the amount of sucralose in such liquid, unit-dose pharmaceutical compositions is about 0.05% to about 0.15% by weight. Suitable single unit-dose containers or multi-dose containers include, but are not limited to, high density polyethylene containers, for example, high density polyethylene containers produced using a blow-fill-seal manufacturing technique with a volume capacity of about 1 mL.

In another embodiment, the present invention provides liquid pharmaceutical compositions for nasal administration, comprising (or consisting essentially of) a therapeutically effective dose of azelastine, or a pharmaceutically acceptable salt or ester thereof, and one or more pharmaceutically acceptable carriers or excipients, wherein at least one of the pharmaceutically acceptable carriers or excipients is sucralose, wherein the composition is free, or substantially free of preservatives, and wherein the composition is provided in either a single unit-dose container or multi-dose container. Suitably, the amount of azelastine in such liquid, unit-dose or multi-dose pharmaceutical compositions is about 0.05% to about 0.15% by weight and the amount of sucralose in such liquid, unit-dose or multi-dose pharmaceutical compositions is about 0.05% to about 0.15% (e.g., 0.05%, 0.10% or 0.15%) by weight. Suitable single unit-dose containers or multi-dose containers include, but are not limited to, high density polyethylene containers, for example, high density polyethylene containers produced using a blow-fill-seal manufacturing technique with a volume capacity of about 1 mL.

The present invention also provides inhalable powder pharmaceutical compositions comprising (or consisting essentially of), a therapeutically effective dose of azelastine, or a pharmaceutically acceptable salt or ester thereof, and one or more pharmaceutically acceptable carriers or excipients, wherein the azelastine is in the form of micronized particles and wherein at least one of the pharmaceutically acceptable carriers or excipients is sucralose, for example, micronized particles of sucralose. Suitable such inhalable powder pharmaceutical compositions comprise micronized particles of azelastine with an average particle size of about 1 µm to about 5 µm, and micronized particles of sucralose with an average particle size of about 1 µm to about 20 µm. Such inhalable powder pharmaceutical compositions of the present invention can be formulated for pulmonary delivery using, for example, a dry powder inhaler. Suitably, the amount of azelastine in such inhalable powder pharmaceutical compositions is about 0.1% to about 20.0% by weight and the amount of sucralose in such inhalable powder pharmaceutical compositions is about 0.05% to about 20.0% by weight.

The present invention also provides inhalable spray pharmaceutical compositions comprising (or consisting essentially of), a suitable concentration to provide a therapeutically effective dose of azelastine, or a pharmaceutically acceptable salt or ester thereof, and one or more pharmaceutically acceptable carrier, stabilizer or excipient, wherein the azelastine is in a solution form and wherein at least one of the pharmaceutically acceptable carriers or excipients is sucralose dissolved in the solution. Such inhalable spray pharmaceutical compositions when used with a suitable device provide a fine spray of the components (including active and non-active components) having an average particle size of about 1 µm to about 5 µm. Such inhalable spray pharmaceutical compositions of the present invention can be formulated for pulmonary delivery using, for example, a suitable device or inhaler. Suitably the amount of azelastine in such inhalable spray pharmaceutical compositions is about 0.1% to about 10% by weight and the amount of sucralose in such inhalable spray pharmaceutical compositions is about 0.05% to about 0.15% (e.g., 0.05%, 0.10% or 0.15%) by weight.

The present invention also provides methods of treating snoring in an animal, comprising administering to the animal a therapeutically effective dose of azelastine, or a pharmaceutically acceptable salt or ester thereof, and one or more pharmaceutically acceptable carriers or excipients, wherein at least one of the pharmaceutically acceptable carriers or excipients is sucralose. The amount of azelastine in such compositions suitably is about 0.05% to about 0.15% by weight, and the amount of sucralose in such compositions is suitably about 0.05% to about 0.15% (e.g., 0.05%, 0.10% or 0.15%) by weight.

The present invention also provides methods of treating or preventing allergic rhinitis, non-allergic vasomotor rhinitis or allergic conjunctivitis in an animal, such as a human, suffering from or predisposed thereto, comprising administering to said animal a pharmaceutical composition comprising an effective amount azelastine and a taste-masking amount of sucralose, thereby avoiding the bitter taste associated with the azelastine.

In suitable embodiments, the present invention provides pharmaceutical compositions comprising (or consisting essentially of) the following:

About 0.05% to about 0.15% (w/v) azelastine hydrochloride; and about 0.01% to about 1.0% (w/v) steroid selected from the group consisting of fluticasone, mometasone, dexamethasone beloxil, loteprednol (e.g., loteprednol etabonate), budesonide and triamcinolone, or a pharmaceutically acceptable salt, ester or derivative thereof (e.g., fluticasone propionate, fluticasone dipropionate, fluticasone furoate, fluticasone maleate, fluticasone valerate, and the like).

About 0.05% to about 0.15% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide and triamcinolone; and about 0.1% to about 0.15% (w/v) sucralose.

About 0.1% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide and triamcinolone; and about 0.1% (w/v) sucralose.

About 0.1% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide and triamcinolone; and about 0.15% (w/v) sucralose.

About 0.15% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide and triamcinolone; and about 0.1% (w/v) sucralose.

About 0.15% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide and triamcinolone; and about 0.15% (w/v) sucralose.

About 0.05% to about 0.15% (w/v) azelastine hydrochloride; and about 0.1% to about 5.0% (w/v) montelukast.

About 0.05% to about 0.15% (w/v) azelastine hydrochloride; about 0.1% to about 5.0% (w/v) montelukast; and about 0.1% to about 0.15% (w/v) sucralose.

About 0.1% (w/v) azelastine hydrochloride; about 0.1% to about 5.0% (w/v) montelukast; and about 0.1% (w/v) sucralose.

About 0.1% (w/v) azelastine hydrochloride; about 0.1% to about 5.0% (w/v) montelukast; and about 0.15% (w/v) sucralose.

About 0.15% (w/v) azelastine hydrochloride; about 0.1% to about 5.0% (w/v) montelukast; and about 0.1% (w/v) sucralose.

About 0.15% (w/v) azelastine hydrochloride; about 0.1% to about 5.0% (w/v) montelukast; and about 0.15% (w/v) sucralose.

About 0.05% to about 0.15% (w/v) azelastine hydrochloride; and about 0.1% to about 1.0% (w/v) decongestant selected from the group consisting of pseudoephedrine and phenylephrine.

About 0.05% to about 0.15% (w/v) azelastine hydrochloride; about 0.1% to about 1.0% (w/v) decongestant selected from the group consisting of pseudoephedrine and phenylephrine; and about 0.1% to about 0.15% (w/v) sucralose.

About 0.1% (w/v) azelastine hydrochloride; about 0.1% to about 1.0% (w/v) decongestant selected from the group consisting of pseudoephedrine and phenylephrine; and about 0.1% (w/v) sucralose.

About 0.1% (w/v) azelastine hydrochloride; about 0.1% to about 1.0% (w/v) decongestant selected from the group consisting of pseudoephedrine and phenylephrine; and about 0.15% (w/v) sucralose.

About 0.15% (w/v) azelastine hydrochloride; about 0.1% to about 1.0% (w/v) decongestant selected from the group consisting of pseudoephedrine and phenylephrine; and about 0.1% (w/v) sucralose.

About 0.15% (w/v) azelastine hydrochloride; about 0.1% to about 1.0% (w/v) decongestant selected from the group consisting of pseudoephedrine and phenylephrine; and about 0.15% (w/v) sucralose.

About 0.05% to about 0.15% (w/v) azelastine hydrochloride; and about 0.1% to about 10.0% (w/v) NSAID selected from the group consisting of ibuprofen, diclofenac, aceclofenac and naproxen.

About 0.05% to about 0.15% (w/v) azelastine hydrochloride; about 0.1% to about 10.0% (w/v) NSAID selected from the group consisting of ibuprofen, diclofenac, aceclofenac and naproxen; and about 0.1% to about 0.15% (w/v) sucralose.

About 0.1% (w/v) azelastine hydrochloride; about 0.1% to about 10.0% (w/v) NSAID selected from the group consisting of ibuprofen, diclofenac, aceclofenac and naproxen; and about 0.1% (w/v) sucralose.

About 0.1% (w/v) azelastine hydrochloride; about 0.1% to about 10.0% (w/v) NSAID selected from the group consisting of ibuprofen, diclofenac, aceclofenac and naproxen; and about 0.15% (w/v) sucralose.

About 0.15% (w/v) azelastine hydrochloride; about 0.1% to about 10.0% (w/v) NSAID selected from the group consisting of ibuprofen, diclofenac, aceclofenac and naproxen; and about 0.1% (w/v) sucralose.

About 0.15% (w/v) azelastine hydrochloride; about 0.1% to about 10.0% (w/v) NSAID selected from the group consisting of ibuprofen, diclofenac, aceclofenac and naproxen; and about 0.15% (w/v) sucralose.

About 0.05% to about 0.15% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; and about 0.1% to about 1.0% (w/v) decongestant selected from the group consisting of pseudoephedrine and phenylephrine.

About 0.05% to about 0.15% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.1% to about 1.0% (w/v) decongestant selected from the group consisting of pseudoephedrine and phenylephrine; and about 0.1% to about 0.15% (w/v) sucralose.

About 0.1% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.1% to about 1.0% (w/v) decongestant selected from the group consisting of pseudoephedrine and phenylephrine; and about 0.1% (w/v) sucralose.

About 0.1% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.1% to about 1.0% (w/v) decongestant selected from the group consisting of pseudoephedrine and phenylephrine; and about 0.15% (w/v) sucralose.

About 0.15% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.1% to about 1.0% (w/v) decongestant selected from the group consisting of pseudoephedrine and phenylephrine; and about 0.1% (w/v) sucralose.

About 0.15% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.1% to about 1.0% (w/v) decongestant selected from the group consisting of pseudoephedrine and phenylephrine; and about 0.15% (w/v) sucralose.

About 0.05% to about 0.15% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; and about 0.1% to about 5.0% (w/v) montelukast.

About 0.05% to about 0.15% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.1% to about 5.0% (w/v) montelukast; and about 0.1% to 0.15% (w/v) sucralose.

About 0.1% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.1% to about 5.0% (w/v) montelukast; and about 0.1% (w/v) sucralose.

About 0.1% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.1% to about 5.0% (w/v) montelukast; and about 0.15% (w/v) sucralose.

About 0.15% (w/v) azelastine hydrochloride; about 0.01% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.1% to about 5.0% (w/v) montelukast; and about 0.1% (w/v) sucralose.

About 0.15% (w/v) azelastine hydrochloride; about 0.1% to about 1.0% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.1% to about 5.0% (w/v) montelukast; and about 0.15% (w/v) sucralose.

About 0.05% to about 0.15% (w/v) azelastine hydrochloride; about 0.01% to about 1% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, and triamcinolone; about 0.001% to about 5.00% (w/v) of a water-soluble polymer; about 0.01% to about 2% of a suspending agent; about 0.01% to about 0.2% of a wetting agent; about 0.01% to about 0.1% (w/v) disodium edetate; about 0.001% to about 0.5% (w/v) of a preservative such as benzalkonium chloride and/or phenethyl alcohol; about 0.1% to about 0.15% sucralose; a sufficient amount of a pharmaceutically acceptable buffer to maintain the pH of the composition within a range of from about 4.5 to about 7.4; a sufficient amount of an isotonicity agent to yield an osmolality of about 220 mosmol/kg to about 350 mosmol/kg; and QS water.

About 0.05% to about 0.15% (w/v) azelastine hydrochloride; about 0.1% to about 5% (w/v) montelukast; about 0.001% to about 5.00% (w/v) of a water-soluble polymer; about 0.01% to about 0.1% (w/v) disodium edetate; about 0.001% to about 0.5% (w/v) benzalkonium chloride; about 0.1% to about 0.15% sucralose; a sufficient amount of a pharmaceutically acceptable buffer to maintain the pH of the composition within a range of from about 4.5 to about 7.4; a sufficient amount of an isotonicity agent to yield an osmolality of about 220 mosmol/kg to about 350 mosmol/kg; and QS water.

About 0.05% to about 0.15% (w/v) azelastine hydrochloride; about 0.1% to about 1% (w/v) decongestant selected from the group consisting of pseudoephedrine and phenylephrine; about 0.001% to about 5.00% (w/v) of a water-soluble polymer; about 0.01% to about 0.1% (w/v) disodium edetate; about 0.001% to about 0.5% (w/v) benzalkonium chloride; about 0.1% to about 0.15% sucralose; a sufficient amount of a pharmaceutically acceptable buffer to maintain the pH of the composition within a range of from about 4.5 to about 7.4; a sufficient amount of an isotonicity agent to yield an osmolality of about 220 mosmol/kg to about 350 mosmol/kg; and QS water.

About 0.05% to about 0.15% (w/v) azelastine hydrochloride; about 0.1% to about 10% (w/v) NSAID selected from the group consisting of ibuprofen, diclofenac, aceclofenac and naproxen; about 0.001% to about 5.00% (w/v) of a water-soluble polymer; about 0.01% to about 0.1% (w/v) disodium edetate; about 0.001% to about 0.5% (w/v) benzalkonium chloride; about 0.1% to about 0.15% sucralose; a sufficient amount of a pharmaceutically acceptable buffer to maintain the pH of the composition within a range of from about 4.5 to about 7.4; a sufficient amount of an isotonicity agent to yield an osmolality of about 220 mosmol/kg to about 350 mosmol/kg; and QS water.

About 0.05% to about 0.15% (w/v) azelastine hydrochloride; about 0.01% to about 1% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide and triamcinolone; about 0.1% to about 1% (w/v) decongestant selected from the group consisting of pseudoephedrine and phenylephrine; about 0.001% to about 5.00% (w/v) of a water-soluble polymer; about 0.01% to about 2% of a suspending agent; about 0.01% to about 0.2% of a wetting agent; about 0.01% to about 0.1% (w/v) disodium edetate; about 0.001% to about 0.5% (w/v) of a preservative such as benzalkonium chloride and/or phenylethyl alcohol; about 0.1% to about 0.15% sucralose; a sufficient amount of a pharmaceutically acceptable buffer to maintain the pH of the composition within a range of from about 4.5 to about 7.4; a sufficient amount of an isotonicity agent to yield an osmolality of about 220 mosmol/kg to about 350 mosmol/kg; and QS water.

About 0.05% to about 0.15% (w/v) azelastine hydrochloride; about 0.01% to about 1% (w/v) steroid selected from the group consisting of fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide and triamcinolone; about 0.1% to about 1% (w/v) montelukast; about 0.001% to about 5.00% (w/v) of a water-soluble polymer; about 0.01% to about 2% of a suspending agent; about 0.01% to about 0.2% of a wetting agent; about 0.01% to about 0.1% (w/v) disodium edetate; about 0.001% to about 0.5% (w/v) of a preservative such as benzalkonium chloride and/or phenylethyl alcohol; about 0.1% to about 0.15% sucralose; a sufficient amount of a pharmaceutically acceptable buffer to maintain the pH of the composition within a range of from about 4.5 to about 7.4; a sufficient amount of an isotonicity agent to yield an osmolality of about 220 mosmol/kg to about 350 mosmol/kg; and QS water.

In another embodiment, the present invention provides methods of treating or preventing a physical disorder in an animal suffering from or predisposed thereto, comprising administering to said animal an effective amount of any one of the pharmaceutical compositions described herein. Suitably the animal is a human, and the physical disorder is selected from the group consisting of allergic rhinitis, non-allergic vasomotor rhinitis and allergic conjunctivitis.

In an additional embodiment, the present invention provides methods of treating or preventing allergic rhinitis, non-allergic vasomotor rhinitis or allergic conjunctivitis in an animal (e.g., a mammal such as a human) suffering from or predisposed thereto, comprising co-administering to the animal an effective amount of azelastine or a salt or ester thereof and an effective amount of one or more steroids. Suitably, the azelastine is azelastine HCl. Examples of steroids for co-administration include, but are not limited to, fluorometha-lone, fluticasone (e.g., fluticasone propionate, fluticasone dipropionate, fluticasone furoate, fluticasone maleate, fluticasone valerate, and the like), mometasone, triamcinolone, betamethasone, flunisolide, budesonide, beclomethasone, budesonide, rimexolone, beloxil, prednisone, loteprednol (e.g., loteprednol etabonate), (e.g., loteprednol (e.g., lotepre-dnol etabonate) etabonate) and dexamethasone, and pharmaceutically acceptable esters, salts, conjugates and other forms of such steroids. Suitably, the co-administration will comprise co-administration of azelastine and fluticasone (e.g., fluticasone propionate, fluticasone dipropionate, fluticasone furoate, fluticasone maleate, fluticasone valerate, and the like). In certain such embodiments, the azelastine (or salt or ester thereof) and the steroid are contained together in a single pharmaceutical composition, for example, a single pharmaceutical composition comprising azelastine (or a salt or ester thereof) and a steroid. In other embodiments, the azelastine (or a salt or ester thereof) is contained in one composition, e.g., a pharmaceutical composition comprising azelastine (or a salt or ester thereof) and the steroid is contained in a different composition, e.g., a pharmaceutical composition comprising a steroid.

In suitable embodiments, the co-administration comprises administering azelastine and one or more steroids (or composition(s) comprising the agents separately or both agents together) at the same time. In further embodiments, the co-administration comprises administering azelastine and one or more steroids (or composition(s) comprising the agents separately or both agents together) within less than about 30 minutes of each other, less than about 20 minutes of each other, or less than about 15 minutes of each other. If administered separately (e.g., in separate compositions), the azelastine and the one or more steroids can be co-administered in any order. Suitably, the azelastine (or a salt or ester thereof) and the one or more steroids are co-administered to the nasal passage.

In certain additional embodiments, the invention provides a unit dosage composition of matter, comprising: (a) a single unit dosage of a pharmaceutical composition; and (b) a unit dosage container comprising: (i) a squeezable chamber holding the single unit dosage of the composition and having an opening wherein the single unit dosage exits the opening when the squeezable chamber is squeezed; and (ii) a closure mechanism removably attached to the opening of the squeezable chamber. In certain embodiments, the unit dosage container is made of a moldable polymer.

In such embodiments, suitable polymers include, but are not limited to, polyethylene, polypropylene (PP), polystyrene (PS), nylon (Ny), polyvinyl chloride (PVC), polyethylene terephthalate (PET), polycarbonate (PC), polyoxymethylene (POM), polysulfon (PSF), polyethersulfon (PES), polyacrylate (PAR), and polyamid (PA). In certain embodiments, polymers include polyethylene, particularly medium-density polyethylene (MDPE) (or branched polyethylene) or high density polyethylene (HDPE) (or linear, polyethylene). In more particular embodiments, wherein the unit dose container is made of high density polyethylene (HDPE) and wherein the single unit dosage of the pharmaceutical composition has a volume of less than about 0.6 ml, and wherein the squeezable chamber has a volume of less than about or equal to about 1.0 ml. Preferred such embodiments include the use of unit dosage container systems wherein the volume of the unit dosage of the pharmaceutical composition within the container is about 0.1 ml to about 1.0 ml (suitably about 0.1 ml, about 0.15 ml, about 0.2 ml, about 0.21 ml, about 0.22 ml, about 0.23 ml, about 0.24 ml, about 0.25 ml, about 0.3 ml, about 0.35 ml, about 0.4 ml, about 0.45 ml, about 0.5 ml, about 0.55 ml, about 0.6 ml, about 0.65 ml, about 0.7 ml, about 0.75 ml, about 0.8 ml, about 0.85 ml, about 0.9 ml, about 0.95 ml or about 1.0 ml), more preferably about 0.1 ml to about 0.5 ml (suitably about 0.1 ml, about 0.15 ml, about 0.2 ml, about 0.21 ml, about 0.22 ml, about 0.23 ml, about 0.24 ml, about 0.25 ml, about 0.3 ml, about 0.35 ml, about 0.4 ml, about 0.45 ml or about 0.5 ml), and the volume of the squeezable chamber is about 0.5 ml to about 1.0 ml.

In additional embodiments, the invention provides such unit dose configurations wherein the unit dosage container further comprises an extension attached to the squeezable chamber having opposed first and second surfaces wherein identification can be located on at least one of the first and second surfaces. Such identification can be engraved, e.g., in writing, on the container extension and may be used to identify the contents of the unit dosage container (e.g., providing the identity and/or volume of the pharmaceutical composition contained therein, the manufacturing lot or control number of the pharmaceutical composition contained therein, the expiration date of the pharmaceutical composition contained therein, etc.).

In one such embodiment, the pharmaceutical formulation contained within the unit dosage container is a composition described herein, such as a pharmaceutical composition that comprises at least one antihistamine, such as, but not limited to, azelastine or a pharmaceutically acceptable salt thereof (such as azelastine hydrochloride), as well as other antihistamines, such as cetirizine, fexofenadine, olopatadine, terfenadine and loratadine, or pharmaceutically acceptable salts thereof, and optionally one or more additional active pharmaceutical ingredients, one or more pharmaceutically acceptable carriers or diluents, one or more taste-masking agents, and/or one or more preservatives, and the like.

In additional embodiments, the present invention provides compositions of matter comprising a plurality of unit dosage containers, each of the individual unit dosage containers comprising a single unit dosage of a pharmaceutical composition, such as one of the pharmaceutical compositions described herein, wherein each unit dosage container comprises: (a) a squeezable chamber holding the single unit dosage and having an opening wherein the single unit dosage exits the opening when the squeezable chamber is squeezed; and (b) a closure mechanism removably attached to the opening of the squeezable chamber. In certain such embodiments, the unit dose container is made of a suitable polymer, including but not limited to, polyethylene, polypropylene (PP), polystyrene (PS), nylon (Ny), polyvinyl chloride (PVC), polyethylene terephthalate (PET), polycarbonate (PC), polyoxymethylene (POM), polysulfon (PSF), polyethersulfon (PES), polyacrylate (PAR), and polyamid (PA). In certain embodiments, the unit dose container is made of polyethylene, particularly medium-density polyethylene (MDPE) (or branched polyethylene) or high density polyethylene (HDPE) (or linear polyethylene). In certain such embodiments, the unit dose container is made of HDPE. In more particular embodiments, the unit dose container is made of HDPE and the single unit dosage of the pharmaceutical composition has a volume of less than about 0.6 ml, and the squeezable chamber has a volume of less than or equal to about 1.0 ml. Preferred such embodiments include the use of a plurality of unit dosage containers wherein the volume of the unit dosage of the pharmaceutical composition within each of the individual containers in the plurality of containers is about 0.1 ml to about 0.5 ml (suitably about 0.1 ml, about 0.15 ml, about 0.2 ml, about 0.21 ml, about 0.22 ml, about 0.23 ml, about 0.24 ml, about 0.25 ml, about 0.3 ml, about 0.35 ml, about 0.4 ml, about 0.45 ml or about 0.5 ml), and the volume of each of the squeezable chambers is about 0.5 ml to about 1.0 ml.

In certain such embodiments, the invention provides an assembly comprising such a plurality of unit dosage containers wherein at least two of the unit dosage containers are removably attached to one another. In particular embodiments the unit dosage containers in the form of a plurality of containers corresponding to the prescribed dosage regime, e.g., two, three, five or 10 containers are removably attached to one another. The plurality of unit dosage containers are separated from one another by a removably attached perforation, demarcation, or similar marking thereof. In certain embodiments, the perforation facilitates removal of a single unit dose container from the plurality of unit dosage containers. Certain embodiments according to this aspect of the invention may further comprise a container (e.g., a box, blister package, foil package, etc.) comprising one or more of the pluralities of containers that comprise the pharmaceutical formulation, in a package or kit format. In additional embodiments, the plurality of containers, for example in a package or kit format, may further comprise instructions for use of the unit dosage containers by the end user.

Non-limiting exemplary unit dosage forms of the present compositions comprise formulations comprising an antihistamine (including $H_1$, $H_2$, $H_3$ and $H_4$ antagonists), such as azelastine or a pharmaceutically acceptable salt thereof such as azelastine hydrochloride. In other embodiments, the formulations comprise two or more active pharmaceutical ingredients, one of which may be an antihistamine such as azelastine hydrochloride and the other of which may be a second active pharmaceutical ingredient including, but not limited to, one or more additional antihistamines (including $H_1$, $H_2$, $H_3$ and $H_4$ receptor antagonists such cetirizine, fexofenadine, olopatadine, terfenadine and loratadine, or pharmaceutically acceptable salts thereof), one or more steroids (e.g., one or more safe steroids), one or more leukotriene antagonists, one or more prostaglandin D2 receptor antagonists, one or more decongestants, one or more anti-fungal agents, triamcinolone and triamcinolone derivatives, one or more non-steroidal immunophilin-dependent immunosuppressants (NSIDIs), one or more anti-inflammatory agents, one or more non-steroidal anti-inflammatory agents (NSAIDs), one or more COX-2 inhibitors, one or more anti-infective agents, one or more mucolytic agents, one or more anticholinergic agents, one or more mast cell stabilizers, one or more antibiotics, one or more non-antibiotic anti-microbial agents, one or more anti-viral agents, one or more antiseptics, one or more neurokinin antagonists, platelet activating factor (PAF) and one or more 5-lipoxygenase (5-LO) inhibitors. In additional embodiments, the pharmaceutical compositions may comprise one or more additional reagents, such as one or more pharmaceutically acceptable carriers, excipients, buffers, salts, isotonicity agents, or taste-masking agents (such as sucralose, sorbitol, xylitol, lactitol, mannitol, menthol, and the like). According to one such aspect of the invention, such formulations are contained in unit dose configuration in the absence of preservatives; however, in other aspects, one or more preservatives such as benzalkonium chloride may be included within the formulation.

In certain additional aspects, the invention provides methods of treating or preventing a physical disorder, condition or symptom thereof, in a patient by administering to the eye, nose, ear, skin, etc. of a patient a unit dosage form of a pharmaceutical composition of the invention comprising an effective amount of one or more active pharmaceutical ingredients in a unit dosage form. Suitably, the methods comprise providing a unit dosage form comprising a unit dosage container made of high density polyethylene, the unit dosage form having a volume of less than about 0.6 ml and said dosage container having a volume of less than or equal to about 1.0 ml. Suitably the unit dose form contains one or more antihistamines (e.g., azelastine HCl) or pharmaceutically acceptable salts thereof, and optionally one or more additional active pharmaceutical ingredients such as those described herein. The unit dosage form is then administered to the subject, and the unit dosage container is then discarded.

In certain such aspects, the physical disorder, condition or symptom thereof treatable or preventable by such methods of the invention includes, but is not limited to, allergic or non-allergic nasal, ocular or skin conditions treatable or preventable using the pharmaceutical compositions of the present invention (preferably in unit dose configuration), such as allergic reactions to plant or insect allergens, environmental allergens, allergic and non-allergic ocular conditions (e.g., hay fever conjunctivitis, perennial allergic conjunctivitis, giant papillary conjunctivitis (including that associated with the use of contact lenses), allergic and non-allergic nasal conditions (e.g., allergic rhinitis (including seasonal allergic rhinitis and perennial allergic rhinitis), non-allergic rhinitis, sinusitis, rhino-sinusitis and the like) non-allergic noninfectious conjunctivitis, vernal keratoconjunctivitis or atopic keratoconjunctivitis) and irritant dermatitis, as well as other related or similar disorders. Other physical conditions, disorders or symptoms thereof suitably treated or prevented using the pharmaceutical compositions of the present invention (preferably in unit dose configuration) include, but are not limited to, nasal and ocular conditions associated with the common cold; nasal, ocular or skin conditions resulting from a reaction to insect bites; postoperative ocular inflammation; acute anterior uveitis; allergic blepharitis; keratitis (such as herpes zoster or superficial punctate keratitis), uticaria and the like; as well as otic conditions such as otitis media, tinnitus, Eustachian tube constriction or blockage, and the like. In another embodiment, the pharmaceutical compositions of the present invention (preferably in unit dose configuration) can be used to treat or prevent motion sickness. In another embodiment, the pharmaceutical compositions of the present invention (preferably in unit dose configuration) can be used to treat or prevent snoring.

Other features and advantages of the invention will be apparent from the following detailed description, and from the claims. The disclosed materials, methods, and examples are for illustrative purposes only and are not intended to be limiting. Skilled artisans will appreciate that methods and materials similar or equivalent to those described herein can be used to practice the invention.

Unless otherwise defined, all technical and scientific terms used herein have the meaning commonly understood by one skilled in the art to which this invention belongs. All publications, patent applications, patents, and other references

BRIEF DESCRIPTION OF THE DRAWINGS/FIGURES

DETAILED DESCRIPTION OF THE INVENTION

Overview

Figure 1:
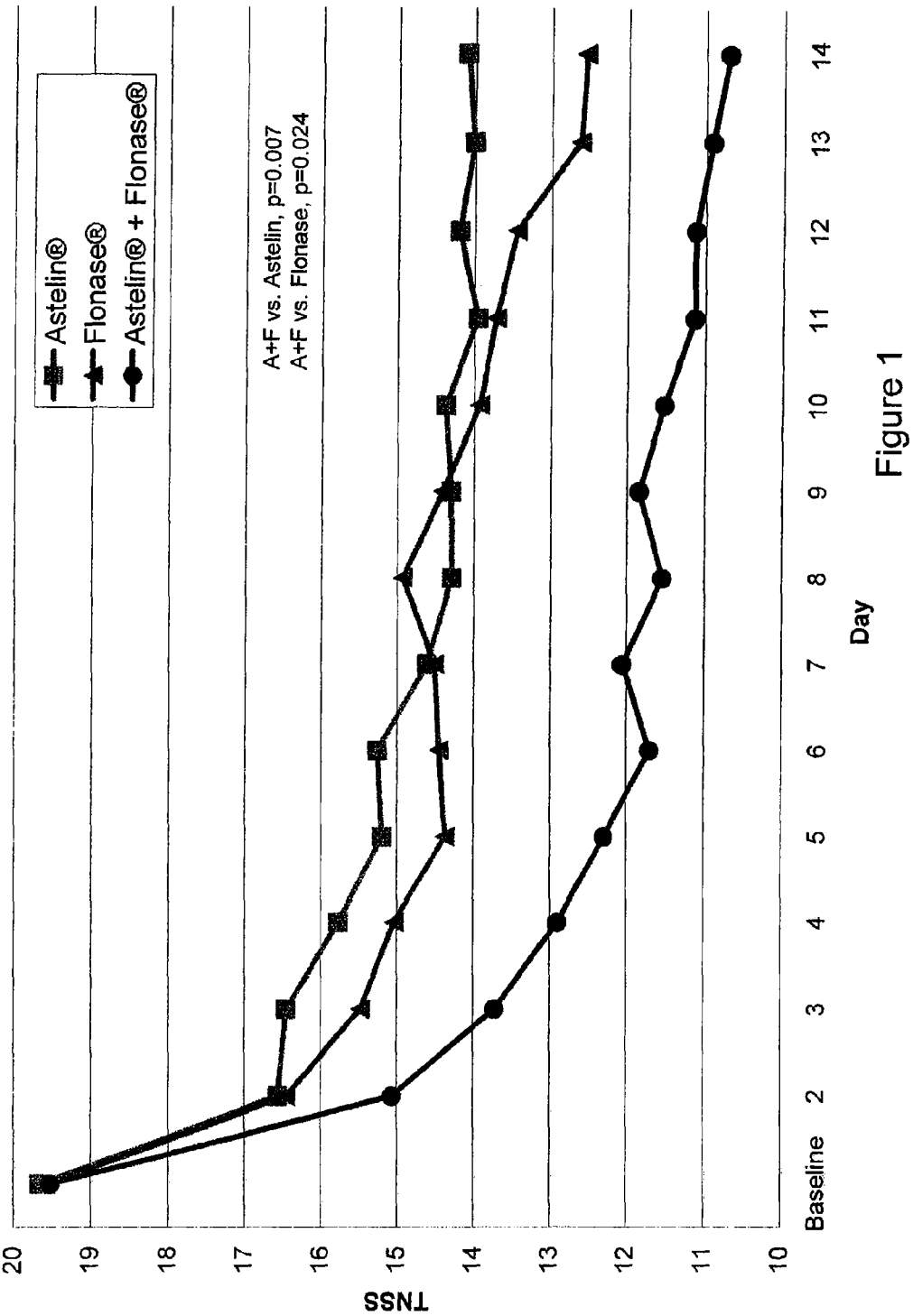
FIG. 1 shows the effects on the total nasal symptom score resulting from the co-administration of azelastine HCl and fluticasone propionate.
Figure 2:
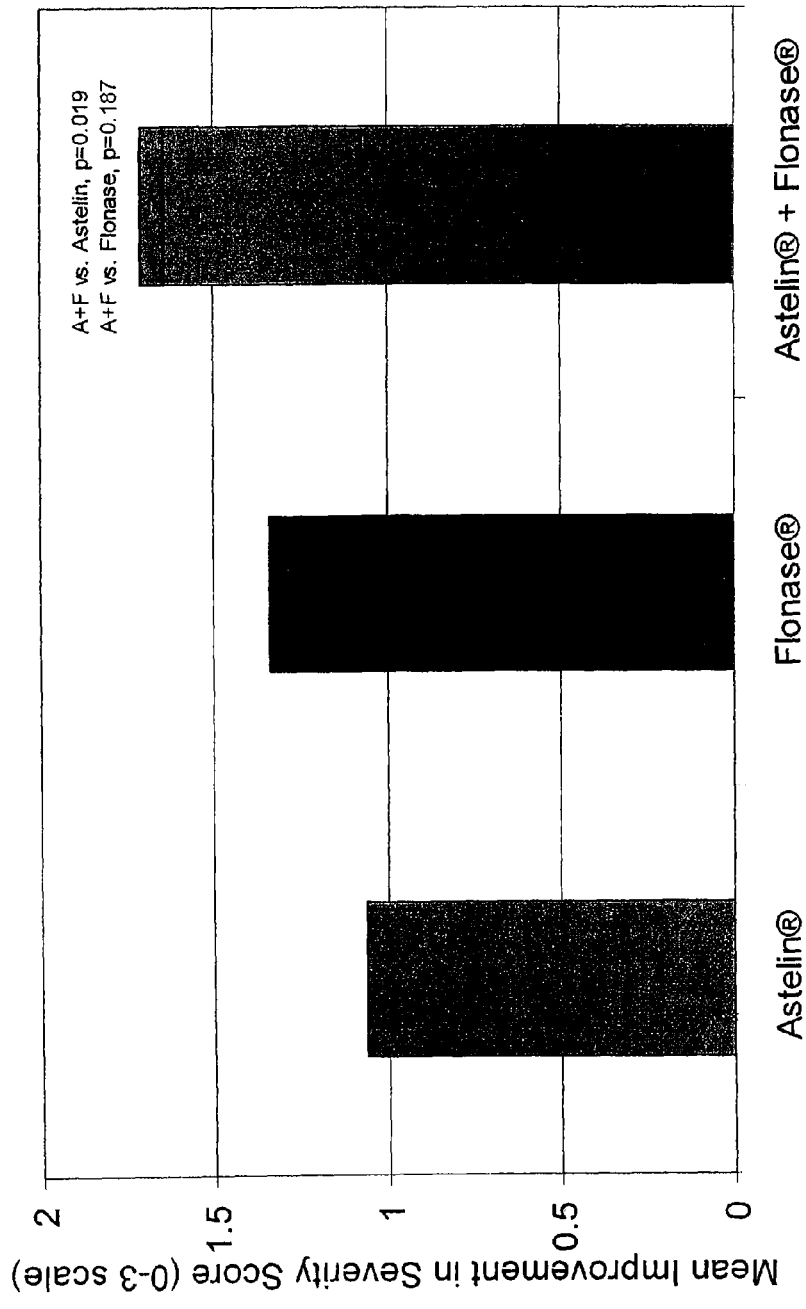
FIG. 2 shows the mean improvement in severity score from baseline for the symptom of runny nose, resulting from the co-administration of azelastine HCl and fluticasone propionate.
Figure 3:
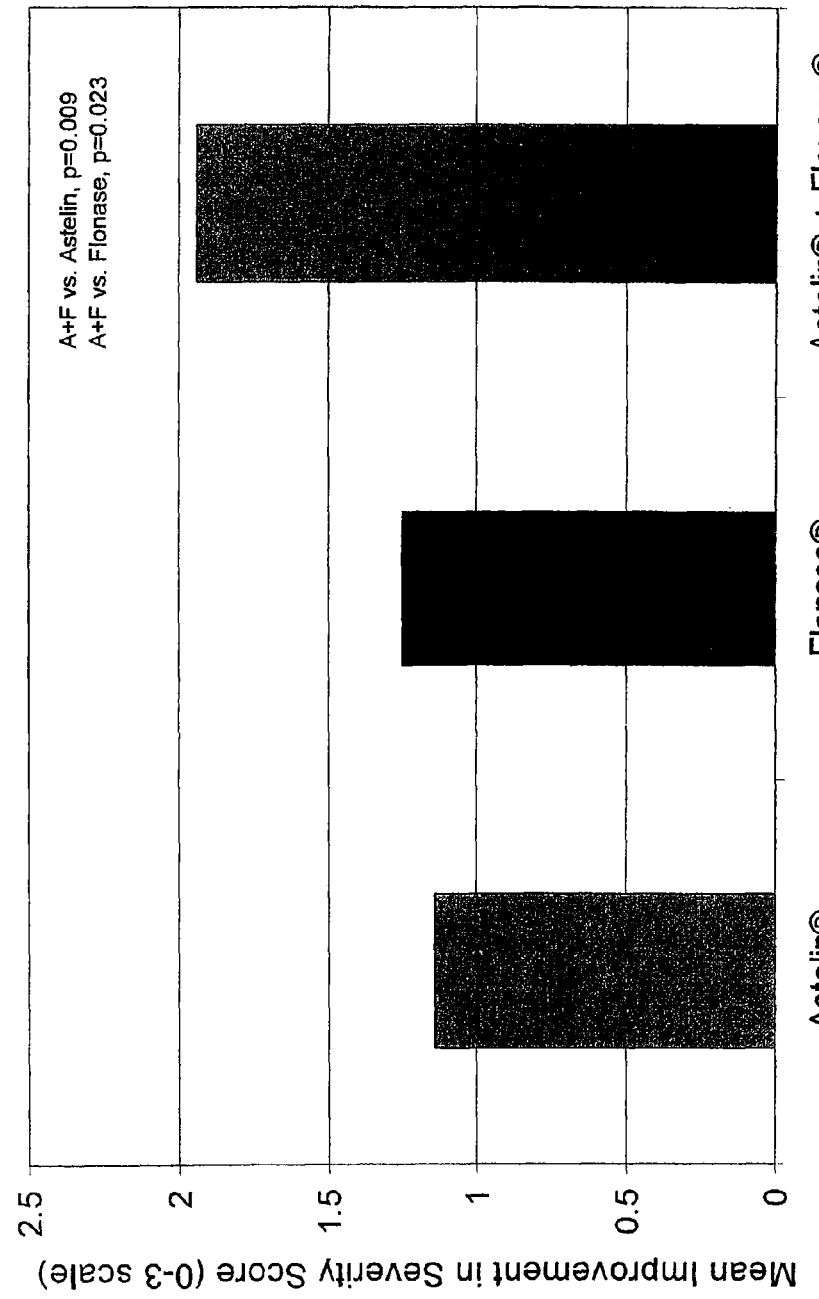
FIG. 3 shows the mean improvement in severity score from baseline for the symptom of itchy nose, resulting from the co-administration of azelastine HCl and fluticasone propionate.
Figure 4:
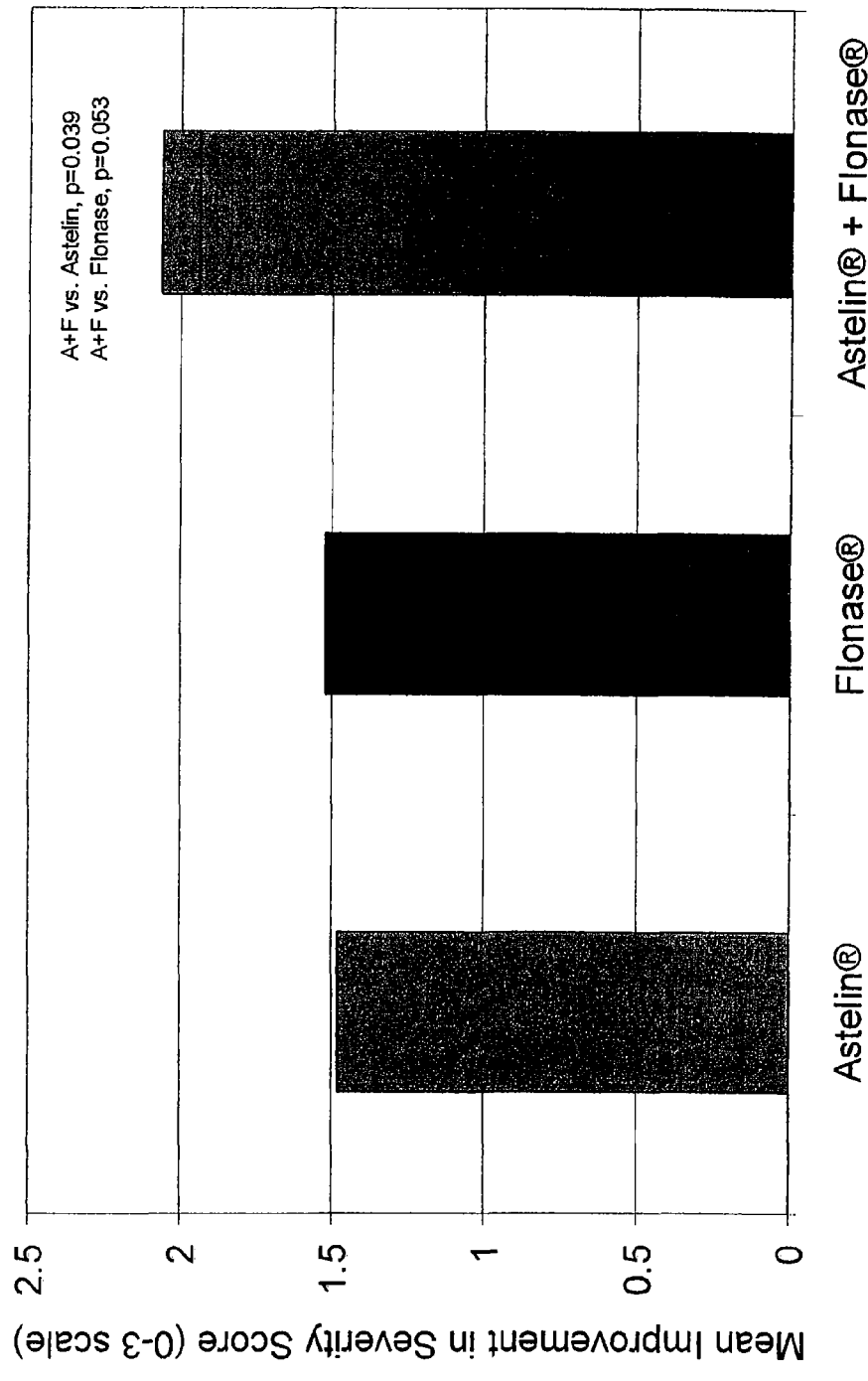
FIG. 4 shows the mean improvement in severity score from baseline for the symptom of sneezing, resulting from the co-administration of azelastine HCl and fluticasone propionate.
Figure 5:
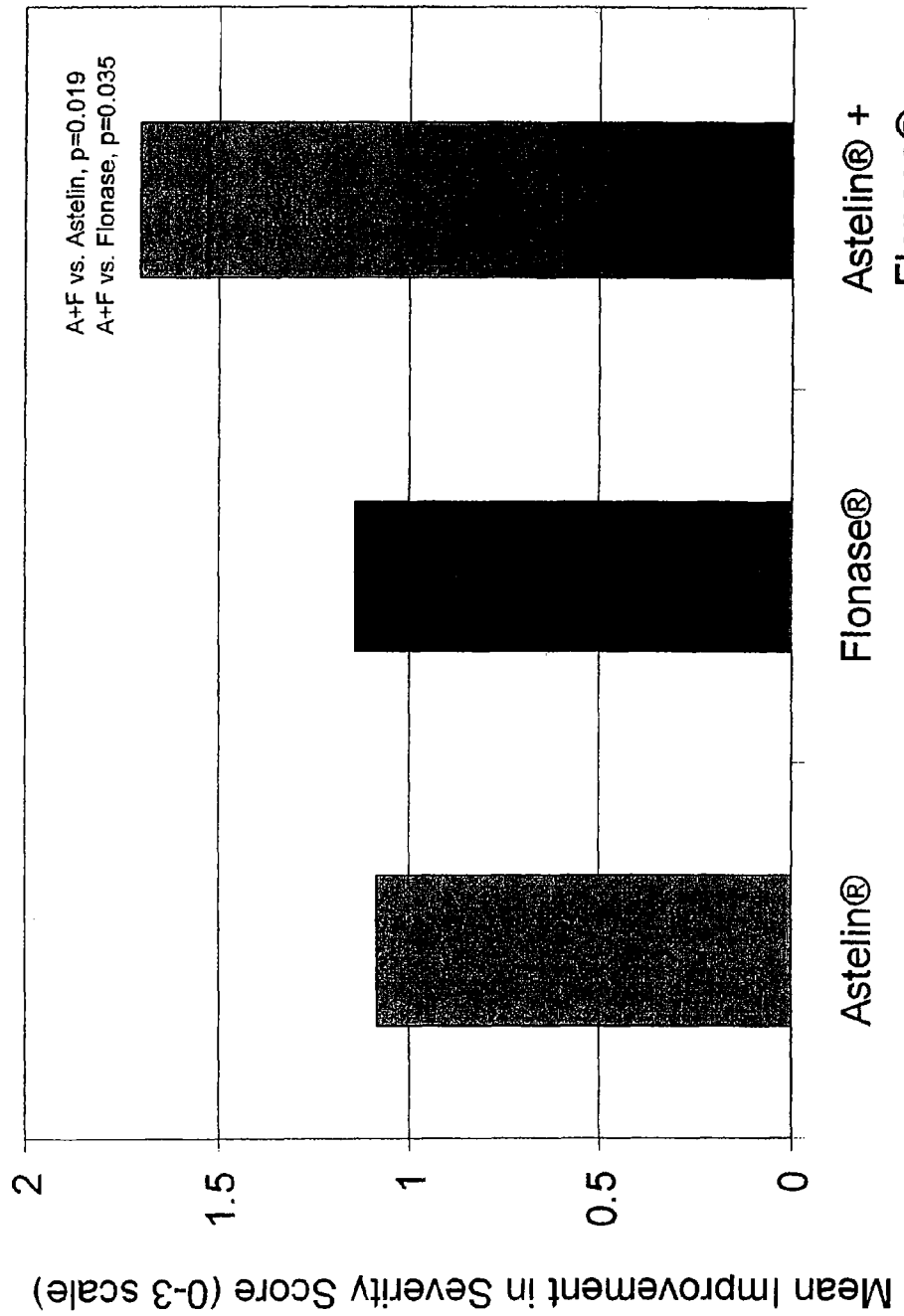
FIG. 5 shows the mean improvement in severity score from baseline for the symptom of congestion, resulting from the co-administration of azelastine HCl and fluticasone propionate.

As used herein when referring to any numerical value, the term "about" means a value falling within a range that is ±10% of the stated value. For example, "about 50° C." encompasses a range of temperatures from 45° C. to 55° C., inclusive; similarly, "about 100 mM" encompasses a range of concentrations from 90 mM to 110 mM, inclusive.

As used herein, the articles "a," "an" and "one" mean "at least one" or "one or more" of the object to which they refer, unless otherwise specified or made clear by the context in which they appear herein.

The present invention provides compositions, particularly pharmaceutical compositions, comprising azelastine and/or one or more of its pharmacologically acceptable salts or esters thereof, particularly azelastine hydrochloride. Preferred such compositions of the invention comprise azelastine hydrochloride as the active ingredient, and may further comprise one or more additional components, such as one or more solvents, one or more preservatives, one or more stabilizers, one or more buffers or buffering agents, one or more bioadhesives, one or more suspending agents (e.g., microcrystalline cellulose, sodium carboxy methyl cellulose, hypromellose carbopol and the like), one or more surfactants or wetting agents and/or one or more isotonicity agents. To reduce or eliminate the bitter taste associated with azelastine (or a salt or ester thereof, such as azelastine hydrochloride), the compositions of the present invention further comprise one or more stable taste-masking, flavoring, or sweetening agents, or a combination of such agents. To reduce the post-nasal drip of the compositions of the present invention for intranasal or ocular administration, the compositions of the present invention may further comprise one or more stable viscosity-increasing agents, one or more stable bioadhesive agents, and/or a combination of viscosity-increasing agents and bioadhesive agents. In other embodiments, the pharmaceutical compositions can comprise one or more additional active agents, such as those described herein, in addition to azelastine, including, but not limited to, additional antihistamines (including $H_1$, $H_3$ and $H_4$ receptor antagonists), steroids (e.g., safe steroids), leukotriene antagonists, prostaglandin D2 receptor antagonists, decongestants, anti-fungal agents, triamcinolone and triamcinolone derivatives, non-steroidal immunophilin-dependent immunosuppressants (NSIDIs), anti-inflammatory agents, non-steroidal anti-inflammatory agents (NSAIDs), COX-2 inhibitors, anti-infective agents, mucolytic agents, anticholinergic agents, mast cell stabilizers, non-antibiotic anti-microbial agents, anti-viral agents, antiseptics, neurokinin antagonists, platelet activating factor (PAF) and 5-lipoxygenase (5-LO) inhibitors.

In certain embodiments, the pharmaceutical compositions comprise one or more pharmaceutically carriers or excipients, particularly one or more such carriers or excipients that are useful in formulating the composition into a form suitable for delivery intranasally via aerosol or spray approaches, or for delivery ocularly via drops. In related embodiments, the invention provides such pharmaceutical compositions in which at least one of the carriers or excipients is a taste-masking agent, such as sucralose, and other compositions in which at least one of the carriers or excipients is a viscosity-increasing agent, such as hypromellose. In certain preferred embodiments, the pharmaceutical compositions provided by the invention comprise at least one taste-masking agent such as sucralose, and at least one viscosity-increasing agent such as hypromellose. The compositions of the invention are particularly useful in treating or preventing the symptoms associated with a variety of conditions such as allergic rhinitis (seasonal and/or perennial), non-allergic rhinitis, vasomotor rhinitis, rhinosinusitis, allergic conjunctivitis, allergic and non-allergic ear conditions (including otitis media, tinnitus, Eustachian tube constriction or blockage, and the like) and other physical disorders as described elsewhere herein and as will be apparent to the ordinarily skilled artisan.

The present invention provides compositions, particularly pharmaceutical compositions, comprising one or more active pharmaceutical ingredients in a pharmaceutically acceptable form, preferably in unit dose configuration. By "unit dose configuration" as used herein is meant that the pharmaceutical formulation is contained within a container which is designed to deliver an effective single dosage of the pharmaceutical formulation to an area of a patient's body that is to be treated with the formulation, and to then be discarded and not reused. The present invention also provides compositions of matter comprising a container (e.g., a unit dose container) comprising one or more pharmaceutical ingredients.

Single dose, disposable, containers for dispensing pharmaceutically active agents to the nose and eyes have been disclosed (see, e.g., U.S. Pat. Nos. 7,185,790, 6,619,516 and 4,469,254), including dispensers comprising integrated nozzles and removable caps (see, e.g., U.S. Pat. No. 6,666, 359). However, for unit dose containers utilizing small volume vessels (e.g., about 1 mL containers containing about 0.1 to about 0.7 mL of solution) in general, more pliable materials, such as low density (high pressure) polyethylene that were easily squeezed were required, thus allowing for dispensing of the solution (see, e.g., U.S. Pat. No. 3,197,120). Prior to the present invention, the use of high density polyethylene in small volume, unit dose containers had not been developed.

Compositions and Modes of Administration

In certain embodiments, the invention provides compositions, particularly pharmaceutical compositions, comprising (or consisting essentially of) a therapeutically or pharmacologically effective amount of azelastine or a pharmaceutically acceptable salt or ester thereof and one or more pharmaceutically acceptable carriers or excipients. Particularly preferred for use in the compositions of the invention is azelastine hydrochloride (see U.S. Pat. Nos. 3,813,384, 4,704,387 and 5,164,194, the disclosures of which are incorporated herein by reference in their entireties). By "pharmaceutically acceptable carrier or excipient" is meant a non-toxic solid, semisolid or liquid filler, diluent, encapsulating material or formulation auxiliary of any type.

The compositions of the present invention can be administered to a patient via any suitable mode of administration, including oral, intranasal, ocular, buccal, sublingual, pulmonary or the like. In certain embodiments, the compositions are administered directly to the nasal mucosa (i.e., intranasally, e.g., in the form of a nasal spray or drops) or to the conjunctival sac of the eye (i.e., ocularly, e.g., in the form of ocular drops) or to the ear canal (i.e., otically, for example, in the form of ear drops, solution, spray, wash, cream or ointment). In alternative embodiments, the compositions are administered topically to the buccal or sublingual cavity or intrapulmonarily, or topically to the skin in the form of drops, spray, ointment, etc. Regardless of their mode of administration, the compositions provided by the present invention suitably comprise from about 0.0001% to about 1.0%, and more suitably from about 0.005% to about 0.5% or most suitably from about 0.05% to about 0.15% (e.g., about 0.05%, about 0.06%, about 0.07%, about 0.08%, about 0.09%, about 0.10%, about 0.11%, about 0.12%, about 0.13%, about 0.14% or about 0.15%), of antihistamine (e.g., $H_1$, $H_2$, $H_3$ and/or $H_4$ antihistamines as disclosed herein) based on the weight of the active ingredient. For example, azelastine-containing compositions provided by the present invention suitably comprise from about 0.0001% to about 1.0%, and more suitably from about 0.005% to about 0.5% or most suitably from about 0.05% to about 0.15% (e.g., about 0.05%, about 0.06%, about 0.07%, about 0.08%, about 0.09%, about 0.10%, about 0.11%, about 0.12%, about 0.13%, about 0.14% or about 0.15%), of pure azelastine salt (e.g., azelastine HCl) based on weight (calculated as the free azelastine base) as the active ingredient. The percentage of active pharmaceutical ingredient (e.g., antihistamines such as azelastine) in a given composition of the invention is calculated as a percentage of the weight of the composition for solid dosage forms (i.e., weight/weight) or as a percentage of the volume of the composition for solution or liquid dosage forms (i.e., weight/volume). The amount of a given salt form of azelastine (e.g., azelastine hydrochloride) to be included in a given composition of the invention is calculated so that the composition contains the amount of pure azelastine noted above. In certain compositions of the invention, e.g., nasal spray formulations, a solution formulated at a higher concentration of azelastine (or salt thereof) can be delivered at a smaller volume to provide a given dosage of azelastine (or salt thereof), thus minimizing the possibility of postnasal drip of the solution into the pharynx which leads to an unpleasant taste sensation by the person to whom the azelastine-containing nasal spray is administered.

In certain embodiments, the compositions of the invention may be formulated into forms for oral administration, including solid dosage forms or liquid dosage forms. In alternative embodiments, the compositions of the invention may be formulated into forms for direct administration to the mucosa, including the nasal mucosa (i.e., intranasal administration), ocular tissue or conjunctival sac (i.e., ocular administration), buccal mucosa (i.e., buccal administration) or oral mucosa under the tongue (i.e., sublingual administration).

Solid dosage forms for oral administration include capsules, tablets, pills, powders, particles and granules. In such solid dosage forms, the active compound(s) (e.g., antihistamines such as azelastine) are mixed with at least one pharmaceutically acceptable excipient or carrier such as (a) fillers or extenders such as starches, lactose, sucrose, glucose, mannitol, dicalcium phosphate and microcrystalline cellulose; (b) binders such as sodium carboxymethylcellulose, alginates, gelatin, polyvinylpyrrolidone, and acacia; (c) disintegrating agents such as agar-agar, calcium carbonate, potato or tapioca starch, alginic acid, certain silicates, sodium carboxymethyl cellulose, pregelatinized starch and sodium starch glycolate; (d) lubricants such as calcium stearate, magnesium stearate, stearic acid, solid polyethylene glycols, sodium lauryl sulfate, and mixtures thereof; and/or (e) glidants such as talc, silicon dioxide and starch. In the case of capsules, tablets and pills, the dosage form may also comprise buffering agents. Solid compositions of a similar type may also be employed as fillers in soft and hard filled gelatin capsules using such excipients as lactose or milk sugar as well as high molecular weight polyethylene glycols, oils and the like. The solid dosage forms of tablets, dragees, capsules, pills, and granules can be prepared with coatings, which may in themselves provide taste-masking, and shells such as enteric coatings and other coatings that are well known in the pharmaceutical formulating art. The solid dosage forms also may optionally contain opacifying, coloring and/or flavoring agents, and can also be formulated such that they release the active azelastine ingredient(s) only, or preferentially, in a certain part of the intestinal tract, optionally in a delayed manner (see U.S. Pat. No. 5,271,946, the disclosure of which is incorporated herein by reference in its entirety). Examples of embedding compositions which can be used include polymeric substances and waxes. The active compounds can also be in micro-encapsulated form, if appropriate, with one or more of the above-mentioned excipients.

Liquid dosage forms for nasal, ocular or oral administration include pharmaceutically acceptable emulsions, solutions, suspensions, syrups and elixirs. In addition to the active pharmaceutical ingredient(s), such as the antihistamine compound(s) (e.g., $H_1$, $H_2$, $H_3$ and/or $H_4$ antagonists, such as azelastine compound(s)), the liquid dosage forms may contain inert diluents and/or solvents commonly used in the art. Water is the solvent of choice for the formulations of the invention; however, combinations of water with other physiologically acceptable solvents as required are also satisfactory for use. Other solvents, solubilizing agents and emulsifiers suitable for use in place of, or in addition to, water include but are not limited to saturated aliphatic mono- and polyvalent alcohols which contain 2-6 carbon atoms (including, but not limited to, ethanol, 1,2-propylene glycol, sorbitol, and glycerine), polyglycols such as polyethylene glycols, and surfactants/emulsifiers like the fatty acid esters of sorbitan, and mixtures thereof. Oils, in particular, cottonseed, peanut, or corn oils, may also be added to the compositions. The combination of the additional solvents in the aqueous solution should preferably not exceed about 15% (w/v) of the total composition. Besides inert diluents, the oral compositions can also include adjuvants such as wetting agents, emulsifying and suspending agents (e.g., microcrystalline cellulose, sodium carboxymethyl cellulose, hypromellose, carbopol and the like), surfactants, sweetening, flavoring, and perfuming agents, including those described in further detail herein below. Liquid dosage forms that provide the active ingredient in suspension may comprise, in addition to the active azelastine compound(s), one or more suspending agents such as microcrystalline cellulose, magnesium aluminum silicate, bentonite, agar-agar, hypromellose, sodium carboxymethyl cellulose, carbopol/carbomer, pectin, acacia, tragacanth or their mixtures.

Certain liquid compositions of the invention may further comprise one or more preservatives and/or one or more stabilizers. Preservatives that are suitable for use in the compositions of the invention include, but are not limited to, edetic acid and their alkali salts such as disodium EDTA (also referred to as "disodium edetate" or "the disodium salt of edetic acid") and calcium EDTA (also referred to as "calcium edetate"), benzyl alcohol, methylparaben, propylparaben, butylparaben, chlorobutanol, phenylethyl alcohol, benzalkonium chloride, thimerosal, propylene glycol, sorbic acid, and benzoic acid derivatives. The preservatives should be used at a concentration of from about 0.001% to about 0.5% (w/v) in the final composition. The combination of benzalkonium chloride, used at a concentration of from about 0.001% to about 0.5% or preferably from about 0.005% to about 0.1% (w/v), and edetic acid (as a disodium salt), used at a concentration of from about 0.005% to about 0.1% (w/v), are the preferred preservative/stabilizer combination used in the compositions of the present invention. Certain compositions of the invention may further comprise one or more solubility-enhancing agents that are used to improve the solubility of the azelastine compound used as an active ingredient. Solubility-enhancing agents that are suitable for use in the compositions of the invention include, but are not limited to, polyvinylpyrrolidone (preferably grades 25, 30, 60, or 90), poloxamer, polysorbate 80, sorbitan monooleate 80, and polyethylene glycols (molecular weights of 200 to 600).

Certain compositions of the invention may further comprise one or more solubility-enhancing agents that are used to improve the solubility of the azelastine compound used as an active ingredient. Solubility-enhancing agents that are suitable for use in the compositions of the invention include, but are not limited to, polyvinylpyrrolidone (preferably grades 25, 30, 60, or 90), poloxamer, polysorbate 80, sorbitan monooleate 80, and polyethylene glycols (molecular weights of 200 to 600).

Certain compositions of the invention may further comprise one or more agents that are used to render the composition isotonic, particularly in those compositions in which water is used as a solvent. Such agents are particularly useful in compositions formulated for nasal or ocular application, since they adjust the osmotic pressure of the formulations to the same osmotic pressure as nasal or ocular secretions. Agents that are suitable for such a use in the compositions of the invention include, but are not limited to, sodium chloride, sorbitol, propylene glycol, dextrose, sucrose, and glycerine, and other isotonicity agents that are known in the art (see, e.g., Reich et al., "Chapter 18: Tonicity, Osmoticity, Osmolality and Osmolarity," in: *Remington: The Science and Practice of Pharmacy*, 20$^{th}$ Edition, Lippincott Williams and Wilkins, Philadelphia, Pa. (2000)).

It is desirable that the compositions of the present invention that are to be administered in liquid form (including intranasally, orally or ocularly applied formulations) have a pH of about 4.5 to about 7.4, and preferably have a pH of about 5.5 to 7.1, for physiological reasons. Accordingly, in additional embodiments, the compositions of the invention may further comprise one or more buffering agents or combinations thereof, that are used to adjust and/or maintain the compositions into the desired pH range. Adjustment of pH or buffering agents that are suitable for use in the compositions of the invention include, but are not limited to, citric acid, sodium citrate, sodium phosphate (dibasic, heptahydrate form), and boric acid or equivalent conventional buffers, or combinations thereof. The appropriate amounts of buffers and buffering agents, or combinations thereof, that are to be used in the compositions of the invention are readily determined by those of ordinary skill without undue experimentation, particularly in view of the guidance contained herein and in standard formularies such as the United States Pharmacopoeia, *Remington: The Science and Practice of Pharmacy*, and the like, the disclosures of which are incorporated herein by reference in their entireties.

As noted above, azelastine salts, particularly azelastine hydrochloride, have a strong bitter taste when the compounds or compositions comprising them are administered intranasally, ocularly, or orally. Thus, in certain embodiments, the liquid formulations of the invention, particularly those that are to be administered intranasally, ocularly, or orally, preferably further comprise one or more taste-masking agents, one or more flavoring agents, and/or one or more sweetening agents, or a combination of such agents. Non-limiting examples of such substances include sucralose (about 0.001 to about 1%), sucrose (about 0.5 to about 10%), saccharin (including the salt forms: sodium, calcium, etc.) (about 0.01 to about 2%), fructose (about 0.5 to about 10%), dextrose (about 0.5 to about 10%), corn syrup (about 0.5 to about 10%), aspartame (about 0.01 to about 2%), acesulfame-K (about 0.01 to about 2%), xylitol (about 0.1 to about 10%), sorbitol (about 0.1 to about 10%), erythritol (about 0.1 to about 10%), ammonium glycyrrhizinate (about 0.01 to about 4%), thaumatin (Talin™) (about 0.01 to about 2%), neotame (about 0.01 to about 2%) mannitol (about 0.5 to about 5%), menthol (about 0.01 to about 0.5%), eucalyptus oil (about 0.01 to about 0.5%), camphor (about 0.01 to about 0.5%), natural and/or artificial flavors such as Artificial Custard Cream Flavor #36184 from International Flavors and Fragrances, Inc. (New York, N.Y.) (about 0.01 to about 1.0%), and the like. Sucralose, an intense sweetener marketed for food and beverage use as SPLENDA® by McNeil Nutritionals LLP (Fort Washington, Pa.), is especially effective as a sweetening and taste-masking agent in the compositions of the present invention, particularly when used at concentrations of from about 0.001% to about 1%, preferably at concentrations of from about 0.01% to about 0.5%, and more preferably at concentrations of from about 0.02% to about 0.2%, and most preferably from about 0.05% to about 0.15% (e.g., about 0.05%, about 0.06%, about 0.07%, about 0.08%, about 0.09%, about 0.10%, about 0.11%, about 0.12%, about 0.13%, about 0.14%, or about 0.15%), of the total composition. Sucralose has been shown to be useful as a taste modifying agent in oral delivery of certain pharmaceutical compositions, for example in sore throat spray products (see U.S. Pat. No. 6,319,513), oral suspensions (see U.S. Pat. Nos. 5,658,919 and 5,621,005), solid dosage forms (see U.S. Pat.

No. 6,149,941), quick melt dosage forms (see U.S. Pat. No. 6,165,512) and mucosal delivery (see U.S. Pat. No. 6,552,024), but has not heretofore been shown to be useful in intranasally or ocularly applied compositions such as those of the present invention. Additional such compositions of the invention may comprise one or more additional taste-masking or flavoring agents such as those described herein, for example menthol at a concentration of from about 0.01% to about 1%, preferably at a concentration of from about 0.05% to about 0.1%. Suitable compositions of the invention include, for example, about 0.1%-0.15% azelastine and about 0.05%-0.15% sucralose, for example, about 0.1% azelastine and about 0.05%-0.15% sucralose, or about 0.125%-0.15% azelastine and about 0.05%-0.15% sucralose, or about 0.10% azelastine and about 0.15% sucralose, or about 0.15% azelastine and about 0.15% sucralose.

As noted above, intranasal or ocular application of azelastine-containing compositions, particularly those containing azelastine hydrochloride, is often complicated by the postnasal drip of the composition into the pharynx following intranasal or ocular administration. Such postnasal drip can induce a very bitter and unpleasant taste experience by the patient. Thus, to avoid, reduce or minimize such issues arising from postnasal drip, certain compositions of the present invention may alternatively or further comprise one or more water-soluble viscosity-increasing agents. Such agents are preferably used at the concentration of about 0.01% to about 5.0% (w/v), in order to typically produce a viscosity of the final solution between about 2 and about 300 centipoise. Use of such viscosity-increasing agents extends the mucocilliary clearance time, increases retention in the nasal cavity, and reduces post nasal drip, of intranasally applied compositions (see U.S. Pat. No. 5,897,858, the disclosure of which is incorporated herein by reference in its entirety) such as those of the present invention. Viscosity-increasing agents that are suitable for use in accordance with the present invention include, but are not limited to, polyvinylpyrrolidones, cellulose derivatives including, but not limited to, hydroxyethyl cellulose, carboxymethyl cellulose or its salts, hypromellose, carrageenan, guar gum, alginates, carbomers, polyethylene glycols, polyvinyl alcohol, and xanthan gum. Particularly preferred is hypromellose, at a concentration of about 0.001% to about 5.00%, preferably at a concentration of about 0.01% to about 1%, more preferably at a concentration of about 0.1% to about 0.5%, and most preferably at a concentration of about 0.1% to about 0.3%.

The compositions of the present invention that are provided in solution form may be preserved, aseptically manufactured and/or sterilized, for example, by filtration through a bacterial-retaining filter.

In exemplary embodiments, the compositions of matter comprise a container (e.g., a unit dose container) comprising azelastine and/or one or more pharmacologically acceptable salts or esters thereof, particularly azelastine hydrochloride. Suitable compositions of matter comprise a unit dose container comprising azelastine hydrochloride, and may further comprise one or more additional components, such as one or more solvents, one or more preservatives, one or more stabilizers, one or more buffers or buffering agents, one or more bioadhesives, one or more suspending agents (e.g., microcrystalline cellulose, sodium carboxymethyl cellulose, hypromellose carbopol and the like), one or more surfactants or wetting agents and/or one or more isotonicity agents.

In exemplary embodiments, the compositions of matter comprise a unit dose container of a moldable polymer, such as a plastic, into which leaching of the pharmaceutical ingredient is limited to an acceptable amount over time. Exemplary unit dose containers are described herein. Polymers suitable for use according to this aspect of the invention include, but are not limited to, polyethylene, polypropylene (PP), polystyrene (PS), nylon (Ny), polyvinyl chloride (PVC), polyethylene terephthalate (PET), polycarbonate (PC), polyoxymethylene (POM), polysulfon (PSF), polyethersulfon (PES), polyacrylate (PAR), and polyamide (PA). In certain embodiments, polymers include polyethylene, particularly medium-density polyethylene (MDPE) (or branched polyethylene) or high density polyethylene (HDPE) (or linear polyethylene). A particularly preferred polymer for use with azelastine-containing pharmaceutical formulations is HDPE, since as discussed hereinbelow, it has been found that azelastine (and salts or esters thereof) has a high degree of undesirable leachability into containers manufactured of other polymers, including polyethylenes having lower densities than HDPE.

Compositions Comprising Additional Active Agents

In addition to azelastine (e.g., azelastine HCl) and the various excipients, taste masking agents, viscosity-increasing agents and the like disclosed herein, the pharmaceutical compositions of the invention can further comprise (or consist essentially of) one or more additional active agents, such as those disclosed throughout U.S. Patent Publication No. 2005/0148562, the disclosure of which is herein incorporated by reference in its entirety. Exemplary additional active agents include, but are not limited to, additional antihistamines (including $H_1$, $H_3$ and $H_4$ receptor antagonists), steroids (e.g., safe steroids), leukotriene antagonists, prostaglandin D2 receptor antagonists, decongestants, expectorants, anti-fungal agents, triamcinolone and triamcinolone derivatives, non-steroidal immunophilin-dependent immunosuppressants (NsIDIs), anti-inflammatory agents, non-steroidal anti-inflammatory agents (NSAIDs), COX-2 inhibitors, anti-infective agents, mucolytic agents, anticholinergic agents, mast cell stabilizers, non-antibiotic anti-microbial agents, anti-viral agents, antiseptics, neurokinin antagonists, platelet activating factor (PAF) and 5-lipoxygenase (5-LO) inhibitors.

Examples of antihistamines in addition to azelastine (e.g., $H_1$ receptor antagonists) suitable for inclusion in the present compositions include, but are not limited to, acrivastine, cyclizine, carebastine, cyproheptadine, carbinoxamine, doxylamine, dimethindene, ebastine, epinastine, efletirizine, ketotifen, levocabastine, mizolastine, mequitazine, mianserin, noberastine, meclizine, norastemizole, olopatadine, picumast, tripelenamine, temelastine, trimeprazine, triprolidine, bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, terfenadine, loratadine, cetirizine, levocetirizine, fexofenadine, descarboethoxyloratadine, desloratadine, dimenhydrinate and hydroxyzine.

Examples of $H_3$ receptor antagonists suitable for inclusion in the present compositions include, but are not limited to, thioperamide, impromidine, burimamide, clobenpropit, impentamine, mifetidine, clozapine, S-sopromidine, R-sopromidine and ciproxifam.

Examples of leukotriene antagonists (e.g., leukotriene D4 antagonists) suitable for inclusion in the present compositions include, but are not limited to, albuterol sulfate, aminophylline, amoxicillin, ampicillin, astemizole, attenuated tubercle *bacillus*, azithromycin, bacampicillin, beclomethasone dipropionate, budesonide, bupropion hydrochloride, cefaclor, cefadroxil, cefixime, cefprozil, cefuroxime axetil, cephalexin, ciprofloxacin hydrochloride, clarithromycin, clindamycin, cloxacillin, doxycycline, erythromycin, ethambutol, fenoterol hydrobromide, fluconazole, flunisolide, fluticasone propionate, formoterol fumarate, gatifloxacin, influenza virus vaccine, ipratropium bromide, isoniazid, isoproterenol hydrochloride, itraconazole, ketoconazole, ketotifen, levofloxacin, minocycline, montelukast (e.g., montelukast sodium), moxifloxacin, nedocromil sodium, nicotine, nystatin, ofloxacin, orciprenaline, oseltamivir, oseltamivir sulfate, oxtriphylline, penicillin, pirbuterol acetate, pivampicillin, pneumococcal conjugate vaccine, pneumococcal polysaccharide vaccine, prednisone, pyrazinamide, rifampin, salbutamol, salmeterol xinafoate, sodium cromoglycate (cromolyn sodium), terbutaline sulfate, terfenadine, theophylline, triamcinolone acetonide, zafirlukast and zanamivir.

Examples of decongestants suitable for inclusion in the present compositions include, but are not limited to, pseudoephedrine, phenylephedrine, phenylephrine, phenylpropanolamine, oxymetazoline, propylhexedrine, xylometazoline, epinephrine, ephedrine, desoxyephedrine, naphazoline, and tetrahydrozoline.

Examples of expectorants suitable for inclusion in the present compositions include, but are not limited to, guaifenesin, codeine phosphate, and isoproternol hydrochloride.

Examples of anti-fungal agents suitable for inclusion in the present compositions include, but are not limited to, amphotericin B, nystatin, fluconazole, ketoconazole, terbinafine, itraconazole, imidazole, triazole, ciclopirox, clotrimazole, and miconazole.

Examples of NSAIDs suitable for inclusion in the present compositions include, but are not limited to, ibuprofen, aceclofenac, diclofenac, naproxen, etodolac, flurbiprofen, fenoprofen, ketoprofen, suprofen, fenbufen, fluprofen, tolmetin sodium, oxaprozin, zomepirac, sulindac, indomethacin, piroxicam, mefenamic acid, nabumetone, meclofenamate sodium, diflunisal, flufenisal, piroxicam, ketorolac, sudoxicam and isoxicam.

By "non-steroidal immunophilin-dependent immunosuppressant" or "NsIDI" is meant any non-steroidal agent that decreases proinflammatory cytokine production or secretion, binds an immunophilin, or causes a down regulation of the proinflammatory reaction. NsIDIs suitable for inclusion in the present compositions include, but are not limited to, calcineurin inhibitors, such as cyclosporine, tacrolimus, ascomycin, pimecrolimus, as well as other agents (peptides, peptide fragments, chemically modified peptides, or peptide mimetics) that inhibit the phosphatase activity of calcineurin. NsIDIs also include rapamycin (sirolimus) and everolimus, which bind to an FK506-binding protein, FKBP-12, and block antigen-induced proliferation of white blood cells and cytokine secretion.

Examples of COX-2 inhibitors suitable for inclusion in the present compositions include, but are not limited to, rofecoxib, celecoxib, valdecoxib, lumiracoxib, meloxicam, and nimesulide.

Examples of steroids suitable for inclusion in the present compositions include but are not limited to, fluoromethalone, fluticasone (e.g., fluticasone propionate, fluticasone dipropionate, fluticasone furoate, fluticasone maleate, fluticasone valerate, and the like), mometasone, triamcinolone, betamethasone, flunisolide, budesonide, beclomethasone, budesonide, rimexolone, beloxil, prednisone, loteprednol (e.g., loteprednol etabonate) (e.g., loteprednol (e.g., loteprednol etabonate) etabonate), dexamethasone and its analogues (e.g., dexamethasone beloxil) described in U.S. Pat. Nos. 5,223,493 and 5,420,120, incorporated herein by reference in their entireties, and other esters, salts, conjugates, derivatives and analogs of such steroids that will be familiar to one of ordinary skill in the art.

Examples of anti-infective agents suitable for inclusion in the present compositions include, but are not limited to, penicillins and other beta lactam antibiotics, cephalosporins, macrolides, ketolides, sulfonamides, quinolones (including haloquinolones such as fluoroquinolones, including ciprofloxacin), aminoglycosides, and linezolid.

Examples of non-antibiotic antimicrobials suitable for inclusion in the present compositions include, but are not limited to, taurolidine.

Examples of mast cell stabilizers suitable for inclusion in the present compositions include, but are not limited to, cromolyn and nedcromil sodium.

Examples of mucolytic agents suitable for inclusion in the present compositions include, but are not limited to, acetylcysteine and dornase alpha.

Examples of antibiotic agents suitable for inclusion in the present compositions include, but are not limited to, cefuroxime, vancomycin, amoxicillin and gentamicin.

Examples of antiseptics suitable for inclusion in the present compositions include, but are not limited to, iodine, chlorhexidine acetate, sodium hypochlorite, and calcium hydroxide.

Examples of anticholinergics suitable for inclusion in the present compositions include, but are not limited to, mivacurium, atracurium, fazadinium, rocuronium, vecuronium, doxacurium, metocurine, pancuronium, pipecuronium, gallamine, hexafluoronium, suxamethonium, succinylcholine, decamethonium, atropine, scopolamine, hyoscyamine, benzatropine, trihexyphenidyl, biperiden, glycopyrrolate, ipratropium, pirenzepine, telenzepine, tiotropium, darifenacin, vedaclidine, tropicamide, cyclopentolate, dicycloverine, tolterodine, oxybutynin, homatropine, orphenadrine, diphenhydramine, hemicholinium-3, vesamicol, pralidoxime, obidoxime, oxitropium, alcuronium, dimethyltubocurarine, tubocurarine and ipratropium.

Examples of prostaglandin D2 receptor antagonists suitable for inclusion in the present compositions include, but are not limited to, non-steroidal anti-inflammatories (NSAIDs), COX-2 inhibitors, bicyclic amino (indole) derivatives (see, e.g., U.S. Pat. Nos. 6,693,203 and 6,498,190, the disclosures of which are incorporated by reference herein in their entireties), thiazoles (see, e.g., U.S. Patent Publication No. 2009/0221604, the disclosure of which is incorporated herein by reference in its entirety), and the like.

Examples of anti-viral agents suitable for inclusion in the present compositions include, but are not limited to, abacavir, acyclovir, adefovir, amantadine, amprenavir, arbidol, atazanavir, atripla boceprevir, cidofovir, combivir, darunavir delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, integrase inhibitor, lamivudine, lopinavir, loviride, maraviroc, moroxydine, nelfinavir, nevirapine, nexavir, oseltamivir, peginterferon alfa-2a, penciclovir, peramivir, pleconaril, podophyllotoxin, raltegravir, ribavirin, rimantadine, ritonavir, saquinavir, stavudine, tenofovir, tipranavir, trifluridine, trizivir, tromantadine, truvada, valaciclovir, valganciclovir, vicriviroc, vidarabine, viramidine, zalcitabine, zanamivir and zidovudine.

Examples of neurokinin antagonists suitable for inclusion in the present compositions include, but are not limited to, oximes, hydrazones, piperidines, piperazines, aryl alkyl amines, hydrazones, nitroalkanes, amides, isoxazolines, quinolines, isoquinolines, azanorbornanes, naphthyridines, and benzodiazepines, such as those disclosed in U.S. Pat. Nos. 5,798,359; 5,795,894; 5,789,422; 5,783,579; 5,719,156; 5,696,267; 5,691,362; 5,688,960; 5,654,316, incorporated by reference herein in their entireties.

Examples of 5-lipoxygenase (5-LO) inhibitors suitable for inclusion in the present compositions include, but are not limited to, zileuton, docebenone, piripost and tenidap.

The concentrations, absolute amounts and relative amounts (i.e., relative to the concentration or absolute amount of azelastine or a salt thereof, e.g. azelastine HCl) of the additional one or more active agents will be familiar to one of ordinary skill in the art. For example, the amounts of additional active agents (e.g., one or more steroid(s), leukotriene antagonist(s), anithistamine(s), decongestant(s), NSAIDs, etc), can be present in any amount, for example about 0.01% to about 99% (e.g., about 0.01%, about 0.1%, about 1%, about 10%, about 20%, about 30%, about 40%, about 50%, about 60%, about 70%, about 80%, or about 90%).

In one embodiment, the present invention provides compositions of matter comprising a container (e.g., a unit dose container) comprising one or more pharmaceutical ingredients, including one or more antihistamines, such as an $H_1$, $H_2$, $H_3$ and $H_4$ antihistamines disclosed herein one or more steroids (e.g., safe steroids), one or more leukotriene antagonists, one or more prostaglandin D2 receptor antagonists, decongestants, one or more anti-fungal agents, one or more non-steroidal immunophilin-dependent immunosuppressants (NSIDIs), one or more anti-inflammatory agents, non-steroidal anti-inflammatory agents (NSAIDs), one or more COX-2 inhibitors, one or more anti-infective agents, mucolytic agents, one or more anticholinergic agents, one or more mast cell stabilizers, one or more non-antibiotic anti-microbial agents, one or more anti-viral agents, one or more antiseptics, one or more neurokinin antagonists, platelet activating factor (PAF) and/or one or more 5-lipoxygenase (5-LO) inhibitors.

In one embodiment, the pharmaceutical compositions comprise (or consisting essentially of) an effective amount of azelastine (suitably azelastine hydrochloride) along with an effective amount of one or more steroids. Exemplary steroids include those discussed throughout. In certain suitable embodiments, the compositions further comprise one or more additional ingredients, such as one or more excipients, one or more taste-masking agents and/or one or more viscosity-increasing agents. Such compositions can be formulated as intranasal or ocular suspensions or solutions, with a pH of about 6.0 to 8.0. In other embodiments, the compositions can be formulated as oral (e.g., tablets or capsules) or topical delivery formulations, such as those disclosed throughout. While the amount of azelastine can be varied and adjusted appropriately by the ordinarily skilled artisan, it is suitably contained in the intranasal or ocular formulations in an amount of about 0.0001% to about 1.0% by weight, and more suitably from about 0.005% to about 0.5% or most suitably from about 0.05% to about 0.15% (e.g., 0.05%, 0.06%, 0.07%, 0.08%, 0.09%. 0.10%, 0.11%, 0.12%, 0.13%, 0.14%, 0.15%), of pure azelastine (calculated as the free azelastine base). The amount of steroid(s) present in the various formulations can be varied and adjusted appropriately by the ordinarily skilled artisan, and can be present in any amount, for example about 0.01% to about 99% (e.g., about 0.01%, about 0.1%, about 1%, about 10%, about 20%, about 30%, about 40%, about 50%, about 60%, about 70%, about 80%, or about 90%). Suitably the amount of steroid is about 0.01% to about 1.5% by weight, more suitably about 0.01% to about 1.0% by weight, or even more suitably about 0.05% to about 0.1% by weight (e.g., about 0.01%, about 0.02%, about 0.03%, about 0.04%, about 0.05%, about 0.06%, about 0.07%, about 0.08%, about 0.09%, or about 0.1% by weight). Preferred steroids for use in the formulations of the present invention are "safe steroids." As used herein, the term "safe steroid" means a steroid which treats eosinophil and neutrophil associated inflammation, reduces papillae formation, and which is effective in treating inflammation, without causing a clinically significant elevation in intraocular pressure (TOP). Exemplary safe steroids that can be used in the various formulations of the present invention, particularly for delivery using nasal spray or ocular drop delivery systems include, but are not limited to, any glucocorticoid which meets the safe steroid definition, including but not limited to, fluoromethalone, fluticasone (and its conjugates, salts, esters, analogues or deriviates, e.g., fluticasone propionate, fluticasone furoate, fluticasone maleate, fluticasone valerate, and the like), rimexolone, loteprednol (e.g., loteprednol etabonate), dexamethasone beloxil and its analogues described in U.S. Pat. Nos. 5,223,493 and 5,420,120, the disclosures of which are incorporated by reference herein in their entireties. Additional "safe steroids" and methods for determining appropriate amounts of such agents for inclusion in the present compositions are disclosed in U.S. Pat. No. 6,649,602, the disclosure of which is incorporated by reference herein in its entirety. Exemplary compositions of the present invention comprising azelastine and a safe steroid comprise about 0.1%-0.15% azelastine, about 0.01%-0.1% of a safe steroid, and optionally about 0.05%-0.15% sucralose.

In one embodiment, the present invention provides pharmaceutical compositions comprising (or consisting essentially of) an effective amount of azelastine (suitably azelastine hydrochloride) along with an effective amount of fluticasone, suitably fluticasone propionate, fluticasone furoate, fluticasone maleate, fluticasone valerate, and the like. In certain suitable embodiments, such compositions further comprise one or more additional ingredients, such as one or more excipients, one or more taste-masking agents and/or one or more viscosity-increasing agents. Such compositions can be formulated as intranasal or ocular suspensions or solutions, with a pH of about 6.0 to 8.0. In other embodiments, the compositions can be formulated as oral (e.g., tablets or capsules) or topical delivery formulations, such as those disclosed throughout. While the amount of azelastine can be varied and adjusted appropriately by the ordinarily skilled artisan, it is suitably contained in the intranasal or ocular formulations in an amount of about 0.0001% to about 1.0% by weight, and more suitably from about 0.005% to about 0.5% or most suitably from about 0.05% to about 0.15% (e.g., 0.05%, 0.06%, 0.07%, 0.08%, 0.09%. 0.10%, 0.11%, 0.12%, 0.13%, 0.14%, 0.15%), of pure azelastine (calculated as the free azelastine base). The amount of fluticasone, suitably fluticasone propionate, fluticasone furoate, fluticasone maleate, fluticasone valerate, and the like, present in the various formulations can be varied and adjusted appropriately by the ordinarily skilled artisan, and can be present in any amount, for example about 0.01% to about 99% (e.g., about 0.01%, about 0.1%, about 1%, about 10%, about 20%, about 30%, about 40%, about 50%, about 60%, about 70%, about 80%, or about 90%). Suitably the amount of fluticasone, suitably fluticasone propionate, fluticasone dipropionate or fluticasone fuorate is about 0.01% to about 1.5% by weight, more suitably about 0.01% to about 1.0% by weight, or even more suitably about 0.05% to about 0.1% by weight (e.g., about 0.01%, about 0.02%, about 0.03%, about 0.04%, about 0.05%, about 0.06%, about 0.07%, about 0.08%, about 0.09%, or about 0.1% by weight).

In another embodiment, the present invention provides pharmaceutical compositions comprising (or consisting essentially of) an effective amount of one or more antihistamines (including $H_1$, $H_2$, $H_3$ and $H_4$ antagonistic antihistamines as disclosed herein) along with an effective amount of loteprednol (e.g., loteprednol etabonate), suitably loteprednol (e.g., loteprednol etabonate) etabonate (see e.g., U.S. Pat. No. 7,022,687, the disclosure of which is incorporated herein by reference in its entirety) In certain suitable embodiments, such compositions further comprise one or more additional ingredients, such as one or more excipients, one or more taste-masking agents and/or one or more viscosity-increasing agents. Such compositions can be formulated as intranasal or ocular suspensions or solutions, with a pH of about 6.0 to 8.0. In other embodiments, the compositions can be formulated as oral (e.g., tablets or capsules) or topical delivery formulations, such as those disclosed throughout. While the amount of azelastine can be varied and adjusted appropriately by the ordinarily skilled artisan, it is suitably contained in the intranasal or ocular formulations in an amount of about 0.0001% to about 1.0% by weight, and more suitably from about 0.005% to about 0.5% or most suitably from about 0.05% to about 0.15% (e.g., 0.05%, 0.06%, 0.07%, 0.08%, 0.09%, 0.10%, 0.11%, 0.12%, 0.13%, 0.14%, 0.15%), of pure azelastine (calculated as the free azelastine base). The amount of loteprednol (e.g., loteprednol etabonate), suitably loteprednol (e.g., loteprednol etabonate) etabonate, present in the various formulations can be varied and adjusted appropriately by the ordinarily skilled artisan, and can be present in any amount, for example about 0.01% to about 99% (e.g., about 0.01%, about 0.1%, about 1%, about 10%, about 20%, about 30%, about 40%, about 50%, about 60%, about 70%, about 80%, or about 90%). Suitably the amount of loteprednol (e.g., loteprednol etabonate), suitably loteprednol (e.g., loteprednol etabonate) etabonate, is about 0.01% to about 1.5% by weight, more suitably about 0.01% to about 1.0% by weight, or even more suitably about 0.05% to about 0.1% by weight (e.g., about 0.01%, about 0.02%, about 0.03%, about 0.04%, about 0.05%, about 0.06%, about 0.07%, about 0.08%, about 0.09%, or about 0.1% by weight).

In another embodiment, the pharmaceutical compositions comprise (or consist essentially of) an effective amount of one or more antihistamines (such as those described herein, including $H_1$, $H_2$, $H_3$ and $H_4$ antagonistic antihistamines) along with an effective amount of one or more steroids, and also an effective amount of one or more decongestants. In suitable such embodiments, the compositions further comprise one or more additional ingredients, such as one or more excipients, one or more taste-masking agents and/or one or more viscosity-increasing agents. Such compositions can be formulated as intranasal or ocular suspensions or solutions, with a pH of about 6.0 to 8.0. In other embodiments, the compositions can be formulated as oral or topical delivery formulations, such as those disclosed throughout. The appropriate amounts of azelastine, steroid and decongestant can be readily determined by those or ordinary skill in the art. Suitably, the amount of steroid and azelastine used will be in the ranges disclosed herein. The amount of decongestant can be present in any amount, for example about 0.01% to about 99% (e.g., about 0.01%, about 0.1%, about 1%, about 10%, about 20%, about 30%, about 40%, about 50%, about 60%, about 70%, about 80%, or about 90%). Suitably the amount of decongestant is about 0.05% to about 1.5% by weight, or more suitably in an amount of about 0.1% to about 1.0% by weight. In addition, the compositions can also comprise sucralose at about 0.05%-0.15%.

In an additional embodiment, the pharmaceutical compositions comprise (or consist essentially of) an effective amount of one or more antihistamines (such as those described herein, including H1, H3 and H4 antagonistic antihistamines) along with an effective amount of one or more additional anti-allergic and/or one or more anti-asthmatic agents. Exemplary anti-allergics and anti-asthmatics include those discussed herein, including, but not limited to, $H_1$ receptor antagonists, $H_3$ receptor antagonists and leukotriene antagonists (e.g., leukotriene D4 antagonists). In suitable such embodiments, the compositions further comprise one or more additional ingredients, such as one or more excipients, one or more taste-masking agents and/or one or more viscosity-increasing agents. Such compositions can be formulated as intranasal or ocular suspensions or solutions, with a pH of about 6.0 to 8.0. In other embodiments, the compositions can be formulated for oral or pulmonary delivery, such as those described herein. While the amount of azelastine can be varied and adjusted appropriately by the ordinarily skilled artisan, it is suitably contained in the intranasal or ocular formulations in an amount of about 0.0001% to about 1.0% by weight, and more suitably from about 0.005% to about 0.5% or most suitably from about 0.05% to about 0.15% (e.g., about 0.05%, 0.06%, 0.07%, 0.08%, 0.09%, 0.10%, 0.11%, 0.12%, 0.13%, 0.14%, 0.15%), of pure azelastine (calculated as the free azelastine base). The amount of one or more additional anti-allergic and/or anti-asthmatics present in the various formulations can be varied and adjusted appropriately by the ordinarily skilled artisan and can be present in any amount, for example about 0.01% to about 99% (e.g., about 0.01%, about 0.1%, about 1%, about 10%, about 20%, about 30%, about 40%, about 50%, about 60%, about 70%, about 80%, or about 90%). Suitably the amount of these additional compounds will be in an amount of about 0.01% to about 10% by weight, or more suitably in an amount of about 0.1% to about 5.0% by weight. In addition, the compositions can also comprise sucralose at about 0.05%-0.15%.

Suitable compositions of the present invention comprise (or consist essentially of), for example (percentages of azelastine refer to weight percentages of azelastine HCl or other suitable salt):

About 0.05% azelastine and about 0.05% sucralose;
About 0.05% azelastine and about 0.1% sucralose;
About 0.05% azelastine and about 0.15% sucralose;
About 0.1% azelastine and about 0.05% sucralose;
About 0.1% azelastine and about 0.1% sucralose;
About 0.1% azelastine and about 0.15% sucralose;
About 0.125% azelastine and about 0.05% sucralose;
About 0.125% azelastine and about 0.1% sucralose;
About 0.125% azelastine and about 0.15% sucralose;
About 0.15% azelastine and about 0.05% sucralose;
About 0.15% azelastine and about 0.1% sucralose;
About 0.15% azelastine and about 0.15% sucralose;
About 0.05% azelastine and about 0.01% steroid;
About 0.1% azelastine and about 0.01% steroid;
About 0.125% azelastine and about 0.01% steroid;
About 0.15% azelastine and about 0.01% steroid;
About 0.05% azelastine and about 0.05% steroid;
About 0.1% azelastine and about 0.05% steroid;
About 0.125% azelastine and about 0.05% steroid;
About 0.15% azelastine and about 0.05% steroid;
About 0.05% azelastine and about 0.1% steroid;
About 0.1% azelastine and about 0.1% steroid;
About 0.125% azelastine and about 0.1% steroid;
About 0.15% azelastine and about 0.1% steroid;
About 0.05% azelastine, about 0.01% steroid and about 0.05% sucralose;

About 0.1% azelastine, about 0.01% steroid and about 0.05% sucralose;
About 0.125% azelastine, about 0.01% steroid and about 0.05% sucralose;
About 0.15% azelastine, about 0.01% steroid and about 0.05% sucralose;
About 0.05% azelastine, about 0.05% steroid and about 0.05% sucralose;
About 0.1% azelastine, about 0.05% steroid and about 0.05% sucralose;
About 0.125% azelastine, about 0.05% steroid and about 0.05% sucralose;
About 0.15% azelastine, about 0.05% steroid and about 0.05% sucralose;
About 0.05% azelastine, about 0.1% steroid and about 0.05% sucralose;
About 0.1% azelastine, about 0.1% steroid and about 0.05% sucralose;
About 0.125% azelastine, about 0.1% steroid and about 0.05% sucralose;
About 0.15% azelastine, about 0.1% steroid and about 0.05% sucralose;
About 0.05% azelastine, about 0.01% steroid and about 0.1% sucralose;
About 0.1% azelastine, about 0.01% steroid and about 0.1% sucralose;
About 0.125% azelastine, about 0.01% steroid and about 0.1% sucralose;
About 0.15% azelastine, about 0.01% steroid and about 0.1% sucralose;
About 0.05% azelastine, about 0.05% steroid and about 0.1% sucralose;
About 0.1% azelastine, about 0.05% steroid and about 0.1% sucralose;
About 0.125% azelastine, about 0.05% steroid and about 0.1% sucralose;
About 0.15% azelastine, about 0.05% steroid and about 0.1% sucralose;
About 0.05% azelastine, about 0.1% steroid and about 0.1% sucralose;
About 0.1% azelastine, about 0.1% steroid and about 0.1% sucralose;
About 0.125% azelastine, about 0.1% steroid and about 0.1% sucralose;
About 0.15% azelastine, about 0.1% steroid and about 0.1% sucralose;
About 0.05% azelastine, about 0.01% steroid and about 0.15% sucralose;
About 0.1% azelastine, about 0.01% steroid and about 0.15% sucralose;
About 0.125% azelastine, about 0.01% steroid and about 0.15% sucralose;
About 0.15% azelastine, about 0.01% steroid and about 0.15% sucralose;
About 0.05% azelastine, about 0.05% steroid and about 0.15% sucralose;
About 0.1% azelastine, about 0.05% steroid and about 0.15% sucralose;
About 0.125% azelastine, about 0.05% steroid and about 0.15% sucralose;
About 0.15% azelastine, about 0.05% steroid and about 0.15% sucralose;
About 0.05% azelastine, about 0.1% steroid and about 0.15% sucralose;
About 0.1% azelastine, about 0.1% steroid and about 0.15% sucralose;
About 0.125% azelastine, about 0.1% steroid and about 0.15% sucralose;
About 0.15% azelastine, about 0.1% steroid and about 0.15% sucralose;
About 0.05% azelastine and about 0.01% fluticasone (e.g., fluticasone propionate, fluticasone dipropionate or fluticasone furoate), mometasone, dexamethasone beloxil, loteprednol (e.g., loteprednol etabonate), budesonide, or triamcinolone;
About 0.1% azelastine and about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.125% azelastine and about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.15% azelastine and about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.05% azelastine and about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.1% azelastine and about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.125% azelastine and about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.15% azelastine and about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.05% azelastine and about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.1% azelastine and about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.125% azelastine and about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.15% azelastine and about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone;
About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.05% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.15% sucralose;

About 0.05% azelastine and about 0.1% leukotriene antagonist;

About 0.1% azelastine and about 0.1% leukotriene antagonist;

About 0.125% azelastine and about 0.1% leukotriene antagonist;

About 0.15% azelastine and about 0.1% leukotriene antagonist;

About 0.05% azelastine and about 0.5% leukotriene antagonist;

About 0.1% azelastine and about 0.5% leukotriene antagonist;

About 0.125% azelastine and about 0.5% leukotriene antagonist;

About 0.15% azelastine and about 0.5% leukotriene antagonist;

About 0.05% azelastine and about 5.0% leukotriene antagonist;

About 0.1% azelastine and about 5.0% leukotriene antagonist;

About 0.125% azelastine and about 5.0% leukotriene antagonist;

About 0.15% azelastine and about 5.0% leukotriene antagonist;

About 0.05% azelastine, about 0.1% leukotriene antagonist and about 0.05% sucralose;

About 0.1% azelastine, about 0.1% leukotriene antagonist and about 0.05% sucralose;

About 0.125% azelastine, about 0.1% leukotriene antagonist and about 0.05% sucralose;

About 0.15% azelastine, about 0.1% leukotriene antagonist and about 0.05% sucralose;

About 0.05% azelastine, about 0.1% leukotriene antagonist and about 0.1% sucralose;

About 0.1% azelastine, about 0.1% leukotriene antagonist and about 0.1% sucralose;

About 0.125% azelastine, about 0.1% leukotriene antagonist and about 0.1% sucralose;

About 0.15% azelastine, about 0.1% leukotriene antagonist and about 0.1% sucralose;

About 0.05% azelastine, about 0.1% leukotriene antagonist and about 0.15% sucralose;

About 0.1% azelastine, about 0.1% leukotriene antagonist and about 0.15% sucralose;

About 0.125% azelastine, about 0.1% leukotriene antagonist and about 0.15% sucralose;

About 0.15% azelastine, about 0.1% leukotriene antagonist and about 0.15% sucralose;

About 0.05% azelastine, about 0.5% leukotriene antagonist and about 0.05% sucralose;

About 0.1% azelastine, about 0.5% leukotriene antagonist and about 0.05% sucralose;

About 0.125% azelastine, about 0.5% leukotriene antagonist and about 0.05% sucralose;
About 0.15% azelastine, about 0.5% leukotriene antagonist and about 0.05% sucralose;
About 0.05% azelastine, about 0.5% leukotriene antagonist and about 0.1% sucralose;
About 0.1% azelastine, about 0.5% leukotriene antagonist and about 0.1% sucralose;
About 0.125% azelastine, about 0.5% leukotriene antagonist and about 0.1% sucralose;
About 0.15% azelastine, about 0.5% leukotriene antagonist and about 0.1% sucralose;
About 0.05% azelastine, about 0.5% leukotriene antagonist and about 0.15% sucralose;
About 0.1% azelastine, about 0.5% leukotriene antagonist and about 0.15% sucralose;
About 0.125% azelastine, about 0.5% leukotriene antagonist and about 0.15% sucralose;
About 0.15% azelastine, about 0.5% leukotriene antagonist and about 0.15% sucralose;
About 0.05% azelastine, about 5.0% leukotriene antagonist and about 0.05% sucralose;
About 0.1% azelastine, about 5.0% leukotriene antagonist and about 0.05% sucralose;
About 0.125% azelastine, about 5.0% leukotriene antagonist and about 0.05% sucralose;
About 0.15% azelastine, about 5.0% leukotriene antagonist and about 0.05% sucralose;
About 0.05% azelastine, about 5.0% leukotriene antagonist and about 0.1% sucralose;
About 0.1% azelastine, about 5.0% leukotriene antagonist and about 0.1% sucralose;
About 0.125% azelastine, about 5.0% leukotriene antagonist and about 0.1% sucralose;
About 0.15% azelastine, about 5.0% leukotriene antagonist and about 0.1% sucralose;
About 0.05% azelastine, about 5.0% leukotriene antagonist and about 0.15% sucralose;
About 0.1% azelastine, about 5.0% leukotriene antagonist and about 0.15% sucralose;
About 0.125% azelastine, about 5.0% leukotriene antagonist and about 0.15% sucralose;
About 0.15% azelastine, about 5.0% leukotriene antagonist and about 0.15% sucralose;
About 0.05% azelastine and about 0.1% montelukast;
About 0.1% azelastine and about 0.1% montelukast;
About 0.125% azelastine and about 0.1% montelukast;
About 0.15% azelastine and about 0.1% montelukast;
About 0.05% azelastine and about 0.5% montelukast;
About 0.1% azelastine and about 0.5% montelukast;
About 0.125% azelastine and about 0.5% montelukast;
About 0.15% azelastine and about 0.5% montelukast;
About 0.05% azelastine and about 5.0% montelukast;
About 0.1% azelastine and about 5.0% montelukast;
About 0.125% azelastine and about 5.0% montelukast;
About 0.15% azelastine and about 5.0% montelukast;
About 0.05% azelastine, about 0.1% montelukast and about 0.05% sucralose;
About 0.1% azelastine, about 0.1% montelukast and about 0.05% sucralose;
About 0.125% azelastine, about 0.1% montelukast and about 0.05% sucralose;
About 0.15% azelastine, about 0.1% montelukast and about 0.05% sucralose;
About 0.05% azelastine, about 0.1% montelukast and about 0.1% sucralose;
About 0.1% azelastine, about 0.1% montelukast and about 0.1% sucralose;
About 0.125% azelastine, about 0.1% montelukast and about 0.1% sucralose;
About 0.15% azelastine, about 0.1% montelukast and about 0.1% sucralose;
About 0.05% azelastine, about 0.1% montelukast and about 0.15% sucralose;
About 0.1% azelastine, about 0.1% montelukast and about 0.15% sucralose;
About 0.125% azelastine, about 0.1% montelukast and about 0.15% sucralose;
About 0.15% azelastine, about 0.1% montelukast and about 0.15% sucralose;
About 0.05% azelastine, about 0.5% montelukast and about 0.05% sucralose;
About 0.1% azelastine, about 0.5% montelukast and about 0.05% sucralose;
About 0.125% azelastine, about 0.5% montelukast and about 0.05% sucralose;
About 0.15% azelastine, about 0.5% montelukast and about 0.05% sucralose;
About 0.05% azelastine, about 0.5% montelukast and about 0.1% sucralose;
About 0.1% azelastine, about 0.5% montelukast and about 0.1% sucralose;
About 0.125% azelastine, about 0.5% montelukast and about 0.1% sucralose;
About 0.15% azelastine, about 0.5% montelukast and about 0.1% sucralose;
About 0.05% azelastine, about 0.5% montelukast and about 0.15% sucralose;
About 0.1% azelastine, about 0.5% montelukast and about 0.15% sucralose;
About 0.125% azelastine, about 0.5% montelukast and about 0.15% sucralose;
About 0.15% azelastine, about 0.5% montelukast and about 0.15% sucralose;
About 0.05% azelastine, about 5.0% montelukast and about 0.05% sucralose;
About 0.1% azelastine, about 5.0% montelukast and about 0.05% sucralose;
About 0.125% azelastine, about 5.0% montelukast and about 0.05% sucralose;
About 0.15% azelastine, about 5.0% montelukast and about 0.05% sucralose;
About 0.05% azelastine, about 5.0% montelukast and about 0.1% sucralose;
About 0.1% azelastine, about 5.0% montelukast and about 0.1% sucralose;
About 0.125% azelastine, about 5.0% montelukast and about 0.1% sucralose;
About 0.15% azelastine, about 5.0% montelukast and about 0.1% sucralose;
About 0.05% azelastine, about 5.0% montelukast and about 0.15% sucralose;
About 0.1% azelastine, about 5.0% montelukast and about 0.15% sucralose;
About 0.125% azelastine, about 5.0% montelukast and about 0.15% sucralose;
About 0.15% azelastine, about 5.0% montelukast and about 0.15% sucralose;
About 0.05% azelastine and about 0.1% decongestant;
About 0.1% azelastine and about 0.1% decongestant;
About 0.125% azelastine and about 0.1% decongestant;
About 0.15% azelastine and about 0.1% decongestant;
About 0.05% azelastine and about 0.5% decongestant;

About 0.1% azelastine and about 0.5% decongestant;
About 0.125% azelastine and about 0.5% decongestant;
About 0.15% azelastine and about 0.5% decongestant;
About 0.05% azelastine and about 1.0% decongestant;
About 0.1% azelastine and about 1.0% decongestant;
About 0.125% azelastine and about 1.0% decongestant;
About 0.15% azelastine and about 1.0% decongestant;
About 0.05% azelastine, about 0.1% decongestant and about 0.05% sucralose;
About 0.1% azelastine, about 0.1% decongestant and about 0.05% sucralose;
About 0.125% azelastine, about 0.1% decongestant and about 0.05% sucralose;
About 0.15% azelastine, about 0.1% decongestant and about 0.05% sucralose;
About 0.05% azelastine, about 0.1% decongestant and about 0.1% sucralose;
About 0.1% azelastine, about 0.1% decongestant and about 0.1% sucralose;
About 0.125% azelastine, about 0.1% decongestant and about 0.1% sucralose;
About 0.15% azelastine, about 0.1% decongestant and about 0.1% sucralose;
About 0.05% azelastine, about 0.1% decongestant and about 0.15% sucralose;
About 0.1% azelastine, about 0.1% decongestant and about 0.15% sucralose;
About 0.125% azelastine, about 0.1% decongestant and about 0.15% sucralose;
About 0.15% azelastine, about 0.1% decongestant and about 0.15% sucralose;
About 0.05% azelastine, about 0.5% decongestant and about 0.05% sucralose;
About 0.1% azelastine, about 0.5% decongestant and about 0.05% sucralose;
About 0.125% azelastine, about 0.5% decongestant and about 0.05% sucralose;
About 0.15% azelastine, about 0.5% decongestant and about 0.05% sucralose;
About 0.05% azelastine, about 0.5% decongestant and about 0.1% sucralose;
About 0.1% azelastine, about 0.5% decongestant and about 0.1% sucralose;
About 0.125% azelastine, about 0.5% decongestant and about 0.1% sucralose;
About 0.15% azelastine, about 0.5% decongestant and about 0.1% sucralose;
About 0.05% azelastine, about 0.5% decongestant and about 0.15% sucralose;
About 0.1% azelastine, about 0.5% decongestant and about 0.15% sucralose;
About 0.125% azelastine, about 0.5% decongestant and about 0.15% sucralose;
About 0.15% azelastine, about 0.5% decongestant and about 0.15% sucralose;
About 0.05% azelastine, about 1.0% decongestant and about 0.05% sucralose;
About 0.1% azelastine, about 1.0% decongestant and about 0.05% sucralose;
About 0.125% azelastine, about 1.0% decongestant and about 0.05% sucralose;
About 0.15% azelastine, about 1.0% decongestant and about 0.05% sucralose;
About 0.05% azelastine, about 1.0% decongestant and about 0.1% sucralose;
About 0.1% azelastine, about 1.0% decongestant and about 0.1% sucralose;
About 0.125% azelastine, about 1.0% decongestant and about 0.1% sucralose;
About 0.15% azelastine, about 1.0% decongestant and about 0.1% sucralose;
About 0.05% azelastine, about 1.0% decongestant and about 0.15% sucralose;
About 0.1% azelastine, about 1.0% decongestant and about 0.15% sucralose;
About 0.125% azelastine, about 1.0% decongestant and about 0.15% sucralose;
About 0.15% azelastine, about 1.0% decongestant and about 0.15% sucralose;
About 0.05% azelastine and about 0.1% pseudoephedrine or phenylephrine;
About 0.1% azelastine and about 0.1% pseudoephedrine or phenylephrine;
About 0.125% azelastine and about 0.1% pseudoephedrine or phenylephrine;
About 0.15% azelastine and about 0.1% pseudoephedrine or phenylephrine;
About 0.05% azelastine and about 0.5% pseudoephedrine or phenylephrine;
About 0.1% azelastine and about 0.5% pseudoephedrine or phenylephrine;
About 0.125% azelastine and about 0.5% pseudoephedrine or phenylephrine;
About 0.15% azelastine and about 0.5% pseudoephedrine or phenylephrine;
About 0.05% azelastine and about 1.0% pseudoephedrine or phenylephrine;
About 0.1% azelastine and about 1.0% pseudoephedrine or phenylephrine;
About 0.125% azelastine and about 1.0% pseudoephedrine or phenylephrine;
About 0.15% azelastine and about 1.0% pseudoephedrine or phenylephrine;
About 0.05% azelastine, about 0.1% pseudoephedrine or phenylephrine and about 0.05% sucralose;
About 0.1% azelastine, about 0.1% pseudoephedrine or phenylephrine and about 0.05% sucralose;
About 0.125% azelastine, about 0.1% pseudoephedrine or phenylephrine and about 0.05% sucralose;
About 0.15% azelastine, about 0.1% pseudoephedrine or phenylephrine and about 0.05% sucralose;
About 0.05% azelastine, about 0.1% pseudoephedrine or phenylephrine and about 0.1% sucralose;
About 0.1% azelastine, about 0.1% pseudoephedrine or phenylephrine and about 0.1% sucralose;
About 0.125% azelastine, about 0.1% pseudoephedrine or phenylephrine and about 0.1% sucralose;
About 0.15% azelastine, about 0.1% pseudoephedrine or phenylephrine and about 0.1% sucralose;
About 0.05% azelastine, about 0.1% pseudoephedrine or phenylephrine and about 0.15% sucralose;
About 0.1% azelastine, about 0.1% pseudoephedrine or phenylephrine and about 0.15% sucralose;
About 0.125% azelastine, about 0.1% pseudoephedrine or phenylephrine and about 0.15% sucralose;
About 0.15% azelastine, about 0.1% pseudoephedrine or phenylephrine and about 0.15% sucralose;
About 0.05% azelastine, about 0.5% pseudoephedrine or phenylephrine and about 0.05% sucralose;
About 0.1% azelastine, about 0.5% pseudoephedrine or phenylephrine and about 0.05% sucralose;
About 0.125% azelastine, about 0.5% pseudoephedrine or phenylephrine and about 0.05% sucralose;

About 0.15% azelastine, about 0.5% pseudoephedrine or phenylephrine and about 0.05% sucralose;
About 0.05% azelastine, about 0.5% pseudoephedrine or phenylephrine or phenylephrine and about 0.1% sucralose;
About 0.1% azelastine, about 0.5% pseudoephedrine or phenylephrine or phenylephrine and about 0.1% sucralose;
About 0.125% azelastine, about 0.5% pseudoephedrine or phenylephrine and about 0.1% sucralose;
About 0.15% azelastine, about 0.5% pseudoephedrine or phenylephrine and about 0.1% sucralose;
About 0.05% azelastine, about 0.5% pseudoephedrine or phenylephrine and about 0.15% sucralose;
About 0.1% azelastine, about 0.5% pseudoephedrine or phenylephrine and about 0.15% sucralose;
About 0.125% azelastine, about 0.5% pseudoephedrine or phenylephrine and about 0.15% sucralose;
About 0.15% azelastine, about 0.5% pseudoephedrine or phenylephrine and about 0.15% sucralose;
About 0.05% azelastine, about 1.0% pseudoephedrine or phenylephrine and about 0.05% sucralose;
About 0.1% azelastine, about 1.0% pseudoephedrine or phenylephrine and about 0.05% sucralose;
About 0.125% azelastine, about 1.0% pseudoephedrine or phenylephrine and about 0.05% sucralose;
About 0.15% azelastine, about 1.0% pseudoephedrine or phenylephrine and about 0.05% sucralose;
About 0.05% azelastine, about 1.0% pseudoephedrine or phenylephrine and about 0.1% sucralose;
About 0.1% azelastine, about 1.0% pseudoephedrine or phenylephrine and about 0.1% sucralose;
About 0.125% azelastine, about 1.0% pseudoephedrine or phenylephrine and about 0.1% sucralose;
About 0.15% azelastine, about 1.0% pseudoephedrine or phenylephrine and about 0.1% sucralose;
About 0.05% azelastine, about 1.0% pseudoephedrine or phenylephrine and about 0.15% sucralose;
About 0.1% azelastine, about 1.0% pseudoephedrine or phenylephrine and about 0.15% sucralose;
About 0.125% azelastine, about 1.0% pseudoephedrine or phenylephrine and about 0.15% sucralose;
About 0.15% azelastine, about 1.0% pseudoephedrine or phenylephrine and about 0.15% sucralose;
About 0.05% azelastine and about 0.1% NSAID;
About 0.1% azelastine and about 0.1% NSAID;
About 0.125% azelastine and about 0.1% NSAID;
About 0.15% azelastine and about 0.1% NSAID;
About 0.05% azelastine and about 0.5% NSAID;
About 0.1% azelastine and about 0.5% NSAID;
About 0.125% azelastine and about 0.5% NSAID;
About 0.15% azelastine and about 0.5% NSAID;
About 0.05% azelastine and about 10.0% NSAID;
About 0.1% azelastine and about 10.0% NSAID;
About 0.125% azelastine and about 10.0% NSAID;
About 0.15% azelastine and about 10.0% NSAID;
About 0.05% azelastine, about 0.1% NSAID and about 0.05% sucralose;
About 0.1% azelastine, about 0.1% NSAID and about 0.05% sucralose;
About 0.125% azelastine, about 0.1% NSAID and about 0.05% sucralose;
About 0.15% azelastine, about 0.1% NSAID and about 0.05% sucralose;
About 0.05% azelastine, about 0.1% NSAID and about 0.1% sucralose;
About 0.1% azelastine, about 0.1% NSAID and about 0.1% sucralose;
About 0.125% azelastine, about 0.1% NSAID and about 0.1% sucralose;
About 0.15% azelastine, about 0.1% NSAID and about 0.1% sucralose;
About 0.05% azelastine, about 0.1% NSAID and about 0.15% sucralose;
About 0.1% azelastine, about 0.1% NSAID and about 0.15% sucralose;
About 0.125% azelastine, about 0.1% NSAID and about 0.15% sucralose;
About 0.15% azelastine, about 0.1% NSAID and about 0.15% sucralose;
About 0.05% azelastine, about 0.5% NSAID and about 0.05% sucralose;
About 0.1% azelastine, about 0.5% NSAID and about 0.05% sucralose;
About 0.125% azelastine, about 0.5% NSAID and about 0.05% sucralose;
About 0.15% azelastine, about 0.5% NSAID and about 0.05% sucralose;
About 0.05% azelastine, about 0.5% NSAID and about 0.1% sucralose;
About 0.1% azelastine, about 0.5% NSAID and about 0.1% sucralose;
About 0.125% azelastine, about 0.5% NSAID and about 0.1% sucralose;
About 0.15% azelastine, about 0.5% NSAID and about 0.1% sucralose;
About 0.05% azelastine, about 0.5% NSAID and about 0.15% sucralose;
About 0.1% azelastine, about 0.5% NSAID and about 0.15% sucralose;
About 0.125% azelastine, about 0.5% NSAID and about 0.15% sucralose;
About 0.15% azelastine, about 0.5% NSAID and about 0.15% sucralose;
About 0.05% azelastine, about 10.0% NSAID and about 0.05% sucralose;
About 0.1% azelastine, about 10.0% NSAID and about 0.05% sucralose;
About 0.125% azelastine, about 10.0% NSAID and about 0.05% sucralose;
About 0.15% azelastine, about 1.0% NSAID and about 0.05% sucralose;
About 0.05% azelastine, about 10.0% NSAID and about 0.1% sucralose;
About 0.1% azelastine, about 10.0% NSAID and about 0.1% sucralose;
About 0.125% azelastine, about 10.0% NSAID and about 0.1% sucralose;
About 0.15% azelastine, about 10.0% NSAID and about 0.1% sucralose;
About 0.05% azelastine, about 10.0% NSAID and about 0.15% sucralose;
About 0.1% azelastine, about 10.0% NSAID and about 0.15% sucralose;
About 0.125% azelastine, about 10.0% NSAID and about 0.15% sucralose;
About 0.15% azelastine, about 10.0% NSAID and about 0.15% sucralose;
About 0.05% azelastine and about 0.1% ibuprofen, diclofenac, aceclofenac or naproxen;
About 0.1% azelastine and about 0.1% ibuprofen, diclofenac, aceclofenac or naproxen;
About 0.125% azelastine and about 0.1% ibuprofen, diclofenac, aceclofenac or naproxen;

About 0.15% azelastine and about 0.1% ibuprofen, diclofenac, aceclofenac or naproxen;
About 0.05% azelastine and about 0.5% ibuprofen, diclofenac, aceclofenac or naproxen;
About 0.1% azelastine and about 0.5% ibuprofen, diclofenac, aceclofenac or naproxen;
About 0.125% azelastine and about 0.5% ibuprofen, diclofenac, aceclofenac or naproxen;
About 0.15% azelastine and about 0.5% ibuprofen, diclofenac, aceclofenac or naproxen;
About 0.05% azelastine and about 10.0% ibuprofen, diclofenac, aceclofenac or naproxen;
About 0.1% azelastine and about 10.0% ibuprofen, diclofenac, aceclofenac or naproxen;
About 0.125% azelastine and about 10.0% ibuprofen, diclofenac, aceclofenac or naproxen;
About 0.15% azelastine and about 10.0% ibuprofen, diclofenac, aceclofenac or naproxen;
About 0.05% azelastine, about 0.1% ibuprofen, diclofenac, aceclofenac or naproxen and about 0.05% sucralose;
About 0.1% azelastine, about 0.1% ibuprofen, diclofenac, aceclofenac or naproxen and about 0.05% sucralose;
About 0.125% azelastine, about 0.1% ibuprofen, diclofenac, aceclofenac or naproxen and about 0.05% sucralose;
About 0.15% azelastine, about 0.1% ibuprofen, diclofenac, aceclofenac or naproxen and about 0.05% sucralose;
About 0.05% azelastine, about 0.1% ibuprofen, diclofenac, aceclofenac or naproxen and about 0.1% sucralose;
About 0.1% azelastine, about 0.1% ibuprofen, diclofenac, aceclofenac or naproxen and about 0.1% sucralose;
About 0.125% azelastine, about 0.1% ibuprofen, diclofenac, aceclofenac or naproxen and about 0.1% sucralose;
About 0.15% azelastine, about 0.1% ibuprofen, diclofenac, aceclofenac or naproxen and about 0.1% sucralose;
About 0.05% azelastine, about 0.1% ibuprofen, diclofenac, aceclofenac or naproxen and about 0.15% sucralose;
About 0.1% azelastine, about 0.1% ibuprofen, diclofenac, aceclofenac or naproxen and about 0.15% sucralose;
About 0.125% azelastine, about 0.1% ibuprofen, diclofenac, aceclofenac or naproxen and about 0.15% sucralose;
About 0.15% azelastine, about 0.1% ibuprofen, diclofenac, aceclofenac or naproxen and about 0.15% sucralose;
About 0.05% azelastine, about 0.5% ibuprofen, diclofenac, aceclofenac or naproxen and about 0.05% sucralose;
About 0.1% azelastine, about 0.5% ibuprofen, diclofenac, aceclofenac or naproxen and about 0.05% sucralose;
About 0.125% azelastine, about 0.5% ibuprofen, diclofenac, aceclofenac or naproxen and about 0.05% sucralose;
About 0.15% azelastine, about 0.5% ibuprofen and about 0.05% sucralose;
About 0.05% azelastine, about 0.5% ibuprofen, diclofenac, aceclofenac or naproxen and about 0.1% sucralose;
About 0.1% azelastine, about 0.5% ibuprofen, diclofenac, aceclofenac or naproxen and about 0.1% sucralose;
About 0.125% azelastine, about 0.5% ibuprofen, diclofenac, aceclofenac or naproxen and about 0.1% sucralose;
About 0.15% azelastine, about 0.5% ibuprofen, diclofenac, aceclofenac or naproxen and about 0.1% sucralose;
About 0.05% azelastine, about 0.5% ibuprofen, diclofenac, aceclofenac or naproxen and about 0.15% sucralose;
About 0.1% azelastine, about 0.5% ibuprofen, diclofenac, aceclofenac or naproxen and about 0.15% sucralose;
About 0.125% azelastine, about 0.5% ibuprofen, diclofenac, aceclofenac or naproxen and about 0.15% sucralose;
About 0.15% azelastine, about 0.5% ibuprofen, diclofenac, aceclofenac or naproxen and about 0.15% sucralose;
About 0.05% azelastine, about 10.0% ibuprofen, diclofenac, aceclofenac or naproxen and about 0.05% sucralose;
About 0.1% azelastine, about 10.0% ibuprofen, diclofenac, aceclofenac or naproxen and about 0.05% sucralose;
About 0.125% azelastine, about 10.0% ibuprofen, diclofenac, aceclofenac or naproxen and about 0.05% sucralose;
About 0.15% azelastine, about 10.0% ibuprofen, diclofenac, aceclofenac or naproxen and about 0.05% sucralose;
About 0.05% azelastine, about 10.0% ibuprofen, diclofenac, aceclofenac or naproxen and about 0.1% sucralose;
About 0.1% azelastine, about 10.0% ibuprofen, diclofenac, aceclofenac or naproxen and about 0.1% sucralose;
About 0.125% azelastine, about 10.0% ibuprofen, diclofenac, aceclofenac or naproxen and about 0.1% sucralose;
About 0.15% azelastine, about 10.0% ibuprofen, diclofenac, aceclofenac or naproxen and about 0.1% sucralose;
About 0.05% azelastine, about 10.0% ibuprofen, diclofenac, aceclofenac or naproxen and about 0.15% sucralose;
About 0.1% azelastine, about 10.0% ibuprofen, diclofenac, aceclofenac or naproxen and about 0.15% sucralose;
About 0.125% azelastine, about 10.0% ibuprofen, diclofenac, aceclofenac or naproxen and about 0.15% sucralose;
About 0.15% azelastine, about 10.0% ibuprofen, diclofenac, aceclofenac or naproxen and about 0.15% sucralose;
About 0.05% azelastine, about 0.01% steroid and about 0.1% decongestant;
About 0.1% azelastine, about 0.01% steroid and about 0.1% decongestant;
About 0.125% azelastine, about 0.01% steroid and about 0.1% decongestant;
About 0.15% azelastine, about 0.01% steroid and about 0.1% decongestant;
About 0.05% azelastine, about 0.05% steroid and about 0.1% decongestant;
About 0.1% azelastine, about 0.05% steroid and about 0.1% decongestant;
About 0.125% azelastine, about 0.05% steroid and about 0.1% decongestant;

About 0.15% azelastine, about 0.05% steroid and about 0.1% decongestant;
About 0.05% azelastine, about 0.1% steroid and about 0.1% decongestant;
About 0.1% azelastine, about 0.1% steroid and about 0.1% decongestant;
About 0.125% azelastine, about 0.1% steroid and about 0.1% decongestant;
About 0.15% azelastine, about 0.1% steroid and about 0.1% decongestant;
About 0.05% azelastine, about 0.01% steroid and about 0.5% decongestant;
About 0.1% azelastine, about 0.01% steroid and about 0.5% decongestant;
About 0.125% azelastine, about 0.01% steroid and about 0.5% decongestant;
About 0.15% azelastine, about 0.01% steroid and about 0.5% decongestant;
About 0.05% azelastine, about 0.05% steroid and about 0.5% decongestant;
About 0.1% azelastine, about 0.05% steroid and about 0.5% decongestant;
About 0.125% azelastine, about 0.05% steroid and about 0.5% decongestant;
About 0.15% azelastine, about 0.05% steroid and about 0.5% decongestant;
About 0.05% azelastine, about 0.1% steroid and about 0.5% decongestant;
About 0.1% azelastine, about 0.1% steroid and about 0.5% decongestant;
About 0.125% azelastine, about 0.1% steroid and about 0.5% decongestant;
About 0.15% azelastine, about 0.1% steroid and about 0.5% decongestant;
About 0.05% azelastine, about 0.01% steroid and about 1.0% decongestant;
About 0.1% azelastine, about 0.01% steroid and about 1.0% decongestant;
About 0.125% azelastine, about 0.01% steroid and about 1.0% decongestant;
About 0.15% azelastine, about 0.01% steroid and about 1.0% decongestant;
About 0.05% azelastine, about 0.05% steroid and about 1.0% decongestant;
About 0.1% azelastine, about 0.05% steroid and about 1.0% decongestant;
About 0.125% azelastine, about 0.05% steroid and about 1.0% decongestant;
About 0.15% azelastine, about 0.05% steroid and about 1.0% decongestant;
About 0.05% azelastine, about 0.1% steroid and about 1.0% decongestant;
About 0.1% azelastine, about 0.1% steroid and about 1.0% decongestant;
About 0.125% azelastine, about 0.1% steroid and about 1.0% decongestant;
About 0.15% azelastine, about 0.1% steroid and about 1.0% decongestant;
About 0.05% azelastine, about 0.01% steroid, about 0.1% decongestant and about 0.05% sucralose;
About 0.1% azelastine, about 0.01% steroid, about 0.1% decongestant and about 0.05% sucralose;
About 0.125% azelastine, about 0.01% steroid, about 0.1% decongestant and about 0.05% sucralose;
About 0.15% azelastine, about 0.01% steroid, about 0.1% decongestant and about 0.05% sucralose;
About 0.05% azelastine, about 0.05% steroid, about 0.1% decongestant and about 0.05% sucralose;
About 0.1% azelastine, about 0.05% steroid, about 0.1% decongestant and about 0.05% sucralose;
About 0.125% azelastine, about 0.05% steroid, about 0.1% decongestant and about 0.05% sucralose;
About 0.15% azelastine, about 0.05% steroid, about 0.1% decongestant and about 0.05% sucralose;
About 0.05% azelastine, about 0.1% steroid, about 0.1% decongestant and about 0.05% sucralose;
About 0.1% azelastine, about 0.1% steroid, about 0.1% decongestant and about 0.05% sucralose;
About 0.125% azelastine, about 0.1% steroid, about 0.1% decongestant and about 0.05% sucralose;
About 0.15% azelastine, about 0.1% steroid, about 0.1% decongestant and about 0.05% sucralose;
About 0.05% azelastine, about 0.01% steroid, about 0.5% decongestant and about 0.05% sucralose;
About 0.1% azelastine, about 0.01% steroid, about 0.5% decongestant and about 0.05% sucralose;
About 0.125% azelastine, about 0.01% steroid, about 0.5% decongestant and about 0.05% sucralose;
About 0.15% azelastine, about 0.01% steroid, about 0.5% decongestant and about 0.05% sucralose;
About 0.05% azelastine, about 0.05% steroid, about 0.5% decongestant and about 0.05% sucralose;
About 0.1% azelastine, about 0.05% steroid, about 0.5% decongestant and about 0.05% sucralose;
About 0.125% azelastine, about 0.05% steroid, about 0.5% decongestant and about 0.05% sucralose;
About 0.15% azelastine, about 0.05% steroid, about 0.5% decongestant and about 0.05% sucralose;
About 0.05% azelastine, about 0.1% steroid, about 0.5% decongestant and about 0.05% sucralose;
About 0.1% azelastine, about 0.1% steroid, about 0.5% decongestant and about 0.05% sucralose;
About 0.125% azelastine, about 0.1% steroid, about 0.5% decongestant and about 0.05% sucralose;
About 0.15% azelastine, about 0.1% steroid, about 0.5% decongestant and about 0.05% sucralose;
About 0.05% azelastine, about 0.01% steroid, about 1.0% decongestant and about 0.05% sucralose;
About 0.1% azelastine, about 0.01% steroid, about 1.0% decongestant and about 0.05% sucralose;
About 0.125% azelastine, about 0.01% steroid, about 1.0% decongestant and about 0.05% sucralose;
About 0.15% azelastine, about 0.01% steroid, about 1.0% decongestant and about 0.05% sucralose;
About 0.05% azelastine, about 0.05% steroid, about 1.0% decongestant and about 0.05% sucralose;
About 0.1% azelastine, about 0.05% steroid, about 1.0% decongestant and about 0.05% sucralose;
About 0.125% azelastine, about 0.05% steroid, about 1.0% decongestant and about 0.05% sucralose;
About 0.15% azelastine, about 0.05% steroid, about 1.0% decongestant and about 0.05% sucralose;
About 0.05% azelastine, about 0.1% steroid, about 1.0% decongestant and about 0.05% sucralose;
About 0.1% azelastine, about 0.1% steroid, about 1.0% decongestant and about 0.05% sucralose;
About 0.125% azelastine, about 0.1% steroid, about 1.0% decongestant and about 0.05% sucralose;
About 0.15% azelastine, about 0.1% steroid, about 1.0% decongestant and about 0.05% sucralose;
About 0.05% azelastine, about 0.01% steroid, about 0.1% decongestant and about 0.1% sucralose;

About 0.1% azelastine, about 0.01% steroid, about 0.1% decongestant and about 0.1% sucralose;
About 0.125% azelastine, about 0.01% steroid, about 0.1% decongestant and about 0.1% sucralose;
About 0.15% azelastine, about 0.01% steroid, about 0.1% decongestant and about 0.1% sucralose;
About 0.05% azelastine, about 0.05% steroid, about 0.1% decongestant and about 0.1% sucralose;
About 0.1% azelastine, about 0.05% steroid, about 0.1% decongestant and about 0.1% sucralose;
About 0.125% azelastine, about 0.05% steroid, about 0.1% decongestant and about 0.1% sucralose;
About 0.15% azelastine, about 0.05% steroid, about 0.1% decongestant and about 0.1% sucralose;
About 0.05% azelastine, about 0.1% steroid, about 0.1% decongestant and about 0.1% sucralose;
About 0.1% azelastine, about 0.1% steroid, about 0.1% decongestant and about 0.1% sucralose;
About 0.125% azelastine, about 0.1% steroid, about 0.1% decongestant and about 0.1% sucralose;
About 0.15% azelastine, about 0.1% steroid, about 0.1% decongestant and about 0.1% sucralose;
About 0.05% azelastine, about 0.01% steroid, about 0.5% decongestant and about 0.1% sucralose;
About 0.1% azelastine, about 0.01% steroid, about 0.5% decongestant and about 0.1% sucralose;
About 0.125% azelastine, about 0.01% steroid, about 0.5% decongestant and about 0.1% sucralose;
About 0.15% azelastine, about 0.01% steroid, about 0.5% decongestant and about 0.1% sucralose;
About 0.05% azelastine, about 0.05% steroid, about 0.5% decongestant and about 0.1% sucralose;
About 0.1% azelastine, about 0.05% steroid, about 0.5% decongestant and about 0.1% sucralose;
About 0.125% azelastine, about 0.05% steroid, about 0.5% decongestant and about 0.1% sucralose;
About 0.15% azelastine, about 0.05% steroid, about 0.5% decongestant and about 0.1% sucralose;
About 0.05% azelastine, about 0.1% steroid, about 0.5% decongestant and about 0.1% sucralose;
About 0.1% azelastine, about 0.1% steroid, about 0.5% decongestant and about 0.1% sucralose;
About 0.125% azelastine, about 0.1% steroid, about 0.5% decongestant and about 0.1% sucralose;
About 0.15% azelastine, about 0.1% steroid, about 0.5% decongestant and about 0.1% sucralose;
About 0.05% azelastine, about 0.01% steroid, about 1.0% decongestant and about 0.1% sucralose;
About 0.1% azelastine, about 0.01% steroid, about 1.0% decongestant and about 0.1% sucralose;
About 0.125% azelastine, about 0.01% steroid, about 1.0% decongestant and about 0.1% sucralose;
About 0.15% azelastine, about 0.01% steroid, about 1.0% decongestant and about 0.1% sucralose;
About 0.05% azelastine, about 0.05% steroid, about 1.0% decongestant and about 0.1% sucralose;
About 0.1% azelastine, about 0.05% steroid, about 1.0% decongestant and about 0.1% sucralose;
About 0.125% azelastine, about 0.05% steroid, about 1.0% decongestant and about 0.1% sucralose;
About 0.15% azelastine, about 0.05% steroid, about 1.0% decongestant and about 0.1% sucralose;
About 0.05% azelastine, about 0.1% steroid, about 1.0% decongestant and about 0.1% sucralose;
About 0.1% azelastine, about 0.1% steroid, about 1.0% decongestant and about 0.1% sucralose;
About 0.125% azelastine, about 0.1% steroid, about 1.0% decongestant and about 0.1% sucralose;
About 0.15% azelastine, about 0.1% steroid, about 1.0% decongestant and about 0.1% sucralose;
About 0.05% azelastine, about 0.01% steroid, about 0.1% decongestant and about 0.15% sucralose;
About 0.1% azelastine, about 0.01% steroid, about 0.1% decongestant and about 0.15% sucralose;
About 0.125% azelastine, about 0.01% steroid, about 0.1% decongestant and about 0.15% sucralose;
About 0.15% azelastine, about 0.01% steroid, about 0.1% decongestant and about 0.15% sucralose;
About 0.05% azelastine, about 0.05% steroid, about 0.1% decongestant and about 0.15% sucralose;
About 0.1% azelastine, about 0.05% steroid, about 0.1% decongestant and about 0.15% sucralose;
About 0.125% azelastine, about 0.05% steroid, about 0.1% decongestant and about 0.15% sucralose;
About 0.15% azelastine, about 0.05% steroid, about 0.1% decongestant and about 0.15% sucralose;
About 0.05% azelastine, about 0.1% steroid, about 0.1% decongestant and about 0.15% sucralose;
About 0.1% azelastine, about 0.1% steroid, about 0.1% decongestant and about 0.15% sucralose;
About 0.125% azelastine, about 0.1% steroid, about 0.1% decongestant and about 0.15% sucralose;
About 0.15% azelastine, about 0.1% steroid, about 0.1% decongestant and about 0.15% sucralose;
About 0.05% azelastine, about 0.01% steroid, about 0.5% decongestant and about 0.15% sucralose;
About 0.1% azelastine, about 0.01% steroid, about 0.5% decongestant and about 0.15% sucralose;
About 0.125% azelastine, about 0.01% steroid, about 0.5% decongestant and about 0.15% sucralose;
About 0.15% azelastine, about 0.01% steroid, about 0.5% decongestant and about 0.15% sucralose;
About 0.05% azelastine, about 0.05% steroid, about 0.5% decongestant and about 0.15% sucralose;
About 0.1% azelastine, about 0.05% steroid, about 0.5% decongestant and about 0.15% sucralose;
About 0.125% azelastine, about 0.05% steroid, about 0.5% decongestant and about 0.15% sucralose;
About 0.15% azelastine, about 0.05% steroid, about 0.5% decongestant and about 0.15% sucralose;
About 0.05% azelastine, about 0.1% steroid, about 0.5% decongestant and about 0.15% sucralose;
About 0.1% azelastine, about 0.1% steroid, about 0.5% decongestant and about 0.15% sucralose;
About 0.125% azelastine, about 0.1% steroid, about 0.5% decongestant and about 0.15% sucralose;
About 0.15% azelastine, about 0.1% steroid, about 0.5% decongestant and about 0.15% sucralose;
About 0.05% azelastine, about 0.01% steroid, about 1.0% decongestant and about 0.15% sucralose;
About 0.1% azelastine, about 0.01% steroid, about 1.0% decongestant and about 0.15% sucralose;
About 0.125% azelastine, about 0.01% steroid, about 1.0% decongestant and about 0.15% sucralose;
About 0.15% azelastine, about 0.01% steroid, about 1.0% decongestant and about 0.15% sucralose;
About 0.05% azelastine, about 0.05% steroid, about 1.0% decongestant and about 0.15% sucralose;
About 0.1% azelastine, about 0.05% steroid, about 1.0% decongestant and about 0.15% sucralose;
About 0.125% azelastine, about 0.05% steroid, about 1.0% decongestant and about 0.15% sucralose;

About 0.15% azelastine, about 0.05% steroid, about 1.0% decongestant and about 0.15% sucralose;

About 0.05% azelastine, about 0.1% steroid, about 1.0% decongestant and about 0.15% sucralose;

About 0.1% azelastine, about 0.1% steroid, about 1.0% decongestant and about 0.15% sucralose;

About 0.125% azelastine, about 0.1% steroid, about 1.0% decongestant and about 0.15% sucralose;

About 0.15% azelastine, about 0.1% steroid, about 1.0% decongestant and about 0.15% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% pseudoephedrine or phenylephrine;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% pseudoephedrine or phenylephrine;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 1.0% pseudoephedrine or phenylephrine;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 1.0% pseudoephedrine or phenylephrine;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 1.0% pseudoephedrine or phenylephrine;

About 0.15% azelastine, about 0.01% fluticasone, mometasone, dexamethasone beloxil, loteprednol (e.g., loteprednol etabonate), budesonide, or triamcinolone and about 1.0% pseudoephedrine or phenylephrine;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 1.0% pseudoephedrine or phenylephrine;

About 0.1% azelastine, about 0.05% fluticasone, mometasone, dexamethasone beloxil, loteprednol (e.g., loteprednol etabonate), budesonide, or triamcinolone and about 1.0% pseudoephedrine or phenylephrine;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 1.0% pseudoephedrine or phenylephrine;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 1.0% pseudoephedrine or phenylephrine;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 1.0% pseudoephedrine or phenylephrine;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 1.0% pseudoephedrine or phenylephrine;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 1.0% pseudoephedrine or phenylephrine;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 1.0% pseudoephedrine or phenylephrine;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, about 0.1% pseudoephedrine or phenylephrine and about 0.05% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.05% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol etabonate), budesonide, or triamcinolone, about 0.5% pseudoephedrine or phenylephrine and about 0.05% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.05% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.05% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.1% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.1% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.1% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine or phenylephrine and about 0.1% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.1% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.1% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.1% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine or phenylephrine and about 0.1% sucralose;

About 0.15% azelastine, about 0.50% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.1% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.1% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.1% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine or phenylephrine and about 0.1% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.1% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.1% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% pseudoephedrine or phenylephrine and about 0.15% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol etabonate), budesonide, or triamcinolone, about 0.5% pseudoephedrine or phenylephrine and about 0.15% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% pseudoephedrine or phenylephrine and about 0.15% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 1.0% pseudoephedrine or phenylephrine and about 0.15% sucralose;

About 0.05% azelastine, about 0.01% steroid and about 0.1% leukotriene antagonist;

About 0.1% azelastine, about 0.01% steroid and about 0.1% leukotriene antagonist;

About 0.125% azelastine, about 0.01% steroid and about 0.1% leukotriene antagonist;

About 0.15% azelastine, about 0.01% steroid and about 0.1% leukotriene antagonist;

About 0.05% azelastine, about 0.05% steroid and about 0.1% leukotriene antagonist;

About 0.1% azelastine, about 0.05% steroid and about 0.1% leukotriene antagonist;

About 0.125% azelastine, about 0.05% steroid and about 0.1% leukotriene antagonist;

About 0.15% azelastine, about 0.05% steroid and about 0.1% leukotriene antagonist;

About 0.05% azelastine, about 0.1% steroid and about 0.1% leukotriene antagonist;

About 0.1% azelastine, about 0.1% steroid and about 0.1% leukotriene antagonist;

About 0.125% azelastine, about 0.1% steroid and about 0.1% leukotriene antagonist;

About 0.15% azelastine, about 0.1% steroid and about 0.1% leukotriene antagonist;

About 0.05% azelastine, about 0.01% steroid and about 0.5% leukotriene antagonist;

About 0.1% azelastine, about 0.01% steroid and about 0.5% leukotriene antagonist;

About 0.125% azelastine, about 0.01% steroid and about 0.5% leukotriene antagonist;

About 0.15% azelastine, about 0.01% steroid and about 0.5% leukotriene antagonist;

About 0.05% azelastine, about 0.05% steroid and about 0.5% leukotriene antagonist;

About 0.1% azelastine, about 0.05% steroid and about 0.5% leukotriene antagonist;

About 0.125% azelastine, about 0.05% steroid and about 0.5% leukotriene antagonist;

About 0.15% azelastine, about 0.05% steroid and about 0.5% leukotriene antagonist;

About 0.05% azelastine, about 0.1% steroid and about 0.5% leukotriene antagonist;

About 0.1% azelastine, about 0.1% steroid and about 0.5% leukotriene antagonist;

About 0.125% azelastine, about 0.1% steroid and about 0.5% leukotriene antagonist;

About 0.15% azelastine, about 0.1% steroid and about 0.5% leukotriene antagonist;

About 0.05% azelastine, about 0.01% steroid and about 5.0% leukotriene antagonist;

About 0.1% azelastine, about 0.01% steroid and about 5.0% leukotriene antagonist;

About 0.125% azelastine, about 0.01% steroid and about 5.0% leukotriene antagonist;

About 0.15% azelastine, about 0.01% steroid and about 5.0% leukotriene antagonist;

About 0.05% azelastine, about 0.05% steroid and about 5.0% leukotriene antagonist;

About 0.1% azelastine, about 0.05% steroid and about 5.0% leukotriene antagonist;

About 0.125% azelastine, about 0.05% steroid and about 5.0% leukotriene antagonist;

About 0.15% azelastine, about 0.05% steroid and about 5.0% leukotriene antagonist;

About 0.05% azelastine, about 0.1% steroid and about 5.0% leukotriene antagonist;

About 0.1% azelastine, about 0.1% steroid and about 5.0% leukotriene antagonist;

About 0.125% azelastine, about 0.1% steroid and about 5.0% leukotriene antagonist;

About 0.15% azelastine, about 0.1% steroid and about 5.0% leukotriene antagonist;

About 0.05% azelastine, about 0.01% steroid, about 0.1% leukotriene antagonist and about 0.05% sucralose;

About 0.1% azelastine, about 0.01% steroid, about 0.1% leukotriene antagonist and about 0.05% sucralose;

About 0.125% azelastine, about 0.01% steroid, about 0.1% leukotriene antagonist and about 0.05% sucralose;

About 0.15% azelastine, about 0.01% steroid, about 0.1% leukotriene antagonist and about 0.05% sucralose;

About 0.05% azelastine, about 0.05% steroid, about 0.1% leukotriene antagonist and about 0.05% sucralose;

About 0.1% azelastine, about 0.05% steroid, about 0.1% leukotriene antagonist and about 0.05% sucralose;

About 0.125% azelastine, about 0.05% steroid, about 0.1% leukotriene antagonist and about 0.05% sucralose;

About 0.15% azelastine, about 0.05% steroid, about 0.1% leukotriene antagonist and about 0.05% sucralose;

About 0.05% azelastine, about 0.1% steroid, about 0.1% leukotriene antagonist and about 0.05% sucralose;
About 0.1% azelastine, about 0.1% steroid, about 0.1% leukotriene antagonist and about 0.05% sucralose;
About 0.125% azelastine, about 0.1% steroid, about 0.1% leukotriene antagonist and about 0.05% sucralose;
About 0.15% azelastine, about 0.1% steroid, about 0.1% leukotriene antagonist and about 0.05% sucralose;
About 0.05% azelastine, about 0.01% steroid, about 0.5% leukotriene antagonist and about 0.05% sucralose;
About 0.1% azelastine, about 0.01% steroid, about 0.5% leukotriene antagonist and about 0.05% sucralose;
About 0.125% azelastine, about 0.01% steroid, about 0.5% leukotriene antagonist and about 0.05% sucralose;
About 0.15% azelastine, about 0.01% steroid, about 0.5% leukotriene antagonist and about 0.05% sucralose;
About 0.05% azelastine, about 0.05% steroid, about 0.5% leukotriene antagonist and about 0.05% sucralose;
About 0.1% azelastine, about 0.05% steroid, about 0.5% leukotriene antagonist and about 0.05% sucralose;
About 0.125% azelastine, about 0.05% steroid, about 0.5% leukotriene antagonist and about 0.05% sucralose;
About 0.15% azelastine, about 0.05% steroid, about 0.5% leukotriene antagonist and about 0.05% sucralose;
About 0.05% azelastine, about 0.1% steroid, about 0.5% leukotriene antagonist and about 0.05% sucralose;
About 0.1% azelastine, about 0.1% steroid, about 0.5% leukotriene antagonist and about 0.05% sucralose;
About 0.125% azelastine, about 0.1% steroid, about 0.5% leukotriene antagonist and about 0.05% sucralose;
About 0.15% azelastine, about 0.1% steroid, about 0.5% leukotriene antagonist and about 0.05% sucralose;
About 0.05% azelastine, about 0.01% steroid, about 5.0% leukotriene antagonist and about 0.05% sucralose;
About 0.1% azelastine, about 0.01% steroid, about 5.0% leukotriene antagonist and about 0.05% sucralose;
About 0.125% azelastine, about 0.01% steroid, about 5.0% leukotriene antagonist and about 0.05% sucralose;
About 0.15% azelastine, about 0.01% steroid, about 5.0% leukotriene antagonist and about 0.05% sucralose;
About 0.05% azelastine, about 0.05% steroid, about 5.0% leukotriene antagonist and about 0.05% sucralose;
About 0.1% azelastine, about 0.05% steroid, about 5.0% leukotriene antagonist and about 0.05% sucralose;
About 0.125% azelastine, about 0.05% steroid, about 5.0% leukotriene antagonist and about 0.05% sucralose;
About 0.15% azelastine, about 0.05% steroid, about 5.0% leukotriene antagonist and about 0.05% sucralose;
About 0.05% azelastine, about 0.1% steroid, about 5.0% leukotriene antagonist and about 0.05% sucralose;
About 0.1% azelastine, about 0.1% steroid, about 5.0% leukotriene antagonist and about 0.05% sucralose;
About 0.125% azelastine, about 0.1% steroid, about 5.0% leukotriene antagonist and about 0.05% sucralose;
About 0.15% azelastine, about 0.1% steroid, about 5.0% leukotriene antagonist and about 0.05% sucralose;
About 0.05% azelastine, about 0.01% steroid, about 0.1% leukotriene antagonist and about 0.1% sucralose;
About 0.1% azelastine, about 0.01% steroid, about 0.1% leukotriene antagonist and about 0.1% sucralose;
About 0.125% azelastine, about 0.01% steroid, about 0.1% leukotriene antagonist and about 0.1% sucralose;
About 0.15% azelastine, about 0.01% steroid, about 0.1% leukotriene antagonist and about 0.1% sucralose;
About 0.05% azelastine, about 0.05% steroid, about 0.1% leukotriene antagonist and about 0.1% sucralose;
About 0.1% azelastine, about 0.05% steroid, about 0.1% leukotriene antagonist and about 0.1% sucralose;
About 0.125% azelastine, about 0.05% steroid, about 0.1% leukotriene antagonist and about 0.1% sucralose;
About 0.15% azelastine, about 0.05% steroid, about 0.1% leukotriene antagonist and about 0.1% sucralose;
About 0.05% azelastine, about 0.1% steroid, about 0.1% leukotriene antagonist and about 0.1% sucralose;
About 0.1% azelastine, about 0.1% steroid, about 0.1% leukotriene antagonist and about 0.1% sucralose;
About 0.125% azelastine, about 0.1% steroid, about 0.1% leukotriene antagonist and about 0.1% sucralose;
About 0.15% azelastine, about 0.1% steroid, about 0.1% leukotriene antagonist and about 0.1% sucralose;
About 0.05% azelastine, about 0.01% steroid, about 0.5% leukotriene antagonist and about 0.1% sucralose;
About 0.1% azelastine, about 0.01% steroid, about 0.5% leukotriene antagonist and about 0.1% sucralose;
About 0.125% azelastine, about 0.01% steroid, about 0.5% leukotriene antagonist and about 0.1% sucralose;
About 0.15% azelastine, about 0.01% steroid, about 0.5% leukotriene antagonist and about 0.1% sucralose;
About 0.05% azelastine, about 0.05% steroid, about 0.5% leukotriene antagonist and about 0.1% sucralose;
About 0.1% azelastine, about 0.05% steroid, about 0.5% leukotriene antagonist and about 0.1% sucralose;
About 0.125% azelastine, about 0.05% steroid, about 0.5% leukotriene antagonist and about 0.1% sucralose;
About 0.15% azelastine, about 0.05% steroid, about 0.5% leukotriene antagonist and about 0.1% sucralose;
About 0.05% azelastine, about 0.1% steroid, about 0.5% leukotriene antagonist and about 0.1% sucralose;
About 0.1% azelastine, about 0.1% steroid, about 0.5% leukotriene antagonist and about 0.1% sucralose;
About 0.125% azelastine, about 0.1% steroid, about 0.5% leukotriene antagonist and about 0.1% sucralose;
About 0.15% azelastine, about 0.1% steroid, about 0.5% leukotriene antagonist and about 0.1% sucralose;
About 0.05% azelastine, about 0.01% steroid, about 5.0% leukotriene antagonist and about 0.1% sucralose;
About 0.1% azelastine, about 0.01% steroid, about 5.0% leukotriene antagonist and about 0.1% sucralose;
About 0.125% azelastine, about 0.01% steroid, about 5.0% leukotriene antagonist and about 0.1% sucralose;
About 0.15% azelastine, about 0.01% steroid, about 5.0% leukotriene antagonist and about 0.1% sucralose;
About 0.05% azelastine, about 0.05% steroid, about 5.0% leukotriene antagonist and about 0.1% sucralose;
About 0.1% azelastine, about 0.05% steroid, about 5.0% leukotriene antagonist and about 0.1% sucralose;
About 0.125% azelastine, about 0.05% steroid, about 5.0% leukotriene antagonist and about 0.1% sucralose;
About 0.15% azelastine, about 0.05% steroid, about 5.0% leukotriene antagonist and about 0.1% sucralose;
About 0.05% azelastine, about 0.1% steroid, about 5.0% leukotriene antagonist and about 0.1% sucralose;
About 0.1% azelastine, about 0.1% steroid, about 5.0% leukotriene antagonist and about 0.1% sucralose;
About 0.125% azelastine, about 0.1% steroid, about 5.0% leukotriene antagonist and about 0.1% sucralose;
About 0.15% azelastine, about 0.1% steroid, about 5.0% leukotriene antagonist and about 0.1% sucralose;
About 0.05% azelastine, about 0.01% steroid, about 0.1% leukotriene antagonist and about 0.15% sucralose;
About 0.1% azelastine, about 0.01% steroid, about 0.1% leukotriene antagonist and about 0.15% sucralose;

About 0.125% azelastine, about 0.01% steroid, about 0.1% leukotriene antagonist and about 0.15% sucralose;
About 0.15% azelastine, about 0.01% steroid, about 0.1% leukotriene antagonist and about 0.15% sucralose;
About 0.05% azelastine, about 0.05% steroid, about 0.1% leukotriene antagonist and about 0.15% sucralose;
About 0.1% azelastine, about 0.05% steroid, about 0.1% leukotriene antagonist and about 0.15% sucralose;
About 0.125% azelastine, about 0.05% steroid, about 0.1% leukotriene antagonist and about 0.15% sucralose;
About 0.15% azelastine, about 0.05% steroid, about 0.1% leukotriene antagonist and about 0.15% sucralose;
About 0.05% azelastine, about 0.1% steroid, about 0.1% leukotriene antagonist and about 0.15% sucralose;
About 0.1% azelastine, about 0.1% steroid, about 0.1% leukotriene antagonist and about 0.15% sucralose;
About 0.125% azelastine, about 0.1% steroid, about 0.1% leukotriene antagonist and about 0.15% sucralose;
About 0.15% azelastine, about 0.1% steroid, about 0.1% leukotriene antagonist and about 0.15% sucralose;
About 0.05% azelastine, about 0.01% steroid, about 0.5% leukotriene antagonist and about 0.15% sucralose;
About 0.1% azelastine, about 0.01% steroid, about 0.5% leukotriene antagonist and about 0.15% sucralose;
About 0.125% azelastine, about 0.01% steroid, about 0.5% leukotriene antagonist and about 0.15% sucralose;
About 0.15% azelastine, about 0.01% steroid, about 0.5% leukotriene antagonist and about 0.15% sucralose;
About 0.05% azelastine, about 0.05% steroid, about 0.5% leukotriene antagonist and about 0.15% sucralose;
About 0.1% azelastine, about 0.05% steroid, about 0.5% leukotriene antagonist and about 0.15% sucralose;
About 0.125% azelastine, about 0.05% steroid, about 0.5% leukotriene antagonist and about 0.15% sucralose;
About 0.15% azelastine, about 0.05% steroid, about 0.5% leukotriene antagonist and about 0.15% sucralose;
About 0.05% azelastine, about 0.1% steroid, about 0.5% leukotriene antagonist and about 0.15% sucralose;
About 0.1% azelastine, about 0.1% steroid, about 0.5% leukotriene antagonist and about 0.15% sucralose;
About 0.125% azelastine, about 0.1% steroid, about 0.5% leukotriene antagonist and about 0.15% sucralose;
About 0.15% azelastine, about 0.1% steroid, about 0.5% leukotriene antagonist and about 0.15% sucralose;
About 0.05% azelastine, about 0.01% steroid, about 5.0% leukotriene antagonist and about 0.15% sucralose;
About 0.1% azelastine, about 0.01% steroid, about 5.0% leukotriene antagonist and about 0.15% sucralose;
About 0.125% azelastine, about 0.01% steroid, about 5.0% leukotriene antagonist and about 0.15% sucralose;
About 0.15% azelastine, about 0.01% steroid, about 5.0% leukotriene antagonist and about 0.15% sucralose;
About 0.05% azelastine, about 0.05% steroid, about 5.0% leukotriene antagonist and about 0.15% sucralose;
About 0.1% azelastine, about 0.05% steroid, about 5.0% leukotriene antagonist and about 0.15% sucralose;
About 0.125% azelastine, about 0.05% steroid, about 5.0% leukotriene antagonist and about 0.15% sucralose;
About 0.15% azelastine, about 0.05% steroid, about 5.0% leukotriene antagonist and about 0.15% sucralose;
About 0.05% azelastine, about 0.1% steroid, about 5.0% leukotriene antagonist and about 0.15% sucralose;
About 0.1% azelastine, about 0.1% steroid, about 5.0% leukotriene antagonist and about 0.15% sucralose;
About 0.125% azelastine, about 0.1% steroid, about 5.0% leukotriene antagonist and about 0.15% sucralose;
About 0.15% azelastine, about 0.1% steroid, about 5.0% leukotriene antagonist and about 0.15% sucralose;
About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;
About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;
About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;
About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;
About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;
About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;
About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;
About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;
About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;
About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;
About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.1% montelukast;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 0.5% montelukast;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone and about 5.0% montelukast;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.05% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.05% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.05% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.1% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.1% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.1% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.125% azelastine, about 0.05% fluticasone, mometasone, dexamethasone beloxil, loteprednol (e.g., loteprednol etabonate), budesonide, or triamcinolone, about 0.1% montelukast and about 0.15% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.1% montelukast and about 0.15% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.125% azelastine, about 0.1% fluticasone, mometasone, dexamethasone beloxil, loteprednol (e.g., loteprednol etabonate), budesonide, or triamcinolone, about 0.5% montelukast and about 0.15% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 0.5% montelukast and about 0.15% sucralose;

About 0.05% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.1% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.125% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.15% azelastine, about 0.01% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.05% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.1% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.125% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.15% azelastine, about 0.05% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.05% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.1% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.125% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose;

About 0.15% azelastine, about 0.1% fluticasone (e.g., fluticasone propionate, fluticasone dipropionate, fluticasone furoate, fluticasone maleate, fluticasone valerate, and the like), mometasone, dexamethasone beloxil, loteprednol (e.g., loteprednol etabonate), budesonide, or triamcinolone, about 5.0% montelukast and about 0.15% sucralose.

Other suitable compositions of the invention include, for example, about 0.1%-0.15% azelastine and about 0.05%-0.15% sucralose, for example, about 0.1% azelastine and about 0.05%-0.15% sucralose, or about 0.125%-0.15% azelastine and about 0.05%-0.15% sucralose, or about 0.10% azelastine and about 0.15% sucralose, or about 0.15% azelastine and about 0.15% sucralose. Additional compositions of the invention include, for example, about 0.1%-0.15% azelastine, about 0.05%-0.15% sucralose and about 0.1%-10% sorbitol, for example, about 0.1% azelastine, about 0.05%-0.15% sucralose and about 0.1%-10% sorbitol, or about 0.125%-0.15% azelastine, about 0.05%-0.15% sucralose and about 0.1%-10% sorbitol, or about 0.10% azelastine, about 0.15% sucralose and about 0.1%-10% sorbitol, or about 0.15% azelastine, about 0.15% sucralose and about 0.1%-10% sorbitol.

Chewable and/or Orally Dissolving Formulations

Chewable Formulations

In addition to the solid dosage forms disclosed throughout, the present invention also provides chewable oral formulations. In certain such embodiments, the formulations will comprise (or consist essentially of) an effective amount of azelastine (e.g., azelastine HCl) along with suitable excipients that allow the formulations to be chewed by the patient. In additional embodiments, the formulations can further comprise one or more taste-masking or sweetening agents, such as those described herein. In one embodiment, sucralose is used in the chewable formulations. Additional active agents, such as those described herein, can also optionally be added to the chewable formulations. The amounts of azelastine, other optional active agents (e.g., steroids, decongestants, leukotriene antagonists, and combinations thereof), and sweetening agents (e.g., sucralose) in the chewable formulations of the present invention are readily determinable by those of ordinary skill in the art, and include those amounts and combinations described herein. For example, the chewable formulations of the present invention comprise (or consist essentially of) about 0.05% to about 5% azelastine, optionally about 0.01% to about 10% other active agent(s) (or more as required), and about 0.05% to about 0.15% sucralose. Such chewable formulations are especially useful in patient populations where compliance is an issue, such as children, the elderly, and patients who may have difficulty swallowing or using spray/inhalable formulations.

The formulations may also contain colorants to improve the appearance of the chewable formulations, especially since an attractive coloration imparted by a colorant may improve patient compliance. The relative amounts of the colorants selected will vary depending upon the particular hue of the individual colorants and the resultant color desired.

Any standard pharmaceutically acceptable excipient can be used in the chewable tablet formulations which provides adequate compression such as diluents (e.g., mannitol, xylitol, maltitol, lactitol, sorbitol, lactose, sucrose, and compressible sugars such as DiPac® (dextrinized sucrose), available from Austin Products Inc. (Holmdel, N.J.), binders, disintegrants, splitting or swelling agents (e.g., polyvinyl polypyrrolidone, croscarmellose sodium (e.g., Ac-Di-Sol available from FMC BioPolymer, Philadelphia, Pa.), starches and derivatives, cellulose and derivatives, microcrystalline celluloses, such as Avicel™ PH 101 or Avicel™ CE-15 (a microcrystalline modified with guar gum), both available from FMC BioPolymer, (Philadelphia, Pa.), lubricating agents (e.g., magnesium stearate), and flow agents (e.g., colloidal silicon dioxide, such as Cab-O-Sil M5® available from Cabot Corporation, Kokomo, Ind.).

Suitable amounts of sweetener (e.g., sucralose) used in the chewable formulations, will be familiar to, and can be readily determined by, those skilled in the art. In certain embodiments, the sweetener is present in an amount from about 0.05% to about 5.0% (e.g., about 0.05%, about 0.1%, about 0.125%, about 0.15%, about 0.2%, about 0.3%, about 0.4%, about 0.5%, about 0.6%, about 0.7%, about 0.8%, about 0.9%, about 1%, about 1.25% about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75% or about 5%). Those or ordinary skill in the art will appreciate that the amount of sweetener may vary depending on the strength of the particular sweetener used and the levels approved by the regulatory authorities for use in pharmaceutical products.

Suitable cyclodextrins for use in the chewable formulations of the present invention include α, β, or γ cyclodextrins, or an alkylated or hydroxyalkylated derivatives thereof, such as heptakis (2,6-di-o-methyl)-β-cyclodextrin (DIMEB), randomly methylated β-cyclodextrin (RAMEB), and hydroxypropyl β-cyclodextrin (HPβCD). A suitable cyclodextrin is β-cyclodextrin (available from Cerestar USA, Inc., Hammond, Ind. or from Roquette America, Inc., Keokuk. IA under the trade name Kleptose™). If desired, the complex of the active substance with cyclodextrin can be prepared in advance, for example, by malaxating or granulating the azelastine and any additional active substance(s) and the cyclodextrin in the presence of water, or by preparing an aqueous solution containing the azelastine and any additional active substance(s) and the cyclodextrin in the desired molar ratio. Alternatively, the azelastine and any additional active substance(s) and the cyclodextrin can be simply mixed with other excipients and adjuvants. The molar ratio of the azelastine and any additional active substance(s) to cyclodextrin is suitably from about 1.0:1.0 to about 4.0:1.0.

A typical manufacturing process for making either a single layer or bi-layer chewable tablet generally involves blending of the desired ingredients to form a uniform distribution of the azelastine (and any other active agent(s)), excipients (e.g., colorants and flavoring agents as well as others). If desired, an inclusion complex of the azelastine and any other active agent (s) and cyclodextrin (e.g., β-cyclodextrin) may be formed prior to blending into the mixture by malaxating the azelastine and any other active agent(s) and cyclodextrin in the presence of water in a planetary mixer for about 20 minutes. The mixture is then dried in a drying oven. After drying, the complex is mixed with any color/flavoring blend. The blend is then compressed into a single layer or bi-layer tablet using standard methods well-known to those skilled in the art (e.g., Kilian T-100 tablet press or Courtoy 292/43 rotary bi-layer press). The colorants and flavoring agents may be added to both layers to form a uniform presentation of the tablet. Methods for preparation of chewable tablets and various components for use in the tablets can be found throughout the detailed description section and the Examples of U.S. Patent Publication No. 2003/0215503, the disclosure of which is incorporated by reference herein for all purposes. Additional chewable/orally dissolving tablets, and methods for their manufacture, are disclosed in U.S. Patent Publication No. 2004/0265372 and U.S. Pat. No. 6,270,790, the disclosures of each of which are incorporated by reference herein for all purposes.

Orally Disintegrating Tablets

In another embodiment, the present invention provides orally disintegrating/orodispersible tablets, such as those disclosed in U.S. Pat. No. 6,723,348, the disclosure of which is incorporated herein by reference in its entirety for all purposes. The orally disintegrating/orodispersible tablets suitably disintegrate in the buccal cavity upon contact with saliva forming an easy-to-swallow suspension. Such tablets comprise (or consist essentially of) azelastine (e.g., azelastine HCl), and optionally, one or more additional active agents (such as those described herein), in the form of coated granules, and a mixture of excipients comprising at least one disintegrating agent, a soluble diluent agent, a lubricant and optionally a swelling agent, an antistatic (fluid flow) agent, a permeabilising agent, taste-masking agents/sweeteners, flavoring agents and colors. In certain such embodiments, the disintegrating/orodispersible tablets comprise the taste-masking agent sucralose. The amounts of azelastine, other optional active agents (e.g., steroids, decongestants, leukotriene antagonists, and combinations thereof), and sweetening agents (e.g., sucralose) in the orally disintegrating tablet formulations of the present invention are readily determinable by those of ordinary skill in the art, and include those amounts and combinations described herein. For example, the orally disintegrating tablet formulations of the present invention comprise about 0.1% to about 0.15% azelastine, optionally about 0.01% to about 10% other active agent(s) (or more as required), and about 0.05% to about 0.15% sucralose.

In suitable embodiments, the particles/granules of azelastine (and any other optional active agents) have a particle size such that about 100% of the particles have an average size of less than about 50 μm. In suitable such embodiments, azelastine (and any other optional active agents) are present as coated granules.

In one embodiment, the disintegrating tablets according to the invention comprise coated granules of azelastine (and optionally, one or more additional active agents) or one of its pharmaceutically acceptable salts (such as azelastine HCl), a taste-masking agent such as sucralose, and a mixture of excipients, the ratio of the mixture of excipients to the coated granules suitably is about 0.4:1 to about 9:1, more suitable about 1.5:1 to about 5:1, or about 2 to 3 parts by weight, the mixture of excipients suitably comprising: at least one disintegrating agent, a soluble diluent agent, a lubricant, and optionally a permeabilising agent, a swelling agent, an antistatic agent, flavoring agents and one or more coloring agents.

In suitable embodiments, the disintegrating agent is selected from the group consisting of croscarmellose, available as e.g. Ac-di-sol™, crospovidone available as e.g. Kollidon CL™, sodium starch glycolate and mixtures thereof.

According to one embodiment of the invention, the soluble diluent is a polyol having less than 13 carbon atoms and being either in the form of a directly compressible product with an average particle size of about 100 to 500 μm, or in the form of a powder with an average particle size of less than about 100 μm, this polyol suitably being selected from the group consisting of mannitol, xylitol, sorbitol and maltitol. The proportion of disintegrating agent suitably is from about 3 to about 15% by weight, e.g., about 5 to about 15% by weight, and in the case of a mixture, each disintegrating agent being present between about 1 and about 10% by weight, e.g., about 5 to about 10% by weight, and the proportion of soluble diluent agent being about 30 to about 90% by weight, e.g., about 40 to about 60% by weight, based in each case on the weight of the tablet.

Suitable lubricants for use in the disintegrating tablets include, but are not limited to, magnesium stearate, stearic acid, sodium stearyl fumarate, micronised polyoxyethyleneglycol (micronised Macrogol 6000), leukine, sodium benzoate and mixtures thereof. The amount of lubricant generally is from about 0 to about 3%, e.g., from about 1 to about 2% by weight, based on the weight of the tablet. The lubricant can be dispersed within the mixture of excipients, or according to one embodiment, sprayed over the outer surface of the tablet. Thus, according to one embodiment of the disintegrating tablets of the invention, the lubricant is in powder form and is, at least in part, disposed on the surface of the tablets.

The permeabilising agent allows the creation of a hydrophilic network which facilitates the penetration of saliva and hence assists the disintegration of the tablet. Suitable permeabilising agent include, but are not limited to, silica with a high affinity for aqueous solvents, such as colloidal silica (Aerosil™), precipitated silica (Syloid™ FP 244), maltodextrins, β-cyclodextrins and mixtures thereof. The amount of permeabilising agent suitably is between about 0 and about 5%, e.g., from about 0.5 to about 2% by weight, based on the weight of the tablet.

A swelling agent can be incorporated in the mixture of excipients. Suitable swelling agents include, but are not limited to, starch, modified starch or microcrystalline cellulose.

An antistatic agent can also be incorporated as a flow aid. Suitable antistatic agents include, but are not limited to, micronised or non-micronised talc, fumed silica (Aerosil™ R972), colloidal silica (Aerosil™ 200), precipitated silica (Syloid™ FP 244), and mixtures thereof.

According to one such embodiment of the invention, the granules of azelastine or one of its pharmaceutically acceptable salts (and optionally, one or more additional active agents such as those described herein) are characterized in that the granules are coated and comprise microcrystals of azelastine or one of its pharmaceutically acceptable salts (e.g., azelastine HCl), sucralose, at least one binder, and optionally a diluent agent, an antistatic agent, and a coloring agent. Furthermore, the granulation excipients can also include disintegrating agents and/or surfactants.

Suitable binders include, but are not limited to, cellulosic polymers, such as ethylcellulose, hydroxypropylcellulose and hydroxypropylmethyl cellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, sucrose and its derivatives, guar gum, polyethylene glycol, for example an acrylic polymer, such as Eudragit™ E100, and mixtures thereof.

Optionally, in order to enhance the granulation of the azelastine (and one or more additional active agents) or one of its pharmaceutically acceptable salts, a diluent agent can be used. Suitable diluent agents include, but are not limited to, microcrystalline cellulose, sucrose, dicalcium phosphate, starches, lactose and polyols of less than 13 carbon atoms, such as mannitol, xylitol, sorbitol, maltitol, pharmaceutically acceptable amino acids, such as glycin, and their mixtures.

In one embodiment, a granule of azelastine or one of its pharmaceutically acceptable salts (as well as any additional active agents, such as those described herein), can be in the form of a core of granulated microcrystals of azelastine, coated with at least one layer comprising azelastine. Such a coated core is characterized in that the core and the layer comprise each from 70% to 95%, preferably 80% to 95% by weight of azelastine, or one of the pharmaceutically acceptable salts thereof, the balance to 100% being formed with at least one binder and optionally sucralose, and that the coated core is suitably a sphere. See e.g., French patent application FR 00 14803, the disclosure of which is incorporated by reference herein.

In one embodiment of the invention, the granules can comprise (or consist essentially of): from about 10% to about 95%, e.g., from about 50% to about 70% of azelastine or a pharmaceutically acceptable salt thereof (e.g., azelastine HCl) and optionally one or more additional active agents, such as those described herein, at most about 20% by weight of the binder, relative to the weight of azelastine, or one of the pharmaceutically acceptable salts thereof, at most about 5%, suitably about 2% by weight of the antistatic agent, relative to the weight of said granules, suitably about 0.05% to about 5% sucralose and optionally a diluent agent for the balance to 100%.

The granules can also be coated with a coating composition comprising at least one coating polymer selected from the group consisting of cellulosic polymers, acrylic polymers and their mixtures. Among the cellulosic polymers, ethylcellulose, hydroxypropylcellulose (HPC) and hydroxypropylmethylcellulose (HPMC), can be used. Among the acrylic polymers, insoluble acrylate ammonio-methacrylate copolymer (Eudragit™ RL100 or RS100 or Eudragit™ RL30D or RS30D), polyacrylate (Eudragit™ NE30D), or methacrylic copolymers (e.g., Eudragit™ L100-55 Eudragit™ L30D, Eudragit™ E100 and Eudragit™ EPO) can be used, alone, in combination, or in admixture with pH-dependent polymers. Eudragit™ E100 or a mixture of Eudragit™ EPO and Eudragit™ NE30D are suitably used. In one embodiment, the binder and the coating polymer are the same polymer.

Optionally, permeabilising agents, plasticizers, soluble agents, disintegrating agents and surfactants, can be added as coating additives. Suitable plasticizers include, but are not limited to, triacetine, triethylacetate, triethylcitrate (Eudraflex™) ethylphthalate, or mixtures thereof. The plasticizer is used in proportions of at most about 30%, preferably 10% by weight of the coating polymers. Suitable soluble agents include polyols having less than 13 carbon atoms. Surfactants may be an anionic, nonionic, cationic, zwitterionic or amphoteric surfactant. Suitable disintegrating agents include, but are not limited to, croscarmellose, available as e.g. Ac-di-sol™, crospovidone available as e.g. Kollidon CL™, and mixtures thereof.

Suitably, the coated granules according to the present invention have a particle size distribution between about 150 μm and about 500 μm, more suitably between about 150 μm and about 425 μm, such that at least 50%, more suitably at least 70% of the granules have a particle size ranging between about 150 and about 425 μm, and less than 15% of the granules have a particle size less than about 150 μm.

In one embodiment, the coated granules according to the invention comprise: from about 10% to about 95%, preferably about 40 to about 75% of granules of azelastine or one of its pharmaceutically acceptable salts, suitably azelastine HCl and optionally one or more optional additional active agents, such as those disclosed herein, sucralose from about 0.05% to about 5%, from about 5 to about 90%, suitably about 10 to about 70% and even more suitably from about 25 to about 55% of a coating polymer, such as Eudragit™ E100, the percentages being expressed by weight relative to the weight of the granules of azelastine, or one of its pharmaceutically acceptable salts, from about 0 to about 10% of a permeabilising agent, such as colloidal silica, the percentages being expressed by weight relative to the weight of the coating polymer.

Effervescent Formulations

In another embodiment, the present invention provides a solid, effervescent, rapidly dissolving dosage form of azelastine for oral administration, such as disclosed in U.S. Pat. No. 6,245,353, the disclosure of which is incorporated by reference herein in its entirety. In such an embodiment, the effervescent formulation comprise (or consist essentially of) (a) azelastine or a pharmaceutically acceptable salt thereof (e.g., azelastine HCl), and optionally one or more additional active agents such as those disclosed herein, (b) an effervescent base comprising at least one of (i) at least one of (1) an organic edible acid and (2) a salt thereof, (ii) at least one of an alkali metal and an alkaline earth metal carbonate and bicarbonate, and (c) optionally a pharmaceutically acceptable auxiliary ingredient. In certain suitable embodiments, the effervescent formulations further comprise one or more taste-masking agents, such as sucralose, and/or other taste-masking agents described herein. The amounts of azelastine, other optional active agents (e.g., steroids, decongestants, leukotriene antagonists, and combinations thereof), and sweetening agents (e.g., sucralose) in the effervescent formulations of the present invention are readily determinable by those of ordinary skill in the art, and include those amounts and combinations described herein. For example, the effervescent formulations of the present invention comprise about 0.1% to about 0.15% azelastine, optionally about 0.01% to about 10% other active agent(s) (or more if required), and about 0.05% to about 0.15% sucralose.

A solution or suspension of azelastine or salt thereof is formed by adding water to the soluble or dispersible effervescent tablets or soluble granules, with evolution of $CO_2$ gas. The resulting effervescent solution or suspension can be ingested very easily, even by patients who have difficulties swallowing. The rapidly disintegrating tablet can also be administered so that it directly disintegrates in the mouth. A rapid release of the active ingredient is of particular importance here, to ensure a rapid onset of action.

Effervescent agents capable of releasing $CO_2$, which can be used in the present invention, include alkali metal carbonates or alkali metal bicarbonates, such as sodium carbonate or sodium bicarbonate. Agents for inducing $CO_2$ release which are suitably employed are edible organic acids, or their acidic salts, which are present in solid form and which can be formulated with the azelastine active ingredient and the other auxiliary ingredients (as well as any other active agents) to provide granules or tablets, without premature evolution of $CO_2$. Edible organic acids which can be so used include for example, tartaric acid, malic acid, fumaric acid, adipic acid, succinic acid, ascorbic acid, maleic acid or citric acid. Pharmaceutically acceptable acidic salts include, for example, salts of polybasic acids which are present in solid form and in which at least one acid function is still present, such as sodium dihydrogen or disodium hydrogen phosphate or monosodium or disodium citrate.

In one embodiment, the present invention provides effervescent azelastine formulations including the formulations and compositions described herein, having an effervescent base comprising (a) a mixture of calcium carbonate with an organic edible acid; (b) a mixture of calcium carbonate, sodium carbonate, sodium bicarbonate and an organic edible acid; or (c) a mixture of sodium bicarbonates, sodium carbonate and an organic edible acid.

The soluble or dispersible effervescent azelastine tablets or the soluble granules suitably comprise (or consisting essentially of) from about 0.5 mg to about 10 mg azelastine (or salt thereof, e.g., azelastine HCl) and from about 50 mg to about 5000 mg, suitably from about 500 mg to about 3000 mg of an effervescent base, optionally, along with other active agents (such as those described herein) and excipients, including taste-masking agents such as sucralose, suitably at about 0.05% to about 5%.

The effervescent base suitably comprises from about 100 mg to about 500 mg calcium ions as, for example, calcium carbonate, and from about 20 mg to about 1500 mg citric acid and/or its salts. In another embodiment, the effervescent base comprises from about 50 mg to about 2000 mg sodium bicarbonate, from about 20 mg to about 200 mg of sodium carbonate and from about 20 mg to about 1500 mg citric acid and/or from about 20 mg to about 500 mg tartaric acid.

An additional suitable composition of the effervescent base comprises from about 50 mg to about 500 mg sodium bicarbonate, from about 20 mg to about 100 mg sodium carbonate, and from about 50 mg to about 750 mg calcium carbonate and from about 100 mg to about 1500 mg of citric acid.

The soluble/dispersible tablets can be prepared by known processes for preparing effervescent bases, such as those disclosed in U.S. Pat. No. 6,245,353, the disclosure of which is incorporated herein by reference in its entirety.

Orally Dissolving/Consumable Films

Another embodiment of the present invention is directed to a physiologically acceptable film that is particularly well-adapted to dissolve in the oral cavity of a warm-blooded animal including humans, and adhere to the mucosa of the oral cavity, to allow delivery of azelastine or a salt thereof, e.g., azelastine HCl, and optionally one or more additional active agents such as those described herein. Such physiologically acceptable films suitable for use in accordance with this aspect of the present invention are disclosed in U.S. Patent Application No. 2004/0247648, the disclosure of which is incorporated herein by reference in its entirety.

In one such embodiment of the present invention, an orally dissolving/consumable film comprises a modified starch, azelastine or a salt thereof, e.g., azelastine HCl, and optionally, one or more additional active agents such as those described herein, suitably, one or more taste-masking agents, such as sucralose, and optionally, at least one water soluble polymer. The amounts of azelastine, other optional active agents (e.g., steroids, decongestants, leukotriene antagonists, and combinations thereof), and sweetening agents (e.g., sucralose) in the orally dissolving/consumable film formulations of the present invention are readily determinable by those of ordinary skill in the art, and include those amounts and combinations described herein. For example, the orally dissolving/consumable film formulations of the present invention comprise about 0.5 mg to about 10 mg azelastine, optionally about 0.5 mg to about 10 mg other active agent(s), and about 0.05% to about 0.15% sucralose.

The consumable films of the present invention may comprise one or more of the following ingredients: water, antimicrobial agents, additional film forming agents or water soluble polymers, plasticizing agents, flavorings, sulfur precipitating agents, saliva stimulating agents, cooling agents, surfactants, stabilizing agents, emulsifying agents, thickening agents, binding agents, coloring agents, triglycerides, polyethylene oxides, propylene glycols, additional taste-masking agents or sweeteners, fragrances, preservatives and the like, as described in U.S. Pat. No. 6,596,298, the disclosure of which is incorporated by reference herein in its entirety.

In one such embodiment, the consumable films of the present invention include a modified starch. The modified starches used in accordance with the present invention can be prepared by mechanically, chemically or thermally modifying unmodified starches. For example, modified starches may be prepared by chemically treating starches to produce, for example, acid treatment starches, enzyme treatment starches, oxidized starches, cross-bonding starches, and other starch derivatives. Starches suitable for modification to produce modified starches may be obtained from natural products such as corn, potatoes, tapioca as well as genetically modified forms of the same such as high amylose and waxy corn as well as sorghum varieties.

Examples of modified starches for use in the practice of the present invention include, but are not limited to, modified corn starches, modified tapioca starches, acid and enzyme hydrolyzed corn and/or potato starches, hypochlorite-oxidized starches, acid-thinned starches, ethylated starches, cross-bonded starches, hydroxypropylated tapioca starches, hydroxypropylated corn starches, pregelatinized modified starches, and the like. Preferred modified starches are selected from pregelatinized modified corn starches and pregelatinized modified tapioca starches.

Representative examples of commercially available modified starches useful in the present invention include PURE-COTE™ modified starches such as PURE-COTE™ B793 (a pregelatinized modified corn starch) and PURE-COTE™ B795 (a pregelatinized modified corn starch), for example, available from Grain Processing Corporation, 1600 Oregon Street, Muscatine, Iowa 52761-1494 USA.

In one such embodiment of the present invention, the modified starch is present in amounts ranging from about 1% to about 90% by weight, in another embodiment about 10% to about 90% by weight, and in yet another embodiment from about 35% to about 80% by weight of the film.

Modified starch may be included in the film alone or optionally in combination with an additional water soluble film forming polymers such as those selected from, for example, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymers, carboxyvinyl polymers, amylose, high amylose starch, hydroxypropylated high amylose starch, pectin, dextrin, chitin, chitosan, levan, elsinan, collagen, gelatin, zein, gluten, soy protein isolate, whey protein isolate, casein and combinations thereof. A preferred water soluble polymer is pullulan. The amount of the water soluble polymer typically is up to about 99% by weight, suitably up to about 80% by weight, more suitably up to about 50% by weight, and most suitably up to about 40% by weight of the film.

Sustained Release Formulations

In another embodiment, the present invention provides sustained release azelastine formulations, such as the formulations and compositions described herein, which also comprise a taste-masking agent, such as sucralose. In additional embodiment, such sustained release formulations of the present invention can further comprise one or more additional active agents, such as those described herein.

Methods for preparing sustained release tablets, capsules, caplets, pellets and the like, as well as excipients for use in the sustained release formulations of the present invention, are well known in the art, and can be found, for example, throughout the detailed description section and the Examples of U.S. Pat. No. 5,271,946, the disclosure of which is incorporated herein by reference in its entirety for all purposes.

As discussed in U.S. Pat. No. 5,271,946, the sustained release formulations of the present invention can be obtained as follows:

1. Through binding of azelastine or a pharmaceutically acceptable salt thereof (e.g., azelastine HCl), and optionally one or more additional active agents such as those described herein, to physiologically acceptable cation exchangers. The following may, for example, be used as such cation exchangers: acrylic and methacrylic resins with exchangeable protons, acid groups: COO⁻ e.g. Amberlite™ IRP-64 Polystyrene resins with exchangeable Na⁺, acid groups: $SO_3^-$, e.g. Amberlite™ IRP-69.

2. Coating of active ingredient particles, granulate or pellet grains or azelastine-containing tablets with coatings of the following substances, or mixtures of the following substances: hydroxypropylmethyl cellulose phthalate- or acetate succinate; cellulose-, starch-, as well as polyvinyl acetate phthalate; carboxymethyl cellulose; hypromellose; carbopol starch acetate; cellulose acetate; polyvinyl acetate; methylcellulose phthalate, methylcellulose succinate, methyl cellulose phthalate succinate as well as methyl cellulose phthalic acid half ester; zein; ethyl cellulose as well as ethyl cellulose succinate; shellac; gluten; ethylcarboxyethyl cellulose; ethacrylate-maleic acid anhydride copolymer; maleic acid anhydride vinyl methyl ether copolymer; sterol maleic acid copolymerizate; 2-ethylhexylacrylate maleic acid anhydride; crotonic acid vinyl acetate copolymer; glutaminic acid/glutaminic acid ester copolymer; carboxymethylethyl cellulose glycerin mono-octanoate; cellulose acetate succinate; polyarginin; fats, oils, waxes, fatty alcohols; anionic polymerizates of methacrylic acid and methacrylic acid esters (Eudragit™ L, Eudragit™ S); copolymerizates of acrylic and methacrylic acid esters with a low ammonium group (Eudragit™ RS) content, as well as copolymers of acrylic and methacrylic acid esters and trimethyl ammonium methacrylate (Eudragit™ RL), copolymerizates of acrylic acid ethyl- and methacrylic acid methyl esters 70:30 (Eudragit™ NE 30 D), copolymerizates of acrylic acid, methacrylic acid as well as their esters (ratio of the free carboxyl groups to the ester groups for example 1:1) (Eudragit™ L 30 D).

Such sustained release formulations may also contain conventional softeners (e.g. dibutyl sebacate, citric and tartaric acid esters, glycerin and glycerin esters, phthalic acid esters and similar substances). It also is possible to add water-soluble substances such as polyethylene glycols, polyvinylpyrrolidone, copolymerizates of polyvinylpyrrolidone and polyvinyl acetate, hydroxypropyl cellulose, hydroxypropylmethyl cellulose. The addition of solids such as talcum and/or magnesium stearate to the coating is also possible.

Organic acids (such as for example citric acid, tartaric acid, maleic, fumaric, ascorbic acid) may also be incorporated into the pellet grains, granulate grains or tablets.

3. Coating of pressed disks, tablets, granulates containing the azelastine or salt thereof, and optionally one or more additional active agents such as those described herein, and one or more osmotically active substances, (e.g. mannitol, sorbitol and the like) with a semi-permeable membrane, e.g. of 70 to 90 weight % of cellulose acetate and hydroxypropylmethyl cellulose or hypromellose (30 to 10 weight %).

Other osmotically active substances that can be used include organic and inorganic compounds or soluble substances which generate an osmotic pressure gradient as compared to the outer liquid via the semi-permeable wall. Osmotically active agents or osmotically active compounds include magnesium sulfate, magnesium chloride, sodium chloride, lithium chloride, potassium sulfate, potassium hydrogen phosphate, urea, saccharose and the like. Other osmotically active agents are disclosed in U.S. Pat. Nos. 3,854,770, 4,077,407 and 4,235,236, the disclosures of each of which are incorporated herein by reference in their entireties.

Semi-permeable materials which can be used as polymers for osmosis and reverse osmosis are, for example: cellulose acylate, cellulose diacylate, cellulose triacylate, cellulose acetate, cellulose diacetate, cellulose triacetate, β-glucan acetate, acetaldehyde dimethyl acetate, cellulose acetate ethyl carbamate, polyamide, polyurethane, sulphonated polystyrene, cellulose acetate phthalate, cellulose acetate methyl carbamate, cellulose acetate succinate, cellulose acetate dimethylamino acetate, cellulose acetate chloracetate, cellulose dipalmitate, cellulose dioctanoate, cellulose dicaprylate, cellulose dipentanate, cellulose acetate valerate, cellulose acetate-p-toluene sulphonate, cellulose acetate butyrate, ethyl cellulose, selectively permeable polymers which are formed by joint precipitation of a polycation and a polyanion as disclosed in U.S. Pat. Nos. 3,173,876, 3,276,586, 3,541,005, 3,541,006 and 3,546,142, the disclosures of which are incorporated by reference herein in their entireties. Coatings of this type in semi-permeable membranes may for example also be effected according to U.S. Pat. Nos. 4,455,143 and 4,449,983, the disclosures of which are incorporated by reference herein.

The proportion of osmotically active substance can be from about 10 to about 800 parts by weight, suitably about 20 to about 600, and more suitably about 50 to about 400 parts by weight, based on 1 part by weight of azelastine. The amount of coating substances applied is such that the semi-permeable membrane is about 50 to about 500 suitably about 100 to about 300 μm thick.

4. Embedding of or binding azelastine (or salt thereof) and/or any other optional additional active agent(s) to the following substances or mixtures of these substances:

Digestible fats, such as triglycerides of saturated fatty acids, $C_8H_{16}O_2$ to $C_{18}H_{36}O_2$, and mixtures thereof, peanut oil and hydrated peanut oil, castor oil and hydrated castor oil, olive oil, sesame oil, cottonseed oil and hydrogenated cottonseed oil, corn oil, wheat germ oil, sunflower seed oil, cod liver oil, mixtures of mono-, di- and triesters of palmitic and stearic acid with glycerine, glycerine trioleate, diglycol stearate, stearic acid.

Indigestible fats or fat-like substances, for example esters of aliphatic saturated or unsaturated fatty acids (2 to 22 carbon atoms, in particular 10 to 18 carbon atoms) with monovalent aliphatic alcohols (1 to 20 carbon atoms), carnauba wax, beeswax, fatty alcohols (straight chain or branched) of chain length $C_8H_{17}OH$ to $C_{30}H_{61}OH$, in particular $C_{12}H_{25}OH$ to $C_{24}H_{49}OH$.

Polymers such as polyvinyl alcohol, polyvinyl chloride, polyacrylic acid (Carbopol™); anionic polymerizates of methacrylic acid and methacrylic acid esters (Eudragit™ L, Eudragit™ S), acrylic and methacrylic acid ester copolymerizates with trimethyl ammonium methacrylate (Eudragit™ RL, Eudragit™ RS).

Copolymerizates of ethyl acrylates and methyl methacrylates (Eudragit™ NE 30 D), as well as of acrylic acid, methacrylic acid as well as esters thereof (ratio of free carboxyl groups to ester groups 1:1) (Eudragit™ L 30 D), polyethylene, polyglycolic acid, polyhydroxybutyric acid, polylactic acid, copolymers of lactic acid and glycolic acid (manufacturer: Boehringer Ingelheim), copolymers of lactic acid and ethylene oxide, copolymers of glycolic acid and ethylene oxide, copolymers of lactic acid and hydroxybutyric acid, hydroxypropylmethyl cellulose-phthalate or -acetate succinate; cellulose acetate phthalate, starch acetate phthalate as well as polyvinyl acetate phthalate; carboxymethyl cellulose; methylcellulose phthalate, -succinate, -phthalate succinate, methyl cellulose phthalic acid half ester; zein; ethyl cellulose; shellac, gluten; ethylcarboxyethyl cellulose; ethacrylate maleic acid anhydride copolymer; maleic acid anhydride vinyl methyl ether copolymer; styrene maleic acid copolymerizate; 2-ethylhexyl acrylate maleic acid anhydride; crotonic acid vinyl acetate copolymer; glutaminic acid/glutaminic acid ester copolymer; carboxymethyl cellulose glycerine mono-octanoate; cellulose acetate succinate; polyarginine; cross-linked alginate; cross-linked gelatin.

Swelling agents such as methyl cellulose, hydroxypropyl cellulose, hydroxypropyl methyl cellulose (Pharmacoat, Methocel E (propylene glycol ether of methyl cellulose)), alginic acid and their salts ($Na^-$, $Ca^-$ salt, also mixtures of sodium alginate and calcium salts such as $CaHPO_4$), starch, carboxymethyl starch, carboxymethyl cellulose and their salts (e.g. $Na^-$ salts), galacto mannan, gum arabic, karaya rubber, ghatti gum, agar-agar, carrageen, xanthan rubber, guar rubber and its derivatives, carob bean flour, propylene glycol alginate, pectin, tragacanth.

The amounts of azelastine or salt thereof, and optionally one or more additional active agents such as those described herein, in the formulations of the invention are about 0.1 mg to about 50 mg, suitably about 0.2 mg to about 30 mg, and more suitably about 0.5 mg to about 20 mg of azelastine.

Suitable exemplary sustained release components are:

a) Cation exchangers: Sodium poly(styrene, divinylbenzene)sulphonate (e.g. Amberlite™ IRP 69). Suitably 3 to 10 parts of Amberlite™ IRP 69 are for example used per 1 part of azelastine (base).

b) Coating substances: Hydroxypropylmethyl cellulose phthalate, suitably at 1.5 to 3 parts of hydroxypropyl methyl cellulose phthalate 55 are used per 1 part of azelastine. Ethyl cellulose, suitably 0.1 to 1 part of ethyl cellulose are used per 1 part of azelastine. Eudragit resins, for example Eudragit™ RS 0.01 to 0.1 part of Eudragit™ RS per 1 part of azelastine.

c) Semi-permeable layers with osmotically acting active substance containing core and outlet openings: Coating with 100 to 300 μm thick layer of 82% cellulose acetate and 18% hydroxypropyl methyl cellulose.

d) Embedding substances: Hydrocolloids e.g. hydroxypropyl methyl cellulose: 2 to 10 parts of hydrocolloid per 1 part of azelastine. Eudragit™ RS: 10 to 15 parts of Eudragit™ RS per 1 part of azelastine. Glycerineditripalmito stearate (e.g. Precirol Ato 5) 1 to 10 parts of Precirol Ato 5 per 1 part of azelastine.

The requisite release of azelastine (and optionally, any additional active agents) of 0.05 to 5 mg per hour suitably occurs within the desired range through the parameters described herein. Should it be desired to achieve a specific release rate within this range it is possible, for example, to proceed as follows:

1. The preparation of the coating or embedding of the active substance in the described manner.

2. Testing of the release of active substance from the dosage form using 0.1 N HCl (2 hours) and phosphate buffer pH 6.8 (subsequently) as release medium.

3. a) Should too much substance be released: Increase of the proportion of the sustained release component and/or reduction of the proportion of water-soluble auxiliary substances. Reduction of the proportion of osmotically active substance.

b) Should too little substance be released: Reduction of the proportion of the sustained release component and/or increase of the proportion of water soluble auxiliary substances. Increase of the proportion of osmotically active substance.

In one embodiment, a release rate of about 0.05 mg of azelastine per hour can be achieved.

Unit Dosage Forms

In additional embodiments, the present invention provides compositions of matter comprising a unit dosage (e.g., single unit dosage) of a pharmaceutical composition and a unit dosage container. In suitable such embodiments, the pharmaceutical composition comprises one or more antihistamines, including $H_1$, $H_2$, $H_3$ and $H_4$ antihistamines as described herein, for example, azelastine and salts thereof, such as azelastine HCl. Suitably, the unit dosage (unit dose, unit dosage, single unit dose and single unit dosage are used interchangeably herein) container will comprise a low volume, e.g., the volume of the unit dosage container will suitably be less than about 5 ml, suitably less than about 4 ml, less than about 3 ml, less than about 2 ml, less than about 1 ml, less than about 0.9 ml, less than about 0.8 ml, less than about 0.7 ml, less than about 0.6 ml, less than about 0.5 ml, less than about 0.4 ml, less than about 0.3 ml, less than about 0.2 ml or less than about 0.1 ml. For example, the unit dosage container can comprise a volume of about 0.05 ml to about 1 ml, about 0.1 ml to about 1 ml, about 0.1 ml to about 0.9 ml, about 0.1 ml to about 0.8 ml, about 0.1 ml to about 0.7 ml, about 0.1 ml to about 0.6 ml, about 0.1 ml to about 0.5 ml, about 0.1 ml to about 0.4 ml, about 0.1 ml to about 0.4 ml, about 0.1 ml to about 0.3 ml, or about 0.1 ml to about 0.2 ml. Exemplary materials that can be used to prepare unit dose container are described herein or otherwise known in the art, and include high density polyethylene. In further embodiments, the unit dosage pharmaceutical composition can further comprise one or more additional active agents, one or more diluents, one or more carriers, one or more taste-masking, etc., as described herein.

Figure 7:
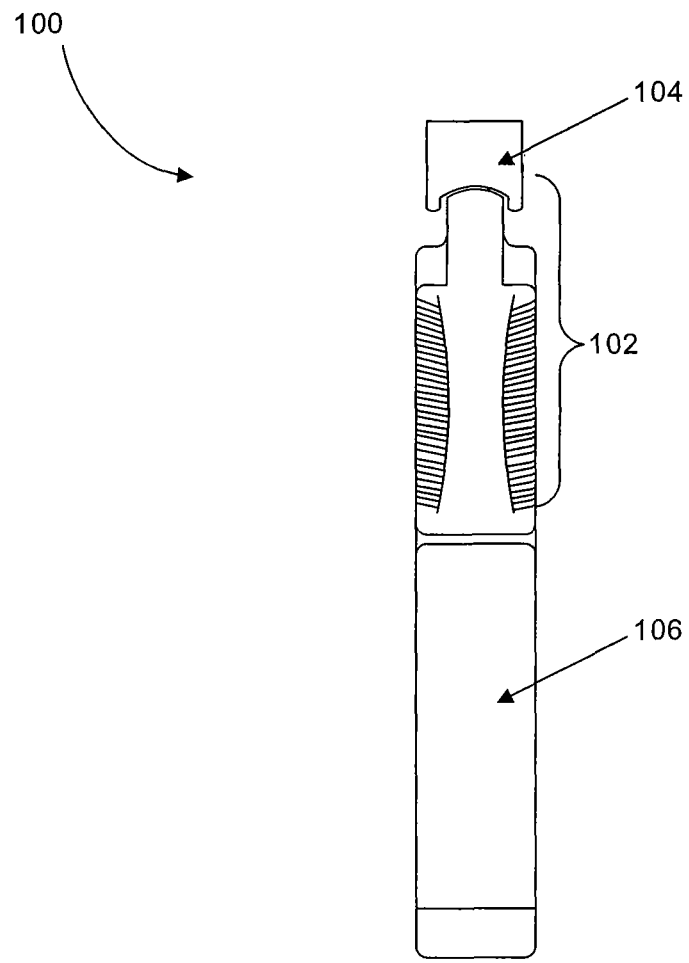
FIG. 7 shows a schematic of an exemplary unit dosage container used in accordance with the invention.
Figure 8:
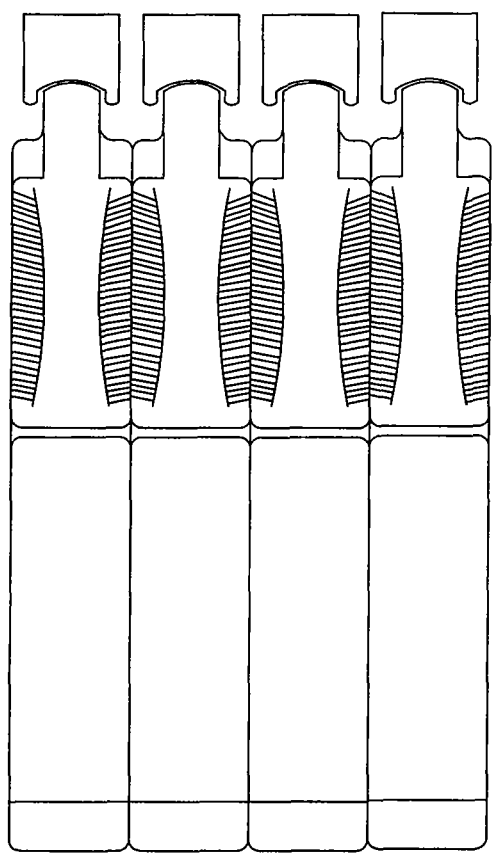
FIG. 8 shows a plurality of unit dosage containers used in accordance with the invention.
Figure 9:
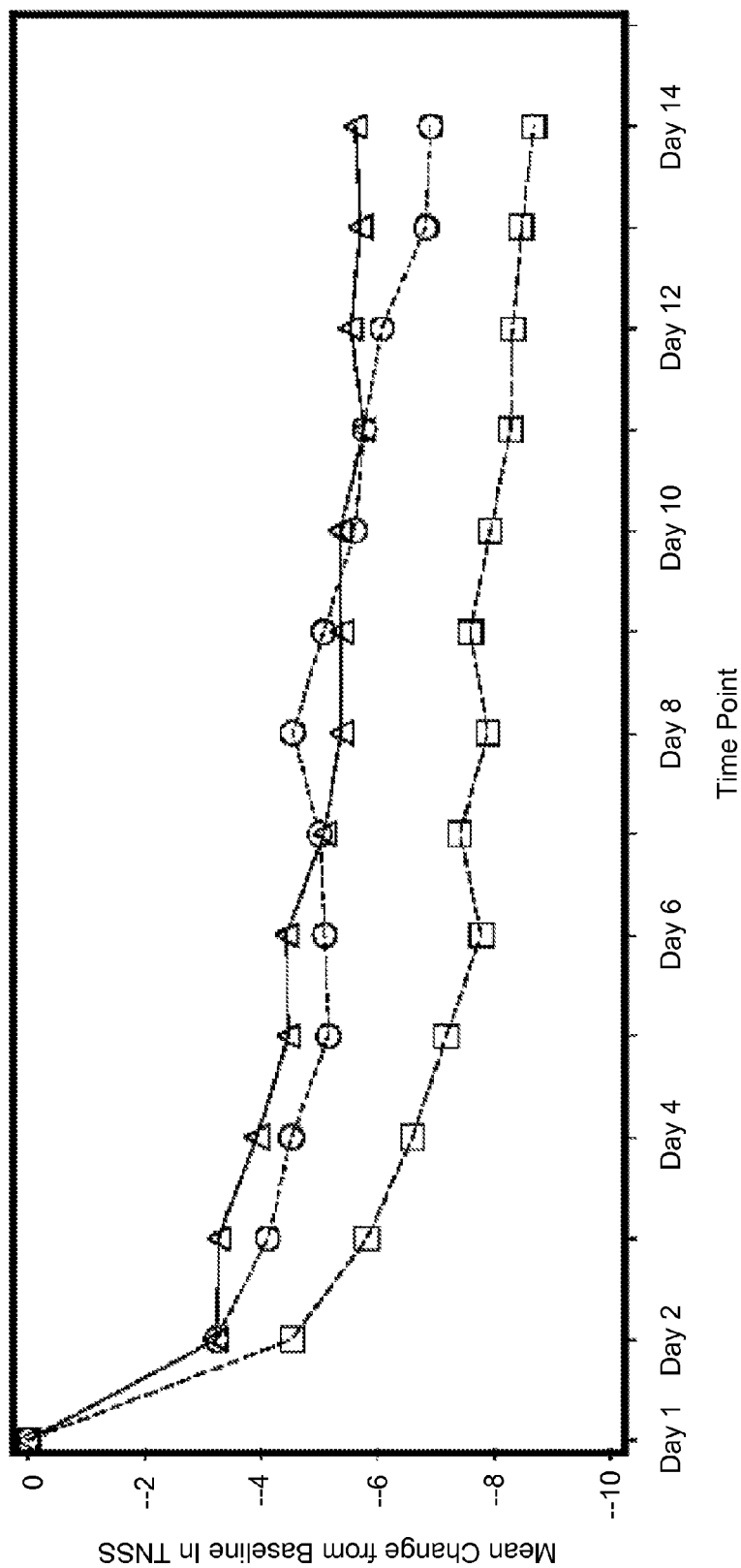
FIG. 9 is a line plot of the mean change from baseline in total nasal symptom score (TNSS) (a.m. and p.m. combined) over a 14 day period, in the intent-to-treat population. (▲–▲–▲) Azelastine; (●–●–●) Fluticasone; and (⊟–⊟–⊟) Azelastine + Fluticasone.
Figure 10:
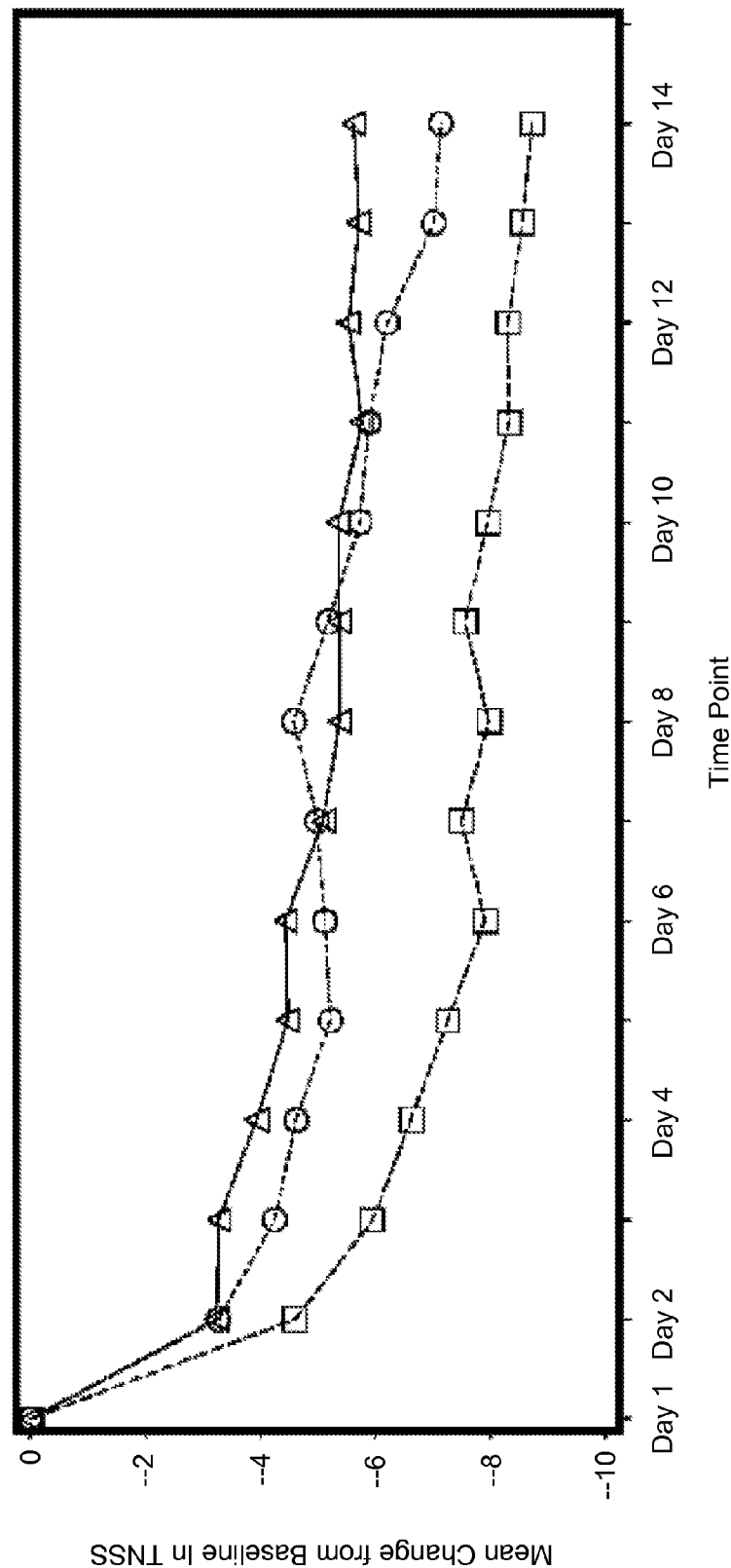
FIG. 10 is a line plot of the mean change from baseline in total nasal symptom score (TNSS) (a.m. and p.m. combined) over a 14 day period, in the per-protocol population. (▲–▲–▲) Azelastine; (●–●–●) Fluticasone; and (⊟–⊟–⊟) Azelastine + Fluticasone.

The pharmaceutical compositions described herein may be stored, and/or delivered for administration to a patient, for example in a unit dosage container. For example, the unit dosage container may have a dimensional configuration similar to those disclosed in U.S. Pat. Nos. 7,185,790, 6,666,359, 6,619,516 and 4,469,254. In particular embodiments, the unit dosage container may have a configuration of unit dosage container 100, as shown in FIGS. 7-8. Unit dosage container 100 may have a squeezable chamber 102, a closure mechanism 104, and an extension 106. The portion of the squeezable chamber 102 that is compressable is indicated by hatch marks.

For ease of description, the container of the invention will be described in a normal (upright) operating position and terms such as upper, lower, horizontal, etc., will be used with reference to this position. It will be understood, however, that the container may be manufactured, stored, transported, used, and sold in an orientation other than the position described herein.

In certain embodiments, the squeezable chamber may be bulbous or flat or substantially flat in shape, having a first surface and a second surface, which may hold a single unit dosage of any of the pharmaceutical compositions described herein. In certain preferred embodiments, the squeezable chamber is flat in shape, as such a geometry renders the squeezable chamber less structurally strong than a squeezable chamber of bulbous shape; this reduced structural strength and flat shape provides excellent squeezability to the chamber while at the same time providing an integral unit dose vial. The squeezable chamber may have a main body with a neck at one end leading to an opening through which the single unit dosage may exit the unit dosage container when squeezable chamber is squeezed. The squeezable chamber has a first surface and a second surface that may have ridges extending therefrom to facilitate gripping the squeezable chamber. In certain embodiments, where the first and second surfaces and are long flat smooth surfaces which impart squeezability but which at the same time could be slippery between the fingers, the integral ridges provide good anti-slip features and control points for the person delivering the medication. The neck of the sqeezable chamber allows for the user to more accurately position the tip of the dosage form, for example, near or into the eyelid area or ear canal.

The squeezable chamber may be sized to have an internal volume of less than or equal to about 1.0 ml, suitably about 0.5 ml to about 1.0 ml. The squeezable chamber may have a length of about 20 mm to about 40 mm, for example, about 32.9 mm; a width of about 5 mm to about 20 mm, suitably about 12.2 mm; and a thickness at its thickest point of about 3 mm to about 10 mm, suitably, about 6.6 mm. The opening may have a diameter of about 1 mm to about 5 mm, for example, about 1.7 mm. These measurements are merely exemplary and may be varied as needed by the ordinarily skilled artisan.

In suitable such embodiments of the invention, the single unit dosage of a pharmaceutical composition held in the squeezable chamber may have a volume in a range of from about 0.1 ml to about 0.6 ml. In more suitable embodiments, the volume of the single unit dosage may be about 0.1 ml, about 0.15 ml, about 0.2 ml, about 0.21 ml, about 0.22 ml, about 0.23 ml, about 0.24 ml, about 0.25 ml, about 0.3 ml, about 0.35 ml, about 0.4 ml, about 0.45 ml, about 0.5 ml, about 0.55 ml or about 0.6 ml. In certain such preferred embodiments, the volume of the single unit dosage enables the patient to dose all the affected eyes, ears, nostrils or other parts of the body with one vial or dosage unit, and then discard the unit dosage container; additional volumes suitable for such a purpose will be readily apparent to those of ordinary skill in the art. In suitable embodiments, the volume of pharmaceutical composition that is provided in a droplet form to the patient via the unit dose forms of the present invention is one the order of about 0.01 to about 0.05 ml, suitably about 0.02, about 0.03, about 0.035, about 0.04 or about 0.05 ml.

The closure mechanism may be removably attached to the opening of the squeezable chamber. The closure mechanism may be a twist-off or pull-off top. In one such embodiment, the closure mechanism is molded as part of the unit dosage container and when the closure mechanism is twisted or pulled by the end-user, it breaks away from the unit dosage container revealing the opening to the squeezable chamber. In this embodiment, the closure mechanism is not able to reseal the opening after use.

The extension may be attached to the squeezable chamber on a side opposite opening. The extension may be a solid flat panel that is sealed from an interior of squeezable chamber. The extension may have a first surface and a second surface, wherein identification can be located on one or both of first surface and second surface. The identification may include, but is not limited to, the name of the pharmaceutical composition held in squeezable chamber, the ingredients of the pharmaceutical composition, the expiration date of the pharmaceutical composition, the name and address of the manufacturer of the pharmaceutical composition, a tracking or lot number, or combinations thereof. The identification may, for example, be written, engraved (e.g., using heat, laser or mechanical engraving), tattooed or otherwise placed on first and/or second surface, or may, for example, be located on a portion of extension which, in certain embodiments, may be referred to in the art as an "engraving section." In further embodiments, the identification may be provided on a label or other item which can then be attached (e.g., via adhesive) to extension on the first and/or second surface.

In one embodiment, the extension may have a length of about 30 mm to about 50 mm, for example, about 42.0 mm; a width of about 5 mm to about 20 mm, for example, about 12.9 mm; and a thickness of about 1 mm to about 10 mm, for example, about 2.5 mm. In one embodiment, the unit dosage container may have a length of about 50 mm to about 100 mm, for example, about 85.5 mm when the closure mechanism is attached and may have a length of about 50 mm to about 100 mm, for example, about 74.9 mm, when the closure mechanism is removed. These measurements are merely exemplary and may be varied as needed. Suitable alternative embodiments employing other container measurements will be readily apparent to one of ordinary skill in the relevant arts in view of the present disclosure, drawings and claims.

The material for the unit dosage container may be a moldable polymer, such as a plastic, that the pharmaceutical composition will not leach into upon storage therein. Polymers suitable for use according to this aspect of the invention include, but are not limited to, polyethylene, polypropylene (PP), polystyrene (PS), nylon (Ny), polyvinyl chloride (PVC), polyethylene terephthalate (PET), polycarbonate (PC), polyoxymethylene (POM), polysulfon (PSF), polyethersulfon (PES), polyacrylate (PAR), and polyamid (PA). In certain embodiments, polymers include polyethylene, particularly medium-density polyethylene (MDPE) (or branched polyethylene) or high density polyethylene (HDPE) (or linear, polyethylene). A particularly preferred polymer for use with azelastine-containing pharmaceutical formulations is HDPE. In general, high-density polyethylene has a specific gravity in the range of about 0.94 to about 0.965; medium-density polyethylene has a specific gravity in the range of about 0.925 to about 0.94; and low-density polyethylene has a specific gravity in the range of about 0.91 to about 0.925.

As the unit dosage container holds a single unit dosage, it is important that the pharmaceutical composition not degrade, dissipate or dissolve by leaching into the material of the unit dosage container to an unacceptable extent, as such would minimize the effectiveness of the pharmaceutical composition. It has unexpectedly been found that a low-volume (e.g., less than about 1 ml), squeezable container can be made according to the present invention which overcomes the problems of pharmaceutical compositions leaching into unit dose containers. Specifically, the problems of antihistamines, more specifically azelastine and azelastine HCl, leaching into lower-density polyethylene unit dose containers (e.g., low density and medium density PE) has been overcome by preparing a low-volume unit dose container of HDPE. In contrast to lower-density PE unit dose containers, HDPE unit dose containers reduce, substantially reduce, or eliminate leaching of azelastine into the material of the container. In further embodiments, a coating or layer (for example a coating of HDPE or other suitably material) can be disposed on the inside of the unit dose container so as to minimize leaching of the pharmaceutical composition into the material of the container.

The container of this aspect of the present invention may be fabricated and assembled with conventional molding apparatus that will provide a container having the structural and functional specifications described herein.

In certain such embodiments, the components of unit dosage container may be molded. For example, the squeezable chamber and extension may be molded in two halves through compression or injection molding and then fused or otherwise joined together around the periphery.

In such embodiments, the unit dosage containers prepared and used in accordance with the present invention can be fabricated by any suitable blow molding technique. The containers preferably are fabricated in a two stage operation by blow molding preforms, which are themselves injection or compression molded. The containers alternatively can be formed in a single stage injection stretch blow molding operation, or in an injection extrusion blow molding operation in which the finish is injection molded and a tube is extruded from the finish and blow molded to form the container body. In molding operations of these types, the container finish typically is injection or compression molded to its final configuration and is of relatively rigid construction, while the container body is blow molded after the finish is formed. The container also can be formed in an extrusion blow molding operation. Other container molding operations familiar to those of ordinary skill in the art can also be employed.

Alternatively, the squeezable chamber and extension may be molded as a single unit wherein the squeezable chamber is formed utilizing a modified blow molding process in which the container is formed by blow molding, the pharmaceutical formulation is filled or introduced into the newly formed container, and the container is sealed and ejected from the manufacturing device such a manufacturing process is frequently referred to in the art as a "blow-fill-seal" process, and will be familiar to those of ordinary skill in the art.

Whether the container is molded as separate halves that are then sealed, or as a single unit, the closure mechanism may be separately molded and then fused to neck to seal opening of squeezable chamber.

The squeezable chamber may be molded such that the wall thickness of the squeezable chamber enables squeezable chamber to be easily squeezed to dispense the pharmaceutical composition out opening. The squeezable chamber may be molded so that application of a compressive force to the squeezable chamber may substantially flatten the squeezable chamber thus facilitating the complete discharge of the pharmaceutical composition. The pharmaceutical composition can be dispensed as a drop (or drops), a stream, a spray, a mist or other suitable method of dispensing. The wall thickness of the squeezable chamber may be from about 0.2 mm to about 7 mm, suitably about 0.4 mm to about 0.5 mm. Suitably, when HDPE is utilized as the material for squeezable chamber, the polymer will have a compressive strength in the range of about 2.7 to about $3.6*10^{-3}$ psi, a flexural yield strength of about $1.0*10^{-3}$ psi, and a flexural modulus of about 1.0 to about $2.6*10^{-5}$ psi.

A plurality of unit dosage containers may be molded together as an assembly. Each of the unit dosage containers are removably attached to assembly and may be broken away from assembly by pulling, twisting or otherwise breaking assembly. Each of the unit dosage containers in assembly may also hold the same pharmaceutical composition or a different pharmaceutical composition from the other unit dosage containers in assembly. For example, the unit dosage containers may hold pharmaceutical composition A and unit dosage containers may hold pharmaceutical composition B. Assembly may be packaged in a container along with instructions for administering the single unit dosages.

In certain embodiments, the unit dose container is filled with liquid product after fabrication and a dispensing closure is applied to the unit dosage container. To dispense the pharmaceutical composition from the squeezable chamber the sides of chamber are gripped by a user, and the squeezable chamber is deformed or squeezed radially inwardly to increase the pressure within the container and thereby dispense product through the dispensing closure. The squeezable chamber in accordance with the present invention is specifically contoured for maximizing the dispensing of liquid from the container. When the squeezable chamber is grasped by a user, the fingers of the user's hand naturally nestle along the squeezable chamber.

The unit dosage container of the present invention is adapted for both cold-fill and hot-fill applications. In hot-fill applications, in which the container is filled with hot liquid product and then capped, an internal vacuum develops as the product cools. The squeezable chamber may distort under the vacuum pressure within the container. The squeezable chamber may assume an oval geometry, or a triangular geometry with the corners of the triangle being randomly located at longitudinally extending channels. However, the fingers of a user will still naturally nestle along the squeezable chamber, so that the container can be readily squeezed to dispense product. Thus, the ergonomic wrap-around grip design of the squeezable chamber is maintained in both hot-fill and cold-fill applications.

The unit dosage container design, in addition to functional convenience, incorporates several other desirable features. The body itself is designed to empty readily without significant hold up. The unit dosage container is produced which retains the pharmaceutical composition until squeezed and can be held in a horizontal or inverted position without dripping. That is, the opening, after removal of the break off tab, is specifically dimensioned in its diameter to allow retention of aqueous-based products until squeezed.

The surfaces of the container body are contoured to allow the contents to be readily expelled without "hold-up" which contrasts to a prior art stand up squeeze bottle in which the contents will typically flow out by gravity should the bottle be inadvertently knocked over or inverted.

After removing the break off tab, the liquid is dispensed from the container preferably in an upright position by pressing or squeezing the main chamber, for example, between thumb and forefinger, thus compressing the air trapped in the main chamber of the container and causing the liquid in the measuring chamber to be sprayed out from the container in a fine stream. All of the contents may be discharged at one time or only a portion may be discharged by controlling the compressive force applied.

After removing the break off tab, the unit dosage container used in accordance with this aspect of the present invention permits the administration of a precisely measured volume of pharmaceutical composition in the unit dosage container by dispensing only the pharmaceutical composition contained in the squeezable chamber. An opening is thus provided through which can be administered precisely measured successive amounts of pharmaceutical composition in a drop format or in a thin, finely divided stream, with the unit dosage container and the head of the patient both in a normal upright position. Another advantage is that, in the case of simultaneous treatment of the nose and eyes, a sterile solution can always be used for the eyes by opening a new container each time. This is not possible with conventional pipette bottles presently in use since they are not adapted for single use. For application to the eyes, ears and other parts of the body, it is also possible to administer the pharmaceutical composition contents of the chamber in the form of drops instead of measured dosages by pointing the measuring chamber downwardly instead of upwardly when administering the contents. Besides the advantage of greater hygiene, in the case of the treatment of a cold, the container according to the present invention is also more pleasant to use than the manipulation with the known containers or dropping pipettes.

In still further embodiments, the unit dosage forms disclosed herein can be used in combination with various nebulizers or other particle dispersion devices. For example, drug delivery devices such as disclosed in U.S. Pat. No. 7,231,919, can be used in combination with the unit dosage forms. In such embodiments, the pharmaceutical composition (e.g., an antihistamine such as azelastine hydrochloride) contained in the unit dosage forms of the present invention can be placed into the particle dispersion devices, and then nebulized for delivery to the patient's nasal passage.

The compositions of the present invention that are provided in solution form may optionally contain a preservative, and/or may be aseptically manufactured and/or sterilized for example by filtration through a bacterial-retaining filter. In certain aspects of the invention, the formulations are aseptically manufactured and/or sterilized and are then sealed within unit dose containers using the "blow-fill-seal" approach described elsewhere herein.

Liquid Dosage Forms Free of Preservatives

While preservatives are useful in limiting concerns related to chemical degradation or bacterial growth in the liquid formulations of the present invention, the presence of these preservatives can themselves cause stinging or irritation, especially when administered to the oral or nasal mucosa, or to ocular tissue or the conjunctival sac. Therefore, in order to reduce this irritation, in one embodiment, the liquid dosage forms disclosed herein, e.g., liquid dosage forms for nasal, ocular or oral administration, such as pharmaceutically acceptable emulsions, solutions, suspensions, syrups and elixirs, can be prepared free, or substantially free, of preservatives. As used herein the phrase "free, or substantially free, of preservatives" means that the liquid formulations contain less than about 0.0001% (weight/volume) of a preservative, more suitably less than about 0.00001% (weight/volume) of a preservative, and most suitably, no preservative.

In order to maintain the integrity of the liquid formulations, and specifically, to protect them from bacterial contamination transferred from the patient or external environment, the delivery systems useful for applying the various liquid formulations can be appropriately engineered to limit bacteria from entering the solutions. For example, in order to limit the introduction of bacteria or particulates that may come from the user of a nasal spray (e.g. from the nasal passage), the spray bottle can be fitted with a filter or other device to limit or prevent the introduction of such bacteria into the bottle and/or formulation. This filter can form part of the spray or dropper nozzle, or can be located within the structure of the spray or dropper bottle itself. The filter allows the various liquid formulations of the present invention to pass through the filter to the patient, but limits bacteria or particulates from the patient or the external environment from entering the nozzle and bottle. Suitable filters are known in the art and are commercially available from well-known sources, and include microporous filtration membranes made from polymers, such as, but not limited to, poly(ethersulfone), poly (vinylidene fluoride), mixed cellulose esters, and poly(tetrafluoroethylene). In general, the pore size of such membranes are on the order of less than about 0.5 microns, more suitably less than about 0.3 microns and most suitably less than or equal to about 0.22 microns. Use of such membrane filters eliminate the need for preservatives in the various liquid formulations of the present invention when utilized in nasal spray or ocular drop delivery systems.

The preservative free liquid formulations and compositions of the present invention can also be provided in single unit-dose containers. Such containers are acceptable to deliver the therapeutic dose of azelastine (or salt or ester thereof, including azelastine hydrochloride) and optionally one or more additional active agents (such as those described herein) to the eyes, nose or mouth. In certain such embodiments of the invention, the compositions can be effectively contained in a package comprising a high density polyethylene (HDPE) container produced using a blow-fill-seal manufacturing technique with a volume capacity of about 1 mL, suitably less than about 0.5 ml, as described in detail herein. As the unit-dose formulations of the present invention are suitably opened, used (i.e., the pharmaceutical composition is administered/delivered to the eye, nose, ear, mouth, skin, etc.), and then discarded, preservatives are an optional component of such formulations. The ability to provide sealed unit dose formulations limits or reduces the ability of bacteria to grow in the formulations. In addition, the use of single unit-dose containers eliminates the concern of contamination for the user (or other outside sources), as once the unit-dose container is opened and a single dose of the present formulations or compositions is delivered, the container is discarded.

The use of single unit-dose containers eliminates the concern of contamination for the user (or other outside sources), as once the unit-dose container is opened and a single dose of the present formulations or compositions is delivered, the container is discarded.

The preservative-free formulations of the present invention can also be used with multi-dose containers, such as, high density polyethylene bottles with a volume capacity of about 10 mL fitted with a spray pump specifically designed for use with preservative free formulations.

Formulations For Pulmonary Delivery

In further embodiments, the present invention provides formulations and compositions for pulmonary delivery of azelastine or a salt thereof, and optionally, one or more additional active agents, such as those described herein. For example, inhalable preparations comprising azelastine or a salt thereof (e.g., azelastine HCl), and optionally, one or more additional active agents such as those described herein, can be produced.

Inhalable preparations include inhalable powders, propellant-containing metering aerosols or propellant-free inhalable solutions. Inhalable powders according to the invention containing azelastine or a salt thereof, and optionally one or more additional active ingredients including those described herein, may comprise the active ingredients on their own, or a mixture of the active ingredients with physiologically acceptable excipients. In certain such embodiments, the inhalable formulas comprise the compositions of the present invention in an inhalable form. Within the scope of the present invention, the term propellant-free inhalable solutions also includes concentrates or sterile inhalable solutions ready for use. The preparations according to the invention may comprise azelastine or a salt thereof and optionally one or more additional active ingredients including those described herein, in one formulation, or in two or more separate formulations.

Physiologically acceptable excipients that may be used to prepare the inhalable powders according to the present invention include, but are not limited to, monosaccharides (e.g., glucose or arabinose), disaccharides (e.g., lactose, saccharose, maltose), oligo- and polysaccharides (e.g., dextran), polyalcohols (e.g., sorbitol, mannitol, xylitol), salts (e.g., sodium chloride, calcium carbonate) or mixtures of these excipients with one another. Suitably, mono- or disaccharides are used, for example, lactose or glucose in the form of their hydrates. Lactose and lactose monohydrate represent exemplary excipients. Excipients for use in the inhalable preparations can have an average particle size of up to about 250 μm, suitably between about 10 μm and about 150 μm, most suitably between about 15 μm and about 80 μm. In certain such embodiments, finer excipient fractions can be added with an average particle size of about 1 μm to about 9 μm. These finer excipients are also selected from the group of possible excipients disclosed throughout. Finally, in order to prepare the inhalable powders according to the present invention, micronised active ingredients (e.g., azelastine and optionally one or more additional agents described throughout), suitably with an average particle size of about 0.5 µm to about 10 µm, more suitably from about 1 µm to about 5 µm, are added to the excipient mixture. Processes for producing the inhalable powders according to the present invention by grinding and micronizing and by finally mixing the ingredients together are routine and well known to those of ordinary skill in the art. The inhalable powders according to the present invention can be prepared and administered either in the form of a single powder mixture which contains azelastine or a salt thereof and optionally one or more additional active agents such as those described herein, or in the form of separate inhalable powders, in which one powder contains only azelastine or a salt thereof, and another powder contains one or more additional active agents such as those described herein. Methods for preparing the inhalable powders of the present invention, as well as devices for their delivery, are disclosed in U.S. Pat. Nos. 6,696,042 and 6,620,438; U.S. Published Patent Application Nos. 2002/0009418, 2005/0121032, 2005/0121027 and 2005/0123486, the disclosures of each of which are incorporated herein by reference in their entireties.

The inhalable powders according to the present invention may be administered using inhalers well known in the art. Inhalable powders according to the present invention which contain a physiologically acceptable excipient in addition to the active agents may be administered, for example, by means of inhalers which deliver a single dose from a supply using a measuring chamber as described in U.S. Pat. No. 4,570,630, or by other means as described in U.S. Pat. Nos. 5,035,237 and 4,811,731, the disclosures of which are incorporated by reference herein in their entireties. The inhalable powders of the present invention can also be administered by dry powder inhalers (DPIs) or pre-metered DPIs (see e.g., U.S. Pat. Nos. 6,779,520, 6,715,486 and 6,328,034, the disclosures of each of which are incorporated herein by reference in their entireties). Suitably, the inhalable powders according to the present invention which contain physiologically acceptable excipients in addition to the active agents are packed into capsules (to produce so-called inhalettes) which are used in inhalers as described, for example, in U.S. Pat. No. 5,947,118, the disclosure of which is incorporated herein by reference in its entirety. An additional DPI that can be used with the powder formulations of the present invention is the Novalizer® by Sofotec (Bad Homburg, Germany). A description of this DPI, as well as methods to formulate powders for use in it, are disclosed in U.S. Pat. Nos. 5,840,279; 5,881,719; 6,071,498; and 6,681,768, the disclosures of which are incorporated herein by reference in their entireties.

According to another embodiment of the present invention, inhalation aerosols containing propellant gas comprising (or consisting essentially of) azelastine or a salt thereof and optionally, one or more additional active ingredients such as those described herein, dissolved in a propellant gas or in dispersed form, can be produced. Azelastine or a salt thereof, and one or more optional active ingredients, such as those disclosed herein, may be present in separate formulations or in a single preparation, in which all active ingredients are each dissolved, each dispersed, or one or more active components are dissolved and any others are dispersed. The propellant gases which may be used to prepare the inhalation aerosols according to the invention are known in the art. Suitable propellant gases include, but are not limited to, hydrocarbons such as n-propane, n-butane or isobutane and halohydrocarbons such as fluorinated derivatives of methane, ethane, propane, butane, cyclopropane or cyclobutane. The propellant gases may be used on their own or in mixtures thereof. Particularly suitable propellant gases are halogenated alkane derivatives selected from TG134a and TG227.

The propellant-driven inhalation aerosols according to the present invention may also contain other ingredients such as co-solvents, stabilizers, surfactants, antioxidants, lubricants and pH adjusters. All of these ingredients, and suitable commercial sources thereof, are well known in the art.

The inhalation aerosols containing propellant gas according to the present invention may contain up to about 5 wt % of active substances (or more if required). Aerosols according to the invention contain, for example, about 0.002 wt. % to about 5 wt. %, about 0.01 wt. % to about 3 wt. %, about 0.015 wt. % to about 2 wt. %, about 0.1 wt. % to about 2 wt. %, about 0.5 wt. % to about 2 wt. %, or about 0.5 wt. % to about 1 wt. % of active substances (e.g., azelastine or a salt thereof and optionally one or more additional active agents such as those described herein).

In embodiments where the active substance(s) are present in dispersed form, the particles of active substance(s) suitably have an average particle size of up to about 10 suitably from about 0.1 µm to about 5 more suitably from about 1 µm to about 5 µm.

Propellant-driven inhalation aerosols according to certain such embodiments of the present invention may be administered using inhalers known in the art (e.g., MDIs: metered dose inhalers, see e.g., U.S. Pat. Nos. 6,380,046, 6,615,826 and 6,260,549, the disclosures of each of which are incorporated herein by reference in their entireties). Accordingly, in another aspect, the present invention provides pharmaceutical compositions in the form of propellant-driven aerosols combined with one or more inhalers suitable for administering these aerosols. In addition, the present invention provides inhalers which are characterized in that they contain the propellant gas-containing aerosols described throughout. The present invention also provides cartridges which are fitted with a suitable valve and can be used in a suitable inhaler and which contain one or more of the propellant gas-containing inhalation aerosols described throughout. Suitable cartridges and methods of filling these cartridges with the inhalable aerosols containing propellant gas according to the invention are known in the art.

In another embodiment, the present invention provides propellant-free inhalable formulations, such as solutions and suspensions, comprising (or consisting essentially of) azelastine or a salt thereof and optionally one or more additional active agents such as those described herein. Suitable solvents for use in such embodiments include aqueous and alcoholic solvents, suitably an ethanolic solution. The solvents may be water on its own or a mixture of water and ethanol. The relative proportion of ethanol compared with water suitably is up to about 70 percent by volume, more suitably up to about 60 percent by volume, or up to about 30 percent by volume. The remainder of the volume is made up of water. The solutions or suspensions containing azelastine or a salt thereof and optionally one or more additional active agents, such as those described herein, separately or together, are adjusted to a pH of 2 to 7, using suitable acids or bases. The pH may be adjusted using acids selected from inorganic or organic acids. Examples of suitable inorganic acids include hydrochloric acid, hydrobromic acid, nitric acid, sulfuric acid and phosphoric acid. Examples of suitable organic acids include ascorbic acid, citric acid, malic acid, tartaric acid, maleic acid, succinic acid, fumaric acid, acetic acid, formic acid, propionic acid, etc. Exemplary inorganic acids include hydrochloric and sulfuric acids. It is also possible to use the acids which have already formed an acid addition salt with one or more of the active substances. Exemplary organic acids include ascorbic acid, fumaric acid and citric acid. If desired, mixtures of the above acids may be used, particularly in the case of acids which have other properties in addition to their acidifying qualities, e.g., as flavorings, antioxidants or complexing agents, such as citric acid or ascorbic acid, for example. Hydrochloric acid can be used to adjust the pH.

Co-solvents and/or other excipients may be added to the propellant-free inhalable formulations of the present invention. Suitable co-solvents are those which contain hydroxyl groups or other polar groups, e.g., alcohols—such as isopropyl alcohol, glycols—such as propylene glycol, polyethylene glycol, polypropylene glycol, glycol ether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Suitably, these substances have no pharmacological effect or, in connection with the desired therapy, no appreciable or at least no undesirable pharmacological effect. The excipients and additives include, for example, surfactants such as soy lecithin, oleic acid, sorbitan esters, such as polysorbates, polyvinylpyrrolidone, other stabilizers, complexing agents, antioxidants and/or preservatives which prolong the shelf life of the finished pharmaceutical formulation, flavorings, vitamins and/or other additives known in the art. The additives also include pharmacologically acceptable salts such as sodium chloride as isotonic agents.

Exemplary excipients include antioxidants such as ascorbic acid, vitamin A, vitamin E, tocopherols and similar vitamins and provitamins occurring in the human body.

Preservatives may be used to protect the inhalable formulations disclosed herein from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are suitably present in concentrations of up to about 50 mg/100 ml, more suitably between about 5 and about 20 mg/100 ml. Alternatively, the inhalable formulations can be prepared without preservatives, for example, in unit-dose forms, such as described herein.

The propellant-free inhalable formulations according to the present invention can be administered using inhalers of the kind which are capable of nebulizing a small amount of a liquid formulation in the therapeutic dose within a few seconds to produce an aerosol suitable for therapeutic inhalation. Suitable inhalers are those in which a quantity of less than about 100 µL, less than about 50 µL, or between about 10 µL and about 30 µL of active substance solution can be nebulized in one spray action to form an aerosol with an average particle size of less than about 20 µm, suitably less than about 10 µm, in such a way that the inhalable part of the aerosol corresponds to the therapeutically effective quantity.

Suitable apparatuses for propellant-free delivery of a metered quantity of a liquid pharmaceutical composition according to the present invention are described for example in U.S. Pat. Nos. 5,497,944; 5,662,271; 5,964,416; 6,402,055; 6,497,373; 6,726,124; and 6,918,547, the disclosures of which are incorporated herein by reference in their entireties. In another embodiment, the present invention provides pharmaceutical formulations in the form of propellant-free inhalable formulations, such as solutions or suspensions, as described herein, combined with a device suitable for administering such formulations.

The propellant-free inhalable formulations, e.g., solutions or suspensions, according to the present invention may take the form of concentrates or sterile inhalable solutions or suspensions ready for use. Formulations ready for use may be produced from the concentrates, for example, by the addition of isotonic saline solutions. Sterile formulations ready for use may be administered using energy-operated fixed or portable nebulizers which produce inhalable aerosols by means of ultrasound or compressed air by the Venturi principle or other principles.

The present invention also provides fine particle dosages of azelastine or a salt thereof (e.g., azelastine HCl) and optionally one or more additional active agents such as those described herein. A delivered fine particle dose (FPD) of azelastine or a salt thereof (e.g., azelastine HCl) administered by inhalation herein is not limited, and may generally be in a range from about 1 to about 50 µg, including about 5, 10, 15, 20, 30 and 40 µg. The correct metered dose loaded into an inhaler to be used for the purpose of administration can be adjusted for predicted losses such as retention and more or less efficient de-aggregation of the inhaled dose.

Excipient particles having a physical median particle size larger than about 25 µm and having a very narrow particle size distribution with generally less than 5% of the particles by mass being below 10 µm generally show good flow properties, and are suitable for use in mixtures together with azelastine or a salt thereof (e.g., azelastine HCl) and optionally one or more additional active agents, such as those described herein. For inhalation purposes, carrier particles having a mass median particle size in a range from about 10 to about 250 µm are typically selected, including about 30, 50, 70, 100, 130, 160, 190, and 220 µm. The median particle size chosen within this range depends on many factors, e.g. type of carrier substance, degree of powder flowability to be attained, type of inhaler and ease of de-aggregation during inhalation of the resulting medicament. Commercial grades of Respitos are available (lactose monohydrate from DMV of several defined particle size distributions up to 400 µm) suitable as particular excipients to be used in formulations containing azelastine, e.g. grade SV003. Uniform homogeneous azelastine powder formulations having a physical median particle size down to about 10 µm can also provide good flow properties when the particles have been modified to have a very smooth surface, thereby improving the flow properties of the formulation.

A practical lower limit for volumetric dose forming for such inhalable powder formulations is in a range of about 0.5 to 1 mg. Smaller doses can be difficult to produce and still maintain a low relative standard deviation between doses in the order of 10%. Typically, though, dose masses range from about 1 to 10 mg.

Suitable excipients for inclusion in the azelastine powder formulations include, but are not limited to, monosaccharides, disaccharides, polylactides, oligo- and polysaccharides, polyalcohols, polymers, salts or mixtures from these groups, e.g. glucose, arabinose, lactose, lactose monohydrate, lactose anhydrous (i.e., no crystalline water present in lactose molecule), saccharose, maltose, dextran, sorbitol, mannitol, xylitol, sodium chloride and calcium carbonate.

Excipients for use with azelastine or a salt thereof (e.g., azelastine HCl) and optionally one or more additional active agents, such as those described herein, generally are selected from among excipients which have good moisture qualities in the sense that the substance will not adversely affect the active agent fine particle dose (FPD) for the shelf life of the product regardless of normal changes in ambient conditions during storage. Suitable "dry" excipients are well known in the art and include those disclosed herein. For example, lactose can be selected as a dry excipient, or lactose monohydrate can be used in a formulation with azelastine or a salt thereof (and optionally one or more additional active agents, such as those described herein). Lactose has the inherent property of having a low and constant water sorption isotherm. Excipients having a similar or lower sorption isotherm can also be used.

As discussed throughout, and in a further aspect of the present invention, azelastine or a salt thereof (e.g., azelastine HCl) may be mixed or formulated with one or more additional active agents such as those described herein in the dry powder or other inhalable formulations. The present invention also encompasses the use of azelastine or a salt thereof where a combination of azelastine or a salt thereof with other agents, such as those described herein, constitute a formulation from which metered doses are then produced, filled and sealed into dry, moisture-tight, high barrier seal containers intended for insertion into a DPI to be administered according to a particular dosing regime or as needed by the user. Suitable additional active agents include those disclosed throughout, for example, inhaled steroids: e.g., budesonide, fluticasone (e.g., fluticasone propionate, fluticasone dipropionate, fluticasone fuorate, fluticasone maleate, fluticasone valerate, and the like), rofleponide, mometasone, and/or ciclesonide; NSAIDs, e.g., ibuprofen; leukotriene antagonists, e.g., montelukast; additional antihistamines, e.g., epinastine, cetirizine, fexofenadine, olopatadine, levocabastine, loratadine, mizolastine, ketotifene, emedastine, dirnetindene, clemastine, bamipine, cexchlorpheniramine, pheniramine, doxylamine, chlorphenoxamine, dimenhydrinate, diphenhydramine, promethazine, ebastine, desloratidine and/or meclozine; beta-mimetics: e.g., formoterol, salmeterol, salbutamol and/or terbutalinsulphate; PDE IV inhibitors: e.g., 3',5'-cyclic nucleotide phosphodiesterases and derivates; adenosine A2a receptor agonists: e.g., Ribofuranosylvanamide derivates, and/or substances described in U.S. Published Patent Application No. 2003/013675, the disclosure of which is incorporated by reference herein in its entirety.

A sealed, dry, high barrier container can be loaded with a powder form azelastine or a salt thereof (e.g., azelastine HCl) and optionally one or more additional active agents, such as those described herein, in the form of a blister and may comprise a flat dose bed or a formed cavity in aluminum foil or a molded cavity in a polymer material, using a high barrier seal foil against ingress of moisture, e.g. of aluminum or a combination of aluminum and polymer materials. The sealed, dry, high barrier container may form a part of an inhaler device or it may form a part of a separate item intended for insertion into an inhaler device for administration of pre-metered doses.

The inhalable pharmaceutical formulations of the present invention that comprise (or consist essentially of) azelastine or a salt thereof (e.g., azelastine HCl) and a suitable steroid (e.g., a safe steroid) are suitably formulated as azelastine: steroid in ratios by weight ranging from about 1:300 to about 50:1, and more suitably from about 1:250 to about 40:1. In exemplary formulations which contain azelastine or a salt thereof (e.g., azelastine HCl) and a steroid selected from among budesonide, fluticasone, mometasone, and ciclesonide, the weight ratio of azelastine (or salt thereof): steroid are suitably in the range of about 1:150 to about 30:1, and more suitably from about 1:50 to 20:1.

The inhalable formulations of the present invention are especially suitable for the treatment of inflammatory (including allergic) or obstructive diseases of the upper or lower respiratory tract, including asthma and chronic obstructive pulmonary disease (COPD), and complications thereof such as pulmonary hypertension, as well as allergic and non-allergic rhinitis. In addition, the inhalable formulations according to the present invention may be used to treat cystic fibrosis and allergic alveolitis (Farmer's Lung).

The present invention also provides inhalable spray pharmaceutical compositions comprising (or consisting essentially of), a suitable concentration to provide a therapeutically effective dose of azelastine, or a pharmaceutically acceptable salt or ester thereof, and one or more pharmaceutically acceptable carrier, stabilizer or excipient, wherein the azelastine is in a solution form and wherein at least one of the pharmaceutically acceptable carriers or excipients is sucralose dissolved in the solution. Such inhalable spray pharmaceutical compositions when used with a suitable device provide a fine spray of the components (including active and non-active components) having an average particle size of about 1 µm to about 5 µm. Such inhalable spray pharmaceutical compositions of the present invention can be formulated for pulmonary delivery using, for example, a suitable device or inhaler. Suitably the amount of azelastine in such inhalable spray pharmaceutical compositions is about 0.1% to about 10% by weight and the amount of sucralose in such inhalable spray pharmaceutical compositions is about 0.05% to about 0.15% by weight, though other suitable amounts will readily be determined by the ordinarily skilled artisan.

Clinical Indications

The compositions provided by the present invention are useful in methods for the treatment of a variety of physical disorders in animals (particularly mammals including humans) that are predisposed to or suffering from a physical disorder that may be delayed, prevented, cured or otherwise treated by the administration of azelastine or a pharmaceutically acceptable salt or ester thereof. Thus, in additional embodiments, the invention provides methods of treating or preventing such physical disorders, comprising administering an effective amount of one or more of the compositions of the invention to an animal (particularly a mammal, including a human) that is predisposed to or suffering from such a physical disorder. As used herein, an animal that is "predisposed to" a physical disorder is defined as an animal that does not exhibit a plurality of overt physical symptoms of the disorder but that is genetically, physiologically or otherwise at risk for developing the disorder. In such situations, the compositions of the present invention may thus be used prophylactically as chemopreventive agents for such disorders.

Suitably, the invention provides methods of treating or preventing a physical disorder, condition or symptom thereof, in a patient by administering to the eye, nose, ear, skin, etc. of a patient a unit dosage form of a pharmaceutical composition of the invention comprising an effective amount of one or more active pharmaceutical ingredients. Suitably, the methods comprise providing a unit dosage form comprising a unit dosage container made of high density polyethylene, the unit dosage form having a volume of less than about 0.6 ml and the dosage container having a volume of less than about 1.0 ml. Suitably the unit dose form contains one or more antihistamines (e.g., azelastine HCl) or pharmaceutically acceptable salts thereof. The unit dosage form is then administered to the subject, and the unit dosage container is then discarded. It should be understood that "discarded" simply means that the unit dosage container is not used for any subsequent dosings.

According to the invention, a mammal (preferably a human) that is predisposed to or suffering from a physical disorder may be treated by administering to the animal an effective dose of one or more of the pharmaceutical compositions of the present invention. Physical disorders treatable with the compositions and methods of the present invention include, but are not limited to, any physical disorder that is characterized by one or more symptoms such allergic rhinitis/rhinosinusitis, vasomotor rhinitis, and/or allergic conjunctivitis, inflammatory or obstructive diseases of the upper or lower respiratory tract, including asthma and chronic obstructive pulmonary diseases (COPD), and complications thereof such as pulmonary hypertension, cystic fibrosis and allergic alveolitis (Farmer's Lung), as well as non-allergic rhinitis or conjunctivitis, or allergic or nonallergic skin conditions. Examples of such allergic nasal, ocular, ear or skin conditions treatable or preventable using the pharmaceutical compositions of the present invention (preferably in unit dose configuration) include, but are not limited to, allergic reactions to plant or insect allergens, environmental allergens, allergic ocular conditions (e.g., hay fever conjunctivitis, perennial allergic conjunctivitis, giant papillary conjunctivitis (including that associated with the use of contact lenses), nonallergic noninfectious conjunctivitis, vernal keratoconjunctivitis or atopic keratoconjunctivitis) and irritant dermatitis, uticaria, and the like, as well as otic conditions such as otitis media, tinnitus, Eustachian tube constriction or blockage, and the like. The compositions of the invention are also useful in treating or preventing the symptoms of such disorders, and thereby provide symptomatic relief to patients suffering from or predisposed to such disorders.

Other physical conditions or disorders suitably treated or prevented using the pharmaceutical compositions of the present invention (preferably in unit dose configuration) include, but are not limited to, nasal and ocular conditions associated with the common cold; nasal, ocular or skin conditions resulting from a reaction to insect bites; postoperative ocular inflammation; acute anterior uveitis; dermatitus/keratisis; allergic blepharitis; keratitis (such as herpes zoster or superficial punctate keratitis), and the like; otic conditions such as uticaria and the like, as well as otitis media, tinnitus, Eustachian tube constriction or blockage, and the like. In another embodiment, the pharmaceutical compositions of the present invention (preferably in unit dose configuration) can be used to treat or prevent motion sickness, such as that associated with travel by boat, airplane, automobile, etc., wherein the composition is administered to (or self-administered by) a person susceptible to motion sickness at least about 15-30 minutes prior to beginning such travel.

The compositions of the invention are also useful in treating or preventing the symptoms of such disorders, and thereby provide symptomatic relief to patients suffering from or predisposed to such disorders.

Dosing

As noted above, by the invention, a composition comprising an effective amount of azelastine or a pharmaceutically acceptable salt or ester thereof (e.g., azelastine HCl), and optionally, one or more additional active agents such as those described herein, can be administered to a patient to provide symptomatic relief from a variety of disorders, including allergic rhinitis, vasomotor rhinitis, allergic conjunctivitis, as well as the various other disorders disclosed throughout and known in the art. One of ordinary skill will appreciate that the amount or concentration of azelastine (or salt or ester thereof, including azelastine hydrochloride) that constitutes "an effective amount" of azelastine can be determined empirically. Non-limiting examples of effective amounts of azelastine (or salt or ester thereof, including azelastine hydrochloride) for use in the pharmaceutical compositions of the present invention include those described in detail herein. It also will be understood that, when administered to a human patient, the total daily usage of the compositions of the present invention will be decided or recommended by the attending physician, pharmacist or other medical practitioner within the scope of sound medical judgment.

The intranasal formulations of this invention are most effective when proper product design is utilized. The preferred product design includes a composition of the invention contained within a delivery system, such as a bottle and a pump, for nasal delivery of the formulation in a mist of spray droplets to coat the mucosa of the nasal cavity upon administration. Preferred pumps for use in such products of the invention are metered multi-dose pumps; however, single unit-dose containers are also acceptable to deliver the therapeutic dose of azelastine (or salt or ester thereof, including azelastine hydrochloride) to the nasal cavity. The selection of the pump is based on the desired dose/spray volume and spray pattern appropriate for local delivery to the nasal mucosa. In certain such embodiments of the invention, the compositions can be effectively contained in a package comprising a high density polyethylene bottle fitted with a screw cap, and are delivered by a metered-dose spray pump designed for intranasal application in volumes of 0.07 to 0.15 ml such as the VP3/140 18/415 or the VP3/140F 18/415 Spigot 522 pumps designed by Valois Pharm, Marly le Roi, France. In addition, the intranasal formulations can be provided in a unit dose form, such as described herein.

The ocular formulations of this invention are also most effective when proper product design is utilized. The preferred product design includes a composition of the invention contained within a delivery system, such as a bottle and a dropper, for ocular delivery of the formulation to coat the conjunctival sac of the eyes upon administration. Preferred packages for use in such products of the invention are multi-dose; however, single unit-dose containers are also acceptable to deliver the therapeutic dose of azelastine (or salt or ester thereof, including azelastine hydrochloride) to the eyes. In certain such embodiments of the invention, the compositions can be effectively contained in a package comprising a high density polyethylene bottle (HDPE) in volume capacity of 10 mL fitted with a low density polyethylene dropper and secured with a HDPE cap closure. In addition, the ocular formulations can be provided in a unit dose form, such as described herein.

Suitable compositions of the present invention include about 0.1%, about 0.125% or about 0.15% azelastine, and about 0.05%-0.15% sucralose. Described below are non-limiting examples of the compositions of the present invention, comprising 0.05%, 0.1% or 0.15% azelastine hydrochloride, 0.1% to 0.3% of hypromellose as a thickener, 0.05% to 0.15% of sucralose as a sweetening and taste-masking agent, and/or 0.05% menthol as a taste-masking/flavoring agent. Suitable such compositions can also comprise one or more additional active agents such as those described herein at the various concentrations and amounts described herein. These compositions are well-tolerated despite the intense bitterness contributed by the presence of azelastine hydrochloride. Thus, use of such compositions of the invention provide symptomatic relief from allergic rhinitis, vasomotor rhinitis, or allergic conjunctivitis, while significantly improving patient acceptability and compliance.

Treatment of Snoring

The present invention also provides a method for treating snoring that in some cases eliminates snoring entirely, and in other cases reduces the intensity and frequency of snoring. The treatment comprises administering a prescribed dosage in one or more doses per day of azelastine or a physiologically acceptable salt thereof along with a taste-masking agent. The azelastine is suitably topically applied to the nasal passage, generally in the form of a nasal spray or in other delivery forms described herein. Azelastine is administered in an amount effective to inhibit snoring and may be administered once or more than once a day. In a suitable embodiment, at least one dose is administered prior to bedtime. Published International Patent Application No. WO 02/056876, the disclosure of which is incorporated by reference herein in its entirety, describes compositions and methods for treatment of snoring that can be used in the practice of the present invention.

In one embodiment, the present invention provides a sterile and stable aqueous solution of azelastine or one or more of its salts (e.g., azelastine HCl), along with one or more taste-masking agents and optionally one or more additional active agents such as those described herein, which can be used in the form of drops, ointments, creams, gels, insufflatable powders or, in a suitable embodiment, in the form of a spray (preferably a nasal spray). The spray can be formed by the use of a conventional spray-squeeze bottle or a pump vaporizer. In addition, it is also possible to use compressed gas aerosols. For example, 0.03 to 3 mg of azelastine base can be released per individual actuation.

In certain such embodiments, the formulations of the present invention for use in treating snoring comprise one or more taste-masking agents, one or more flavoring agents, and/or one or more sweetening agents, or a combination of such agents. Non-limiting examples of such substances include those described herein. For example, sucralose is especially effective as a sweetening and taste-masking agent in the compositions of the present invention for use in treatment of snoring, particularly when used at concentrations of from about 0.001% to about 1%, suitably at concentrations of from about 0.01% to about 0.5%, and more suitably at concentrations of from about 0.02% to about 0.2%, and most suitably from about 0.05% to about 0.15%, of the total composition.

Solvents which may be used for such formulations include, but are not limited to, water, saturated aliphatic mono and polyvalent alcohols which contain 2-3 carbon atoms (for example ethanol. Isopropanol, 1,2-propylene glycol, glycerine), liquid polyglycols (molecular weight 200 to 600). The solvent used is suitably water or mixtures of water with other physiologically acceptable solvents (for example those mentioned above). Suitably, the amount of the latter solvent in the aqueous mixture should not exceed 15% by weight.

Such solutions or formulations suitably can contain preservatives and stabilizers, as well as other excipients disclosed herein. Suitable excipients include, for example: ethylene diamine tetra-acetic acid (eidetic acid) and their alkali salts (for example dialkali salts such as disodium salt, calcium salt, calcium-sodium salt), lower alkyl p-hydroxybenzoates, chlorohexidine (for example in the form of the acetate or gluconate), phenyl mercury borate. Furthermore, it is possible, for example, to use sodium-(2-ethylmercurithio)-benzoate generally known as "thimerosal" which may be present in an amount of 0.001 to 0.05, preferably from 0.005 to 0.02, for example 0.01% (weight/volume in liquid formulations, otherwise weight/weight). Other suitable preservatives are: pharmaceutically useful quaternary ammonium compounds, for example cetylpyridinium chloride, tetradecyltrimethyl ammonium bromide, generally known as "cetrimide," benzyldimethyl-[2-[2-[p-(1,1,3,3-tetramethyl-butyl)]phenoxy]ethoxy]-ammonium chloride, generally known as "benzethonium chloride" and myristyl-:-picolinium chloride. Each of these compounds may be used in a concentration of 0.002 to 0.05, for example 0.02% (weight/volume in liquid formulations, otherwise weight/weight). Preferred preservatives among the quaternary ammonium compounds are alkylbenzyl dimethyl ammonium chloride and mixtures thereof, for example the compounds generally known as "benzalkonium chloride."

Such formulations of the present invention for treatment of snoring (solutions, suspensions as well as oily solutions or suspensions, ointments, emulsions, creams, gels, dosage aerosols) can contain about 0.0005 to about 2, preferably about 0.001 to about 1, or about 0.003 to about 0.5% (weight/weight) of azelastine (related to the free azelastine base). Should azelastine be present as a salt, the amounts should be recalculated as necessary to give the amounts of azelastine, in the free acid form shown above. In the case of powders, the concentration of azelastine base generally is about 0.0005 to about 2 percent by weight relative to the solid carrier substances.

In the case of solutions, the dosage per nostril is, for example, 0.01 to 0.2 ml, in particular 0.05 to 0.15 ml. Such a dosage should be applied once to several times, preferably 1 to 5 times daily (optionally also hourly).

Suitable acid components for azelastine salts are, for example, hydrophilic acids (HCl, HBr), sulfuric acid, phosphoric acids), nitric acid, organic mono-, di- or tricarboxylic acids of aliphatic, alicyclic, aromatic or heterocyclic organic acids (embonic acid, citric acid, tartaric acid), aliphatic and aromatic sulfonic acids (for example camphorsulfonic acid).

It is also suitable to add buffer substances such as citric acid/sodium hydrogensulphate borate buffer, phosphates (sodium hydrogenorthophosphate, disodiumhydrogenphosphate), tromethamol or equivalent conventional buffers in order, for example, to adjust the formulation to a pH value of 6 to 7.5, preferably 6.5 to 7.1.

In one embodiment, snoring is treated by use of a 0.1% or a 0.15% aqueous solution of azelastine hydrochloride, suitably as a nasal spray. The spray is metered to deliver about 137 μg of azelastine hydrochloride (equivalent to 125 μg of azelastine base).

In addition to azelastine, the compositions useful for treating snoring can also optionally contain one or more additional active agents such as those described herein. In addition, the compositions for treating snoring can also further comprise one more sedatives or sleeping aids to help assist the user in falling asleep. Suitable sedatives and sleep aids include, but are not limited to, melatonin (N-acetyl-5-methoxytryptamine), a melatonin agonist, GABA (gamma-aminobutyric acid), other antihistamines (for example, benocten and olopatadine), benzodiazepines (for example, midazolam, diazepam), diazepines, phenobarbiturates, diphenhydramines or methiazoles. Other suitable sleep aids include plant extracts such as: *Valeriana officinalis, Lavandula angustifolia, Humulus lupulus, passiflora incarnate, Ocimum basilicum, Nardostachysjatamamsi, Hypericum perforatum, Corydalis cava, Daliva miltiorrhiza, Cyperipedium pubescens, Cymbopogon flexuosus, Melissa officinalis, Monarda didymia, Citrus aurantii, Psicidia piscioula,* and the like.

Co-Administration of Azelastine and Steroid

In a further embodiment, the present invention provides methods of treating a variety of disorders, including allergic rhinitis, vasomotor rhinitis, allergic conjunctivitis, as well as the various other disorders disclosed throughout and known in the art, by co-administering azelastine (or a pharmaceutically acceptable salt thereof, e.g., azelastine HCl) and one or more steroids. Suitably, azelastine or a pharmaceutically acceptable salt or ester thereof (e.g., azelastine HCl) is administered in the form of a nasal spray, although additional delivery routes and formulations as described throughout can also be used (e.g., oral, ocular, inhalation, etc.). As described throughout, compositions for administration of azelastine via the nasal route (as well as other routes described throughout) can further comprise one or more excipients, for example, a taste-masking agent such as sucralose, as well as one or more additional active agents selected from those described herein or otherwise known in the art, for example a decongestant.

Examples of steroids suitable for co-administration in such embodiments of the present invention include, but are not limited to, fluoromethalone, fluticasone (and its conjugates, esters, variants, salts, derivatives and the like, e.g., fluticasone propionate sold under the brand name FLONASE® by GlaxoSmithKline, Research Triangle Park, N.C., fluticasone dipropionate, fluticasone fuorate, fluticasone maleate, fluticasone valerate, and the like), mometasone, triamcinolone, betamethasone, flunisolide, beclomethasone, budesonide, rimexolone, beloxil, prednisone, loteprednol (e.g., loteprednol etabonate), dexamethasone and its analogues (e.g., dexamethasone beloxil) described in U.S. Pat. Nos. 5,223,493 and 5,420,120, incorporated herein by reference in their entireties, as well as other steroids described throughout. Preferred steroids for use in the formulations of the present invention are "safe steroids." As used herein, the term "safe steroid" means a steroid which treats eosinophil and neurotrophil associated inflammation, reduces papillae formation, and which is effective in treating inflammation, without causing a clinically significant elevation in intraocular pressure (IOP). Exemplary safe steroids that can be used in the various formulations of the present invention, particularly for delivery using nasal spray or ocular drop delivery systems include, but are not limited to, any glucocorticoid which meets the safe steroid definition, including but not limited to, fluorometholone, fluticasone (and its conjugates, esters, variants, salts, derivatives and the like, e.g., fluticasone propionate sold under the brand name FLONASE® by GlaxoSmithKline, Research Triangle Park, N.C., fluticasone dipropionate, fluticasone fuorate, fluticasone maleate, fluticasone valerate, and the like), rimexolone, loteprednol (e.g., loteprednol etabonate), dexamethasone beloxil and its analogues described in U.S. Pat. Nos. 5,223,493 and 5,420,120. Additional "safe steroids" and methods for determining appropriate amounts of such agents for inclusion in the present compositions are disclosed in U.S. Pat. No. 6,649,602, the disclosure of which is incorporated by reference herein in its entirety.

As used herein, the term "co-administration" refers to administering azelastine or a pharmaceutically acceptable salt or ester thereof (e.g., azelastine HCl) by any mode of administration (e.g., intranasally, orally, ocularly, via inhalation, etc.) and one or more steroids also by any mode of administration (e.g., intranasally, orally, ocularly, via inhalation, etc.) simultaneously, i.e., at the same time, or within a suitable time period of one another. More suitably, azelastine and one or more steroids are administered in the form of a nasal spray formulation within less than about 1 minute of each other (and can be administered at the same time), or within less than about 2 minutes of each other, within less than about 3 minutes of each other, within less than about 4 minutes of each other, within less than about 5 minutes of each other, within less than about 6 minutes of each other, within less than about 7 minutes of each other, within less than about 8 minutes of each other, within less than about 9 minutes of each other, within less than about 10 minutes of each other, within less than about 11 minutes of each other, within less than about 12 minutes of each other, within less than about 13 minutes of each other, within less than about 14 minutes of each other, within less than about 15 minutes of each other, within less than about 16 minutes of each other, within less than about 17 minutes of each other, within less than about 18 minutes of each other, within less than about 19 minutes of each other, within less than about 20 minutes of each other, within less than about 25 minutes of each other, within less than about 30 minutes of each other, within less than about 35 minutes of each other, within less than about 40 minutes of each other, within less than about 45 minutes of each other, within less than about 50 minutes of each other, within less than about 55 minutes of each other, or within less than about 60 minutes of each other.

In certain embodiments, azelastine or a pharmaceutically acceptable salt or ester thereof (e.g., azelastine HCl) and one or more steroids are administered at the same time using a spray or dispensing device that allows for administration of both active agents from separated storage containers at the same time. For example, a device comprising two reservoirs, one of which contains azelastine or a pharmaceutically acceptable salt or ester thereof (e.g., azelastine HCl) in a suitable spray formulation, the other of which comprises one or more steroids, also in a suitable spray formulation. By activating the spray or dispensing devise, a dose from each reservoir, i.e., an azelastine dose and a steroid dose, are administered to the nasal passage of the patient at the same time. A device in which each separate reservoir can be dispensed at different times is also envisioned. The dosage and volume of spray from each reservoir can also be controlled and modified as required depending upon the agent being delivered. Additional devices and methods are envisioned for other modes of administration, e.g., for pulmonary delivery via inhalation as described hereinabove, for example using dry powder inhalers (DPIs) or pre-metered DPIs.

In a further embodiment, co-administration comprises administering azelastine or a pharmaceutically acceptable salt or ester thereof (e.g., azelastine HCl) from a first spray or dispensing device, and then administering one or more steroids from a second spray or dispensing device (the devices can be attached or joined to one another, or they can be completely separate dispensing devices) within the time periods set forth herein. For example, azelastine or a pharmaceutically acceptable salt or ester thereof (e.g., azelastine HCl) can be administered by spraying a dose (or one or more sprays can be used depending on the required dose) of active agent into each nasal passage of the patient (or a single nasal passage depending on the required dose). The dose amount is determined by the configuration of the spray device and the concentration of the agent in the spray formulation. Then, within the time periods set forth throughout, (e.g., within less than about 1 minute, less than about 5 minutes, less than about 10 minutes, less than about 15 minutes, less than about 20 minutes, etc.) a dose of steroid is provided to the patient by spraying each nasal passage with a steroid in a nasal spray formulation (or a single nasal passage depending on the required dose). Suitably, two sprays each of azelastine or a pharmaceutically acceptable salt or ester thereof (e.g., azelastine HCl) and a steroid in nasal spray formulations are given to each nasal passage, though in suitable embodiments, a single or multiple sprays can be administered to one or both nasal passages. In further embodiments, doses of additional steroids and/or other agents can be co-administered before or after the administration of azelastine and a first steroid. Similar sequential co-administration of these active ingredients via other modes of administration, e.g., via inhalation for pulmonary delivery as described elsewhere herein, is also contemplated by the present invention.

The present invention also encompasses the co-administration of azelastine and one or more steroids, where the steroids, or both the steroids and azelastine, are administered via a route other than via nasal spray. For example, azelastine (or a salt or ester thereof, e.g. azelastine HCl) can be administered via nasal spray, and one or more steroids administered via oral, inhalation, injection, or other suitable route. Alternatively, azelastine (or a salt or ester thereof, e.g. azelastine HCl) can be administered via pulmonary delivery (e.g., via inhalation as described elsewhere herein), and one or more steroids can be administered via nasal, oral, inhalation, injection or other suitable route. In yet another non-limiting approach, azelastine (or a salt or ester thereof, e.g. azelastine HCl) can be administered ocularly, and one or more steroids can be administered via nasal, oral, inhalation, injection or other suitable route. As one of ordinary skill will be aware, there are other examples of suitable modes of co-administration of azelastine (or a salt or ester thereof, e.g. azelastine HCl) and a steroid, based on the description herein and that will be familiar to the practitioner; such other examples are also encompassed by the present invention.

In a further embodiment, co-administration comprises administration of azelastine (or a salt or ester thereof, e.g. azelastine HCl) and one or more steroids in the same composition. In certain such embodiments, the azelastine (or salt or ester thereof) and the steroid are contained together in a single pharmaceutical composition, for example, a single pharmaceutical composition comprising azelastine (or a salt or ester thereof) and a steroid (either in a solution or a suspension dosage form). Such compositions may take any form, particularly those described herein that are formulated for nasal administration, pulmonary administration (e.g., via inhalation), ocular administration, oral administration, injection and the like.

The amount of azelastine for co-administration can be varied and adjusted appropriately by the ordinarily skilled artisan. Suitably azelastine or a pharmaceutically acceptable salt or ester thereof (e.g., azelastine HCl) is contained in the intranasal formulations for co-administration in an amount of about 0.0001% to about 1.0% by weight, and more suitably from about 0.005% to about 0.5% or most suitably from about 0.05% to about 0.20% (e.g., 0.05%, 0.06%, 0.07%, 0.08%, 0.09%. 0.10%, 0.11%, 0.12%, 0.13%, 0.14%, 0.15%, 0.16%, 0.17%, 0.18%, 0.19%, 0.20%), of pure azelastine (calculated as the free azelastine base). The amount of steroid(s) present in the formulations for co-administration can be varied and adjusted appropriately by the ordinarily skilled artisan. Suitably, one or more steroids are present in any amount in the nasal formulations, for example about 0.01% to about 1.5% (e.g., about 0.01%, about 0.05%, about 0.1%, about 0.25%, about 0.5%, about 0.75%, about 1%, about 1.5%). Suitably the amount of steroid is about 0.01% to about 1.5% by weight, more suitably about 0.01% to about 1.0% by weight, or even more suitably about 0.01% to about 0.1% by weight (e.g., about 0.01%, about 0.02%, about 0.03%, about 0.04%, about 0.05%, about 0.06%, about 0.07%, about 0.08%, about 0.09%, or about 0.1% by weight). Amounts, compositions and selection of buffers, isotonicity-adjusting agents, antioxidants, preservatives, viscosity-increasing agents, chelating agents, and other excipients (including taste-masking agents such as sucralose) and other components of the formulations for use in the co-administration embodiments of the present invention are described herein and readily determinable by those of skill in the art.

It has been found that co-administration of azelastine or a pharmaceutically acceptable salt or ester thereof (e.g., azelastine HCl) and one or more steroids provides a significant improvement in patients suffering from allergic rhinitis, non-allergic vasomotor rhinitis or allergic conjunctivitis, as compared to azelastine or steroid administration alone, in symptoms such as runny nose, itchy nose, sneezing, congestion and total nasal symptom score. (See Example 13). Specifically, it has now been found that the co-administration of azelastine or a pharmaceutically acceptable salt or ester thereof (e.g., azelastine HCl) and one or more steroids unexpectedly results in better therapeutic benefit to patients to whom the agents have been co-administered than would be expected, in that the effect on the symptoms of allergic rhinitis, non-allergic vasomotor rhinitis or allergic conjunctivitis, of the two agents co-administered (whether in the same composition or in separate compositions) is significantly greater than the effects of either agent administered separately.

It will be readily apparent to one of ordinary skill in the relevant arts that other suitable modifications and adaptations to the methods and applications described herein may be made without departing from the scope of the invention or any embodiment thereof. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the claims. Having now described the present invention in detail, the same will be more clearly understood by reference to the following examples, which are included herewith for purposes of illustration only and are not intended to be limiting of the invention.

EXAMPLES

Example 1

Azelastine Hydrochloride Nasal Solution

In one exemplary composition of the invention, a nasal spray formulation containing azelastine hydrochloride was prepared using hypromellose as a thickener, sorbitol as an isotonicity agent and sweetener, and sucralose as both a sweetener and a taste-masking agent.

| Ingredient | % |
| --- | --- |
| Azelastine Hydrochloride | 0.150 |
| Hypromellose 2900, USP 4000 | 0.100 |
| Edetate Disodium, USP | 0.050 |
| Sorbitol 70%, USP | 6.400 |
| Sodium Citrate, USP, Dihydrate | 0.068 |
| Sucralose, NF | 0.150 |
| Benzalkonium Chloride 50% Solution, NF | 0.025 |
| Water Purified or Deionized | Q.S. to 100% |

Following preparation, the composition was filtered, and was packaged into high density polyethylene bottles fitted with a screw cap and comprising a VP3 metered-dose spray pump designed for intranasal application in a volume of about 0.14 ml (Valois). For use, one or two sprays were administered to each nostril two times per day, or as prescribed.

Example 2

Azelastine Hydrochloride Nasal Solution

In another exemplary composition provided by the present invention, a nasal spray formulation containing azelastine hydrochloride was prepared using hypromellose as a thickener and sucralose and menthol as taste-masking agents:

| Ingredient | % |
| --- | --- |
| Azelastine Hydrochloride | 0.100 |
| Hypromellose 2900, USP 4000 | 0.300 |
| Edetate Disodium, USP | 0.050 |
| Sodium Citrate, USP, Dihydrate | 0.068 |
| Sucralose, NF | 0.050 |
| Propylene Glycol, USP | 1.895 |
| Menthol, USP | 0.050 |
| Benzalkonium Chloride 50%, NF | 0.025 |
| Water Purified or Deionized | Q.S. to 100% |

Following preparation, the composition was filtered, and was packaged into high density polyethylene bottles fitted with a screw cap and comprising a VP3 metered-dose spray pump designed for intranasal application in a volume of about 0.14 ml (Valois). For use, one or two sprays were administered to each nostril two times per day, or as prescribed.

Example 3

Azelastine Hydrochloride Nasal Solution

In another exemplary composition of the invention, a nasal spray formulation containing azelastine hydrochloride was prepared using hypromellose as a thickener, sodium chloride as an isotonicity agent, and sucralose as both a sweetener and a taste-masking agent.

| Ingredient | % |
| --- | --- |
| Azelastine Hydrochloride | 0.100 |
| Hypromellose 2900, USP 4000 | 0.100 |
| Edetate Disodium, USP | 0.050 |
| Citric Acid Anhydrous, USP | 0.044 |
| Dibasic Sodium Phosphate Heptahydrate, USP | 0.486 |
| Sodium Chloride, USP | 0.687 |
| Sucralose, NF | 0.150 |
| Benzalkonium Chloride 50% Solution, NF | 0.025 |
| Water Purified or Deionized | Q.S. to 100% |

Following preparation, the composition was filtered, and was packaged into high density polyethylene bottles fitted with a screw cap and comprising a VP3 metered-dose spray pump designed for intranasal application in a volume of about 0.14 ml (Valois). For use, one or two sprays were administered to each nostril about two times per day, or as prescribed.

Example 4

Azelastine Hydrochloride Ocular Solution

In another exemplary composition provided by the present invention, an ocular formulation containing azelastine hydrochloride was prepared using hypromellose as a thickener, sorbitol as an isotonicity agent, and sucralose as a taste-masking agent:

| Ingredient | % |
| --- | --- |
| Azelastine Hydrochloride | 0.050 |
| Hypromellose 2900, USP 4000 | 0.100 |
| Edetate Disodium, USP | 0.050 |
| Sucralose, NF | 0.150 |
| Sorbitol Solution 70%, USP | 6.667 |
| Benzalkonium Chloride 50%, NF | 0.025 |
| Water Purified or Deionized | Q.S. to 100% |

Following preparation, the composition was aseptically filtered, and was packaged into high density polyethylene bottles fitted with low density polyethylene dropper tips and a high density polyethylene protective cap. The droppers were designed for delivery of approximately 0.03 mL per drop. For use, one drop was instilled into each affected eye twice a day, or as prescribed.

Example 5

Sensory Descriptive Bitterness Taste Analysis of Astelin Nasal Spray

To determine effectiveness of masking agents in improving the taste of Astelin®Nasal Spray, a sensory evaluation of various formulations was conducted. Testing was carried out via a randomized, double-blind, placebo-controlled trial to evaluate comparability between the currently FDA-approved Astelin® Nasal Spray formulation and various sweetened azelastine hydrochloride nasal spray formulations. The objective of the study was to determine if a sweetened formulation of azelastine hydrochloride (containing 137 µg azelastine HCl), that includes 0.15% sucralose as a taste masking agent, is equivalent in efficacy and safety to the currently approved formulation of Astelin® Nasal Spray (also containing 137 µg of azelastine HCl).

Methodology:

Panelists: Twelve highly trained descriptive panelists led by a panel leader.

Data Analysis: Data were entered into an Excel spreadsheet and proofed for accuracy. An analysis was conducted with the data using ANOVA and Duncan means separation at a confidence level of 95% using SPSS 13.0 for Windows.

Methodology: Panelists measured the bitterness, noted other flavors perceived as well as observed the length of time the bitterness lasted in the throat.

All solutions were prepared with Milli-Q Water

Standard Solutions 0.05% caffeine, bitter 2

0.08% caffeine, bitter 5

0.11% caffeine, bitter 7.5

Test samples were coded with random three-digit numbers. Panelists scored samples on ballots individually. Samples were evaluated by panelists using a 15-point intensity scale divided into 0.1 point increments with zero indicating no measurable effect and 15 indicating an extremely strong effect.

Product Identification:

(1) Astelin Nasal Spray Batch #1326 (two sprays) (azelastine hydrochloride, 137 µg azelastine HCl per two sprays)

(2) Astelin Nasal Spray Batch #1326 (four sprays) (azelastine hydrochloride, 137 µg azelastine HCl per two sprays)

(3) Astelin Nasal Spray Batch #03-33-01c (two sprays) (azelastine hydrochloride solution 0.1% w/v Investigational Formulation with sorbitol and high concentration of sucralose, 137 µg azelastine HCl per two sprays)

(4) Astelin Nasal Spray Batch #03-33-01c (four sprays) (azelastine hydrochloride solution 0.1% w/v Investigational Formulation with sorbitol and high concentration of sucralose, 137 µg azelastine HCl per two sprays).

(1) Results and Discussion
(A) Commercial Formulation (Standard Azelastine Hydrochloride Commercial Formulation)

This sample and sample 1326 four sprays exhibited the most bitterness with nasal discomfort that fell between mild and moderate. The bitterness was more intense in those who experienced more drainage. However, the bitterness dissipated within 30 minutes for most panelists. A couple of panelists experienced some residual bitterness for 2 to 3 hours after testing. The nasal discomfort was predominately described as tingling, cooling or slight burning.

(B) Sample 1326 Four Sprays

This sample and the Commercial Formulation displayed the most bitterness with nasal discomfort that fell between mild and moderate. Several panelists described this sample as similar or identical to the Commercial Formulation. As with the Commercial Formulation, most panelists did not notice any bitterness after 30 minutes.

(C) Sample 1326 Two Sprays

This sample was significantly less bitter than the Commercial Formulation using four sprays. Additionally, the nasal discomfort was lessened and described as mild. For most, the bitterness lasted less than 30 minutes. Some panelists questioned the effectiveness of two sprays versus four sprays.

(D) Sample 03-33-01c Four Sprays

While this sample was also significantly less bitter than the Commercial

Formulation using four sprays, the sweetness was notable. The nasal discomfort was described as mild and similar to Sample 1326 two sprays and 03-33-01c two sprays. Most panelists described this sample as more sweet than bitter. As they experienced drainage, the sweet flavor intensified overriding any bitterness. Both sweet and bitter flavors dissipated within an hour.

(E) Sample 03-33-01c Two Sprays

This sample exhibited the least bitterness. Although the panelists noted a slight sweetness in this sample, it was not nearly as strong as when using four sprays. The sweetness did not override the slight bitterness as it did when using four sprays. The nasal discomfort was described as mild. Most indicated no bitter or sweet taste after 30 minutes. The bitterness faded faster than the sweetness. As with Sample 1326 two sprays, some panelists questioned the effectiveness of two sprays versus four.

Panelists' Preferences

Of the four test samples, 4 of 11 panelists ranked 03-33-01c two sprays as their first choice. Four panelists ranked it as their second choice. They liked the slight sweetness that masked the bitterness; however, several did question whether two sprays were as effective as four.

Four of eleven panelists chose 03-33-01c four sprays as their first choice with four indicating it would be their second choice. Again, they preferred the sweet flavor that masked the bitterness and they felt it was effective.

Three of eleven panelist chose 1326 two sprays as their first choice, with one choosing it as a second choice. Some did not like the sweetness and preferred a slight bitterness. Some questioned the effectiveness of two sprays.

No panelists ranked 1326 four sprays as their first choice. One panelist chose it as her second choice because she did not like the sweet taste at all.

(2) Conclusions

The panelists recognized the Commercial Formulation and sample 1326 four sprays as the same.

Using two sprays of sample 1326 helped significantly with the bitterness and nasal discomfort.

The 03-33-01c samples were significantly less bitter and gave less nasal discomfort than the Commercial Formulation.

The 03-33-01c samples were equally preferred due to the masking sweetness.

Example 6

Preservative Free Ocular Solution for Unit Dose

One exemplary composition provided by the present invention, is a liquid dosage formulation containing azelastine hydrochloride prepared using hypromellose as a thickener and sucralose and menthol as a taste-masking agent in the ranges provided below:

| Ingredient | % |
|---|---|
| Azelastine Hydrochloride | 0.0500-.150 |
| Hypromellose 2900, USP 4000 | 0.300 |
| Edetate Disodium, USP | 0.050 |
| Sodium Citrate, USP, Dihydrate | 0.068 |
| Sucralose, NF | 0.050-0.150 |
| Propylene Glycol, USP | 1.895 |
| Water Purified or Deionized | Q.S. to 100% |

Following preparation, the solution is filtered, and packaged into high density polyethylene containers. An approximate unit dose volume of about 0.25 mL to 1 mL is filled in the container which has a capacity of about 1 mL. The use of a single unit-dose container eliminates the concerns of contamination and provides the convenience of portability.

Example 7

Azelastine Hydrochloride Nasal Solution Comprising Steroid

One exemplary composition of the invention is a nasal spray formulation containing azelastine hydrochloride prepared using hypromellose as a thickener, a steroid, and sucralose as both a sweetener and a taste-masking agent.

| Ingredient | % |
|---|---|
| Azelastine Hydrochloride | 0.05-0.150 |
| Steroid (fluticasone, mometasone, dexamethasone beloxil, loteprednol (e.g., loteprednol etabonate), budesonide, or triamcinolone) | 0.01-2.0 |
| Hypromellose 2900, USP 4000 | 0.100 |
| Edetate Disodium, USP | 0.050 |
| Sorbitol 70%, USP | 6.400 |
| Sodium Citrate, USP, Dihydrate | 0.068 |
| Sucralose, NF | 0.1-0.15 |
| Benzalkonium Chloride 50% Solution, NF | 0.025 |
| Water Purified or Deionized | Q.S. to 100% |

Following preparation, the solution is packaged into high density polyethylene bottles fitted with a screw cap and comprising a VP3 metered-dose spray pump designed for intranasal application of about 0.14 ml (Valois). For use, one or two sprays can be administered to each nostril two times per day, or as prescribed.

Example 8

Azelastine Hydrochloride Nasal Solution Comprising Leukotriene Antagonist

One exemplary composition of the invention is a nasal spray formulation containing azelastine hydrochloride prepared using hypromellose as a thickener, a leukotriene antagonist, and sucralose as both a sweetener and a taste-masking agent.

| Ingredient | % |
| --- | --- |
| Azelastine Hydrochloride | 0.05-0.150 |
| Leukotriene antagonist (montelukast) | 0.1-5.0 |
| Hypromellose 2900, USP 4000 | 0.100 |
| Edetate Disodium, USP | 0.050 |
| Sorbitol 70%, USP | 6.400 |
| Sodium Citrate, USP, Dihydrate | 0.068 |
| Sucralose, NF | 0.1-0.15 |
| Benzalkonium Chloride 50% Solution, NF | 0.025 |
| Water Purified or Deionized | Q.S. to 100% |

Following preparation, the solution is packaged into high density polyethylene bottles fitted with a screw cap and comprising a VP3 metered-dose spray pump designed for intranasal application of about 0.14 ml (Valois). For use, one or two sprays can be administered to each nostril two times per day, or as prescribed.

Example 9

Azelastine Hydrochloride Nasal Solution Comprising Decongestant

One exemplary composition of the invention is a nasal spray formulation containing azelastine hydrochloride prepared using hypromellose as a thickener, a decongestant, and sucralose as both a sweetener and a taste-masking agent.

| Ingredient | % |
| --- | --- |
| Azelastine Hydrochloride | 0.05-0.150 |
| Decongestant (pseudoephedrine or phenylephrine) | 0.1-2.0 |
| Hypromellose 2900, USP 4000 | 0.100 |
| Edetate Disodium, USP | 0.050 |
| Sorbitol 70%, USP | 6.400 |
| Sodium Citrate, USP, Dihydrate | 0.068 |
| Optionally, Sucralose, NF | 0.1-0.15 |
| Benzalkonium Chloride 50% Solution, NF | 0.025 |
| Water Purified or Deionized | Q.S. to 100% |

Following preparation, the solution is packaged into high density polyethylene bottles fitted with a screw cap and comprising a VP3 metered-dose spray pump designed for intranasal application of about 0.14 ml (Valois). For use, one or two sprays can be administered to each nostril two times per day, or as prescribed.

Example 10

Azelastine Hydrochloride Nasal Solution Comprising NSAID

One exemplary composition of the invention is a nasal spray formulation containing azelastine hydrochloride prepared using hypromellose as a thickener, an NSAID, and sucralose as both a sweetener and a taste-masking agent.

| Ingredient | % |
| --- | --- |
| Azelastine Hydrochloride | 0.05-0.150 |
| NSAID (ibuprofen, diclofenac, aceclofenac or naproxen) | 0.1-10.0 |
| Hypromellose 2900, USP 4000 | 0.100 |
| Edetate Disodium, USP | 0.050 |
| Sorbitol 70%, USP | 6.400 |
| Sodium Citrate, USP, Dihydrate | 0.068 |
| Optionally, Sucralose, NF | 0.1-0.15 |
| Benzalkonium Chloride 50% Solution, NF | 0.025 |
| Water Purified or Deionized | Q.S. to 100% |

Following preparation, the solution is packaged into high density polyethylene bottles fitted with a screw cap and comprising a VP3 metered-dose spray pump designed for intranasal application of about 0.14 ml (Valois). For use, one or two sprays can be administered to each nostril two times per day, or as prescribed.

Example 11

Azelastine Hydrochloride Nasal Solution Comprising Steroid and Decongestant

One exemplary composition of the invention is a nasal spray formulation containing azelastine hydrochloride prepared using hypromellose as a thickener, a steroid, a decongestant, and sucralose as both a sweetener and a taste-masking agent.

| Ingredient | % |
| --- | --- |
| Azelastine Hydrochloride | 0.05-0.150 |
| Steroid (fluticasone, mometasone, dexamethasone beloxil, loteprednol (e.g., loteprednol etabonate), budesonide, or triamcinolone) | 0.01-2.0 |
| Decongestant (pseudoephedrine or phenylephrine) | 0.1-1.0 |
| Hypromellose 2900, USP 4000 | 0.100 |
| Edetate Disodium, USP | 0.050 |
| Sorbitol 70%, USP | 6.400 |
| Sodium Citrate, USP, Dihydrate | 0.068 |
| Optionally, Sucralose, NF | 0.1-0.15 |
| Benzalkonium Chloride 50% Solution, NF | 0.025 |
| Water Purified or Deionized | Q.S. to 100% |

Following preparation, the composition is packaged into high density polyethylene bottles fitted with a screw cap and comprising a VP3 metered-dose spray pump designed for intranasal application of about 0.14 ml (Valois). For use, one or two sprays can be administered to each nostril two times per day, or as prescribed.

Example 12

Azelastine Hydrochloride Nasal Solution Comprising Steroid and Leukotriene antagonist One exemplary composition of the invention is a nasal spray formulation containing azelastine hydrochloride prepared using hypromellose as a thickener, steroid, a leukotriene antagonist, and sucralose as both a sweetener and a taste-masking agent.

| Ingredient | % |
| --- | --- |
| Azelastine Hydrochloride | 0.05-0.150 |
| Steroid (fluticasone, mometasone, dexamethasone beloxil, loteprednol (e.g., loteprednol etabonate), budesonide, or triamcinolone) | 0.01-2.0 |
| Leukotriene antagonist (montelukast) | 0.1-5.0 |
| Hypromellose 2900, USP 4000 | 0.100 |
| Edetate Disodium, USP | 0.050 |
| Sorbitol 70%, USP | 6.400 |
| Sodium Citrate, USP, Dihydrate | 0.068 |
| Optionally, Sucralose, NF | 0.1-0.15 |
| Benzalkonium Chloride 50% Solution, NF | 0.025 |
| Water Purified or Deionized | Q.S. to 100% |

Following preparation, the solution is packaged into high density polyethylene bottles fitted with a screw cap and comprising a VP3 metered-dose spray pump designed for intra-nasal application of about 0.14 ml (Valois). For use, one or two sprays can be administered to each nostril two times per day, or as prescribed.

Example 13

Co-Administration of Azelastine Hydrochloride and Fluticasone Propionate

A two-week, randomized, double-blind study, which evaluated the effects of the co-administration of ASTELIN® (azelastine hydrochloride (HCl)) and FLONASE® (fluticasone propionate) compared to either product alone in patients with seasonal allergic rhinitis (SAR) was conducted during the 2006 Texas mountain cedar season. After a 5-day placebo lead-in period, 151 patients with moderate-to-severe allergic rhinitis symptoms were randomized to either: (1) (49 total patients) ASTELIN® (azelastine hydrochloride (HCl)) plus placebo saline nasal spray 2 sprays per nostril, 15 minutes apart, twice daily (AM & PM); (2) (50 total patients) FLONASE® (fluticasone propionate) plus placebo saline nasal spray, 2 sprays per nostril, 15 minutes apart, once daily (AM) and two sessions of placebo saline nasal spray, 2 sprays per nostril, 15 minutes apart (PM); or (3) (52 total patients) the co-administration of ASTELIN® (azelastine hydrochloride (HCl)) 2 sprays per nostril plus FLONASE® (fluticasone propionate) 2 sprays per nostril (AM), 15 minutes apart, and ASTELIN® (azelastine hydrochloride (HCl)) 2 sprays per nostril plus placebo saline nasal spray, 15 minutes apart, (PM) for a 2-week double-blind treatment period.

The primary efficacy variable was the change from baseline in the Total Nasal Symptom Score (TNSS), which comprised sneezing, itchy nose, runny nose, and nasal congestion (individual symptoms scores were assigned a value between 0 and 3, where 0=no symptoms and 3=severe symptoms). This study was not statistically designed to assess the differences between ASTELIN® and FLONASE®.

The most common adverse events (AEs) were bitter taste (8.2% in ASTELIN® (azelastine hydrochloride (HCl)) group, 2.0% in FLONASE® (fluticasone propionate) group, 13.5% in co-administration group) and headache (4.1% in ASTELIN® (azelastine hydrochloride (HCl)) group, 4.0% in FLONASE® (fluticasone propionate) group, 5.8% in co-administration group). No other AE was reported by more than one patient in any treatment group. There were no discontinuations due to AEs. The significantly higher bitter taste AE score for the co-administration group versus that seen in the groups receiving either agent alone indicates that inclusion of a taste-masking agent, such as sucralose, in the pharmaceutical formulations (whether formulations of each agent alone, or a single formulation containing both agents) is highly desired, to enhance patient compliance and thereby maximize therapeutic benefit.

Figure 6:
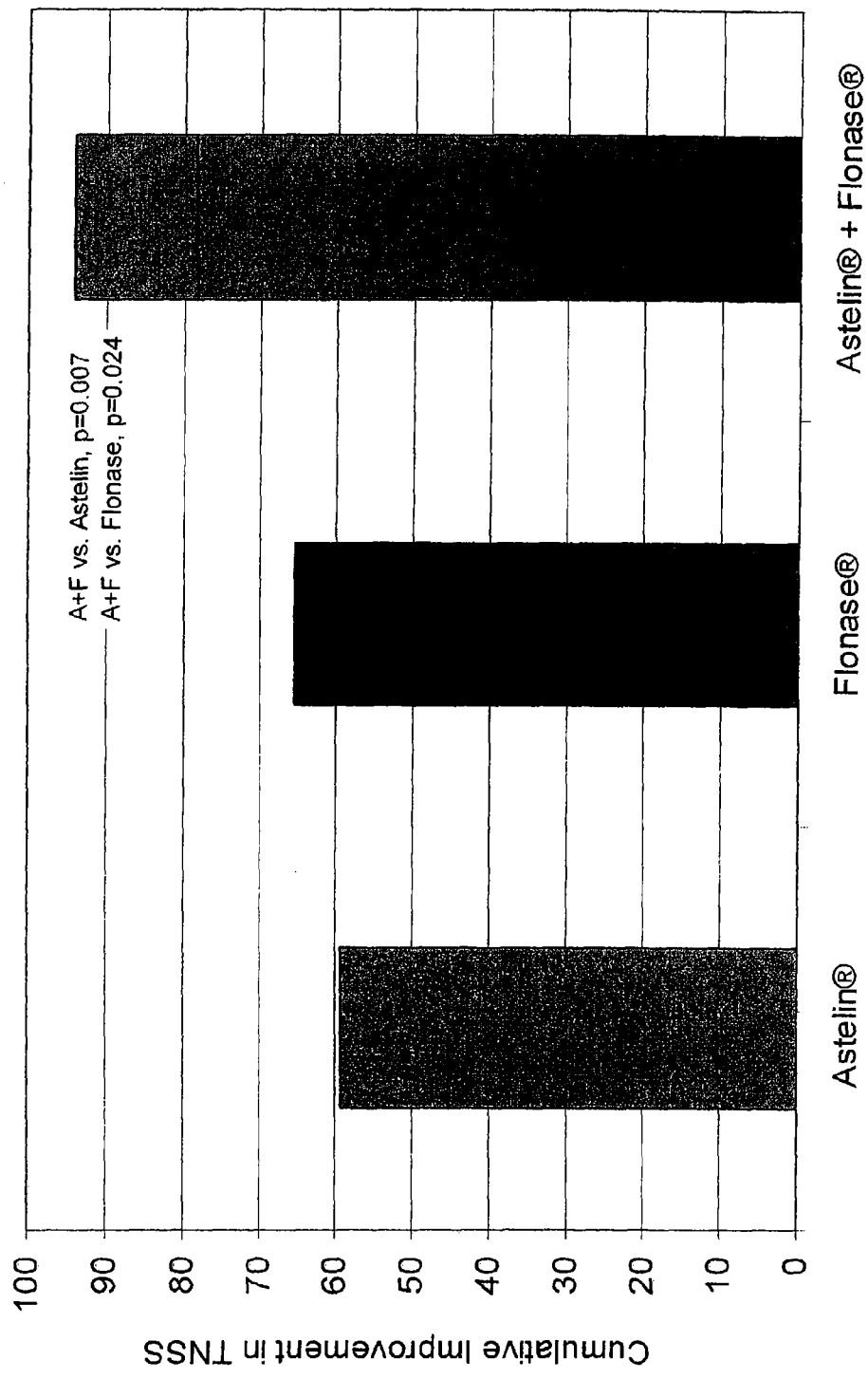
FIG. 6 shows the cumulative improvement in total nasal symptom score versus baseline, resulting from the co-administration of azelastine HCl and fluticasone propionate.

The results of the clinical trial are summarized and presented in Appendix A hereinbelow and in FIGS. 1-6. FIG. 1 shows the effect on the total nasal symptom score (TNSS) for all three treatment groups. The co-administration of (azelastine hydrochloride (HCl)) and (fluticasone propionate) demonstrated a reduction in the TNSS versus either agent alone. FIGS. 2-5 show the mean improvement in severity score (0-3 scale) from baseline for the symptoms of runny nose, itchy nose, sneezing and congestion, respectively. In all cases, the co-administration of (azelastine hydrochloride (HCl)) and (fluticasone propionate) demonstrated a reduction in the severity of the symptom versus either agent alone. FIG. 6 shows the cumulative improvement in TNSS versus baseline using area under the curve (AUC) units, indicating a greater than 40% improvement in TNSS versus either active agent alone. Taken together, these results demonstrate that a significant and unexpected therapeutic benefit is obtained by co-administration of azelastine HCl and fluticasone propionate, beyond the response that was expected based on therapeutic results observed by administration of either agent alone.

A number of studies have examined the additive benefit of combining a nasal steroid with an oral antihistamine or a leukotriene antagonist in rhinitis (Juniper et al., J. Allergy Clin. Immunol. 83(3):627-633 (1989); Ratner et al., J. Fam. Pract. 47(2):118-125 (1998); Simpson, R. J., Ann. Allergy 73(6):497-502 (1994); Backhouse et al., J. Int. Med. Res. 14(1):35-41 (1986); Juniper et al., CMAJ 156(8):1123-1131 (1997); Barnes et al., Clin. Exp. Allergy 36(5):676-684 (May 2006); Di Lorenzo et al., Clin. Exp. Allergy 34(2):259-67 (2004)). The majority of these studies showed that the combination of an oral rhinitis agent with a nasal steroid was no better, with respect to improvement in symptoms and total symptom scores, than the nasal steroid alone; a few of the studies demonstrated only minimal improvement. For example, in a study examining the administration of fluticasone propionate and loratadine alone or in combination, no incremental benefit was observed in TNSS (itchy nose, sneezing, runny nose, nasal congestion) or Rhinitis Quality of Life Questionnaire (RQLQ) when comparing the combination of these agents versus fluticasone propionate alone (Ratner et al., J. Fam. Pract. 47(2):118-125 (1998)). In another study, the addition of levocetirizine to fluticasone propionate did not provide incremental relief in TNSS, RQLQ or peak nasal inspiratory flow relative to results with fluticasone propionate alone (Barnes et al., Clin. Exp. Allergy 36(5):676-684 (May 2006)). In a study examining the effects of administration of fluticasone propionate alone versus co-administration of fluticasone with cetirizine or montelukast, no incremental improvement in TNSS was observed with the combination of fluticasone and cetirizine versus fluticasone alone; similarly, there was no incremental benefit in TNSS with the combination of fluticasone and montelukast versus fluticasone alone (Di Lorenzo et al., Clin. Exp. Allergy 34(2):259-67 (2004)). In contrast, as shown above, in the present studies administration of ASTELIN® brand azelastine HCl nasal spray in combination with fluticasone propionate demonstrated a magnitude of response that is both clinically meaningful and statistically superior to the individual components.

Example 14

Unit Dose Azelastine Hydrochloride Ocular Solution

In one exemplary composition provided by the present invention, a unit dose ocular formulation containing azelastine hydrochloride was prepared using hypromellose as a thickener, sorbitol as an isotonicity agent, and including sucralose as a taste-masking agent:

| Ingredient | % (w/v) |
|---|---|
| Azelastine Hydrochloride | 0.050 |
| Hypromellose 2900, USP 4000 | 0.100 |
| Edetate Disodium, USP | 0.050 |
| Sucralose, NF | 0.150 |
| Sorbitol Solution 70%, USP | 6.667 |
| Benzalkonium Chloride 50%, NF | 0.025 |
| Water Purified or Deionized | Q.S. to 100% |

Following preparation, the composition was aseptically filtered, and was packaged using a "blow-fill-seal" packaging approach into high density polyethylene (HDPE) containers such as those depicted in FIGS. 7-8, at a volume of approximately 0.24 ml per container into the unit dosage containers that had a volume of approximately 1 ml.

The thickness of the walls of the container were optimized so as to allow squeezability to ensure delivery of the appropriate amount of the formulation.

For use, one drop was instilled into each affected eye twice a day, or as prescribed. Following a single use (defined as application of the appropriate number of drops into each eye from a single unit dose container), the container was discarded such that for the next application, a new unit dose container was used. Thus, two separate single unit dose containers were used per day per patient, one for the first dosing and one for the second dosing.

Example 15

Preservative Free Ocular Solution for Unit Dose

Another exemplary composition provided by the present invention is a liquid dosage formulation containing azelastine hydrochloride prepared using hypromellose as a thickener and optionally using one or more taste-masking agents (e.g., sucralose and/or menthol), but without the inclusion of any preservative:

| Ingredient | % |
|---|---|
| Azelastine Hydrochloride | 0.0500-.150 |
| Hypromellose 2900, USP 4000 | 0.300 |
| Edetate Disodium, USP | 0.050 |
| Sodium Citrate, USP, Dihydrate | 0.068 |
| Sucralose, NF | 0.050-0.150 |
| Sorbitol Solution 70%, USP | 6.667 |
| Propylene Glycol, USP | 1.895 |
| Water Purified or Deionized | Q.S. to 100% |

Following preparation, the solution was filtered, and packaged into high density polyethylene containers. Such compositions are particularly amenable for use in the unit dose configurations provided by the present invention since upon single use the container and any residual pharmaceutical composition contained therein is discarded. Thus, in this exemplary embodiment, an approximate unit dose volume of about 0.25 ml to about 0.5 ml was filled into each low volume HDPE container using the "blow-fill-seal" approach described in Example 14 herein. For use, one drop was instilled into each affected eye twice a day, or as prescribed. Following a single use (defined as application of the appropriate number of drops into each eye from a single unit dose container), the container was discarded such that for the next application, a new unit dose container was used. The use of a single unit-dose container eliminates the concerns of contamination (which is particularly important for preservative-free compositions such as those described in this Example), and provides the convenience of portability; both of these aspects have been found to improve patient compliance with prescribing regimens in the treatment of allergic ocular conditions such as allergic conjunctivitis associated with seasonal, vasomotor or perennial allergies.

APPENDIX A

MedPoints Pharmaceuticals
MP 428                                                                                                          Program: PATDISP.SAS
14.1.1 Patient Disposition
All Randomized Patients
(Page 1 of 1)

|  | Azelastine | Fluticasone | Azelastine + Fluticasone | Total |
|---|---|---|---|---|
| All Randomized Patients (N) | 49 | 50 | 52 | 151 |
| Number of Patients Who Completed Study [N (%)] | 49 (100.0) | 48 (96.0) | 50 (96.2) | 147 (97.4) |
| Number of Patients Who Discontinued Study [N (%)] | 0 (0.0) | 2 (4.0) | 2 (3.8) | 4 (2.6) |
| Primary Reason for Discontinuation From Study [N (%)] |  |  |  |  |
| Adverse Event | 0 (0.0) | 0 (0.0) | 0 (0.0) | 0 (0.0) |
| Treatment Failure | 0 (0.0) | 1 (2.0) | 0 (0.0) | 1 (0.7) |
| Non-Compliance | 0 (0.0) | 0 (0.0) | 2 (3.8) | 2 (1.3) |
| Patient Withdrew Consent | 0 (0.0) | 1 (2.0) | 0 (0.0) | 1 (0.7) |
| Lost to Follow-Up | 0 (0.0) | 0 (0.0) | 0 (0.0) | 0 (0.0) |
| Administrative Problems | 0 (0.0) | 0 (0.0) | 0 (0.0) | 0 (0.0) |
| Other | 0 (0.0) | 0 (0.0) | 0 (0.0) | 0 (0.0) |
| Safety Population[a] [N (%)] | 49 (100.0) | 50 (100.0) | 52 (100.0) | 151 (100.0) |
| Intent-to-Treat Population[b] [N (%)] | 49 (100.0) | 50 (100.0) | 52 (100.0) | 151 (100.0) |
| Per-Protocol Population[c] [N (%)] | 49 (100.0) | 47 (94.0) | 48 (92.3) | 144 (95.4) |

[a]Safety Population includes all randomized patients who took at least one dose of the study drug.
[b]Intent-to-Treat Population (ITT) includes all patients who were randomized and had at least one postbaseline observation.
[c]Per-Protocol Population includes all patients who completed the 2-week treatment period per protocol.
Note:
all percentages are based on all randomized patients shown in the same column.
Reference: 16.2.1

MedPointe Pharmaceuticals  
MP 428  
Program: DEMOG.SAS 14.1.2.1 Patient Demographics and Baseline Characteristics  
Intent-to-Treat Population  
(Page 1 of 4)

| Demographics | Category/Statistics | Azelastine (N = 49) | Fluticasone (N = 50) | Azelastine + Fluticasone (N = 52) | Total (N = 151) |
|---|---|---|---|---|---|
| Age (Years) | N | 49 | 50 | 52 | 151 |
| | Mean | 38.4 | 37.4 | 36.0 | 37.2 |
| | Standard Deviation | 15.36 | 14.78 | 14.75 | 14.89 |
| | Median | 36.0 | 37.5 | 36.5 | 37.0 |
| | Min-Max | 12-73 | 12-72 | 13-70 | 12-73 |
| | 12 to <18 [N(%)] | 3 (6.1) | 6 (12.0) | 5 (9.6) | 14 (9.3) |
| | 18 to <65 [N(%)] | 42 (85.7) | 43 (86.0) | 45 (86.5) | 130 (86.1) |
| | 65 or older [N(%)] | 4 (8.2) | 1 (2.0) | 2 (3.8) | 7 (4.6) |
| Sex [N(%)] | Male | 22 (44.9) | 15 (30.0) | 19 (36.5) | 56 (37.1) |
| | Female | 27 (55.1) | 35 (70.0) | 33 (63.5) | 95 (62.9) |
| Race [N(%)] | Asian or Pacific Islander | 0 (0.0) | 3 (6.0) | 1 (1.9) | 4 (2.6) |
| | Hispanic or Latino | 7 (14.3) | 13 (26.0) | 8 (15.4) | 28 (18.5) |
| | Black or African American | 5 (10.2) | 2 (4.0) | 2 (3.8) | 9 (6.0) |
| | American Indian or Alaska Native | 0 (0.0) | 0 (0.0) | 0 (0.0) | 0 (0.0) |
| | White or Caucasian | 36 (73.5) | 32 (64.0) | 41 (78.8) | 109 (72.2) |
| | Other | 1 (2.0) | 0 (0.0) | 0 (0.0) | 1 (0.7) |

MedPointe Pharmaceuticals  
MP 428  
Program: DEMOG.SAS 14.1.2.1 Patient Demographics and Baseline Characteristics  
Intent-to-Treat Population  
(Page 2 of 4)

| Demographics | Category/Statistics | Azelastine (N = 49) | Fluticasone (N = 50) | Azelastine + Fluticasone (N = 52) | Total (N = 151) |
|---|---|---|---|---|---|
| Height (in) | N | 49 | 50 | 52 | 151 |
| | Mean | 65.9 | 65.2 | 65.7 | 65.6 |
| | Standard Deviation | 4.45 | 4.22 | 4.33 | 4.32 |
| | Median | 65.0 | 65.0 | 65.0 | 65.0 |
| | Min-Max | 56-74 | 56-78 | 58-79 | 56-79 |
| Height (in) (Age 12 to <18 Years) | N | 3 | 6 | 5 | 14 |
| | Mean | 59.7 | 63.2 | 63.2 | 62.4 |
| | Standard Deviation | 1.53 | 4.45 | 4.06 | 3.91 |
| | Median | 60.0 | 63.5 | 61.0 | 61.0 |
| | Min-Max | 58-61 | 56-69 | 59-68 | 56-69 |
| Height (in) (Age ≥18 Years) | N | 46 | 44 | 47 | 137 |
| | Mean | 66.3 | 65.5 | 66.0 | 65.9 |
| | Standard Deviation | 4.28 | 4.17 | 4.32 | 4.24 |
| | Median | 65.0 | 65.0 | 65.0 | 65.0 |
| | Min-Max | 56-74 | 56-78 | 58-79 | 56-79 |

MedPointe Pharmaceuticals  
MP 428  
Program: DEMOG.SAS 14.1.2.1 Patient Demographics and Baseline Characteristics  
Intent-to-Treat Population  
(Page 3 of 4)

| Demographics | Category/Statistics | Azelastine (N = 49) | Fluticasone (N = 50) | Azelastine + Fluticasone (N = 52) | Total (N = 151) |
|---|---|---|---|---|---|
| Weight (lb) | N | 49 | 50 | 52 | 151 |
| | Mean | 181.2 | 172.9 | 173.8 | 175.9 |
| | Standard Deviation | 47.09 | 40.42 | 51.05 | 46.30 |
| | Median | 174.0 | 168.5 | 162.5 | 169.0 |
| | Min-Max | 98-284 | 85-269 | 99-303 | 85-303 |
| Weight (lb) (Age 12 to <18 Years) | N | 3 | 6 | 5 | 14 |
| | Mean | 104.7 | 136.3 | 128.1 | 126.6 |
| | Standard Deviation | 7.02 | 46.66 | 21.20 | 33.75 |
| | Median | 104.0 | 122.5 | 121.4 | 118.0 |
| | Min-Max | 98-112 | 85-199 | 108-163 | 85-199 |

| | | | | | |
|---|---|---|---|---|---|
| Weight (lb) | N | 46 | 44 | 47 | 137 |
| (Age ≥18 Years) | Mean | 186.2 | 177.9 | 178.6 | 180.9 |
| | Standard Deviation | 44.12 | 37.37 | 50.99 | 44.49 |
| | Median | 177.8 | 169.5 | 169.0 | 171.0 |
| | Min-Max | 102-284 | 117-269 | 99-303 | 99-303 |

MedPointe Pharmaceuticals
MP 428　　　　　　　　　　　　　　　　　　　　　　　　　　　　　　　　Program: DEMOG.SAS 14.1.2.1 Patient Demographics and Baseline Characteristics
Intent-to-Treat Population
(Page 4 of 4)

| Demographics | Category/Statistics | Azelastine (N = 49) | Fluticasone (N = 50) | Azelastine + Fluticasone (N = 52) | Total (N = 151) |
|---|---|---|---|---|---|
| Total Score[a] | N | 49 | 50 | 52 | 151 |
| | Mean | 19.6 | 19.5 | 19.5 | 19.5 |
| | Standard Deviation | 2.11 | 2.74 | 2.97 | 2.62 |
| | Median | 19.7 | 19.4 | 19.5 | 19.7 |
| | Min-Max | 15-24 | 14-24 | 13-24 | 13-24 |
| Duration of Texas Mountain | N | 49 | 50 | 52 | 151 |
| Cedar Allergy (Years) | Mean | 19.2 | 15.7 | 16.2 | 17.0 |
| | Standard Deviation | 13.32 | 9.69 | 9.15 | 10.87 |
| | Median | 16.0 | 14.0 | 13.5 | 14.0 |
| | Min-Max | 3-50 | 3-51 | 4-40 | 3-51 |

[a]Mean baseline TNSS over 5-day Lead-in Period, including Day 1 AM.
References: 16.2.4.1 and 16.2.6.1

MedPointe Pharmaceuticals
MP 428　　　　　　　　　　　　　　　　　　　　　　　　　　　　　　　　Program: DEMOG.SAS 14.1.2.2 Patient Demographics and Baseline Characteristics
Per-Protocol Population
(Page 1 of 4)

| Demographics | Category/Statistics | Azelastine (N = 49) | Fluticasone (N = 47) | Azelastine + Fluticasone (N = 48) | Total (N = 144) |
|---|---|---|---|---|---|
| Age (Years) | N | 49 | 47 | 48 | 144 |
| | Mean | 38.4 | 35.9 | 35.8 | 36.7 |
| | Standard Deviation | 15.36 | 13.89 | 15.09 | 14.75 |
| | Median | 36.0 | 37.0 | 36.0 | 36.0 |
| | Min-Max | 12-73 | 12-61 | 13-70 | 12-73 |
| | 12 to <18 [N(%)] | 3 (6.1) | 6 (12.8) | 5 (10.4) | 14 (9.7) |
| | 18 to <65 [N(%)] | 42 (85.7) | 41 (87.2) | 41 (85.4) | 124 (86.1) |
| | 65 or older [N(%)] | 4 (8.2) | 0 (0.0) | 2 (4.2) | 6 (4.2) |
| Sex [N(%)] | Male | 22 (44.9) | 15 (31.9) | 19 (39.6) | 56 (38.9) |
| | Female | 27 (55.1) | 32 (68.1) | 29 (60.4) | 88 (61.1) |
| Race [N(%)] | Asian or Pacific Islander | 0 (0.0) | 3 (6.4) | 1 (2.1) | 4 (2.8) |
| | Hispanic or Latino | 7 (14.3) | 13 (27.7) | 6 (12.5) | 26 (18.1) |
| | Black or African American | 5 (10.2) | 2 (4.3) | 2 (4.2) | 9 (6.3) |
| | American Indian or Alaska Native | 0 (0.0) | 0 (0.0) | 0 (0.0) | 0 (0.0) |
| | White or Caucasian | 36 (73.5) | 29 (61.7) | 39 (81.3) | 104 (72.2) |
| | Other | 1 (2.0) | 0 (0.0) | 0 (0.0) | 1 (0.7) |

MedPointe Pharmaceuticals
MP 428　　　　　　　　　　　　　　　　　　　　　　　　　　　　　　　　Program: DEMOG.SAS 14.1.2.2 Patient Demographics and Baseline Characteristics
Per-Protocol Population
(Page 2 of 4)

| Demographics | Category/Statistics | Azelastine (N = 49) | Fluticasone (N = 47) | Azelastine + Fluticasone (N = 48) | Total (N = 144) |
|---|---|---|---|---|---|
| Height (in) | N | 49 | 47 | 48 | 144 |
| | Mean | 65.9 | 65.1 | 65.9 | 65.6 |
| | Standard Deviation | 4.45 | 4.33 | 4.28 | 4.34 |
| | Median | 65.0 | 65.0 | 65.2 | 65.0 |
| | Min-Max | 56-74 | 56-78 | 59-79 | 56-79 |

| | | | | | |
|---|---|---|---|---|---|
| Height (in) | N | 3 | 6 | 5 | 14 |
| (Age 12 to <18 Years) | Mean | 59.7 | 63.2 | 63.2 | 62.4 |
| | Standard Deviation | 1.53 | 4.45 | 4.06 | 3.91 |
| | Median | 60.0 | 63.5 | 61.0 | 61.0 |
| | Min-Max | 58-61 | 56-69 | 59-68 | 56-69 |
| Height (in) | N | 46 | 41 | 43 | 130 |
| (Age ≥18 Years) | Mean | 66.3 | 65.4 | 66.2 | 66.0 |
| | Standard Deviation | 4.28 | 4.30 | 4.25 | 4.26 |
| | Median | 65.0 | 65.0 | 65.4 | 65.0 |
| | Min-Max | 56-74 | 56-78 | 60-79 | 56-79 |

MedPointe Pharmaceuticals  
MP 428  
Program: DEMOG.SAS 14.1.2.2 Patient Demographics and Baseline Characteristics  
Per-Protocol Population  
(Page 3 of 4)

| Demographics | Category/Statistics | Azelastine (N = 49) | Fluticasone (N = 47) | Azelastine + Fluticasone (N = 48) | Total (N = 144) |
|---|---|---|---|---|---|
| Weight (lb) | N | 49 | 47 | 48 | 144 |
| | Mean | 181.2 | 173.4 | 174.0 | 176.3 |
| | Standard Deviation | 47.09 | 40.95 | 50.53 | 46.21 |
| | Median | 174.0 | 169.0 | 162.5 | 169.5 |
| | Min-Max | 98-284 | 85-269 | 108-303 | 85-303 |
| Weight (lb) | N | 3 | 6 | 5 | 14 |
| (Age 12 to <18 Years) | Mean | 104.7 | 136.3 | 128.1 | 126.6 |
| | Standard Deviation | 7.02 | 46.66 | 21.20 | 33.75 |
| | Median | 104.0 | 122.5 | 121.4 | 118.0 |
| | Min-Max | 98-112 | 85-199 | 108-163 | 85-199 |
| Weight (lb) | N | 46 | 41 | 43 | 130 |
| (Age ≥18 Years) | Mean | 186.2 | 178.9 | 179.3 | 181.6 |
| | Standard Deviation | 44.12 | 37.68 | 50.34 | 44.23 |
| | Median | 177.8 | 170.0 | 169.0 | 172.5 |
| | Min-Max | 102-284 | 117-269 | 115-303 | 102-303 |

MedPointe Pharmaceuticals  
MP 428  
Program: DEMOG.SAS 14.1.2.2 Patient Demographics and Baseline Characteristics  
Per-Protocol Population  
(Page 4 of 4)

| Demographics | Category/Statistics | Azelastine (N = 49) | Fluticasone (N = 47) | Azelastine + Fluticasone (N = 48) | Total (N = 144) |
|---|---|---|---|---|---|
| Total Score[a] | N | 49 | 47 | 48 | 144 |
| | Mean | 19.6 | 19.5 | 19.3 | 19.5 |
| | Standard Deviation | 2.11 | 2.74 | 2.97 | 2.62 |
| | Median | 19.7 | 19.2 | 18.8 | 19.5 |
| | Min-Max | 15-24 | 14-24 | 13-24 | 13-24 |
| Duration of Texas Mountain | N | 49 | 47 | 48 | 144 |
| Cedar Allergy (Years) | Mean | 19.2 | 14.5 | 16.5 | 16.8 |
| | Standard Deviation | 13.32 | 8.14 | 9.38 | 10.65 |
| | Median | 16.0 | 14.0 | 14.0 | 14.0 |
| | Min-Max | 3-50 | 3-36 | 4-40 | 3-50 |

[a] Mean baseline TNSS over 5-day Lead-in Period, including Day 1 AM.  
References: 16.2.4.1 and 16.2.6.1

MedPointe Pharmaceuticals  
MP 428  
Program: RHINITIS.SAS 14.1.3 Rhinitis Diagnosis Screening Results  
Intent-to-Treat Population  
(Page 1 of 6)

| Background | Category/Statistics | Azelastine (N = 49) | Fluticasone (N = 50) | Azelastine + Fluticasone (N = 52) | Total (N = 151) |
|---|---|---|---|---|---|
| Current Age (Years) | N | 45 | 44 | 47 | 136 |
| | Mean | 40.5 | 40.6 | 38.3 | 39.8 |
| | Standard Deviation | 14.24 | 12.58 | 13.65 | 13.46 |
| | Median | 42.0 | 39.0 | 38.0 | 39.0 |
| | Min-Max | 18-73 | 18-72 | 18-70 | 18-73 |

-continued

| | | | | | |
|---|---|---|---|---|---|
| Age of Symptoms Onset (Years) | N | 45 | 44 | 47 | 136 |
| | Mean | 21.3 | 23.6 | 20.4 | 21.7 |
| | Standard Deviation | 13.51 | 12.14 | 12.58 | 12.73 |
| | Median | 17.0 | 23.5 | 20.0 | 19.0 |
| | Min-Max | 3-57 | 1-50 | 1-51 | 1-57 |
| Parental History of Allergy [N(%)] | N | 45 (91.8) | 44 (88.0) | 47 (90.4) | 136 (90.1) |
| | Yes | 23 (46.9) | 15 (30.0) | 21 (40.4) | 59 (39.1) |
| | No | 11 (22.4) | 9 (18.0) | 13 (25.0) | 33 (21.9) |
| | Don't Know | 11 (22.4) | 20 (40.0) | 13 (25.0) | 44 (29.1) |
| Parent History of Asthma [N(%)] | N | 45 (91.8) | 44 (88.0) | 47 (90.4) | 136 (90.1) |
| | Yes | 6 (12.2) | 4 (8.0) | 9 (17.3) | 19 (12.6) |
| | No | 30 (61.2) | 30 (60.0) | 34 (65.4) | 94 (62.3) |
| | Don't Know | 9 (18.4) | 10 (20.0) | 4 (7.7) | 23 (15.2) |

MedPointe Pharmaceuticals  
MP 428  
Program: RHINITIS.SAS 14.1.3 Rhinitis Diagnosis Screening Results  
Intent-to-Treat Population  
(Page 2 of 6)

| Background | Category/Statistics | Azelastine (N = 49) | Fluticasone (N = 50) | Azelastine + Fluticasone (N = 52) | Total (N = 151) |
|---|---|---|---|---|---|
| Symptoms Experienced [N(%)] | N | 45 (91.8) | 44 (88.0) | 47 (90.4) | 136 (90.1) |
| (All symptoms that apply) | Sneezing | 43 (87.8) | 39 (78.0) | 46 (88.5) | 128 (84.8) |
| | Stuffy Nose | 41 (83.7) | 43 (86.0) | 47 (90.4) | 131 (86.8) |
| | Runny Nose | 42 (85.7) | 39 (78.0) | 45 (86.5) | 126 (83.4) |
| | Postnasal Drainage | 41 (83.7) | 40 (80.0) | 42 (80.8) | 123 (81.5) |
| | Itchy/watery Eyes | 42 (85.7) | 42 (84.0) | 43 (82.7) | 127 (84.1) |
| | Ear Plugging | 27 (55.1) | 26 (52.0) | 26 (50.0) | 79 (52.3) |
| | Sinus Pressure | 37 (75.5) | 35 (70.0) | 39 (75.0) | 111 (73.5) |

MedPointe Pharmaceuticals  
MP 428  
Program: RHINITIS.SAS 14.1.3 Rhinitis Diagnosis Screening Results  
Intent-to-Treat Population  
(Page 3 of 6)

| Allergic Triggers [N(%)] | Category/Statistics | Azelastine (N = 49) | Fluticasone (N = 50) | Azelastine + Fluticasone (N = 52) | Total (N = 151) |
|---|---|---|---|---|---|
| Cat or Cat Hair | N | 45 (91.8) | 44 (88.0) | 47 (90.4) | 136 (90.1) |
| | Yes | 16 (32.7) | 17 (34.0) | 27 (51.9) | 60 (39.7) |
| | No | 20 (40.8) | 13 (26.0) | 15 (28.8) | 48 (31.8) |
| | Don't Know | 9 (18.4) | 14 (28.0) | 5 (9.6) | 28 (18.5) |
| Dog or Dog Hair | N | 45 (91.8) | 44 (88.0) | 47 (90.4) | 136 (90.1) |
| | Yes | 12 (24.5) | 11 (22.0) | 15 (28.8) | 38 (25.2) |
| | No | 30 (61.2) | 27 (54.0) | 27 (51.9) | 84 (55.6) |
| | Don't Know | 3 (6.1) | 6 (12.0) | 5 (9.6) | 14 (9.3) |
| Other Furry Animals | N | 45 (91.8) | 44 (88.0) | 47 (90.4) | 136 (90.1) |
| | Yes | 6 (12.2) | 9 (18.0) | 13 (25.0) | 28 (18.5) |
| | No | 22 (44.9) | 21 (42.0) | 22 (42.3) | 65 (43.0) |
| | Don't Know | 17 (34.7) | 14 (28.0) | 12 (23.1) | 43 (28.5) |
| Symptoms During Spring Summer, or Fall | N | 45 (91.8) | 44 (88.0) | 47 (90.4) | 136 (90.1) |
| | Yes | 39 (79.6) | 38 (76.0) | 39 (75.0) | 116 (76.8) |
| | No | 5 (10.2) | 3 (6.0) | 6 (11.5) | 14 (9.3) |
| | Don't Know | 1 (2.0) | 3 (6.0) | 2 (3.8) | 6 (4.0) |
| Any Allergic Triggers | N | 45 (91.8) | 44 (88.0) | 47 (90.4) | 136 (90.1) |
| | Yes | 42 (85.7) | 41 (82.0) | 44 (84.6) | 127 (84.1) |
| | No | 3 (6.1) | 3 (6.0) | 3 (5.8) | 9 (6.0) |
| | Don't Know | 0 (0.0) | 0 (0.0) | 0 (0.0) | 0 (0.0) |

MedPointe Pharmaceuticals  
MP 428  
Program: RHINITIS.SAS 14.1.3 Rhinitis Diagnosis Screening Results  
Intent-to-Treat Population  
(Page 4 of 6)

| Non-allergic Triggers [N(%)] | Category/Statistics | Azelastine (N = 49) | Fluticasone (N = 50) | Azelastine + Fluticasone (N = 52) | Total (N = 151) |
|---|---|---|---|---|---|
| Temperature or Humidity Changes | N | 45 (91.8) | 44 (88.0) | 47 (90.4) | 136 (90.1) |
| | Yes | 30 (61.2) | 29 (58.0) | 33 (63.5) | 92 (60.9) |
| | No | 7 (14.3) | 9 (18.0) | 5 (9.6) | 21 (13.9) |
| | Don't Know | 8 (16.3) | 6 (12.0) | 9 (17.3) | 23 (15.2) |

| | | | | | |
|---|---|---|---|---|---|
| Smoke | N | 45 (91.8) | 44 (88.0) | 47 (90.4) | 136 (90.1) |
| | Yes | 25 (51.0) | 22 (44.0) | 27 (51.9) | 74 (49.0) |
| | No | 14 (28.6) | 18 (36.0) | 16 (30.8) | 48 (31.8) |
| | Don't Know | 6 (12.2) | 4 (8.0) | 4 (7.7) | 14 (9.3) |
| Perfumes or Fragrances | N | 45 (91.8) | 44 (88.0) | 47 (90.4) | 136 (90.1) |
| | Yes | 24 (49.0) | 24 (48.0) | 19 (36.5) | 67 (44.4) |
| | No | 19 (38.8) | 16 (32.0) | 22 (42.3) | 57 (37.7) |
| | Don't Know | 2 (4.1) | 4 (8.0) | 6 (11.5) | 12 (7.9) |
| Incense or Candles | N | 45 (91.8) | 44 (88.0) | 47 (90.4) | 136 (90.1) |
| | Yes | 13 (26.5) | 22 (44.0) | 12 (23.1) | 47 (31.1) |
| | No | 28 (57.1) | 18 (36.0) | 29 (55.8) | 75 (49.7) |
| | Don't Know | 4 (8.2) | 4 (8.0) | 6 (11.5) | 14 (9.3) |
| Household Cleaning Products | N | 45 (91.8) | 44 (88.0) | 47 (90.4) | 136 (90.1) |
| | Yes | 16 (32.7) | 20 (40.0) | 18 (34.6) | 54 (35.8) |
| | No | 23 (46.9) | 22 (44.0) | 24 (46.2) | 69 (45.7) |
| | Don't Know | 6 (12.2) | 2 (4.0) | 5 (9.6) | 13 (8.6) |

MedPointe Pharmaceuticals  
MP 428  Program: RHINITIS.SAS  
14.1.3 Rhinitis Diagnosis Screening Results  
Intent-to-Treat Population  
(Page 5 of 6)

| Non-allergic Triggers [N(%)] | Category/Statistics | Azelastine (N = 49) | Fluticasone (N = 50) | Azelastine + Fluticasone (N = 52) | Total (N = 151) |
|---|---|---|---|---|---|
| Any Non-allergic Triggers | N | 45 (91.8) | 44 (88.0) | 47 (90.4) | 136 (90.1) |
| | Yes | 42 (85.7) | 39 (78.0) | 39 (75.0) | 120 (79.5) |
| | No | 3 (6.1) | 5 (10.0) | 7 (13.5) | 15 (9.9) |
| | Don't Know | 0 (0.0) | 0 (0.0) | 1 (1.9) | 1 (0.7) |

MedPointe Pharmaceuticals  
MP 428  Program: RHINITIS.SAS  
14.1.3 Rhinitis Diagnosis Screening Results  
Intent-to-Treat Population  
(Page 6 of 6)

| Drugs That Symptoms Responded Well in the Past [N(%)] | Category/Statistics | Azelastine (N = 49) | Fluticasone (N = 50) | Azelastine + Fluticasone (N = 52) | Total (N = 151) |
|---|---|---|---|---|---|
| Non-Sedating Antihistamines | N | 45 (91.8) | 44 (88.0) | 47 (90.4) | 136 (90.1) |
| | No Effect | 1 (2.0) | 0 (0.0) | 0 (0.0) | 1 (0.7) |
| | Small Effect | 10 (20.4) | 7 (14.0) | 10 (19.2) | 27 (17.9) |
| | Moderate Effect | 18 (36.7) | 19 (38.0) | 21 (40.4) | 58 (38.4) |
| | Big Effect | 9 (18.4) | 11 (22.0) | 9 (17.3) | 29 (19.2) |
| | Don't Know | 7 (14.3) | 7 (14.0) | 7 (13.5) | 21 (13.9) |
| Nasal Corticosteriods | N | 45 (91.8) | 44 (88.0) | 47 (90.4) | 136 (90.1) |
| | No Effect | 1 (2.0) | 0 (0.0) | 0 (0.0) | 1 (0.7) |
| | Small Effect | 5 (10.2) | 1 (2.0) | 6 (11.5) | 12 (7.9) |
| | Moderate Effect | 11 (22.4) | 18 (36.0) | 21 (40.4) | 50 (33.1) |
| | Big Effect | 9 (18.4) | 7 (14.0) | 8 (15.4) | 24 (15.9) |
| | Don't Know | 19 (38.8) | 18 (36.0) | 12 (23.1) | 49 (32.5) |
| Nasal Antihistamines | N | 45 (91.8) | 44 (88.0) | 47 (90.4) | 136 (90.1) |
| | No Effect | 1 (2.0) | 2 (4.0) | 0 (0.0) | 3 (2.0) |
| | Small Effect | 2 (4.1) | 1 (2.0) | 2 (3.8) | 5 (3.3) |
| | Moderate Effect | 9 (18.4) | 12 (24.0) | 13 (25.0) | 34 (22.5) |
| | Big Effect | 2 (4.1) | 2 (4.0) | 2 (3.8) | 6 (4.0) |
| | Don't Know | 31 (63.3) | 27 (54.0) | 30 (57.7) | 88 (58.3) |
| The Best Response From Any of These Drugs | N | 45 (91.8) | 44 (88.0) | 47 (90.4) | 136 (90.1) |
| | No Effect | 2 (4.1) | 0 (0.0) | 0 (0.0) | 2 (1.3) |
| | Small Effect | 8 (16.3) | 2 (4.0) | 8 (15.4) | 18 (11.9) |
| | Moderate Effect | 16 (32.7) | 23 (46.0) | 22 (42.3) | 61 (40.4) |
| | Big Effect | 15 (30.6) | 15 (30.0) | 13 (25.0) | 43 (28.5) |
| | Don't Know | 4 (8.2) | 4 (8.0) | 4 (7.7) | 12 (7.9) |

Reference: 16.2.4.3

MedPointe Pharmaceuticals
MP 428    Program: DUREXPO.SAS

14.1.4 Duration of Exposure and Compliance With Study Drugs
Intent-to-Treat Population
(Page 1 of 1)

|  | Category/Statistics | Azelastine (N = 49) | Fluticasone (N = 50) | Azelastine + Fluticasone (N = 52) | Total (N = 151) |
|---|---|---|---|---|---|
| Duration of Exposure (Days) | N | 49 | 50 | 52 | 151 |
|  | Mean | 14.6 | 14.1 | 14.3 | 14.3 |
|  | Standard Deviation | 0.84 | 2.40 | 1.82 | 1.81 |
|  | Median | 15.0 | 14.0 | 15.0 | 15.0 |
|  | Min-Max | 12-16 | 1-18 | 6-19 | 1-19 |
| Total Number of Doses[a] Taken | N | 49 | 50 | 52 | 151 |
|  | Mean | 42.8 | 40.9 | 41.3 | 41.6 |
|  | Standard Deviation | 2.82 | 6.80 | 6.13 | 5.57 |
|  | Median | 44.0 | 42.0 | 42.0 | 42.0 |
|  | Min-Max | 30-47 | 3-51 | 10-47 | 3-51 |
| Number of Patients With ≥80% Compliance [N(%)] |  | 49 (100.0) | 50 (100.0) | 49 (94.2) | 148 (98.0) |

[a]Each patient recieved 3 bottles of medication at each treatment visit. Two bottles were for AM dosing and the 3$^{rd}$ bottle is for PM dosing. The patients were instructed to administer 2 sprays per nostril from each bottle once daily (3 doses total each day) at the specified time period (AM or PM) with a 15-30 minute wait between dosings from the two AM bottles.
References: 16.2.5.1 and 16.2.6.1

---

MedPointe Pharmaceuticals
MP 428    Program: REFTNSS.SAS

14.2.1.1 AUC of Change from Baseline in TNSS: AM and PM Combined
Intent-to-Treat Population
(Page 1 of 1)

| Variable Time Point | Treatment | N[a] | Mean | LS Mean[b] | Standard Deviation | Minimum | Median | Maximum | Source | ANOVA p-value[c] |
|---|---|---|---|---|---|---|---|---|---|---|
|  |  |  | TNSS (Am and PM Combined) |  |  |  |  |  |  |  |
| Baseline[d] | Azelastine (A) | 49 | 19.60 | 19.66 | 2.113 | 15.3 | 19.70 | 24.0 | Treatment | 0.957 |
|  | Fluticasone (F) | 49 | 19.53 | 19.56 | 2.771 | 13.7 | 19.17 | 24.0 |  |  |
|  | Azelastine + Fluticasone (A + F) | 52 | 19.48 | 19.51 | 2.967 | 13.1 | 19.45 | 24.0 |  |  |
|  |  |  | Change from Baseline in TNSS (AM and PM Combined) |  |  |  |  |  |  |  |
| AUC[e] | Azelastine | 49 | −60.38 | −59.72 | 54.570 | −184.5 | −56.00 | 37.7 | A vs A + F | 0.007 |
|  | Fluticasone | 49 | −64.53 | −65.00 | 58.166 | −231.3 | −51.13 | 49.7 | F vs A + F | 0.024 |
|  | Azelastine + Fluticasone | 52 | −92.21 | −92.85 | 70.981 | −261.5 | −94.50 | 57.8 | Treatment | 0.015 |

[a]Total number of intent-to-treat patients with available data.
[b]LS Mean = Least-Square Mean obtained from analysis of variance (ANOVA) model for baseline or analysis of covariance (ANCOVA) model for change.
[c]p-value for between treatment group comparison, except Baseline, was based on an ANCOVA model containing treatment group and site as fixed effects, and baseline as a covariant. For Baseline, the p-value was based on an ANOVA model containing treatment group and site as fixed effects.
[d]Mean baseline TNSS over 5-day Lead-in Period, including Day 1 AM.
[e]Area-under-the-curve of change from baseline in TNSS from Day 1 to Day 14 with the change on Day 1 set to 0. The last-observation-carried-forward method was applied for missing TNSS scores proir to calculating the AUC.
Reference: 16.2.6.1

---

MedPointe Pharmaceuticals
MP 428    Program: REFTNSS.SAS

14.2.1.2 AUC of Change from Baseline in TNSS: AM and PM Combined
Per-Protocol Population
(Page 1 of 1)

| Variable Time Point | Treatment | N[a] | Mean | LS Mean[b] | Standard Deviation | Minimum | Median | Maximum | Source | ANOVA p-value[c] |
|---|---|---|---|---|---|---|---|---|---|---|
|  |  |  | TNSS (AM and PM Combined) |  |  |  |  |  |  |  |
| Baseline[d] | Azelastine (A) | 49 | 19.60 | 19.66 | 2.113 | 15.3 | 19.70 | 24.0 | Treatment | 0.853 |
|  | Fluticasone (F) | 47 | 19.52 | 19.61 | 2.740 | 13.7 | 19.17 | 24.0 |  |  |
|  | Azelastine + Fluticasone (A + F) | 48 | 19.27 | 19.40 | 2.973 | 13.1 | 18.80 | 24.0 |  |  |

-continued

Change from Baseline in TNSS (AM and PM Combined)

| | | | | | | | | | | | |
|---|---|---|---|---|---|---|---|---|---|---|---|
| AUC[e] | Azelastine | 49 | −60.38 | −59.23 | 54.570 | −184.5 | −56.00 | 37.7 | | A vs A + F | 0.005 |
| | Fluticasone | 47 | −65.66 | −65.38 | 58.782 | −231.3 | −51.13 | 49.7 | | F vs A + F | 0.022 |
| | Azelastine + Fluticasone | 48 | −92.91 | −94.03 | 69.530 | −261.5 | −100.42 | 57.8 | | Treatment | 0.012 |

[a]Total number of per-protocol patients with available data.

[b]LS Mean = Least-Square Mean obtained from analysis of variance (ANOVA) model for baseline or analysis of covariance (ANCOVA) model for change.

[c]p-value for between treatment group comparison, except Baseline, was based on an ANCOVA model containing treatment group and site as fixed effects, and baseline as covariant. For Baseline, the p-value was based on a ANOVA model containing treatment group and site as fixed effects.

[d]Mean baseline TNSS over 5-day Lead-in Period, including Day 1 AM.

[e]Area-under-the-curve of change from baseline in TNSS from Day 1 to Day 14 with the change on Day 1 set to 0. The last-observation-carried-forward method was applied for missing TNSS scores proir to calculating the AUC.

Reference: 16.2.6.1

MedPoints Pharmaceuticals
MP 428                                                                                                              Program: REFTNSS.SAS

14.2.2.1 Change from Baseline in TNSS: AM and PM Combined
Intent-to-Treat Population
(Page 1 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | AM and PM Combined TNSS | | | | | | | |
| Baseline[e] | Azelastine (A) | 49 | 19.60 | 19.66 | 2.113 | 15.3 | 19.70 | 24.0 | | Treatment | 0.958 |
| | Fluticasone (F) | 50 | 19.53 | 19.57 | 2.742 | 13.7 | 19.38 | 24.0 | | | |
| | Azelastine + Fluticasone (A + F) | 52 | 19.48 | 19.52 | 2.967 | 13.1 | 19.45 | 24.0 | | | |
| | | | | Change from Baseline in AM and PM Combined TNSS | | | | | | | |
| Overall[f] | Azelastine | 49 | −4.73 | −4.76 | 4.297 | −14.4 | −4.24 | 3.1 | <0.001 | A vs A + F | 0.008 |
| | Fluticasone | 49 | −5.06 | −5.24 | 4.582 | −18.5 | −3.91 | 3.7 | <0.001 | F vs A + F | 0.029 |
| | Azelastine + Fluticasone | 52 | −7.22 | −7.40 | 5.586 | −20.2 | −7.33 | 4.7 | <0.001 | Treatment | 0.018 |
| | | | | | | | | | | Day | <0.001 |
| | | | | | | | | | | Treatment * Day | 0.182 |
| Day 2 | Azelastine | 49 | −3.23 | −3.10 | 4.330 | −14.2 | −2.67 | 4.1 | <0.001 | A vs A + F | 0.138 |
| | Fluticasone | 49 | −3.24 | −3.12 | 4.331 | −18.5 | −2.00 | 2.7 | <0.001 | F vs A + F | 0.144 |
| | Azelastine + Fluticasone | 52 | −4.53 | −4.46 | 5.391 | −16.1 | −3.01 | 4.1 | <0.001 | Treatment | 0.232 |

MedPoints Pharmaceuticals
MP 428                                                                                                              Program: REFTNSS.SAS

14.2.2.1 Change from Baseline in TNSS: AM and PM Combined
Intent-to-Treat Population
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Change from Baseline in AM and PM Combined TNSS | | | | | | | |
| Day 3 | Azelastine | 49 | −3.28 | −3.21 | 4.610 | −16.2 | −1.67 | 4.1 | <0.001 | A vs A + F | 0.009 |
| | Fluticasone | 49 | −4.12 | −4.09 | 4.931 | −18.5 | −3.20 | 5.3 | <0.001 | F vs A + F | 0.084 |
| | Azelastine + Fluticasone | 52 | −5.82 | −5.80 | 5.520 | −17.1 | −4.68 | 4.3 | <0.001 | Treatment | 0.029 |
| Day 4 | Azelastine | 49 | −3.93 | −3.89 | 5.022 | −17.2 | −2.92 | 4.3 | <0.001 | A vs A + F | 0.009 |
| | Fluticasone | 49 | −4.53 | −4.53 | 4.924 | −18.5 | −4.17 | 4.5 | <0.001 | F vs A + F | 0.045 |
| | Azelastine + Fluticasone | 52 | −6.61 | −6.62 | 5.619 | −17.1 | −6.62 | 4.1 | <0.001 | Treatment | 0.023 |
| Day 5 | Azelastine | 49 | −4.48 | −4.46 | 5.225 | −17.2 | −3.67 | 4.2 | <0.001 | A vs A + F | 0.014 |
| | Fluticasone | 49 | −5.16 | −5.20 | 5.236 | −18.5 | −4.40 | 5.3 | <0.001 | F vs A + F | 0.072 |
| | Azelastine + Fluticasone | 52 | −7.19 | −7.23 | 6.280 | −21.0 | −6.85 | 6.1 | <0.001 | Treatment | 0.039 |

-continued

| | | | | | | | | | | |
|---|---|---|---|---|---|---|---|---|---|---|
| Day 6 | Azelastine | 49 | −4.44 | −4.40 | 5.147 | −16.0 | −3.70 | 5.4 | <0.001 A vs A + F | 0.003 |
| | Fluticasone | 49 | −5.10 | −5.12 | 5.524 | −18.5 | −4.45 | 5.3 | <0.001 F vs A + F | 0.019 |
| | Azelastine + Fluticasone | 52 | −7.78 | −7.82 | 6.225 | −22.0 | −7.99 | 5.1 | <0.001 Treatment | 0.007 |

MedPoints Pharmaceuticals  
MP 428                                                                                               Program: REFTNSS.SAS 14.2.2.1 Change from Baseline in TNSS: AM and PM Combined  
Intent-to-Treat Population  
(Page 3 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Change from Baseline in AM and PM Combined TNSS | | | | | | | |
| Day 7 | Azelastine | 49 | −5.09 | −5.05 | 5.006 | −16.0 | −4.67 | 5.4 | <0.001 | A vs A + F | 0.028 |
| | Fluticasone | 49 | −5.02 | −5.06 | 4.989 | −18.5 | −5.00 | 5.5 | <0.001 | F vs A + F | 0.028 |
| | Azelastine + Fluticasone | 52 | −7.42 | −7.47 | 6.319 | −23.0 | −7.07 | 5.1 | <0.001 | Treatment | 0.039 |
| Day 8 | Azelastine | 49 | −5.38 | −5.37 | 5.056 | −17.0 | −5.00 | 2.4 | <0.001 | A vs A + F | 0.015 |
| | Fluticasone | 49 | −4.55 | −4.64 | 4.647 | −18.5 | −3.70 | 3.7 | <0.001 | F vs A + F | 0.002 |
| | Azelastine + Fluticasone | 52 | −7.90 | −7.98 | 6.035 | −21.0 | −7.11 | 5.1 | <0.001 | Treatment | 0.005 |
| Day 9 | Azelastine | 49 | −5.38 | −5.36 | 4.799 | −18.0 | −3.83 | 2.1 | <0.001 | A vs A + F | 0.033 |
| | Fluticasone | 49 | −5.08 | −5.17 | 5.219 | −18.5 | −4.58 | 2.7 | <0.001 | F vs A + F | 0.021 |
| | Azelastine + Fluticasone | 52 | −7.59 | −7.68 | 6.184 | −23.0 | −7.15 | 4.1 | <0.001 | Treatment | 0.037 |
| Day 10 | Azelastine | 49 | −5.36 | −5.29 | 4.976 | −15.0 | −5.33 | 4.0 | <0.001 | A vs A + F | 0.018 |
| | Fluticasone | 49 | −5.61 | −5.64 | 5.676 | −18.5 | −4.83 | 9.2 | <0.001 | F vs A + F | 0.039 |
| | Azelastine + Fluticasone | 52 | −7.94 | −8.00 | 6.375 | −23.0 | −7.14 | 5.1 | <0.001 | Treatment | 0.035 |

MedPoints Pharmaceuticals  
MP 428                                                                                               Program: REFTNSS.SAS 14.2.2.1 Change from Baseline in TNSS: AM and PM Combined  
Intent-to-Treat Population  
(Page 4 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Change from Baseline in AM and PM Combined TNSS | | | | | | | |
| Day 11 | Azelastine | 49 | −5.77 | −5.70 | 5.576 | −18.1 | −4.70 | 3.8 | <0.001 | A vs A + F | 0.021 |
| | Fluticasone | 49 | −5.77 | −5.85 | 5.742 | −18.5 | −4.83 | 9.2 | <0.001 | F vs A + F | 0.028 |
| | Azelastine + Fluticasone | 52 | −8.28 | −8.39 | 6.459 | −23.0 | −7.72 | 4.3 | <0.001 | Treatment | 0.033 |
| Day 12 | Azelastine | 49 | −5.54 | −5.46 | 6.109 | −19.0 | −5.00 | 4.2 | <0.001 | A vs A + F | 0.017 |
| | Fluticasone | 49 | −6.08 | −6.12 | 5.874 | −18.9 | −5.17 | 9.2 | <0.001 | F vs A + F | 0.062 |
| | Azelastine + Fluticasone | 52 | −8.32 | −8.40 | 6.652 | −24.0 | −7.93 | 4.1 | <0.001 | Treatment | 0.041 |
| Day 13 | Azelastine | 49 | −5.70 | −5.65 | 6.060 | −19.0 | −5.30 | 5.7 | <0.001 | A vs A + F | 0.016 |
| | Fluticasone | 49 | −6.83 | −6.95 | 6.345 | −18.9 | −6.20 | 9.2 | <0.001 | F vs A + F | 0.176 |
| | Azelastine + Fluticasone | 52 | −8.48 | −8.61 | 6.513 | −24.0 | −8.43 | 5.8 | <0.001 | Treatment | 0.054 |
| Day 14 | Azelastine | 49 | −5.62 | −5.56 | 5.890 | −19.0 | −5.30 | 6.7 | <0.001 | A vs A + F | 0.009 |
| | Fluticasone | 49 | −6.91 | −7.02 | 6.614 | −18.5 | −5.85 | 9.2 | <0.001 | F vs A + F | 0.145 |
| | Azelastine + Fluticasone | 52 | −8.69 | −8.82 | 6.517 | −23.0 | −9.34 | 5.8 | <0.001 | Treatment | 0.031 |

[a]Total number of intent-to-treat patients with available data.

[b]LS Mean = Least-Square Mean obtained from analysis of variance (ANOVA) model for baseline or analysis of covariance (ANCOVA) model otherwise.

[c]p-value for the within-patient change was based on a paired t-test.

[d]p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.

[e]Mean baseline TNSS over 5-day Lead-in Period, including Day 1 AM.

[f]Overall includes TNSS scores from Day 2 to Day 14.

Reference: 16.2.6.1

MedPoints Pharmaceuticals
MP 428

Program: REFTNSS.SAS 14.2.2.2 Percent Change from Baseline in TNSS: AM and PM Combined
Intent-to-Treat Population
(Page 1 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| AM and PM Combined TNSS ||||||||||||
| Baseline[e] | Azelastine (A) | 49 | 19.60 | 19.66 | 2.113 | 15.3 | 19.70 | 24.0 | | Treatment | 0.958 |
| | Fluticasone (F) | 50 | 19.53 | 19.57 | 2.742 | 13.7 | 19.38 | 24.0 | | | |
| | Azelastine + Fluticasone (A + F) | 52 | 19.48 | 19.52 | 2.967 | 13.1 | 19.45 | 24.0 | | | |
| Percent Change from Baseline in AM and PM Combined TNSS ||||||||||||
| Overall[f] | Azelastine | 49 | −24.47 | −24.78 | 22.215 | −71.9 | −24.26 | 15.4 | <0.001 | A vs A + F | 0.011 |
| | Fluticasone | 49 | −26.12 | −27.13 | 24.462 | −100.0 | −21.93 | 19.9 | <0.001 | F vs A + F | 0.035 |
| | Azelastine + Fluticasone | 52 | −36.94 | −37.87 | 27.683 | −86.9 | −39.66 | 26.1 | <0.001 | Treatment | 0.024 |
| | | | | | | | | | | Day | <0.001 |
| | | | | | | | | | | Treatment * Day | 0.155 |
| Day 2 | Azelastine | 49 | −16.93 | −16.31 | 22.796 | −70.5 | −12.31 | 20.8 | <0.001 | A vs A + F | 0.207 |
| | Fluticasone | 49 | −16.91 | −16.35 | 23.714 | −100.0 | −12.46 | 18.5 | <0.001 | F vs A + F | 0.210 |
| | Azelastine + Fluticasone | 52 | −22.82 | −22.43 | 27.943 | −84.7 | −14.36 | 22.7 | <0.001 | Treatment | 0.344 |

MedPoints Pharmaceuticals
MP 428

Program: REFTNSS.SAS 14.2.2.2 Percent Change from Baseline in TNSS: AM and PM Combined
Intent-to-Treat Population
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| Percent Change from Baseline in AM and PM Combined TNSS ||||||||||||
| Day 3 | Azelastine | 49 | −17.08 | −16.85 | 24.024 | −76.5 | −8.11 | 20.8 | <0.001 | A vs A + F | 0.014 |
| | Fluticasone | 49 | −22.26 | −22.17 | 26.773 | −100.0 | −16.67 | 28.6 | <0.001 | F vs A + F | 0.151 |
| | Azelastine + Fluticasone | 52 | −29.65 | −29.50 | 27.863 | −94.1 | −25.13 | 23.2 | <0.001 | Treatment | 0.047 |
| Day 4 | Azelastine | 49 | −20.50 | −20.41 | 26.044 | −81.1 | −14.29 | 21.8 | <0.001 | A vs A + F | 0.011 |
| | Fluticasone | 49 | −23.67 | −23.75 | 25.917 | −100.0 | −23.60 | 27.3 | <0.001 | F vs A + F | 0.055 |
| | Azelastine + Fluticasone | 52 | −33.92 | −33.92 | 28.009 | −85.1 | −36.38 | 22.7 | <0.001 | Treatment | 0.029 |
| Day 5 | Azelastine | 49 | −23.15 | −23.20 | 26.633 | −81.1 | −18.64 | 21.0 | <0.001 | A vs A + F | 0.016 |
| | Fluticasone | 49 | −26.89 | −27.20 | 27.945 | −100.0 | −22.77 | 28.6 | <0.001 | F vs A + F | 0.084 |
| | Azelastine + Fluticasone | 52 | −37.02 | −37.22 | 31.706 | −100.0 | −36.34 | 33.8 | <0.001 | Treatment | 0.045 |
| Day 6 | Azelastine | 49 | −23.13 | −23.15 | 26.683 | −80.0 | −18.78 | 29.0 | <0.001 | A vs A + F | 0.003 |
| | Fluticasone | 49 | −26.90 | −27.15 | 29.542 | −100.0 | −22.20 | 28.6 | <0.001 | F vs A + F | 0.024 |
| | Azelastine + Fluticasone | 52 | −40.33 | −40.50 | 31.771 | −100.0 | −45.75 | 28.3 | <0.001 | Treatment | 0.009 |

MedPoints Pharmaceuticals
MP 428

Program: REFTNSS.SAS 14.2.2.2 Percent Change from Baseline in TNSS: AM and PM Combined
Intent-to-Treat Population
(Page 3 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| Percent Change from Baseline in AM and PM Combined TNSS ||||||||||||
| Day 7 | Azelastine | 49 | −26.52 | −26.40 | 26.583 | −84.1 | −23.31 | 29.0 | <0.001 | A vs A + F | 0.037 |
| | Fluticasone | 49 | −25.75 | −26.00 | 26.507 | −100.0 | −23.81 | 33.3 | <0.001 | F vs A + F | 0.031 |
| | Azelastine + Fluticasone | 52 | −38.04 | −38.27 | 31.298 | −95.8 | −41.11 | 28.3 | <0.001 | Treatment | 0.048 |
| Day 8 | Azelastine | 49 | −28.13 | −28.22 | 26.628 | −89.4 | −23.73 | 11.2 | <0.001 | A vs A + F | 0.020 |
| | Fluticasone | 49 | −23.38 | −23.87 | 24.935 | −100.0 | −20.97 | 25.4 | <0.001 | F vs A + F | 0.002 |
| | Azelastine + Fluticasone | 52 | −40.61 | −40.94 | 29.617 | −100.0 | −43.52 | 28.3 | <0.001 | Treatment | 0.005 |
| Day 9 | Azelastine | 49 | −27.72 | −27.79 | 24.151 | −81.8 | −19.35 | 11.1 | <0.001 | A vs A + F | 0.038 |
| | Fluticasone | 49 | −25.94 | −26.50 | 27.382 | −100.0 | −23.40 | 18.5 | <0.001 | F vs A + F | 0.022 |
| | Azelastine + Fluticasone | 52 | −38.97 | −39.40 | 31.247 | −100.0 | −40.03 | 22.7 | <0.001 | Treatment | 0.039 |

| | | | | | | | | | | |
|---|---|---|---|---|---|---|---|---|---|---|
| Day 10 | Azelastine | 49 | −27.81 | −27.60 | 25.985 | −77.9 | −28.93 | 19.7 | <0.001 | A vs A + F | 0.025 |
| | Fluticasone | 49 | −28.76 | −28.93 | 30.182 | −100.0 | −27.10 | 61.6 | <0.001 | F vs A + F | 0.044 |
| | Azelastine + Fluticasone | 52 | −40.56 | −40.78 | 31.425 | −100.0 | −40.01 | 28.3 | <0.001 | Treatment | 0.047 |

MedPoints Pharmaceuticals
MP 428                                                                                                                                    Program: REFTNSS.SAS 14.2.2.2 Percent Change from Baseline in TNSS: AM and PM Combined
Intent-to-Treat Population
(Page 4 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| | | | Percent Change from Baseline in AM and PM Combined TNSS | | | | | | | | |
| Day 11 | Azelastine | 49 | −29.42 | −29.24 | 27.960 | −90.0 | −26.11 | 18.6 | <0.001 | A vs A + F | 0.027 |
| | Fluticasone | 49 | −29.30 | −29.71 | 30.855 | −100.0 | −27.71 | 61.6 | <0.001 | F vs A + F | 0.033 |
| | Azelastine + Fluticasone | 52 | −42.09 | −42.55 | 31.725 | −95.8 | −41.75 | 28.8 | <0.001 | Treatment | 0.042 |
| Day 12 | Azelastine | 49 | −28.25 | −27.99 | 31.095 | −95.0 | −25.86 | 21.0 | <0.001 | A vs A + F | 0.018 |
| | Fluticasone | 49 | −31.04 | −31.31 | 31.574 | −100.0 | −27.78 | 61.6 | <0.001 | F vs A + F | 0.064 |
| | Azelastine + Fluticasone | 52 | −42.62 | −42.96 | 32.096 | −100.0 | −43.60 | 22.7 | <0.001 | Treatment | 0.044 |
| Day 13 | Azelastine | 49 | −29.35 | −29.24 | 31.149 | −95.0 | −26.15 | 32.7 | <0.001 | A vs A + F | 0.024 |
| | Fluticasone | 49 | −34.97 | −35.63 | 33.815 | −100.0 | −30.43 | 61.6 | <0.001 | F vs A + F | 0.205 |
| | Azelastine + Fluticasone | 52 | −43.11 | −43.75 | 32.779 | −100.0 | −44.47 | 43.9 | <0.001 | Treatment | 0.077 |
| Day 14 | Azelastine | 49 | −28.86 | −28.70 | 30.499 | −95.0 | −25.00 | 38.5 | <0.001 | A vs A + F | 0.013 |
| | Fluticasone | 49 | −35.00 | −35.62 | 34.687 | −100.0 | −28.71 | 61.6 | <0.001 | F vs A + F | 0.152 |
| | Azelastine + Fluticasone | 52 | −44.29 | −44.92 | 33.557 | −95.8 | −48.83 | 43.9 | <0.001 | Treatment | 0.044 |

$^a$Total number of intent-to-treat patients with available data.
$^b$LS Mean = Least-Square Mean obtained from analysis of variance (ANOVA) model for baseline or analysis of covariance (ANCOVA) model otherwise.
$^c$p-value for the within-patient change was based on a paired t-test.
$^d$p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.
$^e$Mean baseline TNSS over 5-day Lead-in Period, including Day 1 AM.
$^f$Overall includes TNSS scores from Day 2 to Day 14.

Reference: 16.2.6.1

MedPoints Pharmaceuticals
MP 428                                                                                                                                    Program: REFTNSS.SAS 14.2.3.1 Change from Baseline in TNSS: AM and PM Combined
Per-Protocol Population
(Page 1 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| | | | AM and PM Combined TNSS | | | | | | | | |
| Baseline$^e$ | Azelastine (A) | 49 | 19.60 | 19.66 | 2.113 | 15.3 | 19.70 | 24.0 | | Treatment | 0.853 |
| | Fluticasone (F) | 47 | 19.52 | 19.61 | 2.740 | 13.7 | 19.17 | 24.0 | | | |
| | Azelastine + Fluticasone (A + F) | 48 | 19.27 | 19.40 | 2.973 | 13.1 | 18.80 | 24.0 | | | |
| | | | Change from Baseline in AM and PM Combined TNSS | | | | | | | | |
| Overall$^f$ | Azelastine | 49 | −4.73 | −4.73 | 4.297 | −14.4 | −4.24 | 3.1 | <0.001 | A vs A + F | 0.007 |
| | Fluticasone | 47 | −5.14 | −5.24 | 4.633 | −18.5 | −3.91 | 3.7 | <0.001 | F vs A + F | 0.030 |
| | Azelastine + Fluticasone | 48 | −7.28 | −7.44 | 5.466 | −20.2 | −8.01 | 4.7 | <0.001 | Treatment | 0.017 |
| | | | | | | | | | | Day | <0.001 |
| | | | | | | | | | | Treatment * Day | 0.150 |

| | | | | | | | | | | |
|---|---|---|---|---|---|---|---|---|---|---|
| Day 2 | Azelastine | 49 | −3.23 | −3.08 | 4.330 | −14.2 | −2.67 | 4.1 | <0.001 | A vs A + F | 0.133 |
| | Fluticasone | 47 | −3.27 | −3.10 | 4.412 | −18.5 | −2.00 | 2.7 | <0.001 | F vs A + F | 0.145 |
| | Azelastine + Fluticasone | 48 | −4.60 | −4.48 | 5.326 | −16.1 | −3.46 | 4.1 | <0.001 | Treatment | 0.232 |

MedPoints Pharmaceuticals
MP 428

Program: REFTNSS.SAS 14.2.3.1 Change from Baseline in TNSS: AM and PM Combined
Per-Protocol Population
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | Change from Baseline in AM and PM Combined TNSS | | | | | | |
| Day 3 | Azelastine | 49 | −3.28 | −3.19 | 4.610 | −16.2 | −1.67 | 4.1 | <0.001 | A vs A + F | 0.009 |
| | Fluticasone | 47 | −4.25 | −4.18 | 4.977 | −18.5 | −3.47 | 5.3 | <0.001 | F vs A + F | 0.102 |
| | Azelastine + Fluticasone | 48 | −5.96 | −5.86 | 5.526 | −17.1 | −4.83 | 4.3 | <0.001 | Treatment | 0.031 |
| Day 4 | Azelastine | 49 | −3.93 | −3.87 | 5.022 | −17.2 | −2.92 | 4.3 | <0.001 | A vs A + F | 0.011 |
| | Fluticasone | 47 | −4.63 | −4.61 | 4.961 | −18.5 | −4.17 | 4.5 | <0.001 | F vs A + F | 0.064 |
| | Azelastine + Fluticasone | 48 | −6.62 | −6.59 | 5.566 | −17.1 | −6.93 | 4.1 | <0.001 | Treatment | 0.031 |
| Day 5 | Azelastine | 49 | −4.48 | −4.43 | 5.225 | −17.2 | −3.67 | 4.2 | <0.001 | A vs A + F | 0.013 |
| | Fluticasone | 47 | −5.23 | −5.23 | 5.328 | −18.5 | −4.40 | 5.3 | <0.001 | F vs A + F | 0.074 |
| | Azelastine + Fluticasone | 48 | −7.27 | −7.31 | 6.212 | −21.0 | −7.37 | 6.1 | <0.001 | Treatment | 0.037 |
| Day 6 | Azelastine | 49 | −4.44 | −4.38 | 5.147 | −16.0 | −3.70 | 5.4 | <0.001 | A vs A + F | 0.002 |
| | Fluticasone | 47 | −5.12 | −5.11 | 5.632 | −18.5 | −4.45 | 5.3 | <0.001 | F vs A + F | 0.015 |
| | Azelastine + Fluticasone | 48 | −7.91 | −7.97 | 6.076 | −22.0 | −8.25 | 5.1 | <0.001 | Treatment | 0.006 |

MedPoints Pharmaceuticals
MP 428

Program: REFTNSS.SAS 14.2.3.1 Change from Baseline in TNSS: AM and PM Combined
Per-Protocol Population
(Page 3 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | Change from Baseline in AM and PM Combined TNSS | | | | | | |
| Day 7 | Azelastine | 49 | −5.09 | −5.01 | 5.006 | −16.0 | −4.67 | 5.4 | <0.001 | A vs A + F | 0.020 |
| | Fluticasone | 47 | −4.99 | −4.98 | 5.093 | −18.5 | −5.00 | 5.5 | <0.001 | F vs A + F | 0.020 |
| | Azelastine + Fluticasone | 48 | −7.50 | −7.60 | 6.147 | −23.0 | −7.26 | 5.1 | <0.001 | Treatment | 0.028 |
| Day 8 | Azelastine | 49 | −5.38 | −5.33 | 5.056 | −17.0 | −5.00 | 2.4 | <0.001 | A vs A + F | 0.012 |
| | Fluticasone | 47 | −4.59 | −4.61 | 4.683 | −18.5 | −3.70 | 3.7 | <0.001 | F vs A + F | 0.002 |
| | Azelastine + Fluticasone | 48 | −7.98 | −8.05 | 5.859 | −21.0 | −7.61 | 5.1 | <0.001 | Treatment | 0.004 |
| Day 9 | Azelastine | 49 | −5.38 | −5.32 | 4.799 | −18.0 | −3.83 | 2.1 | <0.001 | A vs A + F | 0.030 |
| | Fluticasone | 47 | −5.18 | −5.21 | 5.252 | −18.5 | −4.58 | 2.7 | <0.001 | F vs A + F | 0.025 |
| | Azelastine + Fluticasone | 48 | −7.56 | −7.69 | 5.978 | −23.0 | −7.33 | 4.1 | <0.001 | Treatment | 0.039 |
| Day 10 | Azelastine | 49 | −5.36 | −5.25 | 4.976 | −15.0 | −5.33 | 4.0 | <0.001 | A vs A + F | 0.013 |
| | Fluticasone | 47 | −5.74 | −5.70 | 5.713 | −18.5 | −4.83 | 9.2 | <0.001 | F vs A + F | 0.038 |
| | Azelastine + Fluticasone | 48 | −7.96 | −8.10 | 6.172 | −23.0 | −7.43 | 5.1 | <0.001 | Treatment | 0.029 |

MedPoints Pharmaceuticals
MP 428

Program: REFTNSS.SAS 14.2.3.1 Change from Baseline in TNSS: AM and PM Combined
Per-Protocol Population
(Page 4 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | Change from Baseline in AM and PM Combined TNSS | | | | | | |
| Day 11 | Azelastine | 49 | −5.77 | −5.64 | 5.576 | −18.1 | −4.70 | 3.8 | <0.001 | A vs A + F | 0.013 |
| | Fluticasone | 47 | −5.89 | −5.89 | 5.775 | −18.5 | −4.83 | 9.2 | <0.001 | F vs A + F | 0.024 |
| | Azelastine + Fluticasone | 48 | −8.33 | −8.58 | 6.485 | −23.0 | −7.80 | 4.3 | <0.001 | Treatment | 0.023 |
| Day 12 | Azelastine | 49 | −5.54 | −5.40 | 6.109 | −19.0 | −5.00 | 4.2 | <0.001 | A vs A + F | 0.013 |
| | Fluticasone | 47 | −6.20 | −6.16 | 5.905 | −18.9 | −5.17 | 9.2 | <0.001 | F vs A + F | 0.061 |
| | Azelastine + Fluticasone | 48 | −8.31 | −8.50 | 6.586 | −24.0 | −8.52 | 4.1 | <0.001 | Treatment | 0.034 |
| Day 13 | Azelastine | 49 | −5.70 | −5.59 | 6.060 | −19.0 | −5.30 | 5.7 | <0.001 | A vs A + F | 0.010 |
| | Fluticasone | 47 | −7.01 | −7.03 | 6.375 | −18.9 | −6.50 | 9.2 | <0.001 | F vs A + F | 0.157 |
| | Azelastine + Fluticasone | 48 | −8.56 | −8.81 | 6.570 | −24.0 | −8.57 | 5.8 | <0.001 | Treatment | 0.037 |

| | | | | | | | | | | |
|---|---|---|---|---|---|---|---|---|---|---|
| Day 14 | Azelastine | 49 | −5.62 | −5.50 | 5.890 | −19.0 | −5.30 | 6.7 | <0.001 | A vs A + F | 0.006 |
| | Fluticasone | 47 | −7.14 | −7.15 | 6.638 | −18.5 | −6.00 | 9.2 | <0.001 | F vs A + F | 0.147 |
| | Azelastine + Fluticasone | 48 | −8.73 | −8.98 | 6.476 | −23.0 | −9.68 | 5.8 | <0.001 | Treatment | 0.022 |

[a] Total number of per-protocol patients with available data.

[b] LS Mean = Least-Square Mean obtained from analysis of variance (ANOVA) model for baseline or analysis of covariance (ANCOVA) model otherwise.

[c] p-value for the within-patient change was based on a paired t-test.

[d] p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.

[e] Mean baseline TNSS over 5-day Lead-in Period, including Day 1 AM.

[f] Overall includes TNSS scores from Day 2 to Day 14.

Reference: 16.2.6.1

MedPoints Pharmaceuticals
MP 428  
Program: REFTNSS.SAS 14.2.3.2 Percent Change from Baseline in TNSS: AM and PM Combined
Per-Protocol Population
(Page 1 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | AM and PM Combined TNSS | | | | | | | |
| Baseline[e] | Azelastine (A) | 49 | 19.60 | 19.66 | 2.113 | 15.3 | 19.70 | 24.0 | | Treatment | 0.853 |
| | Fluticasone (F) | 47 | 19.52 | 19.61 | 2.740 | 13.7 | 19.17 | 24.0 | | | |
| | Azelastine + Fluticasone (A + F) | 48 | 19.27 | 19.40 | 2.973 | 13.1 | 18.80 | 24.0 | | | |
| Percent Change from Baseline in AM and PM Combined TNSS | | | | | | | | | | | |
| Overall[f] | Azelastine | 49 | −24.47 | −24.72 | 22.215 | −71.9 | −24.26 | 15.4 | <0.001 | A vs A + F | 0.010 |
| | Fluticasone | 47 | −26.46 | −27.12 | 24.721 | −100.0 | −21.93 | 19.9 | <0.001 | F vs A + F | 0.036 |
| | Azelastine + Fluticasone | 48 | −37.49 | −38.14 | 27.305 | −86.9 | −42.91 | 26.1 | <0.001 | Treatment | 0.024 |
| | | | | | | | | | | Day | <0.001 |
| | | | | | | | | | | Treatment * Day | 0.121 |
| Day 2 | Azelastine | 49 | −16.93 | −16.25 | 22.796 | −70.5 | −12.31 | 20.8 | <0.001 | A vs A + F | 0.206 |
| | Fluticasone | 47 | −17.11 | −16.38 | 24.182 | −100.0 | −12.46 | 18.5 | <0.001 | F vs A + F | 0.220 |
| | Azelastine + Fluticasone | 48 | −23.31 | −22.55 | 27.918 | −84.7 | −15.83 | 22.7 | <0.001 | Treatment | 0.355 |

MedPoints Pharmaceuticals
MP 428  
Program: REFTNSS.SAS 14.2.3.2 Percent Change from Baseline in TNSS: AM and PM Combined
Per-Protocol Population
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | Percent Change from Baseline in AM and PM Combined TNSS | | | | | | | | |
| Day 3 | Azelastine | 49 | −17.08 | −16.85 | 24.024 | −76.5 | −8.11 | 20.8 | <0.001 | A vs A + F | 0.015 |
| | Fluticasone | 47 | −22.87 | −22.68 | 27.056 | −100.0 | −16.67 | 28.6 | <0.001 | F vs A + F | 0.181 |
| | Azelastine + Fluticasone | 48 | −30.54 | −29.80 | 28.004 | −94.1 | −26.52 | 23.2 | <0.001 | Treatment | 0.050 |
| Day 4 | Azelastine | 49 | −20.50 | −20.39 | 26.044 | −81.1 | −14.29 | 21.8 | <0.001 | A vs A + F | 0.013 |
| | Fluticasone | 47 | −24.08 | −24.10 | 26.117 | −100.0 | −23.60 | 27.3 | <0.001 | F vs A + F | 0.074 |
| | Azelastine + Fluticasone | 48 | −34.28 | −33.89 | 27.955 | −85.1 | −36.87 | 22.7 | <0.001 | Treatment | 0.039 |
| Day 5 | Azelastine | 49 | −23.15 | −23.17 | 26.633 | −81.1 | −18.64 | 21.0 | <0.001 | A vs A + F | 0.015 |
| | Fluticasone | 47 | −27.16 | −27.42 | 28.408 | −100.0 | −22.77 | 28.6 | <0.001 | F vs A + F | 0.086 |
| | Azelastine + Fluticasone | 48 | −37.72 | −37.73 | 31.603 | −100.0 | −38.16 | 33.8 | <0.001 | Treatment | 0.044 |

-continued

| | | | | | | | | | | Paired t-test p-value[c] | Source | ANOVA p-value[d] |
|---|---|---|---|---|---|---|---|---|---|---|---|---|
| Day 6 | Azelastine | | 49 | −23.13 | −23.16 | 26.683 | −80.0 | −18.78 | 29.0 | <0.001 | A vs A + F | 0.003 |
| | Fluticasone | | 47 | −26.95 | −27.15 | 30.062 | −100.0 | −22.20 | 28.6 | <0.001 | F vs A + F | 0.020 |
| | Azelastine + Fluticasone | | 48 | −41.28 | −41.37 | 31.333 | −100.0 | −46.23 | 28.3 | <0.001 | Treatment | 0.007 |

MedPoints Pharmaceuticals  
MP 428  
Program: REFTNSS.SAS 14.2.3.2 Percent Change from Baseline in TNSS: AM and PM Combined  
Per-Protocol Population  
(Page 3 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Percent Change from Baseline in AM and PM Combined TNSS | | | | | | | |
| Day 7 | Azelastine | 49 | −26.52 | −26.32 | 26.583 | −84.1 | −23.31 | 29.0 | <0.001 | A vs A + F | 0.029 |
| | Fluticasone | 47 | −25.57 | −25.63 | 27.007 | −100.0 | −23.81 | 33.3 | <0.001 | F vs A + F | 0.023 |
| | Azelastine + Fluticasone | 48 | −38.70 | −38.96 | 30.725 | −95.8 | −42.41 | 28.3 | <0.001 | Treatment | 0.037 |
| Day 8 | Azelastine | 49 | −28.13 | −28.14 | 26.628 | −89.4 | −23.73 | 11.2 | <0.001 | A vs A + F | 0.017 |
| | Fluticasone | 47 | −23.43 | −23.68 | 25.045 | −100.0 | −20.97 | 25.4 | <0.001 | F vs A + F | 0.002 |
| | Azelastine + Fluticasone | 48 | −41.30 | −41.38 | 28.967 | −100.0 | −44.94 | 28.3 | <0.001 | Treatment | 0.005 |
| Day 9 | Azelastine | 49 | −27.72 | −27.68 | 24.151 | −81.8 | −19.35 | 11.1 | <0.001 | A vs A + F | 0.036 |
| | Fluticasone | 47 | −26.33 | −26.65 | 27.549 | −100.0 | −23.40 | 18.5 | <0.001 | F vs A + F | 0.024 |
| | Azelastine + Fluticasone | 48 | −39.14 | −39.58 | 30.647 | −100.0 | −41.75 | 22.7 | <0.001 | Treatment | 0.043 |
| Day 10 | Azelastine | 49 | −27.81 | −27.49 | 25.985 | −77.9 | −28.93 | 19.7 | <0.001 | A vs A + F | 0.020 |
| | Fluticasone | 47 | −29.26 | −29.19 | 30.406 | −100.0 | −27.10 | 61.6 | <0.001 | F vs A + F | 0.043 |
| | Azelastine + Fluticasone | 48 | −40.96 | −41.38 | 30.734 | −100.0 | −40.26 | 28.3 | <0.001 | Treatment | 0.041 |

MedPoints Pharmaceuticals  
MP 428  
Program: REFTNSS.SAS 14.2.3.2 Percent Change from Baseline in TNSS: AM and PM Combined  
Per-Protocol Population  
(Page 4 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Percent Change from Baseline in AM and PM Combined TNSS | | | | | | | |
| Day 11 | Azelastine | 49 | −29.42 | −29.05 | 27.960 | −90.0 | −26.11 | 18.6 | <0.001 | A vs A + F | 0.018 |
| | Fluticasone | 47 | −29.69 | −29.83 | 31.043 | −100.0 | −27.71 | 61.6 | <0.001 | F vs A + F | 0.027 |
| | Azelastine + Fluticasone | 48 | −42.64 | −43.56 | 31.959 | −95.8 | −42.32 | 28.8 | <0.001 | Treatment | 0.031 |
| Day 12 | Azelastine | 49 | −28.25 | −27.82 | 31.095 | −95.0 | −25.86 | 21.0 | <0.001 | A vs A + F | 0.014 |
| | Fluticasone | 47 | −31.50 | −31.45 | 31.763 | −100.0 | −27.78 | 61.6 | <0.001 | F vs A + F | 0.061 |
| | Azelastine + Fluticasone | 48 | −42.93 | −43.59 | 31.937 | −100.0 | −46.30 | 22.7 | <0.001 | Treatment | 0.038 |
| Day 13 | Azelastine | 49 | −29.35 | −29.06 | 31.149 | −95.0 | −26.15 | 32.7 | <0.001 | A vs A + F | 0.017 |
| | Fluticasone | 47 | −35.73 | −35.99 | 34.040 | −100.0 | −30.43 | 61.6 | <0.001 | F vs A + F | 0.182 |
| | Azelastine + Fluticasone | 48 | −43.85 | −44.83 | 33.178 | −100.0 | −45.75 | 43.9 | <0.001 | Treatment | 0.057 |
| Day 14 | Azelastine | 49 | −28.86 | −28.52 | 30.499 | −95.0 | −25.00 | 38.5 | <0.001 | A vs A + F | 0.010 |
| | Fluticasone | 47 | −36.03 | −36.26 | 34.913 | −100.0 | −34.31 | 61.6 | <0.001 | F vs A + F | 0.153 |
| | Azelastine + Fluticasone | 48 | −44.84 | −45.84 | 33.645 | −95.8 | −49.84 | 43.9 | <0.001 | Treatment | 0.034 |

[a]Total number of per-protocol patients with available data.

[b]LS Mean = Least-Square Mean obtained from analysis of variance (ANOVA) model for baseline or analysis of covariance (ANCOVA) model otherwise.

[c]p-value for the within-patient percent change was based on a paired t-test.

[d]p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.

[e]Mean baseline TNSS over 5-day Lead-in Period, including Day 1 AM.

[f]Overall includes TNSS scores from Day 2 to Day 14.

Reference: 16.2.6.1

MedPoints Pharmaceuticals
MP 428

Program: REFTNSS.SAS 14.2.4.1 Change from Baseline in TNSS: AM
Intent-to-Treat Population
(Page 1 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | AM TNSS | | | | | | | |
| Baseline[e] | Azelastine (A) | 49 | 9.66 | 9.68 | 1.128 | 7.2 | 9.67 | 12.0 | | Treatment | 0.725 |
| | Fluticasone (F) | 50 | 9.79 | 9.81 | 1.369 | 7.2 | 9.78 | 12.0 | | | |
| | Azelastine + Fluticasone (A + F) | 52 | 9.86 | 9.88 | 1.422 | 6.0 | 9.92 | 12.0 | | | |
| | | | | Change from Baseline in AM TNSS | | | | | | | |
| Overall[f] | Azelastine | 49 | −2.21 | −2.22 | 2.157 | −7.3 | −1.86 | 1.8 | <0.001 | A vs A + F | 0.003 |
| | Fluticasone | 49 | −2.57 | −2.55 | 2.403 | −9.5 | −2.14 | 2.5 | <0.001 | F vs A + F | 0.021 |
| | Azelastine + Fluticasone | 52 | −3.76 | −3.70 | 2.891 | −10.8 | −3.67 | 2.3 | <0.001 | Treatment | 0.008 |
| | | | | | | | | | | Day | <0.001 |
| | | | | | | | | | | Treatment * Day | 0.065 |
| Day 2 | Azelastine | 49 | −1.48 | −1.46 | 2.322 | −7.3 | −1.25 | 2.3 | <0.001 | A vs A + F | 0.209 |
| | Fluticasone | 49 | −1.65 | −1.58 | 2.266 | −9.5 | −1.00 | 1.4 | <0.001 | F vs A + F | 0.308 |
| | Azelastine + Fluticasone | 52 | −2.17 | −2.07 | 2.908 | −8.7 | −1.25 | 2.7 | <0.001 | Treatment | 0.406 |

MedPoints Pharmaceuticals
MP 428

Program: REFTNSS.SAS 14.2.4.1 Change from Baseline in TNSS: AM
Intent-to-Treat Population
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Change from Baseline in AM TNSS | | | | | | | |
| Day 3 | Azelastine | 49 | −1.29 | −1.28 | 2.451 | −8.0 | −0.80 | 2.3 | <0.001 | A vs A + F | 0.003 |
| | Fluticasone | 49 | −2.04 | −2.01 | 2.667 | −9.5 | −1.50 | 3.0 | <0.001 | F vs A + F | 0.093 |
| | Azelastine + Fluticasone | 52 | −2.98 | −2.92 | 3.193 | −9.0 | −2.17 | 3.3 | <0.001 | Treatment | 0.011 |
| Day 4 | Azelastine | 49 | −1.76 | −1.79 | 2.623 | −8.3 | −1.33 | 2.5 | <0.001 | A vs A + F | 0.007 |
| | Fluticasone | 49 | −2.41 | −2.43 | 2.401 | −9.5 | −2.67 | 1.5 | <0.001 | F vs A + F | 0.119 |
| | Azelastine + Fluticasone | 52 | −3.28 | −3.27 | 3.080 | −10.3 | −3.08 | 2.3 | <0.001 | Treatment | 0.024 |
| Day 5 | Azelastine | 49 | −2.23 | −2.25 | 2.664 | −8.3 | −1.67 | 2.3 | <0.001 | A vs A + F | 0.030 |
| | Fluticasone | 49 | −2.57 | −2.59 | 2.696 | −9.8 | −2.00 | 3.0 | <0.001 | F vs A + F | 0.110 |
| | Azelastine + Fluticasone | 52 | −3.51 | −3.50 | 3.242 | −10.0 | −3.25 | 2.7 | <0.001 | Treatment | 0.079 |
| Day 6 | Azelastine | 49 | −2.01 | −2.01 | 2.597 | −9.0 | −2.00 | 3.0 | <0.001 | A vs A + F | 0.001 |
| | Fluticasone | 49 | −2.57 | −2.59 | 2.981 | −9.8 | −2.20 | 3.0 | <0.001 | F vs A + F | 0.024 |
| | Azelastine + Fluticasone | 52 | −3.94 | −3.94 | 3.283 | −11.0 | −4.00 | 2.3 | <0.001 | Treatment | 0.005 |

MedPoints Pharmaceuticals
MP 428

Program: REFTNSS.SAS 14.2.4.1 Change from Baseline in TNSS: AM
Intent-to-Treat Population
(Page 3 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Change from Baseline in AM TNSS | | | | | | | |
| Day 7 | Azelastine | 49 | −2.52 | −2.52 | 2.554 | −8.0 | −2.20 | 3.0 | <0.001 | A vs A + F | 0.018 |
| | Fluticasone | 49 | −2.57 | −2.55 | 2.618 | −9.5 | −2.00 | 3.0 | <0.001 | F vs A + F | 0.021 |
| | Azelastine + Fluticasone | 52 | −3.94 | −3.90 | 3.444 | −12.0 | −3.58 | 2.7 | <0001 | Treatment | 0.025 |
| Day 8 | Azelastine | 49 | −2.62 | −2.65 | 2.790 | −9.0 | −2.50 | 2.0 | <0.001 | A vs A + F | 0.014 |
| | Fluticasone | 49 | −2.36 | −2.40 | 2.592 | −9.5 | −1.67 | 3.0 | <0.001 | F vs A + F | 0.004 |
| | Azelastine + Fluticasone | 52 | −4.09 | −4.09 | 3.273 | −11.0 | −3.63 | 2.3 | <0.001 | Treatment | 0.008 |
| Day 9 | Azelastine | 49 | −2.52 | −2.57 | 2.494 | −9.0 | −2.00 | 1.5 | <0.001 | A vs A + F | 0.010 |
| | Fluticasone | 49 | −2.38 | −2.43 | 2.641 | −9.5 | −1.83 | 3.0 | <0.001 | F vs A + F | 0.005 |
| | Azelastine + Fluticasone | 52 | −4.01 | −4.01 | 3.201 | −12.0 | −3.82 | 2.3 | <0.001 | Treatment | 0.008 |

| Day | Treatment | N | Mean | LS Mean | Standard Deviation | Minimum | Median | Maximum | Paired t-test p-value | Source | ANOVA p-value |
|---|---|---|---|---|---|---|---|---|---|---|---|
| Day 10 | Azelastine | 49 | −2.27 | −2.29 | 2.620 | −8.0 | −2.17 | 2.2 | <0.001 | A vs A + F | 0.004 |
|  | Fluticasone | 49 | −2.73 | −2.74 | 2.986 | −9.5 | −2.80 | 4.4 | <0.001 | F vs A + F | 0.034 |
|  | Azelastine + Fluticasone | 52 | −4.01 | −3.99 | 3.301 | −12.0 | −3.70 | 2.7 | <0.001 | Treatment | 0.012 |

MedPoints Pharmaceuticals  
MP 428                                                                                                           Program: REFTNSS.SAS

14.2.4.1 Change from Baseline in TNSS: AM
Intent-to-Treat Population
(Page 4 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | Change from Baseline in AM TNSS | | | | | | |
| Day 11 | Azelastine | 49 | −2.48 | −2.53 | 2.898 | −9.0 | −2.00 | 2.2 | <0.001 | A vs A + F | 0.007 |
|  | Fluticasone | 49 | −2.49 | −2.52 | 3.082 | −9.5 | −2.00 | 4.4 | <0.001 | F vs A + F | 0.007 |
|  | Azelastine + Fluticasone | 52 | −4.19 | −4.16 | 3.362 | −12.0 | −3.63 | 3.3 | <0.001 | Treatment | 0.008 |
| Day 12 | Azelastine | 49 | −2.58 | −2.60 | 2.934 | −9.0 | −2.50 | 2.2 | <0.001 | A vs A + F | 0.012 |
|  | Fluticasone | 49 | −2.98 | −2.99 | 3.121 | −11.3 | −2.75 | 4.4 | <0.001 | F vs A + F | 0.059 |
|  | Azelastine + Fluticasone | 52 | −4.17 | −4.15 | 3.283 | −12.0 | −3.83 | 1.5 | <0.001 | Treatment | 0.032 |
| Day 13 | Azelastine | 49 | −2.50 | −2.55 | 2.992 | −9.0 | −1.80 | 3.0 | <0.001 | A vs A + F | 0.005 |
|  | Fluticasone | 49 | −3.32 | −3.38 | 3.328 | −10.3 | −3.00 | 4.4 | <0.001 | F vs A + F | 0.141 |
|  | Azelastine + Fluticasone | 52 | −4.28 | −4.29 | 3.215 | −12.0 | −4.08 | 3.0 | <0.001 | Treatment | 0.020 |
| Day 14 | Azelastine | 49 | −2.52 | −2.56 | 2.982 | −9.0 | −2.00 | 3.0 | <0.001 | A vs A + F | 0.004 |
|  | Fluticasone | 49 | −3.28 | −3.33 | 3.348 | −9.5 | −3.00 | 4.4 | <0.001 | P vs A + F | 0.103 |
|  | Azelastine + Fluticasone | 52 | −4.34 | −4.34 | 3.245 | −12.0 | −4.63 | 3.3 | <0.001 | Treatment | 0.017 |

[a] Total number of intent-to-treat patients with available data.
[b] LS Mean = Least-Square Mean obtained from analysis of variance (ANOVA) model for baseline of analysis of covariance (ANCOVA) model otherwise.
[c] p-value for the within-patient change was based on an paired t-test.
[d] p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.
[e] Mean baseline TNSS over 5-day Lead-in Period, including Day 1 AM.
[f] Overall includes TNSS scores from Day 2 to Day 14.

Reference 16.2.6.1

MedPoints Pharmaceuticals  
MP 428                                                                                                           Program: REFTNSS.SAS

14.2.4.2 Percent Change from Baseline in TNSS: AM
Intent-to-Treat Population
(Page 1 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | AM TNSS | | | | | | |
| Baseline[e] | Azelastine (A) | 49 | 9.66 | 9.68 | 1.128 | 7.2 | 9.67 | 12.0 |  | Treatment | 0.725 |
|  | Fluticasone (F) | 50 | 9.79 | 9.81 | 1.369 | 7.2 | 9.78 | 12.0 |  |  |  |
|  | Azelastine + Fluticasone (A + F) | 52 | 9.86 | 9.88 | 1.422 | 6.0 | 9.92 | 12.0 |  |  |  |
| | | | | | Percent Change from Baseline in AM TNSS | | | | | | |
| Overall[f] | Azelastine | 49 | −23.29 | −23.13 | 22.865 | −73.1 | −19.23 | 18.6 | <0.001 | A vs A + F | 0.006 |
|  | Fluticasone | 49 | −26.49 | −26.39 | 25.046 | −100.0 | −23.89 | 27.4 | <0.001 | F vs A + F | 0.035 |
|  | Azelastine + Fluticasone | 52 | −37.53 | −37.13 | 28.119 | −90.4 | −40.04 | 26.9 | <0.001 | Treatment | 0.016 |
|  |  |  |  |  |  |  |  |  |  | Day | <0.001 |
|  |  |  |  |  |  |  |  |  |  | Treatment * Day | 0.045 |

-continued

| | | | | | | | | | | | |
|---|---|---|---|---|---|---|---|---|---|---|---|
| Day 2 | Azelastine | 49 | −15.79 | −15.45 | 25.055 | −78.6 | −14.29 | 24.1 | <0.001 | A vs A + F | 0.403 |
| | Fluticasone | 49 | −17.21 | −16.43 | 24.390 | −100.0 | −11.11 | 18.4 | <0.001 | F vs A + F | 0.520 |
| | Azelastine + Fluticasone | 52 | −20.59 | −19.66 | 28.925 | −89.7 | −13.12 | 28.6 | <0.001 | Treatment | 0.678 |

MedPoints Pharmaceuticals
MP 428　　　　　　　　　　　　　　　　　　　　　　　　　　　　　　　　　　　　　　　　Program: REFTNSS.SAS 14.2.4.2 Percent Change from Baseline in TNSS: AM
Intent-to-Treat Population
(Page 2 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| | | | | Percent Change from Baseline in AM TNSS | | | | | | | |
| Day 3 | Azelastine | 49 | −13.75 | −13.37 | 26.139 | −88.9 | −7.89 | 24.1 | <0.001 | A vs A + F | 0.007 |
| | Fluticasone | 49 | −22.09 | −21.72 | 28.857 | −100.0 | −14.29 | 33.3 | <0.001 | F vs A + F | 0.206 |
| | Azelastine + Fluticasone | 52 | −29.29 | −28.86 | 32.070 | −100.0 | −23.79 | 38.5 | <0.001 | Treatment | 0.025 |
| Day 4 | Azelastine | 49 | −18.84 | −18.88 | 27.966 | −89.3 | −14.89 | 26.3 | <0.001 | A vs A + F | 0.011 |
| | Fluticasone | 49 | −25.07 | −25.32 | 24.920 | −100.0 | −27.27 | 17.6 | <0.001 | F vs A + F | 0.168 |
| | Azelastine + Fluticasone | 52 | −32.82 | −32.90 | 30.178 | −91.1 | −32.58 | 26.9 | <0.001 | Treatment | 0.040 |
| Day 5 | Azelastine | 49 | −23.62 | −23.57 | 27.972 | −89.3 | −15.79 | 24.1 | <0.001 | A vs A + F | 0.041 |
| | Fluticasone | 49 | −26.62 | −26.91 | 28.378 | −100.0 | −19.23 | 33.3 | <0.001 | F vs A + F | 0.138 |
| | Azelastine + Fluticasone | 52 | −35.41 | −35.63 | 32.170 | −100.0 | −33.23 | 28.6 | <0.001 | Treatment | 0.106 |
| Day 6 | Azelastine | 49 | −21.35 | −21.14 | 27.405 | −90.0 | −16.67 | 33.3 | <0.001 | A vs A + F | 0.002 |
| | Fluticasone | 49 | −27.12 | −27.42 | 31.284 | −100.0 | −23.81 | 33.3 | <0.001 | F vs A + F | 0.040 |
| | Azelastine + Fluticasone | 52 | −39.68 | −40.06 | 32.703 | −100.0 | −40.66 | 26.9 | <0.001 | Treatment | 0.008 |

MedPoints Pharmaceuticals
MP 428　　　　　　　　　　　　　　　　　　　　　　　　　　　　　　　　　　　　　　　　Program: REFTNSS.SAS 14.2.4.2 Percent Change from Baseline in TNSS: AM
Intent-to-Treat Population
(Page 3 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| | | | | Percent Change from Baseline in AM TNSS | | | | | | | |
| Day 7 | Azelastine | 49 | −26.58 | −26.26 | 27.521 | −80.0 | −25.00 | 33.3 | <0.001 | A vs A + F | 0.027 |
| | Fluticasone | 49 | −26.29 | −26.16 | 27.454 | −100.0 | −22.22 | 33.3 | <0.001 | F vs A + F | 0.026 |
| | Azelastine + Fluticasone | 52 | −39.62 | −39.49 | 33.817 | −100.0 | −40.65 | 28.6 | <0.001 | Treatment | 0.036 |
| Day 8 | Azelastine | 49 | −27.83 | −27.73 | 29.736 | −90.0 | −25.00 | 20.0 | <0.001 | A vs A + F | 0.021 |
| | Fluticasone | 49 | −24.67 | −25.01 | 26.795 | −100.0 | −19.23 | 33.3 | <0.001 | F vs A + F | 0.006 |
| | Azelastine + Fluticasone | 52 | −41.25 | −41.56 | 31.878 | −100.0 | −43.02 | 26.9 | <0.001 | Treatment | 0.012 |
| Day 9 | Azelastine | 49 | −26.20 | −26.38 | 25.942 | −81.8 | −22.22 | 18.4 | <0.001 | A vs A + F | 0.015 |
| | Fluticasone | 49 | −24.52 | −24.94 | 27.327 | −100.0 | −21.95 | 33.3 | <0.001 | F vs A + F | 0.007 |
| | Azelastine + Fluticasone | 52 | −40.21 | −40.39 | 31.450 | −100.0 | −38.98 | 26.9 | <0.001 | Treatment | 0.012 |
| Day 10 | Azelastine | 49 | −23.81 | −23.62 | 28.124 | −80.0 | −23.64 | 25.0 | <0.001 | A vs A + F | 0.008 |
| | Fluticasone | 49 | −28.06 | −28.09 | 31.748 | −100.0 | −28.36 | 57.9 | <0.001 | F vs A + F | 0.052 |
| | Azelastine + Fluticasone | 52 | −40.09 | −40.04 | 32.464 | −100.0 | −39.49 | 33.3 | <0.001 | Treatment | 0.022 |

MedPoints Pharmaceuticals
MP 428　　　　　　　　　　　　　　　　　　　　　　　　　　　　　　　　　　　　　　　　Program: REFTNSS.SAS 14.2.4.2 Percent Change from Baseline in TNSS: AM
Intent-to-Treat Population
(Page 4 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| | | | | Percent Change from Baseline in AM TNSS | | | | | | | |
| Day 11 | Azelastine | 49 | −25.65 | −25.86 | 29.971 | −90.0 | −19.40 | 22.0 | <0.001 | A vs A + F | 0.016 |
| | Fluticasone | 49 | −25.02 | −25.25 | 32.944 | −100.0 | −18.37 | 57.9 | <0.001 | F vs A + F | 0.012 |
| | Azelastine + Fluticasone | 52 | −41.35 | −41.23 | 32.948 | −100.0 | −43.25 | 38.5 | <0.001 | Treatment | 0.017 |
| Day 12 | Azelastine | 49 | −26.72 | −26.61 | 30.825 | −90.0 | −26.32 | 25.0 | <0.001 | A vs A + F | 0.016 |
| | Fluticasone | 49 | −30.49 | −30.64 | 32.747 | −100.0 | −26.83 | 57.9 | <0.001 | F vs A + F | 0.073 |
| | Azelastine + Fluticasone | 52 | −41.84 | −41.89 | 31.114 | −100.0 | −38.98 | 15.4 | <0.001 | Treatment | 0.042 |
| Day 13 | Azelastine | 49 | −26.20 | −26.36 | 31.095 | −90.0 | −18.37 | 33.3 | <0.001 | A vs A + F | 0.011 |
| | Fluticasone | 49 | −34.03 | −34.62 | 34.647 | −100.0 | −28.36 | 57.9 | <0.001 | F vs A + F | 0.203 |
| | Azelastine + Fluticasone | 52 | −42.46 | −42.77 | 32.117 | −100.0 | −43.92 | 50.0 | <0.001 | Treatment | 0.040 |

-continued

| | | | | | | | | | | | |
|---|---|---|---|---|---|---|---|---|---|---|---|
| Day 14 | Azelastine | 49 | −26.44 | −26.51 | 31.727 | −90.0 | −20.00 | 33.3 | <0.001 | A vs A + F | 0.010 |
| | Fluticasone | 49 | −33.12 | −33.54 | 34.789 | −100.0 | −31.03 | 57.9 | <0.001 | F vs A + F | 0.126 |
| | Azelastine + Fluticasone | 52 | −43.30 | −43.48 | 32.821 | −100.0 | −46.19 | 38.5 | <0.001 | Treatment | 0.033 |

[a] Total number of intent-to-treat patients with available data.

[b] LS Mean = Least-Square Mean obtained from analysis of variance (ANOVA) model for baseline or analysis of covariance (ANCOVA) model otherwise.

[c] p-value for the within-patient percent change was based on a paired t-test.

[d] p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.

[e] Mean baseline TNSS over 5-day Lead-in Period, including Day 1 AM.

[f] Overall includes TNSS scores from Day 2 to Day 14.

Reference: 16.2.6.1

MedPoints Pharmaceuticals
MP 428
Program: REFTNSS.SAS 14.2.5.1 Change from Baseline in TNSS: PM
Intent-to-Treat Population
(Page 1 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| | | | | PM TNSS | | | | | | | |
| Baseline$^e$ | Azelastine (A) | 49 | 9.94 | 9.97 | 1.126 | 7.3 | 10.00 | 12.0 | | Treatment | 0.456 |
| | Fluticasone (F) | 50 | 9.74 | 9.77 | 1.436 | 6.5 | 9.63 | 12.0 | | | |
| | Azelastine + Fluticasone (A + F) | 52 | 9.62 | 9.64 | 1.725 | 3.4 | 9.80 | 12.0 | | | |
| | | | | Change from Baseline in PM TNSS | | | | | | | |
| Overall$^f$ | Azelastine | 49 | −2.51 | −2.57 | 2.253 | −7.1 | −2.38 | 1.8 | <0.001 | A vs A + F | 0.023 |
| | Fluticasone | 50 | −2.43 | −2.71 | 2.288 | −9.0 | −1.86 | 1.5 | <0.001 | F vs A + F | 0.042 |
| | Azelastine + Fluticasone | 52 | −3.46 | −3.73 | 2.791 | −9.4 | −3.52 | 2.8 | <0.001 | Treatment | 0.043 |
| | | | | | | | | | | Day | <0.001 |
| | | | | | | | | | | Treatment * Day | 0.563 |
| Day 2 | Azelastine | 49 | −1.76 | −1.65 | 2.490 | −8.2 | −1.00 | 2.0 | <0.001 | A vs A + F | 0.155 |
| | Fluticasone | 49 | −1.59 | −1.54 | 2.465 | −9.0 | −1.00 | 2.3 | <0.001 | F vs A + F | 0.098 |
| | Azelastine + Fluticasone | 52 | −2.37 | −2.37 | 2.732 | −8.8 | −1.67 | 1.4 | <0.001 | Treatment | 0.198 |

MedPoints Pharmaceuticals
MP 428
Program: REFTNSS.SAS 14.2.5.1 Change from Baseline in TNSS: PM
Intent-to-Treat Population
(Page 2 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| | | | | Change from Baseline in PM TNSS | | | | | | | |
| Day 3 | Azelastine | 49 | −1.98 | −1.91 | 2.535 | −8.2 | −1.50 | 2.0 | <0.001 | A vs A + F | 0.060 |
| | Fluticasone | 49 | −2.08 | −2.08 | 2.560 | −9.6 | −1.80 | 2.7 | <0.001 | F vs A + F | 0.118 |
| | Azelastine + Fluticasone | 52 | −2.85 | −2.88 | 2.680 | −8.8 | −2.63 | 2.4 | <0.001 | Treatment | 0.129 |
| Day 4 | Azelastine | 49 | −2.17 | −2.09 | 2.774 | −9.2 | −2.20 | 2.0 | <0.001 | A vs A + F | 0.026 |
| | Fluticasone | 49 | −2.12 | −2.10 | 2.842 | −9.6 | −1.80 | 3.0 | <0.001 | F vs A + F | 0.028 |
| | Azelastine + Fluticasone | 52 | −3.33 | −3.35 | 2.886 | −8.8 | −3.47 | 3.4 | <0.001 | Treatment | 0.037 |
| Day 5 | Azelastine | 49 | −2.25 | −2.19 | 3.062 | −9.2 | −1.20 | 2.5 | <0.001 | A vs A + F | 0.014 |
| | Fluticasone | 49 | −2.59 | −2.61 | 2.675 | −9.0 | −2.00 | 2.3 | <0.001 | F vs A + F | 0.071 |
| | Azelastine + Fluticasone | 52 | −3.67 | −3.73 | 3.392 | −11.0 | −3.60 | 3.4 | <0.001 | Treatment | 0.038 |

| | | | | | | | | | | |
|---|---|---|---|---|---|---|---|---|---|---|
| Day 6 | Azelastine | 49 | −2.43 | −2.38 | 2.763 | −9.0 | −2.00 | 2.4 | <0.001 A vs A + F | 0.011 |
| | Fluticasone | 49 | −2.53 | −2.53 | 2.751 | −9.0 | −2.00 | 2.3 | <0.001 F vs A + F | 0.022 |
| | Azelastine + Fluticasone | 52 | −3.85 | −3.88 | 3.144 | −11.0 | −3.63 | 3.4 | <0.001 Treatment | 0.019 |

MedPoints Pharmaceuticals
MP 428

Program: REFTNSS.SAS 14.2.5.1 Change from Baseline in TNSS: PM
Intent-to-Treat Population
(Page 3 of 4)

| Variable Time Point | Treatment | N[a] | Mean | LS Mean[b] | Standard Deviation | Minimum | Median | Maximum | Paired t-test p-value[c] Source | ANOVA p-value[d] |
|---|---|---|---|---|---|---|---|---|---|---|
| | | | | | Change from Baseline in PM TNSS | | | | | |
| Day 7 | Azelastine | 49 | −2.57 | −2.54 | 2.705 | −8.4 | −2.25 | 2.4 | <0.001 A vs A + F | 0.074 |
| | Fluticasone | 49 | −2.45 | −2.50 | 2.632 | −9.0 | −2.00 | 3.0 | <0.001 F vs A + F | 0.064 |
| | Azelastine + Fluticasone | 52 | −3.48 | −3.57 | 3.178 | −11.0 | −3.13 | 2.4 | <0.001 Treatment | 0.107 |
| Day 8 | Azelastine | 49 | −2.76 | −2.69 | 2.584 | −8.5 | −2.75 | 1.8 | <0.001 A vs A + F | 0.027 |
| | Fluticasone | 49 | −2.18 | −2.24 | 2.575 | −9.0 | −2.00 | 4.3 | <0.001 F vs A + F | 0.003 |
| | Azelastine + Fluticasone | 52 | −3.81 | −3.91 | 3.062 | −10.0 | −3.43 | 3.4 | <0.001 Treatment | 0.007 |
| Day 9 | Azelastine | 49 | −2.86 | −2.78 | 2.675 | −9.0 | −2.33 | 1.2 | <0.001 A vs A + F | 0.128 |
| | Fluticasone | 49 | −2.69 | −2.73 | 2.852 | −9.0 | −2.00 | 3.3 | <0.001 F vs A + F | 0.107 |
| | Azelastine + Fluticasone | 52 | −3.58 | −3.67 | 3.226 | −11.0 | −3.50 | 3.4 | <0.001 Treatment | 0.191 |
| Day 10 | Azelastine | 49 | −3.08 | −3.01 | 2.812 | −9.0 | −3.00 | 2.8 | <0.001 A vs A + F | 0.102 |
| | Fluticasone | 49 | −2.88 | −2.90 | 2.900 | −9.0 | −2.60 | 4.8 | <0.001 F vs A + F | 0.067 |
| | Azelastine + Fluticasone | 52 | −3.92 | −4.00 | 3.265 | −11.0 | −3.43 | 2.4 | <0.001 Treatment | 0.130 |

MedPoints Pharmaceuticals
MP 428

Program: REFTNSS.SAS 14.2.5.1 Change from Baseline in TNSS: PM
Intent-to-Treat Population
(Page 4 of 4)

| Variable Time Point | Treatment | N[a] | Mean | LS Mean[b] | Standard Deviation | Minimum | Median | Maximum | Paired t-test p-value[c] Source | ANOVA p-value[d] |
|---|---|---|---|---|---|---|---|---|---|---|
| | | | | | Change from Baseline in PM TNSS | | | | | |
| Day 11 | Azelastine | 49 | −3.29 | −3.20 | 3.122 | −9.5 | −3.33 | 2.4 | <0.001 A vs A + F | 0.099 |
| | Fluticasone | 49 | −3.29 | −3.33 | 2.862 | −9.7 | −3.00 | 4.8 | <0.001 F vs A + F | 0.148 |
| | Azelastine + Fluticasone | 52 | −4.10 | −4.21 | 3.338 | −11.0 | −3.50 | 1.8 | <0.001 Treatment | 0.195 |
| Day 12 | Azelastine | 49 | −2.96 | −2.85 | 3.340 | −10.0 | −2.40 | 2.8 | <0.001 A vs A + F | 0.031 |
| | Fluticasone | 49 | −3.10 | −3.13 | 3.029 | −9.0 | −3.00 | 4.8 | <0.001 F vs A + F | 0.081 |
| | Azelastine + Fluticasone | 52 | −4.15 | −4.26 | 3.553 | −12.0 | −3.63 | 3.4 | <0.001 Treatment | 0.071 |
| Day 13 | Azelastine | 49 | −3.21 | −3.11 | 3.248 | −10.0 | −3.00 | 3.7 | <0.001 A vs A + F | 0.062 |
| | Fluticasone | 49 | −3.51 | −3.57 | 3.187 | −9.3 | −3.00 | 4.8 | <0.001 F vs A + F | 0.244 |
| | Azelastine + Fluticasone | 52 | −4.19 | −4.32 | 3.505 | −12.0 | −3.90 | 2.8 | <0.001 Treatment | 0.167 |
| Day 14 | Azelastine | 49 | −3.10 | −3.00 | 3.142 | −10.0 | −2.80 | 3.7 | <0.001 A vs A + F | 0.025 |
| | Fluticasone | 49 | −3.63 | −3.70 | 3.473 | −9.3 | −3.00 | 4.8 | <0.001 F vs A + F | 0.228 |
| | Azelastine + Fluticasone | 52 | −4.35 | −4.48 | 3.448 | −11.0 | −4.10 | 3.8 | <0.001 Treatment | 0.079 |

[a] Total number of intent-to-treat patients with available data.
[b] LS Mean = Least-Square Mean obtained from analysis of variance (ANOVA) model for baseline or analysis of covariance (ANCOVA) model otherwise.
[c] p-value for the within-patient change was based on a paired t-test.
[d] p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.
[e] Mean baseline TNSS over 5-day Lead-in Period, including Day 1 AM.
[f] Overall includes TNSS scores from Day 2 to Day 14.
Reference: 16.2.6.1

MedPoints Pharmaceuticals
MP 428

Program: REFTNSS.SAS

14.2.5.2 Percent Change from Baseline in TNSS: PM
Intent-to-Treat Population
(Page 1 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | PM TNSS | | | | | | | |
| Baseline[e] | Azelastine (A) | 49 | 9.94 | 9.97 | 1.126 | 7.3 | 10.00 | 12.0 | | Treatment | 0.456 |
| | Fluticasone (F) | 50 | 9.74 | 9.77 | 1.436 | 6.5 | 9.63 | 12.0 | | | |
| | Azelastine + Fluticasone (A + F) | 52 | 9.62 | 9.64 | 1.725 | 3.4 | 9.80 | 12.0 | | | |
| | | | Percent Change from Baseline in PM TNSS | | | | | | | | |
| Overall[f] | Azelastine | 49 | −25.39 | −26.45 | 22.390 | −70.8 | −21.68 | 18.9 | <0.001 | A vs A + F | 0.020 |
| | Fluticasone | 50 | −24.98 | −27.75 | 24.983 | −100.0 | −20.34 | 21.9 | <0.001 | F vs A + F | 0.037 |
| | Azelastine + Fluticasone | 52 | −36.18 | −38.67 | 27.800 | −86.3 | −35.94 | 32.4 | <0.001 | Treatment | 0.037 |
| | | | | | | | | | | Day | <0.001 |
| | | | | | | | | | | Treatment * Day | 0.575 |
| Day 2 | Azelastine | 49 | −17.76 | −17.15 | 24.989 | −73.2 | −10.00 | 20.0 | <0.001 | A vs A + F | 0.166 |
| | Fluticasone | 49 | −16.52 | −16.05 | 26.828 | −100.0 | −11.11 | 25.0 | <0.001 | F vs A + F | 0.110 |
| | Azelastine + Fluticasone | 52 | −24.74 | −24.49 | 28.552 | −89.8 | −16.15 | 16.3 | <0.001 | Treatment | 0.219 |

MedPoints Pharmaceuticals
MP 428

Program: REFTNSS.SAS

14.2.5.2 Percent Change from Baseline in TNSS: PM
Intent-to-Treat Population
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | Percent Change from Baseline in PM TNSS | | | | | | | | |
| Day 3 | Azelastine | 49 | −20.01 | −19.66 | 25.506 | −73.2 | −15.15 | 20.0 | <0.001 | A vs A + F | 0.074 |
| | Fluticasone | 49 | −22.28 | −22.22 | 27.434 | −100.0 | −20.00 | 28.6 | <0.001 | F vs A + F | 0.190 |
| | Azelastine + Fluticasone | 52 | −29.10 | −29.08 | 26.759 | −89.8 | −28.08 | 27.9 | <0.001 | Treatment | 0.178 |
| Day 4 | Azelastine | 49 | −21.99 | −21.42 | 27.647 | −82.1 | −23.08 | 20.0 | <0.001 | A vs A + F | 0.034 |
| | Fluticasone | 49 | −22.22 | −21.91 | 30.751 | −100.0 | −20.00 | 37.5 | <0.001 | F vs A + F | 0.040 |
| | Azelastine + Fluticasone | 52 | −34.16 | −34.05 | 30.123 | −89.8 | −36.04 | 39.5 | <0.001 | Treatment | 0.054 |
| Day 5 | Azelastine | 49 | −22.50 | −22.87 | 30.099 | −82.1 | −13.04 | 26.3 | <0.001 | A vs A + F | 0.012 |
| | Fluticasone | 49 | −27.06 | −27.51 | 29.028 | −100.0 | −22.22 | 33.3 | <0.001 | F vs A + F | 0.072 |
| | Azelastine + Fluticasone | 52 | −38.96 | −39.10 | 35.621 | −100.0 | −41.86 | 39.5 | <0.001 | Treatment | 0.035 |
| Day 6 | Azelastine | 49 | −24.82 | −25.18 | 28.081 | −81.8 | −20.45 | 25.0 | <0.001 | A vs A + F | 0.011 |
| | Fluticasone | 49 | −26.62 | −26.81 | 29.839 | −100.0 | −22.22 | 25.0 | <0.001 | F vs A + F | 0.022 |
| | Azelastine + Fluticasone | 52 | −40.94 | −40.78 | 32.866 | −100.0 | −41.86 | 39.5 | <0.001 | Treatment | 0.019 |

MedPoints Pharmaceuticals
MP 428

Program: REFTNSS.SAS

14.2.5.2 Percent Change from Baseline in TNSS: PM
Intent-to-Treat Population
(Page 3 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | Percent Change from Baseline in PM TNSS | | | | | | | | |
| Day 7 | Azelastine | 49 | −26.20 | −26.39 | 28.186 | −89.4 | −23.81 | 25.0 | <0.001 | A vs A + F | 0.085 |
| | Fluticasone | 49 | −25.18 | −25.72 | 28.316 | −100.0 | −20.45 | 37.5 | <0.001 | F vs A + F | 0.066 |
| | Azelastine + Fluticasone | 52 | −36.25 | −36.65 | 31.573 | −91.7 | −36.50 | 27.9 | <0.001 | Treatment | 0.117 |
| Day 8 | Azelastine | 49 | −28.17 | −27.94 | 26.451 | −89.4 | −27.27 | 18.9 | <0.001 | A vs A + F | 0.036 |
| | Fluticasone | 49 | −21.91 | −22.44 | 28.831 | −100.0 | −21.95 | 63.0 | <0.001 | F vs A + F | 0.002 |
| | Azelastine + Fluticasone | 52 | −39.45 | −40.02 | 29.932 | −100.0 | −36.70 | 39.5 | <0.001 | Treatment | 0.008 |
| Day 9 | Azelastine | 49 | −28.91 | −28.94 | 25.922 | −81.8 | −25.00 | 12.2 | <0.001 | A vs A + F | 0.127 |
| | Fluticasone | 49 | −27.18 | −27.82 | 30.627 | −100.0 | −22.22 | 48.1 | <0.001 | F vs A + F | 0.086 |
| | Azelastine + Fluticasone | 52 | −37.64 | −38.21 | 33.093 | −100.0 | −39.83 | 39.5 | <0.001 | Treatment | 0.167 |

| | | | | | | | | | Paired t-test | | ANOVA |
|---|---|---|---|---|---|---|---|---|---|---|---|
| | Treatment | N | Mean | | Standard Deviation | Minimum | Median | Maximum | p-value | Source | p-value |

-continued

| Day 10 | Azelastine | 49 | −31.29 | −31.30 | 28.433 | −88.6 | −33.33 | 29.7 | <0.001 | A vs A + F | 0.109 |
|---|---|---|---|---|---|---|---|---|---|---|---|
| | Fluticasone | 49 | −29.48 | −29.73 | 31.092 | −100.0 | −27.27 | 65.5 | <0.001 | F vs A + F | 0.063 |
| | Azelastine + Fluticasone | 52 | −41.03 | −41.24 | 32.243 | −100.0 | −41.86 | 27.9 | <0.001 | Treatment | 0.129 |

MedPoints Pharmaceuticals
MP 428

Program: REFTNSS.SAS 14.2.5.2 Percent Change from Baseline in TNSS: PM
Intent-to-Treat Population
(Page 4 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Percent Change from Baseline in PM TNSS | | | | | | | |
| Day 11 | Azelastine | 49 | −32.77 | −32.80 | 30.202 | −90.0 | −33.96 | 25.0 | <0.001 | A vs A + F | 0.084 |
| | Fluticasone | 49 | −33.54 | −34.15 | 30.853 | −100.0 | −33.33 | 65.5 | <0.001 | F vs A + F | 0.128 |
| | Azelastine + Fluticasone | 52 | −43.12 | −43.71 | 33.524 | −100.0 | −39.11 | 25.0 | <0.001 | Treatment | 0.166 |
| Day 12 | Azelastine | 49 | −29.44 | −29.18 | 32.936 | −100.0 | −25.00 | 29.7 | <0.001 | A vs A + F | 0.027 |
| | Fluticasone | 49 | −31.52 | −32.00 | 33.300 | −100.0 | −31.82 | 65.5 | <0.001 | F vs A + F | 0.071 |
| | Azelastine + Fluticasone | 52 | −43.65 | −44.26 | 35.487 | −100.0 | −44.95 | 39.5 | <0.001 | Treatment | 0.062 |
| Day 13 | Azelastine | 49 | −32.27 | −32.19 | 33.207 | −100.0 | −33.33 | 44.0 | <0.001 | A vs A + F | 0.067 |
| | Fluticasone | 49 | −35.75 | −36.56 | 34.708 | −100.0 | −33.33 | 65.5 | <0.001 | F vs A + F | 0.227 |
| | Azelastine + Fluticasone | 52 | −44.03 | −44.83 | 36.109 | −100.0 | −43.68 | 38.9 | <0.001 | Treatment | 0.174 |
| Day 14 | Azelastine | 49 | −31.14 | −31.07 | 31.947 | −100.0 | −28.57 | 44.0 | <0.001 | A vs A + F | 0.028 |
| | Fluticasone | 49 | −36.79 | −37.70 | 37.211 | −100.0 | −33.33 | 65.5 | <0.001 | F vs A + F | 0.206 |
| | Azelastine + Fluticasone | 52 | −45.57 | −46.50 | 36.136 | −100.0 | −44.51 | 52.8 | <0.001 | Treatment | 0.087 |

[a]Total number of intent-to-treat patients with available data.
[b]LS Mean = Least-Square Mean obtained from analysis of variance (ANOVA) model for baseline or analysis of covariance (ANCOVA) model otherwise.
[c]p-value for the within-patient percent change was based on a paired t-test.
[d]p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.
[e]Mean baseline TNSS over 5-day Lead-in Period, including Day 1 AM.
[f]Overall includes TNSS scores from Day 2 to Day 14.

Reference: 16.2.6.1

MedPoints Pharmaceuticals
MP 428

Program: REFTNSS.SAS 14.2.6.1 Change from Baseline in Individual Nasal Symptom Score (AM and PM Combined): Itchy Nose
Intent-to-Treat Population
(Page 1 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | AM and PM Combined Nasal Symptom Score: Itchy Nose | | | | | | | | |
| Baseline[e] | Azelastine (A) | 49 | 4.74 | 4.76 | 0.807 | 2.9 | 4.73 | 6.0 | | Treatment | 0.982 |
| | Fluticasone (F) | 50 | 4.76 | 4.78 | 1.309 | 0.0 | 5.16 | 6.0 | | | |
| | Azelastine + Fluticasone (A + F) | 52 | 4.72 | 4.74 | 1.047 | 1.5 | 4.76 | 6.0 | | | |
| | | | Change from Baseline in AM and PM Combined Nasal Symptom Score: Itchy Nose | | | | | | | | |
| Overall[f] | Azelastine | 49 | −1.16 | −1.14 | 1.358 | −4.5 | −0.98 | 1.1 | <0.001 | A vs A + F | 0.009 |
| | Fluticasone | 49 | −1.24 | −1.25 | 1.464 | −5.4 | −0.95 | 2.2 | <0.001 | F vs A + F | 0.023 |
| | Azelastine + Fluticasone | 52 | −1.94 | −1.94 | 1.730 | −5.8 | −1.89 | 2.3 | <0.001 | Treatment | 0.017 |
| | | | | | | | | | | Day | <0.001 |
| | | | | | | | | | | Treatment * Day | 0.889 |
| Day 2 | Azelastine | 49 | −0.61 | −0.58 | 1.245 | −4.2 | −0.50 | 1.8 | 0.001 | A vs A + F | 0.022 |
| | Fluticasone | 49 | −0.66 | −0.61 | 1.600 | −5.4 | −0.40 | 3.2 | 0.006 | F vs A + F | 0.027 |
| | Azelastine + Fluticasone | 52 | −1.28 | −1.25 | 1.742 | −5.1 | −1.00 | 2.0 | <0.001 | Treatment | 0.033 |

MedPoints Pharmaceuticals  
MP 428  
Program: REFTNSS.SAS 14.2.6.1 Change from Baseline in Individual Nasal Symptom Score (AM and PM Combined): Itchy Nose  
Intent-to-Treat Population  
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | Change from Baseline in AM and PM Combined Nasal Symptom Score: Itchy Nose | | | | | | | | | | |
| Day 3 | Azelastine | 49 | −0.84 | −0.85 | 1.364 | −4.2 | −0.75 | 1.3 | <0.001 | A vs A + F | 0.020 |
| | Fluticasone | 49 | −0.97 | −0.99 | 1.533 | −5.4 | −0.67 | 2.2 | <0.001 | F vs A + F | 0.061 |
| | Azelastine + Fluticasone | 52 | −1.53 | −1.55 | 1.770 | −6.0 | −1.38 | 1.9 | <0.001 | Treatment | 0.046 |
| Day 4 | Azelastine | 49 | −1.00 | −1.01 | 1.606 | −4.8 | −0.73 | 2.2 | <0.001 | A vs A + F | 0.030 |
| | Fluticasone | 49 | −0.97 | −0.98 | 1.638 | −5.4 | −0.90 | 2.3 | <0.001 | F vs A + F | 0.024 |
| | Azelastine + Fluticasone | 52 | −1.69 | −1.71 | 1.683 | −6.0 | −1.67 | 1.0 | <0.001 | Treatment | 0.037 |
| Day 5 | Azelastine | 49 | −1.10 | −1.11 | 1.690 | −4.8 | −0.75 | 1.3 | <0.001 | A vs A + F | 0.031 |
| | Fluticasone | 49 | −1.15 | −1.16 | 1.650 | −5.4 | −1.00 | 2.3 | <0.001 | F vs A + F | 0.042 |
| | Azelastine + Fluticasone | 52 | −1.86 | −1.88 | 1.998 | −6.0 | −1.81 | 1.9 | <0.001 | Treatment | 0.052 |
| Day 6 | Azelastine | 49 | −1.14 | −1.14 | 1.650 | −4.8 | −0.73 | 1.4 | <0.001 | A vs A + F | 0.019 |
| | Fluticasone | 49 | −1.21 | −1.21 | 1.630 | −5.4 | −1.00 | 1.6 | <0.001 | F vs A + F | 0.032 |
| | Azelastine + Fluticasone | 52 | −1.94 | −1.95 | 1.923 | −6.0 | −2.00 | 1.9 | <0.001 | Treatment | 0.033 |

MedPoints Pharmaceuticals  
MP 428  
Program: REFTNSS.SAS 14.2.6.1 Change from Baseline in Individual Nasal Symptom Score (AM and PM Combined): Itchy Nose  
Intent-to-Treat Population  
(Page 3 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | Change from Baseline in AM and PM Combined Nasal Symptom Score: Itchy Nose | | | | | | | | | | |
| Day 7 | Azelastine | 49 | −1.17 | −1.18 | 1.464 | −4.8 | −0.90 | 1.3 | <0.001 | A vs A + F | 0.009 |
| | Fluticasone | 49 | −1.27 | −1.30 | 1.580 | −5.4 | −1.00 | 2.3 | <0.001 | F vs A + F | 0.024 |
| | Azelastine + Fluticasone | 52 | −2.03 | −2.06 | 1.993 | −6.0 | −2.00 | 2.9 | <0.001 | Treatment | 0.017 |
| Day 8 | Azelastine | 49 | −1.12 | −1.15 | 1.497 | −4.8 | −0.83 | 1.4 | <0.001 | A vs A + F | 0.004 |
| | Fluticasone | 49 | −1.29 | −1.33 | 1.643 | −5.4 | −1.15 | 3.2 | <0.001 | F vs A + F | 0.018 |
| | Azelastine + Fluticasone | 52 | −2.11 | −2.15 | 2.059 | −6.0 | −1.95 | 2.9 | <0.001 | Treatment | 0.009 |
| Day 9 | Azelastine | 49 | −1.27 | −1.29 | 1.472 | −5.4 | −0.93 | 1.3 | <0.001 | A vs A + F | 0.019 |
| | Fluticasone | 49 | −1.35 | −1.40 | 1.624 | −5.4 | −1.30 | 2.2 | <0.001 | F vs A + F | 0.040 |
| | Azelastine + Fluticasone | 52 | −2.05 | −2.10 | 2.025 | −6.0 | −2.00 | 2.9 | <0.001 | Treatment | 0.037 |
| Day 10 | Azelastine | 49 | −1.35 | −1.35 | 1.743 | −5.0 | −1.10 | 1.3 | <0.001 | A vs A + F | 0.041 |
| | Fluticasone | 49 | −1.19 | −1.21 | 1.817 | −5.4 | −1.00 | 3.4 | <0.001 | F vs A + F | 0.015 |
| | Azelastine + Fluticasone | 52 | −2.05 | −2.08 | 1.904 | −6.0 | −2.00 | 2.0 | <0.001 | Treatment | 0.032 |

MedPoints Pharmaceuticals  
MP 428  
Program: REFTNSS.SAS 14.2.6.1 Change from Baseline in Individual Nasal Symptom Score (AM and PM Combined): Itchy Nose  
Intent-to-Treat Population  
(Page 4 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | Change from Baseline in AM and PM Combined Nasal Symptom Score: Itchy Nose | | | | | | | | | | |
| Day 11 | Azelastine | 49 | −1.37 | −1.39 | 1.803 | −5.0 | −1.10 | 1.4 | <0.001 | A vs A + F | 0.028 |
| | Fluticasone | 49 | −1.29 | −1.33 | 1.810 | −5.4 | −1.08 | 3.4 | <0.001 | F vs A + F | 0.019 |
| | Azelastine + Fluticasone | 52 | −2.13 | −2.18 | 1.908 | −6.0 | −2.12 | 2.9 | <0.001 | Treatment | 0.030 |
| Day 12 | Azelastine | 49 | −1.33 | −1.33 | 1.930 | −6.0 | −1.00 | 1.3 | <0.001 | A vs A + F | 0.017 |
| | Fluticasone | 49 | −1.48 | −1.50 | 1.945 | −5.4 | −1.17 | 3.4 | <0.001 | F vs A + F | 0.051 |
| | Azelastine + Fluticasone | 52 | −2.19 | −2.23 | 1.883 | −6.0 | −2.23 | 2.0 | <0.001 | Treatment | 0.039 |
| Day 13 | Azelastine | 49 | −1.43 | −1.44 | 1.842 | −5.4 | −1.15 | 1.8 | <0.001 | A vs A + F | 0.078 |
| | Fluticasone | 49 | −1.62 | −1.64 | 2.031 | −6.0 | −1.42 | 3.4 | <0.001 | F vs A + F | 0.224 |
| | Azelastine + Fluticasone | 52 | −2.05 | −2.10 | 1.978 | −6.0 | −2.25 | 2.9 | <0.001 | Treatment | 0.194 |

| | | | | | | | | | | |
|---|---|---|---|---|---|---|---|---|---|---|
| Day 14 | Azelastine | 49 | −1.39 | −1.39 | 1.903 | −6.0 | −1.15 | 1.8 | <0.001 A vs A + F | 0.017 |
| | Fluticasone | 49 | −1.74 | −1.76 | 2.052 | −6.0 | −1.57 | 3.4 | <0.001 F vs A + F | 0.146 |
| | Azelastine + Fluticasone | 52 | −2.26 | −2.30 | 1.946 | −6.0 | −2.56 | 2.9 | <0.001 Treatment | 0.053 |

[a] Total number of intent-to-treat patients with available data.

[b] LS Mean = Least-Square Mean obtained from analysis of variance (ANOVA) model for baseline or analysis of covariance (ANCOVA) model otherwise.

[c] p-value for the within-patient change was based on a paired t-test.

[d] p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.

[e] Mean baseline TNSS over 5-day Lead-in Period, including Day 1 AM.

[f] Overall includes TNSS scores from Day 2 to Day 14.

Reference: 16.2.6.1

MedPoints Pharmaceuticals
MP 428
Program: REFTNSS.SAS
14.2.6.2 Change from Baseline in Individual Nasal Symptom Score (AM and PM Combined): Congestion
Intent-to-Treat Population
(Page 1 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | AM and PM Combined Nasal Symptom Score: Congestion | | | | | | | | |
| Baseline[e] | Azelastine (A) | 49 | 5.48 | 5.48 | 0.511 | 4.5 | 5.47 | 6.0 | | Treatment | 0.505 |
| | Fluticasone (F) | 50 | 5.51 | 5.51 | 0.388 | 4.5 | 5.55 | 6.0 | | | |
| | Azelastine + Fluticasone (A + F) | 52 | 5.40 | 5.40 | 0.578 | 3.8 | 5.45 | 6.0 | | | |
| | | | Change from Baseline in AM and PM Combined Nasal Symptom Score: Congestion | | | | | | | | |
| Overall[f] | Azelastine | 49 | −1.12 | −1.08 | 1.452 | −5.0 | −0.77 | 1.5 | <0.001 | A vs A + F | 0.019 |
| | Fluticasone | 49 | −1.19 | −1.14 | 1.243 | −5.2 | −0.99 | 0.9 | <0.001 | F vs A + F | 0.035 |
| | Azelastine + Fluticasone | 52 | −1.70 | −1.70 | 1.349 | −4.6 | −1.54 | 1.2 | <0.001 | Treatment | 0.034 |
| | | | | | | | | | | Day | <0.001 |
| | | | | | | | | | | Treatment * Day | 0.220 |
| Day 2 | Azelastine | 49 | −0.78 | −0.73 | 1.386 | −4.1 | −0.17 | 1.5 | <0.001 | A vs A + F | 0.717 |
| | Fluticasone | 49 | −0.65 | −0.59 | 1.380 | −5.4 | −0.30 | 1.2 | 0.002 | F vs A + F | 0.349 |
| | Azelastine + Fluticasone | 52 | −0.84 | −0.83 | 1.243 | −3.7 | −0.88 | 1.9 | <0.001 | Treatment | 0.641 |

MedPoints Pharmaceuticals
MP 428
Program: REFTNSS.SAS
14.2.6.2 Change from Baseline in Individual Nasal Symptom Score (AM and PM Combined): Congestion
Intent-to-Treat Population
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | Change from Baseline in AM and PM Combined Nasal Symptom Score: Congestion | | | | | | | | |
| Day 3 | Azelastine | 49 | −0.68 | −0.62 | 1.701 | −5.8 | 0.00 | 1.5 | 0.007 | A vs A + F | 0.011 |
| | Fluticasone | 49 | −0.90 | −0.81 | 1.457 | −5.4 | −0.67 | 1.1 | <0.001 | F vs A + F | 0.059 |
| | Azelastine + Fluticasone | 52 | −1.38 | −1.37 | 1.511 | −5.4 | −1.43 | 1.9 | <0.001 | Treatment | 0.030 |
| Day 4 | Azelastine | 49 | −0.82 | −0.78 | 1.533 | −5.1 | −0.92 | 1.5 | <0.001 | A vs A + F | 0.010 |
| | Fluticasone | 49 | −1.06 | −1.00 | 1.388 | −5.2 | −1.00 | 1.4 | <0.001 | F vs A + F | 0.070 |
| | Azelastine + Fluticasone | 52 | −1.53 | −1.53 | 1.497 | −5.0 | −1.48 | 1.8 | <0.001 | Treatment | 0.031 |
| Day 5 | Azelastine | 49 | −1.07 | −1.02 | 1.680 | −5.1 | −0.90 | 1.5 | <0.001 | A vs A + F | 0.110 |
| | Fluticasone | 49 | −1.06 | −1.00 | 1.462 | −5.4 | −0.83 | 1.1 | <0.001 | F vs A + F | 0.099 |
| | Azelastine + Fluticasone | 52 | −1.53 | −1.53 | 1.679 | −5.4 | −1.55 | 1.8 | <0.001 | Treatment | 0.169 |
| Day 6 | Azelastine | 49 | −1.09 | −1.04 | 1.771 | −5.8 | −0.92 | 1.5 | <0.001 | A vs A + F | 0.044 |
| | Fluticasone | 49 | −1.10 | −1.03 | 1.563 | −5.4 | −0.83 | 1.1 | <0.001 | F vs A + F | 0.042 |
| | Azelastine + Fluticasone | 52 | −1.69 | −1.69 | 1.569 | −5.0 | −1.57 | 1.8 | <0.001 | Treatment | 0.064 |

MedPoints Pharmaceuticals  
MP 428  
Program: REFTNSS.SAS 14.2.6.2 Change from Baseline in Individual Nasal Symptom Score (AM and PM Combined): Congestion  
Intent-to-Treat Population  
(Page 3 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | Change from Baseline in AM and PM Combined Nasal Symptom Score: Congestion | | | | | | |
| Day 7 | Azelastine | 49 | −1.23 | −1.17 | 1.791 | −5.8 | −1.00 | 1.5 | <0.001 | A vs A + F | 0.102 |
| | Fluticasone | 49 | −1.10 | −1.03 | 1.392 | −5.2 | −1.08 | 1.1 | <0.001 | F vs A + F | 0.040 |
| | Azelastine + Fluticasone | 52 | −1.71 | −1.69 | 1.663 | −6.0 | −1.67 | 1.8 | <0.001 | Treatment | 0.093 |
| Day 8 | Azelastine | 49 | −1.27 | −1.24 | 1.670 | −5.8 | −1.00 | 1.5 | <0.001 | A vs A + F | 0.079 |
| | Fluticasone | 49 | −0.98 | −0.94 | 1.361 | −5.2 | −0.83 | 1.1 | <0.001 | F vs A + F | 0.006 |
| | Azelastine + Fluticasone | 52 | −1.74 | −1.76 | 1.495 | −4.8 | −1.70 | 1.8 | <0.001 | Treatment | 0.021 |
| Day 9 | Azelastine | 49 | −1.23 | −1.20 | 1.515 | −5.8 | −1.00 | 1.5 | <0.001 | A vs A + F | 0.023 |
| | Fluticasone | 49 | −1.22 | −1.19 | 1.311 | −5.2 | −1.27 | 0.9 | <0.001 | F vs A + F | 0.021 |
| | Azelastine + Fluticasone | 52 | −1.84 | −1.86 | 1.569 | −6.0 | −1.73 | 0.9 | <0.001 | Treatment | 0.030 |
| Day 10 | Azelastine | 49 | −1.17 | −1.12 | 1.574 | −5.3 | −1.00 | 1.5 | <0.001 | A vs A + F | 0.010 |
| | Fluticasone | 49 | −1.39 | −1.34 | 1.463 | −5.2 | −1.50 | 1.4 | <0.001 | F vs A + F | 0.061 |
| | Azelastine + Fluticasone | 52 | −1.90 | −1.92 | 1.701 | −5.1 | −1.67 | 1.8 | <0.001 | Treatment | 0.028 |

MedPoints Pharmaceuticals  
MP 428  
Program: REFTNSS.SAS 14.2.6.2 Change from Baseline in Individual Nasal Symptom Score (AM and PM Combined): Congestion  
Intent-to-Treat Population  
(Page 4 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | Change from Baseline in AM and PM Combined Nasal Symptom Score: Congestion | | | | | | |
| Day 11 | Azelastine | 49 | −1.23 | −1.18 | 1.762 | −6.0 | −0.92 | 1.5 | <0.001 | A vs A + F | 0.009 |
| | Fluticasone | 49 | −1.28 | −1.22 | 1.367 | −5.2 | −1.27 | 1.4 | <0.001 | F vs A + F | 0.013 |
| | Azelastine + Fluticasone | 52 | −1.96 | −1.98 | 1.599 | −5.0 | −1.74 | 0.8 | <0.001 | Treatment | 0.013 |
| Day 12 | Azelastine | 49 | −1.27 | −1.21 | 1.844 | −6.0 | −1.00 | 1.5 | <0.001 | A vs A + F | 0.045 |
| | Fluticasone | 49 | −1.49 | −1.41 | 1.579 | −5.2 | −1.55 | 1.4 | <0.001 | F vs A + F | 0.157 |
| | Azelastine + Fluticasone | 52 | −1.88 | −1.88 | 1.707 | −6.0 | −1.90 | 1.1 | <0.001 | Treatment | 0.119 |
| Day 13 | Azelastine | 49 | −1.29 | −1.25 | 1.690 | −5.0 | −1.00 | 1.5 | <0.001 | A vs A + F | 0.009 |
| | Fluticasone | 49 | −1.59 | −1.55 | 1.648 | −5.2 | −1.43 | 1.4 | <0.001 | F vs A + F | 0.080 |
| | Azelastine + Fluticasone | 52 | −2.11 | −2.14 | 1.791 | −6.0 | −2.00 | 1.8 | <0.001 | Treatment | 0.028 |
| Day 14 | Azelastine | 49 | −1.39 | −1.33 | 1.827 | −6.0 | −1.05 | 1.5 | <0.001 | A vs A + F | 0.032 |
| | Fluticasone | 49 | −1.59 | −1.53 | 1.749 | −5.4 | −1.30 | 1.4 | <0.001 | F vs A + F | 0.116 |
| | Azelastine + Fluticasone | 52 | −2.05 | −2.06 | 1.671 | −5.1 | −2.00 | 0.8 | <0.001 | Treatment | 0.084 |

[a] Total number of intent-to-treat patients with available data.

[b] LS Mean = Least-Square Mean obtained from analysis of variance (ANOVA) model for baseline or analysis of covariance (ANCOVA) model otherwise.

[c] p-value for the within-patient change was based on a paired t-test.

[d] p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.

[e] Mean baseline TNSS over 5-day Lead-in Period, including Day 1 AM.

[f] Overall includes TNSS scores from Day 2 to Day 14.

Reference: 16.2.6.1

MedPoints Pharmaceuticals  
MP 428  
Program: REFTNSS.SAS 14.2.6.3 Change from Baseline in Individual Nasal Symptom Score (AM and PM Combined): Runny Nose  
Intent-to-Treat Population  
(Page 1 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| \multicolumn{12}{c}{AM and PM Combined Nasal Symptom Score: Runny Nose} |
| Baseline$^e$ | Azelastine (A) | 49 | 4.91 | 4.92 | 0.780 | 2.1 | 4.92 | 6.0 | | Treatment | 0.843 |
| | Fluticasone (F) | 50 | 4.96 | 4.97 | 0.950 | 0.7 | 5.16 | 6.0 | | | |
| | Azelastine + Fluticasone (A + F) | 52 | 4.86 | 4.87 | 0.961 | 1.5 | 4.92 | 6.0 | | | |
| \multicolumn{12}{c}{Change from Baseline in AM and PM Combined Nasal Symptom Score: Runny Nose} |
| Overall$^f$ | Azelastine | 49 | −1.08 | −1.06 | 1.409 | −4.4 | −0.67 | 1.6 | <0.001 | A vs A + F | 0.019 |
| | Fluticasone | 49 | −1.36 | −1.34 | 1.244 | −4.3 | −1.04 | 2.1 | <0.001 | F vs A + F | 0.187 |
| | Azelastine + Fluticasone | 52 | −1.73 | −1.71 | 1.563 | −5.5 | −1.35 | 1.7 | <0.001 | Treatment | 0.063 |
| | | | | | | | | | | Day | <0.001 |
| | | | | | | | | | | Treatment * Day | 0.084 |
| Day 2 | Azelastine | 49 | −0.72 | −0.70 | 1.513 | −4.7 | −0.42 | 1.8 | 0.002 | A vs A + F | 0.354 |
| | Fluticasone | 49 | −0.90 | −0.86 | 1.300 | −4.3 | −1.00 | 2.3 | <0.001 | F vs A + F | 0.708 |
| | Azelastine + Fluticasone | 52 | −0.98 | −0.97 | 1.639 | −4.5 | −0.53 | 2.2 | <0.001 | Treatment | 0.647 |

MedPoints Pharmaceuticals  
MP 428  
Program: REFTNSS.SAS 14.2.6.3 Change from Baseline in Individual Nasal Symptom Score (AM and PM Combined): Runny Nose  
Intent-to-Treat Population  
(Page 2 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| \multicolumn{12}{c}{Change from Baseline in AM and PM Combined Nasal Symptom Score: Runny Nose} |
| Day 3 | Azelastine | 49 | −0.79 | −0.74 | 1.583 | −5.7 | −1.00 | 1.8 | 0.001 | A vs A + F | 0.074 |
| | Fluticasone | 49 | −1.05 | −0.96 | 1.421 | −5.0 | −0.80 | 2.0 | <0.001 | F vs A + F | 0.302 |
| | Azelastine + Fluticasone | 52 | −1.30 | −1.27 | 1.646 | −5.2 | −1.21 | 2.2 | <0.001 | Treatment | 0.199 |
| Day 4 | Azelastine | 49 | −0.79 | −0.76 | 1.402 | −4.8 | −0.43 | 1.6 | <0.001 | A vs A + F | 0.018 |
| | Fluticasone | 49 | −1.17 | −1.12 | 1.534 | −6.0 | −1.15 | 2.3 | <0.001 | F vs A + F | 0.237 |
| | Azelastine + Fluticasone | 52 | −1.49 | −1.48 | 1.611 | −5.2 | −1.27 | 2.4 | <0.001 | Treatment | 0.061 |
| Day 5 | Azelastine | 49 | −0.97 | −0.96 | 1.450 | −4.0 | −0.67 | 1.6 | <0.001 | A vs A + F | 0.025 |
| | Fluticasone | 49 | −1.43 | −1.42 | 1.660 | −5.0 | −1.05 | 3.3 | <0.001 | F vs A + F | 0.391 |
| | Azelastine + Fluticasone | 52 | −1.69 | −1.70 | 1.818 | −6.0 | −1.53 | 2.2 | <0.001 | Treatment | 0.079 |
| Day 6 | Azelastine | 49 | −0.95 | −0.94 | 1.406 | −4.1 | −1.00 | 1.8 | <0.001 | A vs A + F | 0.003 |
| | Fluticasone | 49 | −1.35 | −1.35 | 1.630 | −5.0 | −1.00 | 2.3 | <0.001 | F vs A + F | 0.083 |
| | Azelastine + Fluticasone | 52 | −1.90 | −1.92 | 1.859 | −6.0 | −1.38 | 1.2 | <0.001 | Treatment | 0.012 |

MedPoints Pharmaceuticals  
MP 428  
Program: REFTNSS.SAS 14.2.6.3 Change from Baseline in Individual Nasal Symptom Score (AM and PM Combined): Runny Nose  
Intent-to-Treat Population  
(Page 3 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| \multicolumn{12}{c}{Change from Baseline in AM and PM Combined Nasal Symptom Score: Runny Nose} |
| Day 7 | Azelastine | 49 | −0.95 | −0.93 | 1.601 | −4.1 | −1.07 | 1.8 | <0.001 | A vs A + F | 0.017 |
| | Fluticasone | 49 | −1.31 | −1.28 | 1.553 | −4.3 | −1.45 | 3.3 | <0.001 | F vs A + F | 0.189 |
| | Azelastine + Fluticasone | 52 | −1.71 | −1.72 | 1.804 | −6.0 | −1.53 | 2.2 | <0.001 | Treatment | 0.058 |
| Day 8 | Azelastine | 49 | −1.25 | −1.23 | 1.711 | −5.1 | −1.00 | 1.8 | <0.001 | A vs A + F | 0.065 |
| | Fluticasone | 49 | −0.98 | −0.95 | 1.430 | −4.3 | −0.73 | 3.3 | <0.001 | F vs A + F | 0.007 |
| | Azelastine + Fluticasone | 52 | −1.84 | −1.84 | 1.776 | −6.0 | −1.70 | 1.6 | <0.001 | Treatment | 0.023 |
| Day 9 | Azelastine | 49 | −1.15 | −1.14 | 1.637 | −4.8 | −0.90 | 1.8 | <0.001 | A vs A + F | 0.101 |
| | Fluticasone | 49 | −1.21 | −1.18 | 1.674 | −5.5 | −1.00 | 2.3 | <0.001 | F vs A + F | 0.133 |
| | Azelastine + Fluticasone | 52 | −1.69 | −1.69 | 1.744 | −6.0 | −1.38 | 1.2 | <0.001 | Treatment | 0.188 |

| | | N<sup>a</sup> | Mean | LS Mean<sup>b</sup> | Standard Deviation | Minimum | Median | Maximum | Paired t-test p-value<sup>c</sup> | Source | ANOVA p-value<sup>d</sup> |
|---|---|---|---|---|---|---|---|---|---|---|---|
| Day 10 | Azelastine | 49 | −1.13 | −1.11 | 1.843 | −5.1 | −0.83 | 1.8 | <0.001 | A vs A + F | 0.038 |
| | Fluticasone | 49 | −1.54 | −1.52 | 1.672 | −4.5 | −1.45 | 2.3 | <0.001 | F vs A + F | 0.343 |
| | Azelastine + Fluticasone | 52 | −1.84 | −1.85 | 1.764 | −6.0 | −1.68 | 1.2 | <0.001 | Treatment | 0.115 |

MedPoints Pharmaceuticals
MP 428
Program: REFTNSS.SAS 14.2.6.3 Change from Baseline in Individual Nasal Symptom Score (AM and PM Combined): Runny Nose
Intent-to-Treat Population
(Page 4 of 4)

| Variable Time Point | Treatment | N<sup>a</sup> | Mean | LS Mean<sup>b</sup> | Standard Deviation | Minimum | Median | Maximum | Paired t-test p-value<sup>c</sup> | Source | ANOVA p-value<sup>d</sup> |
|---|---|---|---|---|---|---|---|---|---|---|---|
| | | | | Change from Baseline in AM and PM Combined Nasal Symptom Score: Runny Nose | | | | | | | |
| Day 11 | Azelastine | 49 | −1.38 | −1.35 | 2.018 | −6.0 | −1.10 | 1.8 | <0.001 | A vs A + F | 0.062 |
| | Fluticasone | 49 | −1.54 | −1.51 | 1.656 | −5.5 | −1.42 | 1.6 | <0.001 | F vs A + F | 0.151 |
| | Azelastine + Fluticasone | 52 | −2.03 | −2.05 | 1.956 | −6.0 | −1.90 | 1.2 | <0.001 | Treatment | 0.145 |
| Day 12 | Azelastine | 49 | −1.25 | −1.22 | 2.133 | −6.0 | −0.43 | 2.0 | <0.001 | A vs A + F | 0.043 |
| | Fluticasone | 49 | −1.58 | −1.54 | 1.434 | −4.3 | −1.35 | 1.6 | <0.001 | F vs A + F | 0.244 |
| | Azelastine + Fluticasone | 52 | −1.96 | −1.97 | 2.008 | −6.0 | −1.58 | 2.2 | <0.001 | Treatment | 0.126 |
| Day 13 | Azelastine | 49 | −1.38 | −1.36 | 1.949 | −5.4 | −1.07 | 1.8 | <0.001 | A vs A + F | 0.061 |
| | Fluticasone | 49 | −1.78 | −1.78 | 1.677 | −4.5 | −2.00 | 2.3 | <0.001 | F vs A + F | 0.478 |
| | Azelastine + Fluticasone | 52 | −1.99 | −2.03 | 1.893 | −6.0 | −1.90 | 2.2 | <0.001 | Treatment | 0.168 |
| Day 14 | Azelastine | 49 | −1.34 | −1.32 | 1.829 | −5.4 | −1.43 | 1.9 | <0.001 | A vs A + F | 0.037 |
| | Fluticasone | 49 | −1.88 | −1.89 | 1.791 | −5.8 | −2.15 | 1.6 | <0.001 | F vs A + F | 0.604 |
| | Azelastine + Fluticasone | 52 | −2.03 | −2.07 | 1.894 | −6.0 | −2.22 | 2.2 | <0.001 | Treatment | 0.096 |

<sup>a</sup>Total number of intent-to-treat patients with available data.
<sup>b</sup>LS Mean = Least-Square Mean obtained from analysis of variance (ANOVA) model for baseline or analysis of covariance (ANCOVA) model otherwise.
<sup>c</sup>p-value for the within-patient change was based on a paired t-test.
<sup>d</sup>p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.
<sup>e</sup>Mean baseline TNSS over 5-day Lead-in Period, including Day 1 AM.
<sup>f</sup>Overall includes TNSS scores from Day 2 to Day 14.

Reference: 16.2.6.1

MedPoints Pharmaceuticals
MP 428
Program: REFTNSS.SAS 14.2.6.4 Change from Baseline in Individual Nasal Symptom Score (AM and PM Combined): Sneezing
Intent-to-Treat Population
(Page 1 of 4)

| Variable Time Point | Treatment | N<sup>a</sup> | Mean | LS Mean<sup>b</sup> | Standard Deviation | Minimum | Median | Maximum | Paired t-test p-value<sup>c</sup> | Source | ANOVA p-value<sup>d</sup> |
|---|---|---|---|---|---|---|---|---|---|---|---|
| | | | AM and PM Combined Nasal Symptom Score: Sneezing | | | | | | | | |
| Baseline<sup>e</sup> | Azelastine (A) | 49 | 4.48 | 4.51 | 1.102 | 1.2 | 4.42 | 6.0 | | Treatment | 0.625 |
| | Fluticasone (F) | 50 | 4.29 | 4.31 | 1.283 | 0.0 | 4.34 | 6.0 | | | |
| | Azelastine + Fluticasone (A + F) | 52 | 4.49 | 4.51 | 1.199 | 2.2 | 4.58 | 6.0 | | | |
| | | | Change from Baseline in AM and PM Combined Nasal Symptom Score: Sneezing | | | | | | | | |
| Overall<sup>f</sup> | Azelastine | 49 | −1.49 | −1.48 | 1.029 | −4.0 | −1.31 | 0.4 | <0.001 | A vs A + F | 0.039 |
| | Fluticasone | 49 | −1.44 | −1.52 | 1.500 | −5.0 | −1.34 | 1.3 | <0.001 | F vs A + F | 0.053 |
| | Azelastine + Fluticasone | 52 | −2.06 | −2.06 | 1.712 | −5.7 | −2.12 | 1.2 | <0.001 | Treatment | 0.067 |
| | | | | | | | | | | Day | <0.001 |
| | | | | | | | | | | Treatment * Day | 0.092 |
| Day 2 | Azelastine | 49 | −1.11 | −1.09 | 1.275 | −4.3 | −0.90 | 1.0 | <0.001 | A vs A + F | 0.255 |
| | Fluticasone | 49 | −1.03 | −1.06 | 1.280 | −4.4 | −1.00 | 1.6 | <0.001 | F vs A + F | 0.218 |
| | Azelastine + Fluticasone | 52 | −1.44 | −1.42 | 1.777 | −5.0 | −1.21 | 1.9 | <0.001 | Treatment | 0.386 |

MedPoints Pharmaceuticals
MP 428

Program: REFTNSS.SAS 14.2.6.4 Change from Baseline in Individual Nasal Symptom Score (AM and PM Combined): Sneezing
Intent-to-Treat Population
(Page 2 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| \multicolumn{12}{l}{Change from Baseline in AM and PM Combined Nasal Symptom Score: Sneezing} |
| Day 3 | Azelastine | 49 | −0.97 | −0.99 | 1.363 | −4.8 | −0.77 | 2.0 | <0.001 | A vs A + F | 0.040 |
|  | Fluticasone | 49 | −1.21 | −1.29 | 1.484 | −4.0 | −1.00 | 1.5 | <0.001 | F vs A + F | 0.282 |
|  | Azelastine + Fluticasone | 52 | −1.61 | −1.63 | 1.793 | −5.0 | −1.36 | 2.0 | <0.001 | Treatment | 0.119 |
| Day 4 | Azelastine | 49 | −1.32 | −1.34 | 1.668 | −5.8 | −1.00 | 2.0 | <0.001 | A vs A + F | 0.097 |
|  | Fluticasone | 49 | −1.33 | −1.42 | 1.579 | −5.4 | −1.10 | 2.0 | <0.001 | F vs A + F | 0.159 |
|  | Azelastine + Fluticasone | 52 | −1.90 | −1.92 | 2.007 | −6.0 | −2.00 | 2.0 | <0.001 | Treatment | 0.199 |
| Day 5 | Azelastine | 49 | −1.34 | −1.36 | 1.431 | −4.3 | −1.03 | 0.9 | <0.001 | A vs A + F | 0.023 |
|  | Fluticasone | 49 | −1.52 | −1.61 | 1.649 | −5.4 | −1.33 | 1.5 | <0.001 | F vs A + F | 0.121 |
|  | Azelastine + Fluticasone | 52 | −2.11 | −2.14 | 2.017 | −6.0 | −2.18 | 1.1 | <0.001 | Treatment | 0.066 |
| Day 6 | Azelastine | 49 | −1.26 | −1.27 | 1.352 | −4.3 | −1.30 | 1.6 | <0.001 | A vs A + F | 0.003 |
|  | Fluticasone | 49 | −1.44 | −1.51 | 1.769 | −5.4 | −1.27 | 2.0 | <0.001 | F vs A + F | 0.024 |
|  | Azelastine + Fluticasone | 52 | −2.26 | −2.28 | 1.892 | −6.0 | −2.38 | 1.0 | <0.001 | Treatment | 0.009 |

MedPoints Pharmaceuticals
MP 428

Program: REFTNSS.SAS 14.2.6.4 Change from Baseline in Individual Nasal Symptom Score (AM and PM Combined): Sneezing
Intent-to-Treat Population
(Page 3 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| \multicolumn{12}{l}{Change from Baseline in AM and PM Combined Nasal Symptom Score: Sneezing} |
| Day 7 | Azelastine | 49 | −1.75 | −1.76 | 1.501 | −4.3 | −1.55 | 1.6 | <0.001 | A vs A + F | 0.491 |
|  | Fluticasone | 49 | −1.33 | −1.44 | 1.751 | −5.4 | −1.20 | 2.0 | <0.001 | F vs A + F | 0.111 |
|  | Azelastine + Fluticasone | 52 | −1.97 | −2.00 | 2.029 | −6.0 | −2.13 | 2.9 | <0.001 | Treatment | 0.278 |
| Day 8 | Azelastine | 49 | −1.73 | −1.74 | 1.465 | −4.3 | −1.55 | 2.8 | <0.001 | A vs A + F | 0.124 |
|  | Fluticasone | 49 | −1.29 | −1.41 | 1.677 | −5.4 | −1.25 | 3.0 | <0.001 | F vs A + F | 0.011 |
|  | Azelastine + Fluticasone | 52 | −2.21 | −2.23 | 1.750 | −5.3 | −2.00 | 1.0 | <0.001 | Treatment | 0.037 |
| Day 9 | Azelastine | 49 | −1.73 | −1.72 | 1.598 | −5.8 | −1.67 | 1.8 | <0.001 | A vs A + F | 0.382 |
|  | Fluticasone | 49 | −1.29 | −1.40 | 1.831 | −5.4 | −1.40 | 2.0 | <0.001 | F vs A + F | 0.071 |
|  | Azelastine + Fluticasone | 52 | −2.01 | −2.02 | 1.852 | −6.0 | −2.10 | 2.0 | <0.001 | Treatment | 0.196 |
| Day 10 | Azelastine | 49 | −1.71 | −1.70 | 1.309 | −4.2 | −1.75 | 0.7 | <0.001 | A vs A + F | 0.176 |
|  | Fluticasone | 49 | −1.50 | −1.57 | 1.833 | −5.4 | −1.58 | 3.0 | <0.001 | F vs A + F | 0.081 |
|  | Azelastine + Fluticasone | 52 | −2.15 | −2.15 | 1.904 | −6.0 | −2.18 | 1.4 | <0.001 | Treatment | 0.183 |

MedPoints Pharmaceuticals
MP 428

Program: REFTNSS.SAS 14.2.6.4 Change from Baseline in Individual Nasal Symptom Score (AM and PM Combined): Sneezing
Intent-to-Treat Population
(Page 4 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| \multicolumn{12}{l}{Change from Baseline in AM and PM Combined Nasal Symptom Score: Sneezing} |
| Day 11 | Azelastine | 49 | −1.79 | −1.79 | 1.590 | −6.0 | −1.55 | 0.8 | <0.001 | A vs A + F | 0.259 |
|  | Fluticasone | 49 | −1.66 | −1.78 | 1.966 | −5.4 | −1.83 | 3.0 | <0.001 | F vs A + F | 0.243 |
|  | Azelastine + Fluticasone | 52 | −2.17 | −2.19 | 1.946 | −6.0 | −2.10 | 2.0 | <0.001 | Treatment | 0.410 |
| Day 12 | Azelastine | 49 | −1.63 | −1.63 | 1.589 | −5.3 | −1.73 | 2.8 | <0.001 | A vs A + F | 0.046 |
|  | Fluticasone | 49 | −1.54 | −1.68 | 1.982 | −5.4 | −1.80 | 2.8 | <0.001 | F vs A + F | 0.064 |
|  | Azelastine + Fluticasone | 52 | −2.30 | −2.33 | 1.917 | −6.0 | −2.20 | 1.0 | <0.001 | Treatment | 0.082 |
| Day 13 | Azelastine | 49 | −1.60 | −1.60 | 1.682 | −5.1 | −1.75 | 2.5 | <0.001 | A vs A + F | 0.033 |
|  | Fluticasone | 49 | −1.84 | −1.98 | 1.963 | −5.4 | −1.83 | 2.8 | <0.001 | F vs A + F | 0.293 |
|  | Azelastine + Fluticasone | 52 | −2.32 | −2.34 | 1.854 | −6.0 | −2.18 | 2.0 | <0.001 | Treatment | 0.102 |

| | | | | | | | | | | |
|---|---|---|---|---|---|---|---|---|---|---|
| Day 14 | Azelastine | 49 | −1.50 | −1.51 | 1.794 | −5.8 | −1.35 | 3.5 | <0.001 A vs A + F | 0.020 |
| | Fluticasone | 49 | −1.70 | −1.87 | 2.046 | −5.4 | −1.83 | 3.6 | <0.001 F vs A + F | 0.181 |
| | Azelastine + Fluticasone | 52 | −2.34 | −2.37 | 2.108 | −6.0 | −2.28 | 3.4 | <0.001 Treatment | 0.065 |

[a] Total number of intent-to-treat patients with available data.

[b] LS Mean = Least-Square Mean obtained from analysis of variance (ANOVA) model for baseline or analysis of covariance (ANCOVA) model otherwise.

[c] p-value for the within-patient change was based on a paired t-test.

[d] p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.

[e] Mean baseline TNSS over 5-day Lead-in Period, including Day 1 AM.

[f] Overall includes TNSS scores from Day 2 to Day 14.

Reference: 16.2.6.1

---

MedPoints Pharmaceuticals
MP 428                                                                                                    Program: REFTNSS.SAS 14.2.7.1 Percent Change from Baseline in Individual Nasal Symptom Score (AM and PM Combined): Itchy Nose
Intent-to-Treat Population
(Page 1 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | AM and PM Combined Nasal Symptom Score: Itchy Nose | | | | | | | | |
| Baseline[e] | Azelastine (A) | 49 | 4.74 | 4.76 | 0.807 | 2.9 | 4.73 | 6.0 | | Treatment | 0.982 |
| | Fluticasone (F) | 50 | 4.76 | 4.78 | 1.309 | 0.0 | 5.16 | 6.0 | | | |
| | Azelastine + Fluticasone (A + F) | 52 | 4.72 | 4.74 | 1.047 | 1.5 | 4.76 | 6.0 | | | |
| | | | Percent Change from Baseline in AM and PM Combined Nasal Symptom Score: Itchy Nose | | | | | | | | |
| Overall[f] | Azelastine | 49 | −25.53 | −25.36 | 29.667 | −100.0 | −19.66 | 24.4 | <0.001 | A vs A + F | 0.033 |
| | Fluticasone | 48 | −25.67 | −25.54 | 32.846 | −100.0 | −25.54 | 78.1 | <0.001 | F vs A + F | 0.037 |
| | Azelastine + Fluticasone | 52 | −39.65 | −39.86 | 38.963 | −98.0 | −41.67 | 73.7 | <0.001 | Treatment | 0.050 |
| | | | | | | | | | | Day | <0.001 |
| | | | | | | | | | | Treatment * Day | 0.912 |
| Day 2 | Azelastine | 49 | −13.55 | −13.14 | 28.296 | −100.0 | −11.11 | 44.0 | 0.002 | A vs A + F | 0.101 |
| | Fluticasone | 48 | −14.27 | −12.72 | 39.625 | −100.0 | −8.39 | 110.5 | 0.016 | F vs A + F | 0.092 |
| | Azelastine + Fluticasone | 52 | −25.04 | −24.76 | 41.506 | −100.0 | −16.67 | 96.7 | <0.001 | Treatment | 0.154 |

MedPoints Pharmaceuticals
MP 428                                                                                                    Program: REFTNSS.SAS 14.2.7.1 Percent Change from Baseline in Individual Nasal Symptom Score (AM and PM Combined): Itchy Nose
Intent-to-Treat Population
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | Percent Change from Baseline in AM and PM Combined Nasal Symptom Score: Itchy Nose | | | | | | | | |
| Day 3 | Azelastine | 49 | −18.60 | −19.04 | 31.661 | −100.0 | −16.67 | 27.7 | <0.001 | A vs A + F | 0.111 |
| | Fluticasone | 48 | −22.41 | −22.88 | 36.902 | −100.0 | −15.32 | 75.4 | <0.001 | F vs A + F | 0.289 |
| | Azelastine + Fluticasone | 52 | −29.89 | −30.63 | 42.602 | −100.0 | −28.99 | 104.5 | <0.001 | Treatment | 0.265 |
| Day 4 | Azelastine | 49 | −22.23 | −22.54 | 37.258 | −100.0 | −13.79 | 56.5 | <0.001 | A vs A + F | 0.072 |
| | Fluticasone | 48 | −20.31 | −20.59 | 38.528 | −100.0 | −16.67 | 75.4 | <0.001 | F vs A + F | 0.041 |
| | Azelastine + Fluticasone | 52 | −35.17 | −35.72 | 36.235 | −100.0 | −33.94 | 36.4 | <0.001 | Treatment | 0.080 |
| Day 5 | Azelastine | 49 | −24.24 | −24.75 | 37.297 | −100.0 | −15.49 | 27.7 | <0.001 | A vs A + F | 0.100 |
| | Fluticasone | 48 | −24.64 | −25.02 | 38.416 | −100.0 | −25.00 | 75.4 | <0.001 | F vs A + F | 0.109 |
| | Azelastine + Fluticasone | 52 | −37.54 | −38.19 | 45.751 | −100.0 | −33.33 | 104.5 | <0.001 | Treatment | 0.168 |
| Day 6 | Azelastine | 49 | −25.00 | −24.98 | 35.189 | −100.0 | −15.49 | 30.9 | <0.001 | A vs A + F | 0.047 |
| | Fluticasone | 48 | −26.87 | −27.12 | 37.321 | −100.0 | −24.76 | 40.4 | <0.001 | F vs A + F | 0.089 |
| | Azelastine + Fluticasone | 52 | −39.77 | −40.13 | 41.232 | −100.0 | −46.22 | 61.3 | <0.001 | Treatment | 0.097 |

MedPoints Pharmaceuticals  
MP 428  
Program: REFTNSS.SAS 14.2.7.1 Percent Change from Baseline in Individual Nasal Symptom Score (AM and PM Combined): Itchy Nose  
Intent-to-Treat Population  
(Page 3 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | | | | | | | |

Percent Change from Baseline in AM and PM Combined Nasal Symptom Score: Itchy Nose

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| Day 7 | Azelastine | 49 | −25.83 | −26.35 | 32.567 | −100.0 | −21.57 | 27.7 | <0.001 | A vs A + F | 0.033 |
| | Fluticasone | 48 | −26.92 | −27.79 | 36.738 | −100.0 | −23.55 | 75.4 | <0.001 | F vs A + F | 0.053 |
| | Azelastine + Fluticasone | 52 | −41.85 | −42.66 | 43.566 | −100.0 | −50.00 | 93.5 | <0.001 | Treatment | 0.060 |
| Day 8 | Azelastine | 49 | −24.80 | −25.37 | 32.681 | −100.0 | −18.92 | 30.9 | <0.001 | A vs A + F | 0.018 |
| | Fluticasone | 48 | −27.33 | −28.16 | 39.760 | −100.0 | −30.22 | 110.5 | <0.001 | F vs A + F | 0.045 |
| | Azelastine + Fluticasone | 52 | −43.28 | −44.15 | 44.339 | −100.0 | −47.47 | 93.5 | <0.001 | Treatment | 0.037 |
| Day 9 | Azelastine | 49 | −26.97 | −27.69 | 30.150 | −100.0 | −21.57 | 27.7 | <0.001 | A vs A + F | 0.033 |
| | Fluticasone | 48 | −28.73 | −29.96 | 35.790 | −100.0 | −31.23 | 75.4 | <0.001 | F vs A + F | 0.069 |
| | Azelastine + Fluticasone | 52 | −42.78 | −43.85 | 45.194 | −100.0 | −43.46 | 93.5 | <0.001 | Treatment | 0.069 |
| Day 10 | Azelastine | 49 | −29.56 | −29.83 | 38.926 | −100.0 | −21.57 | 30.4 | <0.001 | A vs A + F | 0.083 |
| | Fluticasone | 48 | −22.79 | −23.04 | 41.732 | −100.0 | −18.99 | 126.4 | <0.001 | F vs A + F | 0.012 |
| | Azelastine + Fluticasone | 52 | −43.11 | −43.96 | 41.925 | −100.0 | −44.14 | 61.3 | <0.001 | Treatment | 0.035 |

MedPoints Pharmaceuticals  
MP 428  
Program: REFTNSS.SAS 14.2.7.1 Percent Change from Baseline in Individual Nasal Symptom Score (AM and PM Combined): Itchy Nose  
Intent-to-Treat Population  
(Page 4 of 4)

Percent Change from Baseline in AM and PM Combined Nasal Symptom Score: Itchy Nose

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| Day 11 | Azelastine | 49 | −29.59 | −30.38 | 39.232 | −100.0 | −22.33 | 31.4 | <0.001 | A vs A + F | 0.080 |
| | Fluticasone | 48 | −25.70 | −26.56 | 41.558 | −100.0 | −27.36 | 126.4 | <0.001 | F vs A + F | 0.029 |
| | Azelastine + Fluticasone | 52 | −43.70 | −45.12 | 45.931 | −100.0 | −50.00 | 104.5 | <0.001 | Treatment | 0.067 |
| Day 12 | Azelastine | 49 | −28.74 | −29.11 | 41.037 | −100.0 | −16.67 | 27.7 | <0.001 | A vs A + F | 0.037 |
| | Fluticasone | 48 | −29.58 | −29.96 | 45.257 | −100.0 | −30.22 | 126.4 | <0.001 | F vs A + F | 0.048 |
| | Azelastine + Fluticasone | 52 | −45.74 | −46.77 | 41.579 | −100.0 | −50.00 | 61.3 | <0.001 | Treatment | 0.061 |
| Day 13 | Azelastine | 49 | −31.63 | −32.25 | 40.192 | −100.0 | −22.33 | 44.0 | <0.001 | A vs A + F | 0.209 |
| | Fluticasone | 48 | −30.81 | −31.14 | 45.786 | −100.0 | −31.23 | 126.4 | <0.001 | F vs A + F | 0.170 |
| | Azelastine + Fluticasone | 52 | −41.85 | −43.24 | 47.158 | −100.0 | −52.66 | 104.5 | <0.001 | Treatment | 0.309 |
| Day 14 | Azelastine | 49 | −31.14 | −31.60 | 41.995 | −100.0 | −25.00 | 44.0 | <0.001 | A vs A + F | 0.085 |
| | Fluticasone | 48 | −33.38 | −33.39 | 46.398 | −100.0 | −33.33 | 126.4 | <0.001 | F vs A + F | 0.130 |
| | Azelastine + Fluticasone | 52 | −45.77 | −46.96 | 46.575 | −100.0 | −56.91 | 104.5 | <0.001 | Treatment | 0.167 |

[a]Total number of intent-to-treat patients with available data.

[b]LS Mean = Least-Square Mean obtained from analysis of variance (ANOVA) model for baseline or analysis of covariance (ANCOVA) model otherwise.

[c]p-value for the within-patient percent change was based on a paired t-test.

[d]p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.

[e]Mean baseline TNSS over 5-day Lead-in Period, including Day 1 AM.

[f]Overall includes TNSS scores from Day 2 to Day 14.

Reference: 16.2.6.1

MedPoints Pharmaceuticals  
MP 428  
Program: REFTNSS.SAS 14.2.7.2 Percent Change from Baseline in Individual Nasal Symptom Score (AM and PM Combined): Congestion  
Intent-to-Treat Population  
(Page 1 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| | | | AM and PM Combined Nasal Symptom Score: Congestion | | | | | | | | |
| Baseline$^e$ | Azelastine (A) | 49 | 5.48 | 5.48 | 0.511 | 4.5 | 5.47 | 6.0 | | Treatment | 0.505 |
| | Fluticasone (F) | 50 | 5.51 | 5.51 | 0.388 | 4.5 | 5.55 | 6.0 | | | |
| | Azelastine + Fluticasone (A + F) | 52 | 5.40 | 5.40 | 0.578 | 3.8 | 5.45 | 6.0 | | | |
| | | | Percent Change from Baseline in AM and PM Combined Nasal Symptom Score: Congestion | | | | | | | | |
| Overall$^f$ | Azelastine | 49 | −19.82 | −19.23 | 26.640 | −85.5 | −12.82 | 32.4 | <0.001 | A vs A + F | 0.016 |
| | Fluticasone | 49 | −21.68 | −21.11 | 23.391 | −100.0 | −18.72 | 17.3 | <0.001 | F vs A + F | 0.042 |
| | Azelastine + Fluticasone | 52 | −31.49 | −31.19 | 25.710 | −91.8 | −26.01 | 29.2 | <0.001 | Treatment | 0.034 |
| | | | | | | | | | | Day | <0.001 |
| | | | | | | | | | | Treatment * Day | 0.197 |
| Day 2 | Azelastine | 49 | −14.05 | −13.19 | 26.251 | −80.4 | −3.23 | 32.4 | <0.001 | A vs A + F | 0.740 |
| | Fluticasone | 49 | −11.97 | −10.84 | 26.153 | −100.0 | −5.66 | 24.1 | 0.002 | F vs A + F | 0.418 |
| | Azelastine + Fluticasone | 52 | −15.18 | −14.81 | 23.853 | −64.7 | −16.67 | 45.2 | <0.001 | Treatment | 0.718 |

MedPoints Pharmaceuticals  
MP 428  
Program: REFTNSS.SAS 14.2.7.2 Percent Change from Baseline in Individual Nasal Symptom Score (AM and PM Combined): Congestion  
Intent-to-Treat Population  
(Page 2 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| | | | Percent Change from Baseline in AM and PM Combined Nasal Symptom Score: Congestion | | | | | | | | |
| Day 3 | Azelastine | 49 | −11.70 | −10.71 | 31.360 | −100.0 | 0.00 | 32.4 | 0.012 | A vs A + F | 0.012 |
| | Fluticasone | 49 | −16.63 | −15.34 | 27.665 | −100.0 | −11.76 | 22.0 | <0.001 | F vs A + F | 0.089 |
| | Azelastine + Fluticasone | 52 | −25.04 | −24.87 | 28.329 | −100.0 | −26.38 | 45.2 | <0.001 | Treatment | 0.036 |
| Day 4 | Azelastine | 49 | −14.44 | −13.79 | 28.821 | −100.0 | −16.67 | 32.4 | <0.001 | A vs A + F | 0.010 |
| | Fluticasone | 49 | −19.51 | −18.75 | 26.344 | −100.0 | −16.67 | 30.4 | <0.001 | F vs A + F | 0.090 |
| | Azelastine + Fluticasone | 52 | −28.34 | −28.13 | 28.168 | −83.3 | −27.90 | 44.0 | <0.001 | Treatment | 0.031 |
| Day 5 | Azelastine | 49 | −18.92 | −18.24 | 31.108 | −100.0 | −16.67 | 32.4 | <0.001 | A vs A + F | 0.094 |
| | Fluticasone | 49 | −19.38 | −18.74 | 27.542 | −100.0 | −14.29 | 23.3 | <0.001 | F vs A + F | 0.112 |
| | Azelastine + Fluticasone | 52 | −28.54 | −28.40 | 32.252 | −100.0 | −28.42 | 44.0 | <0.001 | Treatment | 0.166 |
| Day 6 | Azelastine | 49 | −18.97 | −18.26 | 32.497 | −100.0 | −18.37 | 32.4 | <0.001 | A vs A + F | 0.035 |
| | Fluticasone | 49 | −20.16 | −19.32 | 29.269 | −100.0 | −14.29 | 22.0 | <0.001 | F vs A + F | 0.053 |
| | Azelastine + Fluticasone | 52 | −31.14 | −31.21 | 29.999 | −100.0 | −28.12 | 44.0 | <0.001 | Treatment | 0.063 |

MedPoints Pharmaceuticals  
MP 428  
Program: REFTNSS.SAS 14.2.7.2 Percent Change from Baseline in Individual Nasal Symptom Score (AM and PM Combined): Congestion  
Intent-to-Treat Population  
(Page 3 of 4)

| Variable Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| | | | Percent Change from Baseline in AM and PM Combined Nasal Symptom Score: Congestion | | | | | | | | |
| Day 7 | Azelastine | 49 | −22.02 | −21.14 | 33.150 | −100.0 | −18.37 | 32.4 | <0.001 | A vs A + F | 0.086 |
| | Fluticasone | 49 | −20.17 | −19.42 | 25.842 | −100.0 | −21.31 | 22.0 | <0.001 | F vs A + F | 0.046 |
| | Azelastine + Fluticasone | 52 | −31.85 | −31.47 | 32.137 | −100.0 | −29.41 | 44.0 | <0.001 | Treatment | 0.096 |
| Day 8 | Azelastine | 49 | −22.68 | −22.22 | 30.873 | −100.0 | −18.64 | 32.4 | <0.001 | A vs A + F | 0.070 |
| | Fluticasone | 49 | −17.88 | −17.55 | 25.284 | −100.0 | −14.29 | 23.3 | <0.001 | F vs A + F | 0.009 |
| | Azelastine + Fluticasone | 52 | −32.28 | −32.46 | 29.026 | −100.0 | −29.92 | 44.0 | <0.001 | Treatment | 0.027 |
| Day 9 | Azelastine | 49 | −22.05 | −21.68 | 27.567 | −100.0 | −18.64 | 32.4 | <0.001 | A vs A + F | 0.020 |
| | Fluticasone | 49 | −22.28 | −22.17 | 24.501 | −100.0 | −24.05 | 18.0 | <0.001 | F vs A + F | 0.026 |
| | Azelastine + Fluticasone | 52 | −34.18 | −34.36 | 29.937 | −100.0 | −30.22 | 20.0 | <0.001 | Treatment | 0.031 |

| | | | | | | | | | | |
|---|---|---|---|---|---|---|---|---|---|---|
| Day 10 | Azelastine | 49 | −20.94 | −20.32 | 29.482 | −100.0 | −16.67 | 32.4 | <0.001 A vs A + F | 0.011 |
| | Fluticasone | 49 | −25.31 | −24.97 | 27.721 | −100.0 | −27.27 | 30.4 | <0.001 F vs A + F | 0.080 |
| | Azelastine + Fluticasone | 52 | −35.02 | −35.22 | 32.451 | −100.0 | −29.92 | 44.0 | <0.001 Treatment | 0.034 |

MedPoints Pharmaceuticals
MP 428                                                                                                           Program: REFTNSS.SAS
14.2.7.2 Percent Change from Baseline in Individual Nasal Symptom Score (AM and PM Combined): Congestion
Intent-to-Treat Population
(Page 4 of 4)

| Variable Time Point | Treatment | $N^a$ | Mean | LS Mean$^b$ | Standard Deviation | Minimum | Median | Maximum | Paired t-test p-value$^c$ Source | ANOVA p-value$^d$ |
|---|---|---|---|---|---|---|---|---|---|---|
| | Percent Change from Baseline in AM and PM Combined Nasal Symptom Score: Congestion | | | | | | | | | |
| Day 11 | Azelastine | 49 | −21.53 | −20.72 | 31.552 | −100.0 | −16.67 | 32.4 | <0.001 A vs A + F | 0.007 |
| | Fluticasone | 49 | −23.45 | −22.54 | 25.792 | −100.0 | −24.05 | 30.4 | <0.001 F vs A + F | 0.017 |
| | Azelastine + Fluticasone | 52 | −35.97 | −36.20 | 29.653 | −100.0 | −31.03 | 20.0 | <0.001 Treatment | 0.013 |
| Day 12 | Azelastine | 49 | −22.63 | −21.71 | 33.872 | −100.0 | −16.67 | 32.4 | <0.001 A vs A + F | 0.041 |
| | Fluticasone | 49 | −27.05 | −26.02 | 29.299 | −100.0 | −27.93 | 30.4 | <0.001 F vs A + F | 0.173 |
| | Azelastine + Fluticasone | 52 | −34.65 | −34.57 | 31.613 | −100.0 | −33.33 | 22.4 | <0.001 Treatment | 0.112 |
| Day 13 | Azelastine | 49 | −23.01 | −22.44 | 31.203 | −83.3 | −18.64 | 32.4 | <0.001 A vs A + F | 0.009 |
| | Fluticasone | 49 | −28.95 | −28.59 | 30.706 | −100.0 | −26.38 | 30.4 | <0.001 F vs A + F | 0.093 |
| | Azelastine + Fluticasone | 52 | −38.96 | −39.28 | 33.996 | −100.0 | −33.33 | 42.9 | <0.001 Treatment | 0.028 |
| Day 14 | Azelastine | 49 | −24.78 | −23.87 | 33.330 | −100.0 | −20.79 | 32.4 | <0.001 A vs A + F | 0.027 |
| | Fluticasone | 49 | −29.09 | −28.37 | 32.768 | −100.0 | −24.53 | 30.4 | <0.001 F vs A + F | 0.129 |
| | Azelastine + Fluticasone | 52 | −38.15 | −38.04 | 32.039 | −100.0 | −33.33 | 19.0 | <0.001 Treatment | 0.075 |

$^a$Total number of intent-to-treat patients with available data.
$^b$LS Mean = Least-Square Mean obtained from analysis of variance (ANOVA) model for baseline or analysis of covariance (ANCOVA) model otherwise.
$^c$p-value for the within-patient percent change was based on a paired t-test.
$^d$p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.
$^e$Mean baseline TNSS over 5-day Lead-in Period, including Day 1 AM.
$^f$Overall includes TNSS scores from Day 2 to Day 14.
Reference: 16.2.6.1

MedPoints Pharmaceuticals
MP 428                                                                                                           Program: REFINSS.SAS
14.2.7.3 Percent Change from Baseline in Individual Nasal Symptom Score (AM and PM Combined): Runny Nose
Intent-to-Treat Population
(Page 1 of 4)

| Variable Time Point | Treatment | $N^a$ | Mean | LS Mean$^b$ | Standard Deviation | Minimum | Median | Maximum | Paired t-test p-value$^c$ Source | ANOVA p-value$^d$ |
|---|---|---|---|---|---|---|---|---|---|---|
| | AM and PM Combined Nasal Symptom Score: Runny Nose | | | | | | | | | |
| Baseline$^e$ | Azelastine (A) | 49 | 4.91 | 4.92 | 0.780 | 2.1 | 4.92 | 6.0 | Treatment | 0.843 |
| | Fluticasone (F) | 50 | 4.96 | 4.97 | 0.950 | 0.7 | 5.16 | 6.0 | | |
| | Azelastine + Fluticasone (A + F) | 52 | 4.86 | 4.87 | 0.961 | 1.5 | 4.92 | 6.0 | | |
| | Percent Change from Baseline in AM and PM Combined Nasal Symptom Score: Runny Nose | | | | | | | | | |
| Overall$^f$ | Azelastine | 49 | −21.06 | −20.47 | 27.637 | −77.3 | −15.44 | 37.4 | <0.001 A vs A + F | 0.045 |
| | Fluticasone | 49 | −23.19 | −23.02 | 53.352 | −100.0 | −21.99 | 295.6 | 0.004 F vs A + F | 0.091 |
| | Azelastine + Fluticasone | 52 | −36.87 | −36.40 | 32.928 | −100.0 | −31.06 | 45.7 | <0.001 Treatment | 0.096 |
| | | | | | | | | | Day | <0.001 |
| | | | | | | | | | Treatment * Day | 0.064 |

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| Day 2 | Azelastine | 49 | −14.08 | −13.68 | 30.566 | −100.0 | −7.98 | 41.2 | 0.002 | A vs A + F | 0.394 |
|  | Fluticasone | 49 | −12.95 | −12.11 | 57.175 | −100.0 | −16.67 | 328.6 | 0.119 | F vs A + F | 0.300 |
|  | Azelastine + Fluticasone | 52 | −20.64 | −20.90 | 37.053 | −100.0 | −12.73 | 57.9 | <0.001 | Treatment | 0.539 |

MedPoints Pharmaceuticals
MP 428                                                                                                     Program: REFINSS.SAS
14.2.7.3 Percent Change from Baseline in Individual Nasal Symptom Score (AM and PM Combined): Runny Nose
Intent-to-Treat Population
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | Percent Change from Baseline in AM and PM Combined Nasal Symptom Score: Runny Nose | | | | | | |
| Day 3 | Azelastine | 49 | −14.69 | −13.72 | 31.227 | −100.0 | −16.67 | 41.2 | 0.002 | A vs A + F | 0.079 |
|  | Fluticasone | 49 | −18.81 | −17.15 | 43.046 | −100.0 | −13.79 | 185.7 | 0.004 | F vs A + F | 0.198 |
|  | Azelastine + Fluticasone | 52 | −26.99 | −26.42 | 35.215 | −100.0 | −23.93 | 57.9 | <0.001 | Treatment | 0.188 |
| Day 4 | Azelastine | 49 | −16.23 | −15.76 | 30.087 | −100.0 | −7.98 | 37.4 | <0.001 | A vs A + F | 0.063 |
|  | Fluticasone | 49 | −18.21 | −17.17 | 59.211 | −100.0 | −22.33 | 328.6 | 0.036 | F vs A + F | 0.090 |
|  | Azelastine + Fluticasone | 52 | −32.13 | −31.97 | 35.962 | −100.0 | −24.29 | 66.7 | <0.001 | Treatment | 0.118 |
| Day 5 | Azelastine | 49 | −18.42 | −18.46 | 28.691 | −76.0 | −11.76 | 37.4 | <0.001 | A vs A + F | 0.084 |
|  | Fluticasone | 49 | −22.31 | −22.06 | 79.601 | −100.0 | −21.31 | 471.4 | 0.056 | F vs A + F | 0.164 |
|  | Azelastine + Fluticasone | 52 | −36.01 | −36.84 | 39.297 | −100.0 | −33.33 | 57.9 | <0.001 | Treatment | 0.184 |
| Day 6 | Azelastine | 49 | −18.89 | −18.89 | 28.555 | −80.4 | −21.74 | 42.9 | <0.001 | A vs A + F | 0.014 |
|  | Fluticasone | 49 | −22.47 | −22.60 | 61.486 | −100.0 | −18.64 | 328.6 | 0.014 | F vs A + F | 0.039 |
|  | Azelastine + Fluticasone | 52 | −40.73 | −41.46 | 40.234 | −100.0 | −28.93 | 31.6 | <0.001 | Treatment | 0.030 |

MedPoints Pharmaceuticals
MP 428                                                                                                     Program: REFINSS.SAS
14.2.7.3 Percent Change from Baseline in Individual Nasal Symptom Score (AM and PM Combined): Runny Nose
Intent-to-Treat Population
(Page 3 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | Percent Change from Baseline in AM and PM Combined Nasal Symptom Score: Runny Nose | | | | | | |
| Day 7 | Azelastine | 49 | −18.92 | −18.66 | 32.863 | −80.4 | −25.00 | 42.9 | <0.001 | A vs A + F | 0.082 |
|  | Fluticasone | 49 | −18.63 | −18.01 | 78.054 | −100.0 | −28.99 | 471.4 | 0.101 | F vs A + F | 0.072 |
|  | Azelastine + Fluticasone | 52 | −36.57 | −37.21 | 39.658 | −100.0 | −35.36 | 57.9 | <0.001 | Treatment | 0.121 |
| Day 8 | Azelastine | 49 | −24.97 | −24.85 | 34.586 | −100.0 | −25.00 | 42.9 | <0.001 | A vs A + F | 0.153 |
|  | Fluticasone | 49 | −12.38 | −11.82 | 76.230 | −100.0 | −14.29 | 471.4 | 0.261 | F vs A + F | 0.008 |
|  | Azelastine + Fluticasone | 52 | −39.04 | −39.68 | 37.171 | −100.0 | −36.17 | 36.4 | <0.001 | Treatment | 0.029 |
| Day 9 | Azelastine | 49 | −23.25 | −23.07 | 34.072 | −100.0 | −21.74 | 42.9 | <0.001 | A vs A + F | 0.140 |
|  | Fluticasone | 49 | −19.22 | −18.79 | 61.104 | −100.0 | −16.67 | 328.6 | 0.033 | F vs A + F | 0.053 |
|  | Azelastine + Fluticasone | 52 | −36.32 | −36.62 | 37.348 | −100.0 | −34.41 | 31.6 | <0.001 | Treatment | 0.127 |
| Day 10 | Azelastine | 49 | −22.22 | −22.00 | 37.229 | −100.0 | −16.67 | 42.9 | <0.001 | A vs A + F | 0.056 |
|  | Fluticasone | 49 | −26.39 | −26.05 | 62.505 | −100.0 | −29.13 | 328.6 | 0.005 | F vs A + F | 0.138 |
|  | Azelastine + Fluticasone | 52 | −39.75 | −40.12 | 37.259 | −100.0 | −34.41 | 31.6 | <0.001 | Treatment | 0.132 |

MedPoints Pharmaceuticals
MP 428                                                                                                     Program: REFINSS.SAS
14.2.7.3 Percent Change from Baseline in Individual Nasal Symptom Score (AM and PM Combined): Runny Nose
Intent-to-Treat Population
(Page 4 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | | Percent Change from Baseline in AM and PM Combined Nasal Symptom Score: Runny Nose | | | | | | |
| Day 11 | Azelastine | 49 | −25.83 | −25.36 | 39.046 | −100.0 | −21.57 | 42.9 | <0.001 | A vs A + F | 0.020 |
|  | Fluticasone | 49 | −31.74 | −31.56 | 37.692 | −100.0 | −33.33 | 42.9 | <0.001 | F vs A + F | 0.121 |
|  | Azelastine + Fluticasone | 52 | −43.68 | −43.71 | 40.451 | −100.0 | −40.29 | 31.6 | <0.001 | Treatment | 0.059 |
| Day 12 | Azelastine | 49 | −23.43 | −22.75 | 41.313 | −100.0 | −8.40 | 50.0 | <0.001 | A vs A + F | 0.014 |
|  | Fluticasone | 49 | −31.86 | −31.33 | 32.712 | −100.0 | −25.62 | 42.9 | <0.001 | F vs A + F | 0.175 |
|  | Azelastine + Fluticasone | 52 | −41.90 | −41.82 | 41.487 | −100.0 | −37.47 | 57.9 | <0.001 | Treatment | 0.049 |
| Day 13 | Azelastine | 49 | −27.57 | −27.36 | 39.121 | −100.0 | −24.05 | 42.9 | <0.001 | A vs A + F | 0.094 |
|  | Fluticasone | 49 | −30.84 | −30.96 | 62.521 | −100.0 | −33.33 | 328.6 | 0.001 | F vs A + F | 0.195 |
|  | Azelastine + Fluticasone | 52 | −42.30 | −43.25 | 39.438 | −100.0 | −42.11 | 57.9 | <0.001 | Treatment | 0.211 |

| | | | | | | | | | | |
|---|---|---|---|---|---|---|---|---|---|---|
| Day 14 | Azelastine | 49 | −25.22 | −25.17 | 39.838 | −100.0 | −29.41 | 93.5 | <0.001 | A vs A + F | 0.027 |
| | Fluticasone | 49 | −35.65 | −36.10 | 49.133 | −100.0 | −41.75 | 185.7 | <0.001 | F vs A + F | 0.344 |
| | Azelastine + Fluticasone | 52 | −43.18 | −44.15 | 40.256 | −100.0 | −47.22 | 57.9 | <0.001 | Treatment | 0.084 |

[a] Total number of intent-to-treat patients with available data.

[b] LS Mean = Least-Square Mean obtained from analysis of variance (ANOVA) model for baseline or analysis of covariance (ANCOVA) model otherwise.

[c] p-value for the within-patient percent change was based on a paired t-test.

[d] p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient effect, treatment group and site as the between-patient effects, treatment-by-study day interaction, and baseline as a covariate. For Baseline, the p-value was based on an ANOVA model containing treatment group and site as fixed effects.

[e] Mean baseline TNSS over 5-day Lead-in Period, including Day 1 AM.

[f] Overall includes TNSS scores from Day 2 to Day 14.

Reference: 16.2.6.1

MedPoints Pharmaceuticals
MP 428                                                                                                    Program: REFINSS.SAS
14.2.7.4 Percent Change from Baseline in Individual Nasal Symptom Score (AM and PM Combined): Sneezing
Intent-to-Treat Population
(Page 1 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| AM and PM Combined Nasal Symptom Score: Sneezing ||||||||||||
| Baseline[e] | Azelastine (A) | 49 | 4.48 | 4.51 | 1.102 | 1.2 | 4.42 | 6.0 | | Treatment | 0.625 |
| | Fluticasone (F) | 50 | 4.29 | 4.31 | 1.283 | 0.0 | 4.34 | 6.0 | | | |
| | Azelastine + Fluticasone (A + F) | 52 | 4.49 | 4.51 | 1.199 | 2.2 | 4.58 | 6.0 | | | |
| Percent Change from Baseline in AM and PM Combined Nasal Symptom Score: Sneezing ||||||||||||
| Overall[f] | Azelastine | 49 | −33.98 | −34.20 | 25.752 | −92.9 | −33.20 | 31.9 | <0.001 | A vs A + F | 0.077 |
| | Fluticasone | 48 | −31.11 | −31.80 | 38.116 | −100.0 | −33.13 | 83.6 | <0.001 | F vs A + F | 0.036 |
| | Azelastine + Fluticasone | 52 | −45.98 | −46.38 | 37.157 | −94.9 | −52.92 | 28.8 | <0.001 | Treatment | 0.077 |
| | | | | | | | | | | Day | <0.001 |
| | | | | | | | | | | Treatment * Day | 0.166 |
| Day 2 | Azelastine | 49 | −26.94 | −26.72 | 32.849 | −100.0 | −21.05 | 28.6 | <0.001 | A vs A + F | 0.476 |
| | Fluticasone | 48 | −22.69 | −22.64 | 32.208 | −100.0 | −16.67 | 63.3 | <0.001 | F vs A + F | 0.201 |
| | Azelastine + Fluticasone | 52 | −31.69 | −31.74 | 39.544 | −100.0 | −29.41 | 61.3 | <0.001 | Treatment | 0.438 |

MedPoints Pharmaceuticals
MP 428                                                                                                    Program: REFINSS.SAS
14.2.7.4 Percent Change from Baseline in Individual Nasal Symptom Score (AM and PM Combined): Sneezing
Intent-to-Treat Population
(Page 2 of 4)

| Variable Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| Percent Change from Baseline in AM and PM Combined Nasal Symptom Score: Sneezing ||||||||||||
| Day 3 | Azelastine | 49 | −22.81 | −23.56 | 32.550 | −100.0 | −16.08 | 50.0 | <0.001 | A vs A + F | 0.071 |
| | Fluticasone | 48 | −28.44 | −29.62 | 39.779 | −100.0 | −30.09 | 93.5 | <0.001 | F vs A + F | 0.322 |
| | Azelastine + Fluticasone | 52 | −36.24 | −37.05 | 39.298 | −100.0 | −33.33 | 50.0 | <0.001 | Treatment | 0.194 |
| Day 4 | Azelastine | 49 | −31.90 | −32.76 | 41.004 | −100.0 | −25.00 | 48.8 | <0.001 | A vs A + F | 0.177 |
| | Fluticasone | 48 | −30.67 | −31.80 | 36.729 | −100.0 | −27.36 | 50.0 | <0.001 | F vs A + F | 0.146 |
| | Azelastine + Fluticasone | 52 | −42.90 | −43.88 | 44.936 | −100.0 | −43.42 | 61.3 | <0.001 | Treatment | 0.264 |
| Day 5 | Azelastine | 49 | −32.23 | −33.21 | 33.600 | −100.0 | −25.23 | 17.6 | <0.001 | A vs A + F | 0.048 |
| | Fluticasone | 48 | −34.14 | −35.40 | 40.666 | −100.0 | −33.33 | 93.5 | <0.001 | F vs A + F | 0.090 |
| | Azelastine + Fluticasone | 52 | −47.78 | −48.95 | 44.067 | −100.0 | −50.00 | 29.0 | <0.001 | Treatment | 0.099 |

| | | | | | | | | | | |
|---|---|---|---|---|---|---|---|---|---|---|
| Day 6 | Azelastine | 49 | −31.52 | −32.36 | 34.306 | −100.0 | −28.00 | 37.4 | <0.001 A vs A + F | 0.012 |
| | Fluticasone | 48 | −31.22 | −32.10 | 46.825 | −100.0 | −32.77 | 100.0 | <0.001 F vs A + F | 0.012 |
| | Azelastine + Fluticasone | 52 | −52.55 | −53.59 | 43.193 | −100.0 | −56.28 | 28.6 | <0.001 Treatment | 0.014 |

MedPoints Pharmaceuticals
MP 428                                                                                                                                                   Program: REFINSS.SAS
14.2.7.4 Percent Change from Baseline in Individual Nasal Symptom Score (AM and PM Combined): Sneezing
Intent-to-Treat Population
(Page 3 of 4)

| Variable Time Point | Treatment | N[a] | Mean | LS Mean[b] | Standard Deviation | Minimum | Median | Maximum | Paired t-test p-value[c] Source | ANOVA p-value[d] |
|---|---|---|---|---|---|---|---|---|---|---|
| *Percent Change from Baseline in AM and PM Combined Nasal Symptom Score: Sneezing* | | | | | | | | | | |
| Day 7 | Azelastine | 49 | −39.73 | −40.66 | 40.109 | −100.0 | −38.78 | 71.4 | <0.001 A vs A + F | 0.623 |
| | Fluticasone | 48 | −30.14 | −31.86 | 39.516 | −100.0 | −31.32 | 50.0 | <0.001 F vs A + F | 0.133 |
| | Azelastine + Fluticasone | 52 | −43.58 | −44.87 | 47.974 | −100.0 | −51.00 | 93.5 | <0.001 Treatment | 0.310 |
| Day 8 | Azelastine | 49 | −37.78 | −38.54 | 53.003 | −100.0 | −33.33 | 242.9 | <0.001 A vs A + F | 0.152 |
| | Fluticasone | 48 | −26.04 | −28.16 | 46.403 | −100.0 | −31.03 | 150.0 | <0.001 F vs A + F | 0.012 |
| | Azelastine + Fluticasone | 52 | −50.63 | −51.74 | 38.420 | −100.0 | −51.00 | 25.0 | <0.001 Treatment | 0.040 |
| Day 9 | Azelastine | 49 | −36.04 | −36.31 | 46.303 | −100.0 | −35.48 | 157.1 | <0.001 A vs A + F | 0.256 |
| | Fluticasone | 48 | −28.22 | −29.73 | 44.136 | −100.0 | −32.58 | 93.5 | <0.001 F vs A + F | 0.060 |
| | Azelastine + Fluticasone | 52 | −45.43 | −46.13 | 39.919 | −100.0 | −50.00 | 50.0 | <0.001 Treatment | 0.165 |
| Day 10 | Azelastine | 49 | −40.82 | −41.13 | 32.513 | −100.0 | −38.78 | 16.3 | <0.001 A vs A + F | 0.377 |
| | Fluticasone | 48 | −31.17 | −31.65 | 49.076 | −100.0 | −33.33 | 150.0 | <0.001 F vs A + F | 0.046 |
| | Azelastine + Fluticasone | 52 | −47.87 | −48.50 | 42.235 | −100.0 | −50.00 | 53.8 | <0.001 Treatment | 0.135 |

MedPoints Pharmaceuticals
MP 428                                                                                                                                                   Program: REFINSS.SAS
14.2.7.4 Percent Change from Baseline in Individual Nasal Symptom Score (AM and PM Combined): Sneezing
Intent-to-Treat Population
(Page 4 of 4)

| Variable Time Point | Treatment | N[a] | Mean | LS Mean[b] | Standard Deviation | Minimum | Median | Maximum | Paired t-test p-value[c] Source | ANOVA p-value[d] |
|---|---|---|---|---|---|---|---|---|---|---|
| *Percent Change from Baseline in AM and PM Combined Nasal Symptom Score: Sneezing* | | | | | | | | | | |
| Day 11 | Azelastine | 49 | −42.70 | −43.40 | 37.450 | −100.0 | −38.78 | 28.6 | <0.001 A vs A + F | 0.598 |
| | Fluticasone | 48 | −33.52 | −35.11 | 58.224 | −100.0 | −36.05 | 158.1 | <0.001 F vs A + F | 0.158 |
| | Azelastine + Fluticasone | 52 | −47.10 | −48.26 | 41.763 | −100.0 | −50.00 | 53.8 | <0.001 Treatment | 0.362 |
| Day 12 | Azelastine | 49 | −34.06 | −34.92 | 53.768 | −100.0 | −33.33 | 242.9 | <0.001 A vs A + F | 0.076 |
| | Fluticasone | 48 | −31.18 | −33.86 | 56.246 | −100.0 | −35.69 | 158.1 | <0.001 F vs A + F | 0.062 |
| | Azelastine + Fluticasone | 52 | −51.04 | −52.43 | 40.279 | −100.0 | −52.19 | 28.6 | <0.001 Treatment | 0.107 |
| Day 13 | Azelastine | 49 | −35.28 | −35.90 | 44.192 | −100.0 | −30.43 | 100.0 | <0.001 A vs A + F | 0.057 |
| | Fluticasone | 48 | −40.87 | −42.84 | 48.895 | −100.0 | −35.42 | 93.5 | <0.001 F vs A + F | 0.267 |
| | Azelastine + Fluticasone | 52 | −51.26 | −52.60 | 40.496 | −100.0 | −51.00 | 53.8 | <0.001 Treatment | 0.159 |
| Day 14 | Azelastine | 49 | −29.95 | −30.86 | 58.715 | −100.0 | −27.93 | 242.9 | <0.001 A vs A + F | 0.054 |
| | Fluticasone | 48 | −36.07 | −39.31 | 52.487 | −100.0 | −33.94 | 144.9 | <0.001 F vs A + F | 0.262 |
| | Azelastine + Fluticasone | 52 | −49.62 | −51.14 | 51.854 | −100.0 | −57.14 | 130.8 | <0.001 Treatment | 0.152 |

[a]Total number of intent-to-treat patients with available data.
[b]LS Mean = Least-Square Mean obtained from analysis of variance (ANOVA) model for baseline or analysis of covariance (ANCOVA) model otherwise.
[c]p-value for the within-patient percent change was based on a paired t-test.
[d]p-value for between treatment group comparison, except Overall and Baseline, was based on an ANCOVA model containing treatment group and site as fixed effects, and baseline as a covariate. For Overall, the p-value was based on a repeated measures ANCOVA model containing study day as the within-patient efffect, treatment group and site as the between-patient effects, treatment-by-study day interaction, and baseline as a covariate. For Baseline, the p-value was based on an ANOVA model containing treatment group and site as fixed effects.
[e]Mean baseline TNSS over 5-day Lead-in Period, including Day 1 AM.
[f]Overall includes TNSS scores from Day 2 to Day 14.
Reference 16.2.6.1

MedPoints Pharmaceuticals  
MP 428  
Program: RQLQO.SAS 14.2.8 Adult Rhinoconjunctivitis Quality of Life Questionnaire Outcomes  
Intent-to-Treat Population  
(Page 1 of 4)

| Domain Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Activity | | | | | | | |
| Baseline | Azelastine (A) | 44 | 4.17 | 4.17 | 1.180 | 1.3 | 4.33 | 6.0 | | Treatment | 0.216 |
| | Fluticasone (F) | 41 | 4.49 | 4.45 | 0.966 | 2.3 | 4.67 | 6.0 | | | |
| | Azelastine + Fluticasone (A + F) | 47 | 4.55 | 4.55 | 1.104 | 1.3 | 4.67 | 6.0 | | | |
| | | | Change From Baseline in Activity | | | | | | | | |
| Day 14/ET | Azelastine | 43 | −1.25 | −1.37 | 1.386 | −5.0 | −1.00 | 1.3 | <0.001 | A vs A + F | 0.041 |
| | Fluticasone | 41 | −1.50 | −1.52 | 1.638 | −4.3 | −1.33 | 1.7 | <0.001 | F vs A + F | 0.116 |
| | Azelastine + Fluticasone | 47 | −2.07 | −2.03 | 1.702 | −6.0 | −2.00 | 1.0 | <0.001 | Treatment | 0.098 |
| | | | | Sleep | | | | | | | |
| Baseline | Azelastine | 45 | 3.23 | 3.25 | 1.241 | 0.0 | 3.33 | 5.7 | | Treatment | 0.024 |
| | Fluticasone | 44 | 3.93 | 3.91 | 1.397 | 0.0 | 4.17 | 6.0 | | | |
| | Azelastine + Fluticasone | 47 | 3.78 | 3.81 | 1.265 | 0.7 | 4.00 | 6.0 | | | |
| | | | Change From Baseline in Sleep | | | | | | | | |
| Day 14/ET | Azelastine | 44 | −1.02 | −1.23 | 1.081 | −3.0 | −1.00 | 1.0 | <0.001 | A vs A + F | 0.024 |
| | Fluticasone | 43 | −1.26 | −1.23 | 1.558 | −4.3 | −1.33 | 1.7 | <0.001 | F vs A + F | 0.023 |
| | Azelastine + Fluticasone | 47 | −1.90 | −1.88 | 1.658 | −6.0 | −1.33 | 1.0 | <0.001 | Treatment | 0.031 |

MedPoints Pharmaceuticals  
MP 428  
Program: RQLQO.SAS 14.2.8 Adult Rhinoconjunctivitis Quality of Life Questionnaire Outcomes  
Intent-to-Treat Population  
(Page 2 of 4)

| Domain Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Non-nose/eye Symptoms | | | | | | | |
| Baseline | Azelastine | 44 | 3.22 | 3.22 | 1.281 | 0.3 | 3.21 | 5.9 | | Treatment | 0.598 |
| | Fluticasone | 44 | 3.53 | 3.48 | 1.299 | 0.3 | 3.57 | 5.6 | | | |
| | Azelastine + Fluticasone | 47 | 3.39 | 3.40 | 1.375 | 0.6 | 3.71 | 5.7 | | | |
| | | | Change From Baseline in Non-nose/eye Symptoms | | | | | | | | |
| Day 14/ET | Azelastine | 43 | −0.82 | −0.88 | 1.226 | −3.4 | −0.86 | 1.7 | <0.001 | A vs A + F | 0.014 |
| | Fluticasone | 43 | −1.23 | −1.19 | 1.355 | −4.4 | −1.14 | 2.3 | <0.001 | F vs A + F | 0.203 |
| | Azelastine + Fluticasone | 47 | −1.52 | −1.52 | 1.462 | −4.6 | −1.29 | 1.1 | <0.001 | Treatment | 0.048 |
| | | | | Practical Problems | | | | | | | |
| Baseline | Azelastine | 44 | 4.27 | 4.28 | 1.297 | 0.3 | 4.33 | 6.0 | | Treatment | 0.555 |
| | Fluticasone | 44 | 4.59 | 4.55 | 1.325 | 1.3 | 5.00 | 6.0 | | | |
| | Azelastine + Fluticasone | 46 | 4.48 | 4.48 | 1.231 | 1.7 | 4.33 | 6.0 | | | |
| | | | Change From Baseline in Practical Problems | | | | | | | | |
| Day 14/ET | Azelastine | 43 | −1.50 | −1.59 | 1.581 | −5.7 | −1.33 | 2.7 | <0.001 | A vs A + F | 0.024 |
| | Fluticasone | 43 | −1.76 | −1.74 | 1.511 | −4.7 | −1.67 | 0.7 | <0.001 | F vs A + F | 0.073 |
| | Azelastine + Fluticasone | 46 | −2.29 | −2.29 | 1.622 | −5.7 | −2.33 | 0.3 | <0.001 | Treatment | 0.056 |

MedPoints Pharmaceuticals  
MP 428  
Program: RQLQO.SAS 14.2.8 Adult Rhinoconjunctivitis Quality of Life Questionnaire Outcomes  
Intent-to-Treat Population  
(Page 3 of 4)

| Domain Time Point | Treatment | N[a] | Mean | LS Mean[b] | Standard Deviation | Minimum | Median | Maximum | Paired t-test p-value[c] | Source | ANOVA p-value[d] |
|---|---|---|---|---|---|---|---|---|---|---|---|
| | | | | Nasal Symptoms | | | | | | | |
| Baseline | Azelastine | 44 | 4.29 | 4.31 | 1.251 | 1.3 | 4.50 | 6.0 | | Treatment | 0.290 |
| | Fluticasone | 44 | 4.69 | 4.65 | 1.190 | 1.3 | 5.00 | 6.0 | | | |
| | Azelastine + Fluticasone | 47 | 4.59 | 4.62 | 1.242 | 1.8 | 5.00 | 6.0 | | | |

-continued

| | | | | | | | | | | | |
|---|---|---|---|---|---|---|---|---|---|---|---|
| Change From Baseline in Nasal Symptoms | | | | | | | | | | | |
| Day 14/ET | Azelastine | 43 | −1.31 | −1.46 | 1.309 | −4.3 | −1.25 | 1.8 | <0.001 | A vs A + F | 0.006 |
| | Fluticasone | 43 | −1.74 | −1.72 | 1.377 | −4.8 | −1.50 | 0.3 | <0.001 | F vs A + F | 0.075 |
| | Azelastine + Fluticasone | 47 | −2.21 | −2.19 | 1.512 | −5.0 | −1.75 | 0.3 | <0.001 | Treatment | 0.020 |
| Eye Symptoms | | | | | | | | | | | |
| Baseline | Azelastine | 44 | 3.77 | 3.78 | 1.550 | 0.0 | 4.00 | 6.0 | | Treatment | 0.627 |
| | Fluticasone | 44 | 4.11 | 4.02 | 1.558 | 0.0 | 4.25 | 6.0 | | | |
| | Azelastine + Fluticasone | 47 | 4.03 | 4.04 | 1.583 | 0.5 | 4.25 | 6.0 | | | |
| Change From Baseline in Eye Symptoms | | | | | | | | | | | |
| Day 14/ET | Azelastine | 43 | −1.49 | −1.64 | 1.555 | −6.0 | −1.25 | 2.5 | <0.001 | A vs A + F | 0.069 |
| | Fluticasone | 43 | −1.53 | −1.51 | 1.372 | −4.5 | −1.75 | 1.0 | <0.001 | F vs A + F | 0.025 |
| | Azelastine + Fluticasone | 47 | −2.18 | −2.18 | 1.862 | −6.0 | −2.25 | 1.0 | <0.001 | Treatment | 0.056 |

MedPoints Pharmaceuticals
MP 428  Program: RQLQO.SAS
14.2.8 Adult Rhinoconjunctivitis Quality of Life Questionnaire Outcomes
Intent-to-Treat Population
(Page 4 of 4)

| Domain Time Point | Treatment | $N^a$ | Mean | LS Mean$^b$ | Standard Deviation | Minimum | Median | Maximum | Paired t-test p-value$^c$ | Source | ANOVA p-value$^d$ |
|---|---|---|---|---|---|---|---|---|---|---|---|
| Emotional | | | | | | | | | | | |
| Baseline | Azelastine | 44 | 3.19 | 3.20 | 1.597 | 0.0 | 3.25 | 6.0 | | Treatment | 0.516 |
| | Fluticasone | 44 | 3.61 | 3.55 | 1.507 | 0.0 | 4.00 | 6.0 | | | |
| | Azelastine + Fluticasone | 47 | 3.41 | 3.43 | 1.474 | 0.5 | 3.25 | 6.0 | | | |
| Change From Baseline in Emotional | | | | | | | | | | | |
| Day 14/ET | Azelastine | 43 | −1.13 | −1.26 | 1.189 | −3.5 | −1.00 | 1.8 | <0.001 | A vs A + F | 0.149 |
| | Fluticasone | 43 | −1.50 | −1.42 | 1.534 | −5.5 | −1.25 | 1.5 | <0.001 | F vs A + F | 0.397 |
| | Azelastine + Fluticasone | 47 | −1.64 | −1.66 | 1.722 | −5.8 | −1.00 | 1.5 | <0.001 | Treatment | 0.345 |
| Overall Score | | | | | | | | | | | |
| Baseline | Azelastine | 43 | 3.65 | 3.66 | 1.126 | 0.5 | 3.75 | 5.5 | | Treatment | 0.335 |
| | Fluticasone | 41 | 3.99 | 3.95 | 1.138 | 0.9 | 4.26 | 5.6 | | | |
| | Azelastine + Fluticasone | 46 | 3.93 | 3.93 | 1.092 | 1.6 | 4.23 | 5.5 | | | |
| Change From Baseline in Overall Score | | | | | | | | | | | |
| Day 14/ET | Azelastine | 42 | −1.11 | −1.21 | 1.018 | −3.9 | −1.13 | 1.5 | <0.001 | A vs A + F | 0.005 |
| | Fluticasone | 41 | −1.49 | −1.47 | 1.214 | −4.4 | −1.37 | 0.6 | <0.001 | F vs A + F | 0.075 |
| | Azelastine + Fluticasone | 46 | −1.93 | −1.92 | 1.464 | −5.1 | −1.55 | 0.2 | <0.001 | Treatment | 0.018 |

$^a$Total number of intent-to-treat patients with available data.
$^b$LS Mean = Least-Square Mean obtained from analysis of variance (ANOVA) model for baseline or analysis of covariance (ANCOVA) model otherwise.
$^c$p-value for the within-patient change was based on a paired t-test.
$^d$p-value for between treatment group comparison, except Baseline, was based on an ANCOVA model containing treatment group and site as fixed effects, and baseline as a covariate. For Baseline, the p-value was based on an ANOVA model containing treatment group and site as fixed effects.
Reference: 16.2.6.2

MedPoints Pharmaceuticals
MP 428  Program: AEALL.SAS
14.3.1.1 Overview of Adverse Events
Safety Population
(Page 1 of 1)

| | Azelastine (N = 49) | Fluticasone (N = 50) | Azelastine + Fluticasone (N = 52) | Total (N = 151) |
|---|---|---|---|---|
| Number of Adverse Events (AE) Reported | | | | |
| All Treatment-Emergent$^a$ AEs | 9 | 5 | 17 | 31 |
| All Treatment-Related$^b$ AEs | 4 | 4 | 13 | 21 |
| Number (%) Patients With Any AEs | | | | |
| All Treatment-Emergent AEs | 8 (16.3) | 5 (10.0) | 12 (23.1) | 25 (16.6) |
| All Treatment-Related AEs | 4 (8.2) | 4 (8.0) | 10 (19.2) | 18 (11.9) |
| Number (%) of Patients With Serious AEs | 0 (0.0) | 0 (0.0) | 0 (0.0) | 0 (0.0) |
| Number (%) of Deaths | 0 (0.0) | 0 (0.0) | 0 (0.0) | 0 (0.0) |

MedPoints Pharmaceuticals
MP 428     Program: AEALL.SAS

14.3.1.1 Overview of Adverse Events
Safety Population
(Page 1 of 1)

| | Azelastine (N = 49) | Fluticasone (N = 50) | Azelastine + Fluticasone (N = 52) | Total (N = 151) |
|---|---|---|---|---|
| Number (%) Patients With AEs by Maximum Severity | | | | |
| *All Treatment-Emergent AEs* | | | | |
| Mild | 3 (6.1) | 4 (8.0) | 5 (9.6) | 12 (7.9) |
| Moderate | 2 (4.1) | 1 (2.0) | 2 (3.8) | 5 (3.3) |
| Severe | 3 (6.1) | 0 (0.0) | 5 (9.6) | 8 (5.3) |
| *All Treatment-Related AEs* | | | | |
| Mild | 1 (2.0) | 3 (6.0) | 4 (7.7) | 8 (5.3) |
| Moderate | 0 (0.0) | 1 (2.0) | 1 (1.9) | 2 (1.3) |
| Severe | 3 (6.1) | 0 (0.0) | 5 (9.6) | 8 (5.3) |

$^a$Treatment-emergent adverse event was an adverse event (AE) with an onset date on or after the first dose of study drug (Azelastine or Fluticasone), or an AE that is worsened (increased in severity) after taking the study drug.
$^b$Treatment-related adverse event was a treatment-emergent adverse event considered possibly or probably related to the study drug by an investigator.
Reference: 16.2.7

---

MedPoints Pharmaceuticals
MP 428     Program: AESEV.SAS

14.3.1.2 Treatment-Emergent Adverse Events by System Organ Class, Preferred Term, and Maximum Severity
Safety Population
(Page 1 of 4)

| System Organ Class / Preferred Term | Azelastine (N = 49) No. of Patients (%) | | | | Fluticasone (N = 50) No. of Patients (%) | | | |
|---|---|---|---|---|---|---|---|---|
| | Mild | Moderate | Severe | Total | Mild | Moderate | Severe | Total |
| Any Adverse Event | 3 (0.1) | 2 (4.1) | 3 (6.1) | 8 (16.3) | 4 (8.0) | 1 (2.0) | 0 (0.0) | 5 (10.0) |
| EAR AND LABYRINTH DISORDERS | | | | | | | | |
| Any Preferred Term | 0 (0.0) | 1 (2.0) | 0 (0.0) | 1 (2.0) | 0 (0.0) | 0 (0.0) | 0 (0.0) | 0 (0.0) |
| EAR PAIN | 0 (0.0) | 1 (2.0) | 0 (0.0) | 1 (2.0) | 0 (0.0) | 0 (0.0) | 0 (0.0) | 0 (0.0) |
| GASTROINTESTINAL DISORDERS | | | | | | | | |
| Any Preferred Term | 1 (2.0) | 0 (0.0) | 3 (6.1) | 4 (8.2) | 2 (4.0) | 1 (2.0) | 0 (0.0) | 3 (6.0) |
| DRY MOUTH | 0 (0.0) | 0 (0.0) | 0 (0.0) | 0 (0.0) | 1 (2.0) | 0 (0.0) | 0 (0.0) | 1 (2.0) |
| DYSGEUSIA | 1 (2.0) | 0 (0.0) | 3 (6.1) | 4 (8.2) | 1 (2.0) | 0 (0.0) | 0 (0.0) | 1 (2.0) |
| STOMACH DISCOMFORT | 0 (0.0) | 0 (0.0) | 0 (0.0) | 0 (0.0) | 0 (0.0) | 1 (2.0) | 0 (0.0) | 1 (2.0) |
| MUSCULOSKELETAL AND CONNECTIVE TISSUE DISORDERS | | | | | | | | |
| Any Preferred Term | 1 (2.0) | 0 (0.0) | 0 (0.0) | 1 (2.0) | 0 (0.0) | 0 (0.0) | 0 (0.0) | 0 (0.0) |
| MYALGIA | 0 (0.0) | 0 (0.0) | 0 (0.0) | 0 (0.0) | 0 (0.0) | 0 (0.0) | 0 (0.0) | 0 (0.0) |
| NECK PAIN | 1 (2.0) | 0 (0.0) | 0 (0.0) | 1 (2.0) | 0 (0.0) | 0 (0.0) | 0 (0.0) | 0 (0.0) |

---

MedPoints Pharmaceuticals
MP 428     Program: AESEV.SAS

14.3.1.2 Treatment-Emergent Adverse Events by System Organ Class, Preferred Term, and Maximum Severity
Safety Population
(Page 2 of 4)

| System Organ Class / Preferred Term | Azelastine + Fluticasone (N = 52) No. of Patients (%) | | | |
|---|---|---|---|---|
| | Mild | Moderate | Severe | Total |
| Any Adverse Event | 5 (9.6) | 2 (3.8) | 5 (9.6) | 12 (23.1) |
| EAR AND LABYRINTH DISORDERS | | | | |
| Any Preferred Term | 0 (0.0) | 0 (0.0) | 0 (0.0) | 0 (0.0) |
| EAR PAIN | 0 (0.0) | 0 (0.0) | 0 (0.0) | 0 (0.0) |
| GASTROINTESTINAL DISORDERS | | | | |
| Any Preferred Term | 1 (1.9) | 1 (1.9) | 5 (9.6) | 7 (13.5) |
| DRY MOUTH | 0 (0.0) | 0 (0.0) | 0 (0.0) | 0 (0.0) |

-continued

|  | | | | |
|---|---|---|---|---|
| DYSGEUSIA | 1 (1.9) | 1 (1.9) | 5 (9.6) | 7 (13.5) |
| STOMACH DISCOMFORT | 0 (0.0) | 0 (0.0) | 0 (0.0) | 0 (0.0) |
| MUSCULOSKELETAL AND CONNECTIVE TISSUE DISORDERS | | | | |
| Any Preferred Term | 0 (0.0) | 1 (1.9) | 0 (0.0) | 1 (1.9) |
| MYALGIA | 0 (0.0) | 1 (1.9) | 0 (0.0) | 1 (1.9) |
| NECK PAIN | 0 (0.0) | 0 (0.0) | 0 (0.0) | 0 (0.0) |

MedPoints Pharmaceuticals
MP 428                                                                                                           Program: AESEV.SAS
14.3.1.2 Treatment-Emergent Adverse Events by System Organ Class, Preferred Term, and Maximum Severity
Safety Population
(Page 3 of 4)

| System Organ Class Preferred Term | Azelastine (N = 49) No. of Patients (%) | | | | Fluticasone (N = 50) No. of Patients (%) | | | |
|---|---|---|---|---|---|---|---|---|
|  | Mild | Moderate | Severe | Total | Mild | Moderate | Severe | Total |
| NERVOUS SYSTEM DISORDERS | | | | | | | | |
| Any Preferred Term | 1 (2.0) | 1 (2.0) | 0 (0.0) | 2 (4.1) | 2 (4.0) | 0 (0.0) | 0 (0.0) | 2 (4.0) |
| HEADACHE | 1 (2.0) | 1 (2.0) | 0 (0.0) | 2 (4.1) | 2 (4.0) | 0 (0.0) | 0 (0.0) | 2 (4.0) |
| RESPIRATORY, THORACIC AND MEDIASTINAL DISORDERS | | | | | | | | |
| Any Preferred Term | 0 (0.0) | 1 (2.0) | 0 (0.0) | 1 (2.0) | 0 (0.0) | 0 (0.0) | 0 (0.0) | 0 (0.0) |
| EPISTAXIS | 0 (0.0) | 0 (0.0) | 0 (0.0) | 0 (0.0) | 0 (0.0) | 0 (0.0) | 0 (0.0) | 0 (0.0) |
| NASAL DISCOMFORT | 0 (0.0) | 0 (0.0) | 0 (0.0) | 0 (0.0) | 0 (0.0) | 0 (0.0) | 0 (0.0) | 0 (0.0) |
| PHARYNGOLARYNGEAL PAIN | 0 (0.0) | 1 (2.0) | 0 (0.0) | 1 (2.0) | 0 (0.0) | 0 (0.0) | 0 (0.0) | 0 (0.0) |

MedPoints Pharmaceuticals
MP 428                                                                                                           Program: AESEV.SAS
14.3.1.2 Treatment-Emergent Adverse Events by System Organ Class, Preferred Term, and Maximum Severity
Safety Population
(Page 4 of 4)

| System Organ Class Preferred Term | Azelastine + Fluticasone (N = 52) No. of Patients (%) | | | |
|---|---|---|---|---|
|  | Mild | Moderate | Severe | Total |
| NERVOUS SYSTEM DISORDERS | | | | |
| Any Preferred Term | 2 (3.8) | 1 (1.9) | 0 (0.0) | 3 (5.8) |
| HEADACHE | 2 (3.8) | 1 (1.9) | 0 (0.0) | 3 (5.8) |
| RESPIRATORY, THORACIC AND MEDIASTINAL DISORDERS | | | | |
| Any Preferred Term | 3 (5.8) | 0 (0.0) | 0 (0.0) | 3 (5.8) |
| EPISTAXIS | 1 (1.9) | 0 (0.0) | 0 (0.0) | 1 (1.9) |
| NASAL DISCOMFORT | 1 (1.9) | 0 (0.0) | 0 (0.0) | 1 (1.9) |
| PHARYNGOLARYNGEAL PAIN | 1 (1.9) | 0 (0.0) | 0 (0.0) | 1 (1.9) |

Note:
Adverse Events (AEs) coded using the MedDRA dictionary. A patient with multiple AEs is counted only once under the maximum severity experienced and once under the Total in any AE row.
Reference: 16.2.7

MedPoints Pharmaceuticals
MP 428                                                                                                           Program: AEREL.SAS
14.3.1.3 Treatment-Related Adverse Events by System Organ Class, Preferred Term, and Relationship
to Study Drug Safety Population
(Page 1 of 2)

| System Organ Class Preferred Term | Azelastine (N = 49) No. of Patients (%) | | | Fluticasone (N = 50) No. of Patients (%) | | |
|---|---|---|---|---|---|---|
|  | Possibly | Probably | Total | Possibly | Probably | Total |
| Any Adverse Event | 1 (2.0) | 3 (6.1) | 4 (8.2) | 4 (8.0) | 0 (0.0) | 4 (8.0) |
| GASTROINTESTINAL DISORDERS | | | | | | |
| Any Preferred Term | 1 (2.0) | 3 (6.1) | 4 (8.2) | 3 (6.0) | 0 (0.0) | 3 (6.0) |
| DRY MOUTH | 0 (0.0) | 0 (0.0) | 0 (0.0) | 1 (2.0) | 0 (0.0) | 1 (2.0) |
| DYSGEUSIA | 1 (2.0) | 3 (6.1) | 4 (8.2) | 1 (2.0) | 0 (0.0) | 1 (2.0) |
| STOMACH DISCOMFORT | 0 (0.0) | 0 (0.0) | 0 (0.0) | 1 (2.0) | 0 (0.0) | 1 (2.0) |

-continued

| | | | | | | |
|---|---|---|---|---|---|---|
| NERVOUS SYSTEM DISORDERS | | | | | | |
| Any Preferred Term | 0 (0.0) | 0 (0.0) | 0 (0.0) | 1 (2.0) | 0 (0.0) | 1 (2.0) |
| HEADACHE | 0 (0.0) | 0 (0.0) | 0 (0.0) | 1 (2.0) | 0 (0.0) | 1 (2.0) |
| RESPIRATORY, THORACIC AND MEDIASTINAL DISORDERS | | | | | | |
| Any Preferred Term | 0 (0.0) | 0 (0.0) | 0 (0.0) | 0 (0.0) | 0 (0.0) | 0 (0.0) |
| EPISTAXIS | 0 (0.0) | 0 (0.0) | 0 (0.0) | 0 (0.0) | 0 (0.0) | 0 (0.0) |
| NASAL DISCOMFORT | 0 (0.0) | 0 (0.0) | 0 (0.0) | 0 (0.0) | 0 (0.0) | 0 (0.0) |

MedPoints Pharmaceuticals
MP 428                                                                                                                           Program: AEREL.SAS
14.3.1.3 Treatment-Related Adverse Events by System Organ Class, Preferred Term, and Relationship to Study Drug Safety Population
(Page 2 of 2)

| System Organ Class<br>Preferred Term | Azelastine + Fluticasone (N = 52) No. of Patients (%) | | |
|---|---|---|---|
| | Possibly | Probably | Total |
| Any Adverse Event | 1 (1.9) | 9 (17.3) | 10 (19.2) |
| GASTROINTESTINAL DISORDERS | | | |
| Any Preferred Term | 0 (0.0) | 7 (13.5) | 7 (13.5) |
| DRY MOUTH | 0 (0.0) | 0 (0.0) | 0 (0.0) |
| DYSGEUSIA | 0 (0.0) | 7 (13.5) | 7 (13.5) |
| STOMACH DISCOMFORT | 0 (0.0) | 0 (0.0) | 0 (0.0) |
| NERVOUS SYSTEM DISORDERS | | | |
| Any Preferred Term | 0 (0.0) | 2 (3.8) | 2 (3.8) |
| HEADACHE | 0 (0.0) | 2 (3.8) | 2 (3.8) |
| RESPIRATORY, THORACIC AND MEDIASTINAL DISORDERS | | | |
| Any Preferred Term | 1 (1.9) | 1 (1.9) | 2 (3.8) |
| EPISTAXIS | 1 (1.9) | 0 (0.0) | 1 (1.9) |
| NASAL DISCOMFORT | 0 (0.0) | 1 (1.9) | 1 (1.9) |

Note:
Adverse Events (AEs) coded using the MedDRA dictionary. Treatment-related adverse event was a treatment-emergent adverse event considered possibly or probably related to the study drug by an investigator. A patient with multiple AEs is counted only once under the closest relationship to the study drug and under the Total in any AE row.
Reference: 16.2.7

MedPoints Pharmaceuticals
MP 428                                                                                                                         Program: AEFREQ.SAS
14.3.1.4 Treatment-Emergent Adverse Events by Decreasing Order of Frequency
Safety Population
(Page 1 of 1)

| Preferred Term | Azelastine (N = 49) No. of Patients (%) | Fluticasone (N = 50) No. of Patients (%) | Azelastine + Fluticasone (N = 52) No. of Patients (%) |
|---|---|---|---|
| Any Adverse Event | 8 (16.3) | 5 (10.0) | 12 (23.1) |
| DYSGEUSIA | 4 (8.2) | 1 (2.0) | 7 (13.5) |
| HEADACHE | 2 (4.1) | 2 (4.0) | 3 (5.8) |
| PHARYNGOLARYNGEAL PAIN | 1 (2.0) | 0 (0.0) | 1 (1.9) |
| EAR PAIN | 1 (2.0) | 0 (0.0) | 0 (0.0) |
| NECK PAIN | 1 (2.0) | 0 (0.0) | 0 (0.0) |
| DRY MOUTH | 0 (0.0) | 1 (2.0) | 0 (0.0) |
| STOMACH DISCOMFORT | 0 (0.0) | 1 (2.0) | 0 (0.0) |
| EPISTAXIS | 0 (0.0) | 0 (0.0) | 1 (1.9) |
| MYALGIA | 0 (0.0) | 0 (0.0) | 1 (1.9) |
| NASAL DISCOMFORT | 0 (0.0) | 0 (0.0) | 1 (1.9) |

Note:
Adverse Events (AEs) coded using the MedDRA dictionary. A patient with multiple AEs is counted only once in any row.
Reference: 16.2.7

MedPoints Pharmaceuticals
MP 428                                                                                                   Program: AELIS.SAS
                    14.3.2.1 Listing of Adverse Events Resulting in Death
                                         (Page 1 of 1)

Treatment Group:

|  | Sex | Investigator Term | Start Date (Day) | | | |
|---|---|---|---|---|---|---|
| Site- | Age (years) | Preferred Term | Stop Date (Day) | Serious AE?/ | Relationship/ | |
| Patient | Race | System Organ Class | Duration of AE | Severity | Treatment for AE | Action |
| | NO OBSERVATIONS IN THE DATABASE | | | | | |

+ Treatment-Emergent Adverse Event.
Reference: CRF Pages 1 and 10

---

MedPoints Pharmaceuticals
MP 428                                                                                                   Program: AELIS.SAS
                          14.3.2.2 Listing of Serious Adverse Events
                                         (Page 1 of 1)

Treatment Group:

|  | Sex | Investigator Term | Start Date (Day) | | | |
|---|---|---|---|---|---|---|
| Site- | Age (years) | Preferred Term | Stop Date (Day) | | Relationship/ | Action/ |
| Patient | Race | System Organ Class | Duration of AE | Severity | Treatment for AE | Outcome |
| | NO OBSERVATIONS IN THE DATABASE | | | | | |

+ Treatment-Emergent Adverse Event.
Reference: CRF Pages 1 and 10

---

MedPoints Pharmaceuticals
MP 428                                                                                                   Program: AELIS.SAS
              14.3.2.3 Listing of Adverse Events Resulting in Discontinuation
                                         (Page 1 of 1)

Treatment Group:

|  | Sex | Investigator Term | Start Date (Day) | | | |
|---|---|---|---|---|---|---|
| Site- | Age (years) | Preferred Term | Stop Date (Day) | Serious AE?/ | Relationship/ | |
| Patient | Race | System Organ Class | Duration of AE | Severity | Treatment for AE | Outcome |
| | NO OBSERVATIONS IN THE DATABASE | | | | | |

+ Treatment-Emergent Adverse Event.
Reference: CRF Pages 1 and 10

---

MedPoints Pharmaceuticals
MP 428                                                                                                   Program: VITALS.SAS
                              14.3.5 Vital Sign Assessments
                                      Safety Population
                                         (Page 1 of 8)

Systolic Blood Pressure (mmHg)

| | | Azelastine (N = 49) | | Fluticasone (N = 50) | | Azelastine + Fluticasone (N = 52) | |
|---|---|---|---|---|---|---|---|
| Visit | Statistics | Actual | Change$^a$ | Actual | Change$^a$ | Actual | Change$^a$ |
| Screening | N | 49 | | 50 | | 52 | |
| | Mean | 124.0 | | 121.2 | | 120.5 | |
| | Standard Deviation | 14.06 | | 13.96 | | 13.25 | |
| | Median | 123.0 | | 119.5 | | 119.5 | |
| | Min-Max | 96-162 | | 96-156 | | 97-154 | |
| Day 1 | N | 49 | | 50 | | 52 | |
| | Mean | 120.2 | | 117.9 | | 119.7 | |

-continued

|  |  | Azelastine | | Fluticasone | | Azelastine + Fluticasone | |
|---|---|---|---|---|---|---|---|
|  |  | Actual | Change | Actual | Change | Actual | Change |
|  | Standard Deviation | 13.90 |  | 12.82 |  | 13.29 |  |
|  | Median | 120.0 |  | 118.5 |  | 120.0 |  |
|  | Min-Max | 96-156 |  | 93-142 |  | 80-147 |  |
| Day 7 | N | 49 | 49 | 48 | 48 | 50 | 50 |
|  | Mean | 121.9 | 1.7 | 116.7 | −1.4 | 118.3 | −1.8 |
|  | Standard Deviation | 13.66 | 10.20 | 11.99 | 9.26 | 14.13 | 9.86 |
|  | Median | 120.0 | 2.0 | 116.0 | −0.5 | 118.0 | −2.5 |
|  | Min-Max | 96-156 | −23-28 | 95-142 | −21-15 | 90-144 | −23-20 |
| Day 14 | N | 49 | 49 | 50 | 50 | 52 | 52 |
|  | Mean | 122.6 | 2.4 | 118.9 | 1.0 | 119.0 | −0.7 |
|  | Standard Deviation | 12.38 | 10.50 | 13.81 | 11.69 | 14.40 | 10.98 |
|  | Median | 121.0 | 3.0 | 117.0 | 1.5 | 117.5 | −0.5 |
|  | Min-Max | 98-150 | −20-22 | 98-170 | −20-40 | 93-154 | −33-24 |

MedPoints Pharmaceuticals  
MP 428                                                                                   Program: VITALS.SAS 14.3.5 Vital Sign Assessments  
Safety Population  
(Page 2 of 8)

Diastolic Blood Pressure (mmHg)

|  |  | Azelastine (N = 49) | | Fluticasone (N = 50) | | Azelastine + Fluticasone (N = 52) | |
|---|---|---|---|---|---|---|---|
| Visit | Statistics | Actual | Change[a] | Actual | Change[a] | Actual | Change[a] |
| Screening | N | 49 |  | 50 |  | 52 |  |
|  | Mean | 75.9 |  | 75.6 |  | 75.2 |  |
|  | Standard Deviation | 8.47 |  | 9.76 |  | 8.88 |  |
|  | Median | 75.0 |  | 78.0 |  | 73.5 |  |
|  | Min-Max | 50-96 |  | 50-95 |  | 60-95 |  |
| Day 1 | N | 49 |  | 50 |  | 52 |  |
|  | Mean | 74.6 |  | 74.0 |  | 74.4 |  |
|  | Standard Deviation | 8.57 |  | 9.75 |  | 7.92 |  |
|  | Median | 74.0 |  | 76.0 |  | 74.0 |  |
|  | Min-Max | 54-90 |  | 41-89 |  | 50-90 |  |
| Day 7 | N | 49 | 49 | 48 | 48 | 50 | 50 |
|  | Mean | 75.5 | 0.8 | 72.7 | −1.5 | 72.4 | −2.1 |
|  | Standard Deviation | 8.39 | 7.50 | 7.37 | 6.97 | 9.51 | 7.94 |
|  | Median | 76.0 | 1.0 | 74.0 | −1.5 | 72.0 | −1.0 |
|  | Min-Max | 56-90 | −16-20 | 58-86 | −15-19 | 52-90 | −21-16 |
| Day 14 | N | 49 | 49 | 50 | 50 | 52 | 52 |
|  | Mean | 75.9 | 1.3 | 73.6 | −0.4 | 72.8 | −1.5 |
|  | Standard Deviation | 7.93 | 6.39 | 9.01 | 7.52 | 8.28 | 7.16 |
|  | Median | 78.0 | 0.0 | 74.0 | 0.0 | 72.0 | 0.0 |
|  | Min-Max | 60-90 | −13-18 | 54-90 | −24-22 | 56-90 | −18-15 |

MedPoints Pharmaceuticals  
MP 428                                                                                   Program: VITALS.SAS 14.3.5 Vital Sign Assessments  
Safety Population  
(Page 3 of 8)

Pulse Rate (bpm)

|  |  | Azelastine (N = 49) | | Fluticasone (N = 50) | | Azelastine + Fluticasone (N = 52) | |
|---|---|---|---|---|---|---|---|
| Visit | Statistics | Actual | Change[a] | Actual | Change[a] | Actual | Change[a] |
| Screening | N | 49 |  | 50 |  | 52 |  |
|  | Mean | 73.7 |  | 75.5 |  | 76.0 |  |
|  | Standard Deviation | 9.95 |  | 10.47 |  | 7.94 |  |
|  | Median | 74.0 |  | 78.0 |  | 75.0 |  |
|  | Min-Max | 52-100 |  | 50-103 |  | 59-94 |  |
| Day 1 | N | 49 |  | 50 |  | 52 |  |
|  | Mean | 73.4 |  | 75.0 |  | 76.8 |  |
|  | Standard Deviation | 10.38 |  | 8.87 |  | 9.45 |  |
|  | Median | 73.0 |  | 75.0 |  | 74.0 |  |
|  | Min-Max | 56-98 |  | 57-92 |  | 60-107 |  |
| Day 7 | N | 49 | 49 | 48 | 48 | 50 | 50 |
|  | Mean | 75.7 | 2.3 | 75.5 | 0.5 | 74.7 | −1.7 |
|  | Standard Deviation | 9.09 | 8.78 | 10.85 | 10.77 | 9.95 | 10.69 |
|  | Median | 75.0 | 3.0 | 74.0 | −2.0 | 74.0 | −3.5 |
|  | Min-Max | 60-95 | −18-22 | 52-102 | −29-38 | 60-104 | −25-30 |

-continued

| | | | | | | | |
|---|---|---|---|---|---|---|---|
| Day 14 | N | 49 | 49 | 50 | 50 | 52 | 52 |
| | Mean | 75.4 | 2.0 | 75.3 | 0.3 | 75.9 | −0.9 |
| | Standard Deviation | 8.51 | 9.57 | 9.38 | 8.77 | 10.44 | 10.46 |
| | Median | 76.0 | 1.0 | 74.0 | 1.0 | 74.0 | −2.0 |
| | Min-Max | 60-96 | −23-24 | 53-95 | −22-23 | 60-102 | −26-22 |

MedPoints Pharmaceuticals  
MP 428  
Program: VITALS.SAS 14.3.5 Vital Sign Assessments  
Safety Population  
(Page 4 of 8)

Respiration (bpm)

| | | Azelastine (N = 49) | | Fluticasone (N = 50) | | Azelastine + Fluticasone (N = 52) | |
|---|---|---|---|---|---|---|---|
| Visit | Statistics | Actual | Change$^a$ | Actual | Change$^a$ | Actual | Change$^a$ |
| Screening | N | 49 | | 50 | | 52 | |
| | Mean | 16.1 | | 15.7 | | 16.2 | |
| | Standard Deviation | 2.14 | | 2.29 | | 2.58 | |
| | Median | 16.0 | | 16.0 | | 16.0 | |
| | Min-Max | 12-20 | | 12-20 | | 12-24 | |
| Day 1 | N | 49 | | 50 | | 52 | |
| | Mean | 15.8 | | 15.8 | | 15.5 | |
| | Standard Deviation | 2.00 | | 1.43 | | 1.99 | |
| | Median | 16.0 | | 16.0 | | 16.0 | |
| | Min-Max | 12-20 | | 12-18 | | 12-18 | |
| Day 7 | N | 49 | 49 | 48 | 48 | 50 | 50 |
| | Mean | 15.9 | 0.1 | 16.0 | 0.2 | 16.0 | 0.4 |
| | Standard Deviation | 1.67 | 1.93 | 1.62 | 1.73 | 1.59 | 2.18 |
| | Median | 16.0 | 0.0 | 16.0 | 0.0 | 16.0 | 0.0 |
| | Min-Max | 12-18 | −4-4 | 12-20 | −4-4 | 12-20 | −4-6 |
| Day 14 | N | 49 | 49 | 50 | 50 | 52 | 52 |
| | Mean | 15.9 | 0.2 | 15.8 | 0.0 | 15.9 | 0.3 |
| | Standard Deviation | 1.64 | 1.89 | 1.56 | 1.76 | 1.70 | 1.89 |
| | Median | 16.0 | 0.0 | 16.0 | 0.0 | 16.0 | 0.0 |
| | Min-Max | 12-18 | −4-4 | 12-20 | −4-4 | 12-20 | −4-4 |

MedPoints Pharmaceuticals  
MP 428  
Program: VITALS.SAS 14.3.5 Vital Sign Assessments  
Safety Population  
(Page 5 of 8)

Temperature (° F.)

| | | Azelastine (N = 49) | | Fluticasone (N = 50) | | Azelastine + Fluticasone (N = 52) | |
|---|---|---|---|---|---|---|---|
| Visit | Statistics | Actual | Change$^a$ | Actual | Change$^a$ | Actual | Change$^a$ |
| Screening | N | 49 | | 50 | | 52 | |
| | Mean | 97.91 | | 98.04 | | 97.75 | |
| | Standard Deviation | 0.623 | | 0.646 | | 0.623 | |
| | Median | 98.00 | | 98.00 | | 97.80 | |
| | Min-Max | 96.2-99.3 | | 96.9-99.3 | | 96.2-99.3 | |
| Day 1 | N | 49 | | 50 | | 52 | |
| | Mean | 97.73 | | 97.89 | | 97.81 | |
| | Standard Deviation | 0.583 | | 0.667 | | 0.541 | |
| | Median | 97.80 | | 97.85 | | 97.70 | |
| | Min-Max | 96.5-99.4 | | 97.0-99.8 | | 96.8-99.0 | |
| Day 7 | N | 49 | 49 | 48 | 48 | 50 | 50 |
| | Mean | 97.82 | 0.09 | 97.90 | −0.03 | 97.85 | 0.02 |
| | Standard Deviation | 0.621 | 0.642 | 0.567 | 0.743 | 0.526 | 0.642 |
| | Median | 97.80 | 0.10 | 97.95 | 0.00 | 97.80 | 0.00 |
| | Min-Max | 96.3-99.0 | −2.0-1.3 | 96.0-98.9 | −1.8-1.8 | 96.5-98.9 | −1.6-1.4 |

-continued

| | | | | | | | |
|---|---|---|---|---|---|---|---|
| Day 14 | N | 49 | 49 | 50 | 50 | 52 | 52 |
| | Mean | 97.94 | 0.21 | 97.86 | −0.03 | 97.89 | 0.09 |
| | Standard Deviation | 0.630 | 0.750 | 0.578 | 0.765 | 0.536 | 0.683 |
| | Median | 98.00 | 0.30 | 97.90 | 0.10 | 97.90 | 0.10 |
| | Min-Max | 96.0-99.5 | −1.1-1.8 | 96.2-99.1 | −1.6-2.0 | 96.8-99.0 | −1.3-1.7 |

MedPoints Pharmaceuticals  
MP 428  
Program: VITALS.SAS 14.3.5 Vital Sign Assessments  
Safety Population  
(Page 6 of 8)

Body Weight (lb)

| | | Azelastine (N = 49) | | Fluticasone (N = 50) | | Azelastine + Fluticasone (N = 52) | |
|---|---|---|---|---|---|---|---|
| Visit | Statistics | Actual | Change$^a$ | Actual | Change$^a$ | Actual | Change$^a$ |
| Screening | N | 49 | | 50 | | 52 | |
| | Mean | 181.2 | | 172.9 | | 173.8 | |
| | Standard Deviation | 47.09 | | 40.42 | | 51.05 | |
| | Median | 174.0 | | 168.5 | | 162.5 | |
| | Min-Max | 98-284 | | 85-269 | | 99-303 | |
| Day 14 | N | 49 | 49 | 49 | 49 | 52 | 52 |
| | Mean | 180.9 | −0.3 | 173.0 | −0.5 | 174.2 | 0.4 |
| | Standard Deviation | 46.60 | 2.18 | 40.04 | 2.35 | 50.14 | 3.42 |
| | Median | 174.0 | −1.0 | 168.0 | 0.0 | 162.0 | 0.0 |
| | Min-Max | 98-282 | −5-7 | 87-265 | −6-7 | 103-302 | −8-15 |

MedPoints Pharmaceuticals  
MP 428  
Program: VITALS.SAS 14.3.5 Vital Sign Assessments  
Safety Population  
(Page 7 of 8)

Body Weight (lb) for Patients of Age 12 to 17

| | | Azelastine (N = 49) | | Fluticasone (N = 50) | | Azelastine + Fluticasone (N = 52) | |
|---|---|---|---|---|---|---|---|
| Visit | Statistics | Actual | Change$^a$ | Actual | Change$^a$ | Actual | Change$^a$ |
| Screening | N | 3 | | 6 | | 5 | |
| | Mean | 104.7 | | 136.3 | | 128.1 | |
| | Standard Deviation | 7.02 | | 46.66 | | 21.20 | |
| | Median | 104.0 | | 122.5 | | 121.4 | |
| | Min-Max | 98-112 | | 85-199 | | 108-163 | |
| Day 14 | N | 3 | 3 | 6 | 6 | 5 | 5 |
| | Mean | 105.7 | 1.0 | 135.8 | −0.5 | 130.6 | 2.5 |
| | Standard Deviation | 9.29 | 2.65 | 45.95 | 1.52 | 21.09 | 7.29 |
| | Median | 103.0 | 0.0 | 121.5 | −0.5 | 131.0 | 0.0 |
| | Min-Max | 98-116 | −1-4 | 87-197 | −2-2 | 108-162 | −2-15 |

MedPoints Pharmaceuticals  
MP 428  
Program: VITALS.SAS 14.3.5 Vital Sign Assessments  
Safety Population  
(Page 8 of 8)

Body Weight (lb) for Patients of Age 18 and Beyond

| | | Azelastine (N = 49) | | Fluticasone (N = 50) | | Azelastine + Fluticasone (N = 52) | |
|---|---|---|---|---|---|---|---|
| Visit | Statistics | Actual | Change$^a$ | Actual | Change$^a$ | Actual | Change$^a$ |
| Screening | N | 46 | | 44 | | 47 | |
| | Mean | 186.2 | | 177.9 | | 178.6 | |
| | Standard Deviation | 44.12 | | 37.37 | | 50.99 | |
| | Median | 177.8 | | 169.5 | | 169.0 | |
| | Min-Max | 102-284 | | 117-269 | | 99-303 | |

| | | | | | | |
|---|---|---|---|---|---|---|
| Day 14 | N | 46 | 46 | 43 | 43 | 47 | 47 |
| | Mean | 185.8 | −0.4 | 178.2 | −0.5 | 178.8 | 0.2 |
| | Standard Deviation | 43.70 | 2.15 | 36.83 | 2.46 | 50.20 | 2.80 |
| | Median | 176.2 | −1.0 | 172.0 | 0.0 | 169.0 | 0.0 |
| | Min-Max | 102-282 | −5-7 | 115-265 | −6-7 | 103-302 | −8-7 |

[a]Change from baseline where baseline was measured at Screening.

Reference: 16.2.9

MedPoints Pharmaceuticals
MP 428                                                                                                               Program: MEDS.SAS 14.3.6 Concomitant Medications
Intent-to-Treat Population
(Page 1 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| Any Concomitant Medications | 44 (89.8) | 40 (80.0) | 41 (78.8) | 125 (82.8) |
| ACE INHIBITORS AND DIURETICS | | | | |
|   Any Preferred Term | 0 (0.0) | 0 (0.0) | 1 (1.9) | 1 (0.7) |
|   PRINZIDE /00977901/ | 0 (0.0) | 0 (0.0) | 1 (1.9) | 1 (0.7) |
| ACE INHIBITORS, PLAIN | | | | |
|   Any Preferred Term | 3 (6.1) | 4 (8.0) | 1 (1.9) | 8 (5.3) |
|   BENAZEPRIL HYDROCHLORIDE | 0 (0.0) | 1 (2.0) | 0 (0.0) | 1 (0.7) |
|   LISINOPRIL | 2 (4.1) | 3 (6.0) | 1 (1.9) | 6 (4.0) |
|   QUINAPRIL HYDROCHLORIDE | 1 (2.0) | 0 (0.0) | 0 (0.0) | 1 (0.7) |
| ALLERGEN EXTRACTS | | | | |
|   Any Preferred Term | 1 (2.0) | 0 (0.0) | 2 (3.8) | 3 (2.0) |
|   ALLERGENS NOS | 1 (2.0) | 0 (0.0) | 2 (3.8) | 3 (2.0) |
| AMINO ACIDS AND DERIVATIVES | | | | |
|   Any Preferred Term | 1 (2.0) | 0 (0.0) | 0 (0.0) | 1 (0.7) |
|   LEVOGLUTAMIDE | 1 (2.0) | 0 (0.0) | 0 (0.0) | 1 (0.7) |

Note:
Concomitant medications were coded using the WHO Drug dictionary. A patient who took multiple medications is counted only once in each row.
Reference: 16.2.5.2

MedPoints Pharmaceuticals
MP 428                                                                                                               Program: MEDS.SAS 14.3.6 Concomitant Medications
Intent-to-Treat Population
(Page 2 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| AMINOALKYL ETHERS | | | | |
|   Any Preferred Term | 2 (4.1) | 3 (6.0) | 2 (3.8) | 7 (4.6) |
|   CLEMASTINE FUMARATE | 0 (0.0) | 2 (4.0) | 0 (0.0) | 2 (1.3) |
|   DIPHENHYDRAMINE | 0 (0.0) | 1 (2.0) | 0 (0.0) | 1 (0.7) |
|   DIPHENHYDRAMINE HYDROCHLORIDE | 2 (4.1) | 0 (0.0) | 2 (3.8) | 4 (2.6) |
| AMINOSALICYLIC ACID AND SIMILAR AGENTS | | | | |
|   Any Preferred Term | 0 (0.0) | 0 (0.0) | 1 (1.9) | 1 (0.7) |
|   SULFASALAZINE | 0 (0.0) | 0 (0.0) | 1 (1.9) | 1 (0.7) |
| ANDROGENS AND ESTROGENS | | | | |
|   Any Preferred Term | 0 (0.0) | 1 (2.0) | 1 (1.9) | 2 (1.3) |
|   ESTRATEST HS | 0 (0.0) | 1 (2.0) | 1 (1.9) | 2 (1.3) |

-continued

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| ANGIOTENSIN II ANTAGONISTS AND DIURETICS | | | | |
| Any Preferred Term | 1 (2.0) | 0 (0.0) | 1 (1.9) | 2 (1.3) |
| CO-DIOVAN | 0 (0.0) | 0 (0.0) | 1 (1.9) | 1 (0.7) |
| PRITOR /01506701/ | 1 (2.0) | 0 (0.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428                                                                                               Program: MEDS.SAS 14.3.6 Concomitant Medications
Intent-to-Treat Population
(Page 3 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| ANGIOTENSIN II ANTAGONISTS, PLAIN | | | | |
| Any Preferred Term | 1 (2.0) | 1 (2.0) | 0 (0.0) | 2 (1.3) |
| OLMESARTAN MEDOXOMIL | 0 (0.0) | 1 (2.0) | 0 (0.0) | 1 (0.7) |
| VALSARTAN | 1 (2.0) | 0 (0.0) | 0 (0.0) | 1 (0.7) |
| ANILIDES | | | | |
| Any Preferred Term | 9 (18.4) | 12 (24.0) | 9 (17.3) | 30 (19.9) |
| AXOTAL /00727001/ | 0 (0.0) | 1 (2.0) | 1 (1.9) | 2 (1.3) |
| CO-TYLENOL | 0 (0.0) | 0 (0.0) | 1 (1.9) | 1 (0.7) |
| MEDINITE | 0 (0.0) | 1 (2.0) | 0 (0.0) | 1 (0.7) |
| MIDOL /00095101/ | 0 (0.0) | 1 (2.0) | 0 (0.0) | 1 (0.7) |
| PAMPRIN | 0 (0.0) | 0 (0.0) | 1 (1.9) | 1 (0.7) |
| PARACETAMOL | 9 (18.4) | 8 (16.0) | 9 (17.3) | 26 (17.2) |
| THOMAPYRIN N | 0 (0.0) | 2 (4.0) | 0 (0.0) | 2 (1.3) |
| ANTACIDS WITH ANTIFLATULENTS | | | | |
| Any Preferred Term | 0 (0.0) | 1 (2.0) | 0 (0.0) | 1 (0.7) |
| MYLANTA /0036701/ | 0 (0.0) | 1 (2.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428                                                                                               Program: MEDS.SAS 14.3.6 Concomitant Medications
Intent-to-Treat Population
(Page 4 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| ANTIALLERGIC AGENTS, EXCL. CORTICOSTEROIDS | | | | |
| Any Preferred Term | 1 (2.0) | 0 (0.0) | 0 (0.0) | 1 (0.7) |
| AZELASTINE HYDROCHLORIDE | 1 (2.0) | 0 (0.0) | 0 (0.0) | 1 (0.7) |
| ANTIINFLAMMATORY/ANTIRHEUMATIC PROD., NON-STEROIDS | | | | |
| Any Preferred Term | 1 (2.0) | 0 (0.0) | 0 (0.0) | 1 (0.7) |
| GLUCOSAMINE W/CHONDROITIN | 1 (2.0) | 0 (0.0) | 0 (0.0) | 1 (0.7) |
| ANTIPROPULSIVES | | | | |
| Any Preferred Term | 1 (2.0) | 0 (0.0) | 0 (0.0) | 1 (0.7) |
| LOPERAMIDE HYDROCHLORIDE | 1 (2.0) | 0 (0.0) | 0 (0.0) | 1 (0.7) |
| ASCORBIC ACID (VITAMIN C), PLAIN | | | | |
| Any Preferred Term | 1 (2.0) | 1 (2.0) | 2 (3.8) | 4 (2.6) |
| ASCORBIC ACID | 1 (2.0) | 1 (2.0) | 2 (3.8) | 4 (2.6) |

-continued

| | | | | |
|---|---|---|---|---|
| BETA BLOCKING AGENTS, SELECTIVE | | | | |
|   Any Preferred Term | 0 (0.0) | 0 (0.0) | 1 (1.9) | 1 (0.7) |
|   METOPROLOL TARTRATE | 0 (0.0) | 0 (0.0) | 1 (1.9) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428     Program: MEDS.SAS 14.3.6 Concomitant Medications
Intent-to-Treat Population
(Page 5 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| BIGUANIDES | | | | |
|   Any Preferred Term | 2 (4.1) | 0 (0.0) | 0 (0.0) | 2 (1.3) |
|   METFORMIN | 1 (2.0) | 0 (0.0) | 0 (0.0) | 1 (0.7) |
|   METFORMIN HYDROCHLORIDE | 1 (2.0) | 0 (0.0) | 0 (0.0) | 1 (0.7) |
| BISMUTH PREPARATIONS | | | | |
|   Any Preferred Term | 1 (2.0) | 0 (0.0) | 0 (0.0) | 1 (0.7) |
|   BISMUTH SUBSALICYLATE | 1 (2.0) | 0 (0.0) | 0 (0.0) | 1 (0.7) |
| BISPHOSPHONATES | | | | |
|   Any Preferred Term | 0 (0.0) | 1 (2.0) | 0 (0.0) | 1 (0.7) |
|   ALENDRONATE SODIUM | 0 (0.0) | 1 (2.0) | 0 (0.0) | 1 (0.7) |
| CALCIUM | | | | |
|   Any Preferred Term | 4 (8.2) | 2 (4.0) | 3 (5.8) | 9 (6.0) |
|   CALCIUM | 3 (6.1) | 2 (4.0) | 3 (5.8) | 8 (5.3) |
|   CALCIUM CARBONATE | 1 (2.0) | 0 (0.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428     Program: MEDS.SAS 14.3.6 Concomitant Medications
Intent-to-Treat Population
(Page 6 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| CARBAMIC ACID ESTERS | | | | |
|   Any Preferred Term | 0 (0.0) | 1 (2.0) | 0 (0.0) | 1 (0.7) |
|   METHOCARBAMOL | 0 (0.0) | 1 (2.0) | 0 (0.0) | 1 (0.7) |
| COMB AND COMPL OF ALUMIN., CALC<br>AND MAGNES COMP | | | | |
|   Any Preferred Term | 0 (0.0) | 0 (0.0) | 1 (1.9) | 1 (0.7) |
|   MAALOX /00091001/ | 0 (0.0) | 0 (0.0) | 1 (1.9) | 1 (0.7) |
| DIHYDROPYRIDINE DERIVATIVES | | | | |
|   Any Preferred Term | 0 (0.0) | 1 (2.0) | 0 (0.0) | 1 (0.7) |
|   AMLODIPINE BESILATE | 0 (0.0) | 1 (2.0) | 0 (0.0) | 1 (0.7) |
| DIPHENYLPROPYLAMINE DERIVATIVES | | | | |
|   Any Preferred Term | 0 (0.0) | 0 (0.0) | 1 (1.9) | 1 (0.7) |
|   PROPACET | 0 (0.0) | 0 (0.0) | 1 (1.9) | 1 (0.7) |
| DRUGS USED IN ERECTILE DYSFUNCTION | | | | |
|   Any Preferred Term | 0 (0.0) | 1 (2.0) | 0 (0.0) | 1 (0.7) |
|   TADALAFIL | 0 (0.0) | 1 (2.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428     Program: MEDS.SAS 14.3.6 Concomitant Medications
Intent-to-Treat Population
(Page 7 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| DRUGS USED IN NICOTINE DEPENDENCE | | | | |
|   Any Preferred Term | 0 (0.0) | 1 (2.0) | 1 (1.9) | 2 (1.3) |
|   BUPROPION HYDROCHLORIDE | 0 (0.0) | 1 (2.0) | 1 (1.9) | 2 (1.3) |

-continued

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| ESTREN DERIVATIVES | | | | |
|   Any Preferred Term | 0 (0.0) | 0 (0.0) | 1 (1.9) | 1 (0.7) |
|   NORETHISTERONE ACETATE | 0 (0.0) | 0 (0.0) | 1 (1.9) | 1 (0.7) |
| FLUOROQUINOLONES | | | | |
|   Any Preferred Term | 0 (0.0) | 0 (0.0) | 1 (1.9) | 1 (0.7) |
|   LEVOFLOXACIN | 0 (0.0) | 0 (0.0) | 1 (1.9) | 1 (0.7) |
| FOLIC ACID AND DERIVATIVES | | | | |
|   Any Preferred Term | 1 (2.0) | 0 (0.0) | 0 (0.0) | 1 (0.7) |
|   FOLIC ACID | 1 (2.0) | 0 (0.0) | 0 (0.0) | 1 (0.7) |
| GLUCOCORTICOIDS | | | | |
|   Any Preferred Term | 2 (4.1) | 0 (0.0) | 0 (0.0) | 2 (1.3) |
|   FLUTICASONE PROPIONATE | 1 (2.0) | 0 (0.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428    Program: MEDS.SAS 14.3.6 Concomitant Medications
Intent-to-Treat Population
(Page 8 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| GLUCOCORTICOIDS | | | | |
|   TRIAMCINOLONE ACETONIDE | 1 (2.0) | 0 (0.0) | 0 (0.0) | 1 (0.7) |
| H2-RECEPTOR ANTAGONISTS | | | | |
|   Any Preferred Term | 0 (0.0) | 0 (0.0) | 1 (1.9) | 1 (0.7) |
|   RANITIDINE HYDROCHLORIDE | 0 (0.0) | 0 (0.0) | 1 (1.9) | 1 (0.7) |
| HMG COA REDUCTASE INHIBITORS | | | | |
|   Any Preferred Term | 3 (6.1) | 3 (6.0) | 4 (7.7) | 10 (6.6) |
|   ATORVASTATIN CALCIUM | 1 (2.0) | 2 (4.0) | 2 (3.8) | 5 (3.3) |
|   INEGY | 1 (2.0) | 0 (0.0) | 0 (0.0) | 1 (0.7) |
|   LOVASTATIN | 0 (0.0) | 1 (2.0) | 0 (0.0) | 1 (0.7) |
|   PRAVASTATIN SODIUM | 0 (0.0) | 0 (0.0) | 1 (1.9) | 1 (0.7) |
|   SIMVASTATIN | 1 (2.0) | 0 (0.0) | 1 (1.9) | 2 (1.3) |
| INTRAUTERINE CONTRACEPTIVES | | | | |
|   Any Preferred Term | 1 (2.0) | 0 (0.0) | 0 (0.0) | 1 (0.7) |
|   INTRAUTERINE CONTRACEPTIVE DEVICE | 1 (2.0) | 0 (0.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428    Program: MEDS.SAS 14.3.6 Concomitant Medications
Intent-to-Treat Population
(Page 9 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Petients (%) |
|---|---|---|---|---|
| LOW-CEILING DIURETICS AND POTASSIUM-SPARING AGENTS | | | | |
|   Any Preferred Term | 0 (0.0) | 1 (2.0) | 1 (1.9) | 2 (1.3) |
|   ALDACTAZIDE A | 0 (0.0) | 1 (2.0) | 0 (0.0) | 1 (0.7) |
|   DYAZIDE | 0 (0.0) | 0 (0.0) | 1 (1.9) | 1 (0.7) |
| MULTIVITAMINS WITH MINERALS | | | | |
|   Any Preferred Term | 1 (2.0) | 0 (0.0) | 0 (0.0) | 1 (0.7) |
|   CENTRUM /00554501/ | 1 (2.0) | 0 (0.0) | 0 (0.0) | 1 (0.7) |
| MULTIVITAMINS, PLAIN | | | | |
|   Any Preferred Term | 5 (10.2) | 2 (4.0) | 5 (9.6) | 12 (7.9) |
|   MULTIVITAMINS, PLAIN | 5 (10.2) | 2 (4.0) | 5 (9.6) | 12 (7.9) |

-continued

| | | | | |
|---|---|---|---|---|
| NATURAL AND SEMISYNTHETIC ESTROGENS, PLAIN | | | | |
|   Any Preferred Term | 2 (4.1) | 1 (2.0) | 3 (5.8) | 6 (4.0) |
|   ESTRADIOL | 0 (0.0) | 0 (0.0) | 1 (1.9) | 1 (0.7) |
|   ESTROGENS CONJUGATED | 2 (4.1) | 1 (2.0) | 2 (3.8) | 5 (3.3) |

Note:
Concomitant medications were coded using the WHO Drug dictionary. A patient who took multiple medications is counted only once in each row.
Reference: 16.2.5.2
MedPoints Pharmaceuticals
MP 428              Program: MEDS.SAS 14.3.6 Concomitant Medications
Intent-to-Treat Population
(Page 10 of 19)

| Anatomical Therapeutic Class<br>  Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| NATURAL OPIUM ALKALOIDS | | | | |
|   Any Preferred Term | 1 (2.0) | 0 (0.0) | 0 (0.0) | 1 (0.7) |
|   VICODIN | 1 (2.0) | 0 (0.0) | 0 (0.0) | 1 (0.7) |
| NUCLEOSIDES AND NUCLEOTIDES | | | | |
| EXCL REV. TRANSCR INHIB | | | | |
|   Any Preferred Term | 0 (0.0) | 0 (0.0) | 1 (1.9) | 1 (0.7) |
|   ACICLOVIR | 0 (0.0) | 0 (0.0) | 1 (1.9) | 1 (0.7) |
| OPIUM ALKALOIDS AND DERIVATIVES | | | | |
|   Any Preferred Term | 0 (0.0) | 1 (2.0) | 0 (0.0) | 1 (0.7) |
|   HYDROCODONE | 0 (0.0) | 1 (2.0) | 0 (0.0) | 1 (0.7) |
| OTHER ANTIALLERGICS | | | | |
|   Any Preferred Term | 1 (2.0) | 1 (2.0) | 0 (0.0) | 2 (1.3) |
|   OLOPATADINE HYDROCHLORIDE | 1 (2.0) | 1 (2.0) | 0 (0.0) | 2 (1.3) |
| OTHER ANTIDEPRESSANTS | | | | |
|   Any Preferred Term | 0 (0.0) | 1 (2.0) | 0 (0.0) | 1 (0.7) |
|   VENLAFAXINE HYDROCHLORIDE | 0 (0.0) | 1 (2.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428              Program: MEDS.SAS 14.3.6 Concomitant Medications
Intent-to-Treat Population
(Page 11 of 19)

| Anatomical Therapeutic Class<br>  Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| OTHER ANTIEPILEPTICS | | | | |
|   Any Preferred Term | 1 (2.0) | 1 (2.0) | 1 (1.9) | 3 (2.0) |
|   GABAPENTIN | 0 (0.0) | 1 (2.0) | 1 (1.9) | 2 (1.3) |
|   TOPIRAMATE | 1 (2.0) | 0 (0.0) | 0 (0.0) | 1 (0.7) |
| OTHER ANTIHISTAMINES FOR SYSTEMIC USE | | | | |
|   Any Preferred Term | 6 (12.2) | 4 (8.0) | 5 (9.6) | 15 (9.9) |
|   ALLEGRA-D /01413301/ | 0 (0.0) | 1 (2.0) | 2 (3.8) | 3 (2.0) |
|   DESLORATADINE | 0 (0.0) | 0 (0.0) | 1 (1.9) | 1 (0.7) |
|   FEXOFENADINE HYDROCHLORIDE | 4 (8.2) | 1 (2.0) | 0 (0.0) | 5 (3.3) |
|   LORATADINE | 2 (4.1) | 3 (6.0) | 2 (3.8) | 7 (4.6) |
| OTHER ANTIINFL/ANTIRHEUMATIC AGENTS, | | | | |
| NON-STEROIDS | | | | |
|   Any Preferred Term | 1 (2.0) | 0 (0.0) | 1 (1.9) | 2 (1.3) |
|   GLUCOSAMINE | 1 (2.0) | 0 (0.0) | 1 (1.9) | 2 (1.3) |

-continued

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| OTHER CHOLESTEROL AND TRIGLYCERIDE REDUCERS | | | | |
|   Any Preferred Term | 2 (4.1) | 1 (2.0) | 1 (1.9) | 4 (2.6) |
|   EZETIMIBE | 0 (0.0) | 1 (2.0) | 0 (0.0) | 1 (0.7) |
|   FISH OIL | 2 (4.1) | 0 (0.0) | 1 (1.9) | 3 (2.0) |

Note:
Concomitant medications were coded using the WHO Drug dictionary. A patient who took multiple medications is counted only once in each row.
Reference: 16.2.5.2
MedPoints Pharmaceuticals
MP 428      Program: MEDS.SAS 14.3.6 Concomitant Medications
Intent-to-Treat Population
(Page 12 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| OTHER OPHTHALMOLOGICALS | | | | |
|   Any Preferred Term | 1 (2.0) | 0 (0.0) | 0 (0.0) | 1 (0.7) |
|   OTHER OPHTHALMOLOGICALS | 1 (2.0) | 0 (0.0) | 0 (0.0) | 1 (0.7) |
| OTHER PLAIN VITAMIN PREPARATIONS | | | | |
|   Any Preferred Term | 3 (6.1) | 1 (2.0) | 1 (1.9) | 5 (3.3) |
|   PYRIDOXINE HYDROCHLORIDE | 2 (4.1) | 0 (0.0) | 0 (0.0) | 2 (1.3) |
|   TOCOPHERYL ACETATE | 1 (2.0) | 1 (2.0) | 1 (1.9) | 3 (2.0) |
| OTHER POTASSIUM-SPARING AGENTS | | | | |
|   Any Preferred Term | 1 (2.0) | 0 (0.0) | 0 (0.0) | 1 (0.7) |
|   TRIAMTERENE | 1 (2.0) | 0 (0.0) | 0 (0.0) | 1 (0.7) |
| OXAZOL, THIAZINE, AND TRIAZINE DERIVATIVES | | | | |
|   Any Preferred Term | 0 (0.0) | 1 (2.0) | 0 (0.0) | 1 (0.7) |
|   METAXALONE | 0 (0.0) | 1 (2.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428      Program: MEDS.SAS 14.3.6 Concomitant Medications
Intent-to-Treat Population
(Page 13 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| OXICAMS | | | | |
|   Any Preferred Term | 2 (4.1) | 1 (2.0) | 0 (0.0) | 3 (2.0) |
|   MELOXICAM | 2 (4.1) | 1 (2.0) | 0 (0.0) | 3 (2.0) |
| PHENYLALKYLAMINE DERIVATIVES | | | | |
|   Any Preferred Term | 1 (2.0) | 0 (0.0) | 0 (0.0) | 1 (0.7) |
|   VERAPAMIL | 1 (2.0) | 0 (0.0) | 0 (0.0) | 1 (0.7) |
| PIPERAZINE DERIVATIVES | | | | |
|   Any Preferred Term | 1 (2.0) | 4 (8.0) | 6 (11.5) | 11 (7.3) |
|   CETIRIZINE HYDROCHLORIDE | 1 (2.0) | 4 (8.0) | 6 (11.5) | 11 (7.3) |
| POTASSIUM | | | | |
|   Any Preferred Term | 0 (0.0) | 1 (2.0) | 1 (1.9) | 2 (1.3) |
|   POTASSIUM | 0 (0.0) | 1 (2.0) | 1 (1.9) | 2 (1.3) |
| PREGNEN (4) DERIVATIVES | | | | |
|   Any Preferred Term | 1 (2.0) | 2 (4.0) | 1 (1.9) | 4 (2.6) |
|   MEDROXYPROGESTERONE ACETATE | 1 (2.0) | 2 (4.0) | 1 (1.9) | 4 (2.6) |

Note:
Concomitant medications were coded using the WHO Drug dictionary. A patient who took multiple medications is counted only once in each row.
Reference: 16.2.5.2
MedPoints Pharmaceuticals
MP 428      Program: MEDS.SAS 14.3.6 Concomitant Medications
Intent-to-Treat Population
(Page 14 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| PROGESTOGENS AND ESTROGENS, FIXED COMBINATIONS | | | | |
|   Any Preferred Term | 2 (4.1) | 2 (4.0) | 6 (11.5) | 10 (6.6) |
|   ANOVLAR | 1 (2.0) | 1 (2.0) | 1 (1.9) | 3 (2.0) |
|   CILEST | 1 (2.0) | 0 (0.0) | 2 (3.8) | 3 (2.0) |
|   CONLUNETT | 0 (0.0) | 1 (2.0) | 0 (0.0) | 1 (0.7) |

| | | | | |
|---|---|---|---|---|
| EUGYNON /00022701/ | 0 (0.0) | 0 (0.0) | 1 (1.9) | 1 (0.7) |
| EVRA | 0 (0.0) | 0 (0.0) | 1 (1.9) | 1 (0.7) |
| NORMENSAL | 0 (0.0) | 0 (0.0) | 1 (1.9) | 1 (0.7) |
| PROPIONIC ACID DERIVATIVES | | | | |
| Any Preferred Term | 14 (28.6) | 12 (24.0) | 14 (26.9) | 40 (26.5) |
| CO-ADVIL | 2 (4.1) | 0 (0.0) | 0 (0.0) | 2 (1.3) |
| IBUPROFEN | 13 (26.5) | 11 (22.0) | 11 (21.2) | 35 (23.2) |
| NAPROXEN | 0 (0.0) | 0 (0.0) | 1 (1.9) | 1 (0.7) |
| NAPROXEN SODIUM | 1 (2.0) | 1 (2.0) | 3 (5.8) | 5 (3.3) |
| PROTEIN SUPPLEMENTS | | | | |
| Any Preferred Term | 1 (2.0) | 0 (0.0) | 0 (0.0) | 1 (0.7) |
| PROTEIN SUPPLEMENTS | 1 (2.0) | 0 (0.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428  Program: MEDS.SAS 14.3.6 Concomitant Medications
Intent-to-Treat Population
(Page 15 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| PROTON PUMP INHIBITORS | | | | |
| Any Preferred Term | 2 (4.1) | 5 (10.0) | 2 (3.8) | 9 (6.0) |
| ESOMEPRAZOLE MAGNESIUM | 2 (4.1) | 0 (0.0) | 1 (1.9) | 3 (2.0) |
| OMEPRAZOLE | 0 (0.0) | 3 (6.0) | 1 (1.9) | 4 (2.6) |
| PANTOPRAZOLE SODIUM | 0 (0.0) | 1 (2.0) | 0 (0.0) | 1 (0.7) |
| RABEPRAZOLE SODIUM | 0 (0.0) | 1 (2.0) | 0 (0.0) | 1 (0.7) |
| PYRAZOLONES | | | | |
| Any Preferred Term | 1 (2.0) | 1 (2.0) | 2 (3.8) | 4 (2.6) |
| TYLENOL SINUS MEDICATION | 1 (2.0) | 1 (2.0) | 2 (3.8) | 4 (2.6) |
| SALICYLIC ACID AND DERIVATIVES | | | | |
| Any Preferred Term | 7 (14.3) | 5 (10.0) | 3 (5.8) | 15 (9.9) |
| ACETYLSALICYLIC ACID | 7 (14.3) | 5 (10.0) | 3 (5.8) | 15 (9.9) |
| SELECTIVE BETA-2-ADRENORECEPTOR AGONISTS | | | | |
| Any Preferred Term | 1 (2.0) | 2 (4.0) | 1 (1.9) | 4 (2.6) |
| SALBUTAMOL | 1 (2.0) | 1 (2.0) | 1 (1.9) | 3 (2.0) |
| SALBUTAMOL SULFATE | 0 (0.0) | 1 (2.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428  Program: MEDS.SAS 14.3.6 Concomitant Medications
Intent-to-Treat Population
(Page 16 of 19)

| Anatomical Therapeutic Class<br>Preferred Term | Azelastine<br>(N = 49)<br>No. of Patients (%) | Fluticasone<br>(N = 50)<br>No. of Patients (%) | Azelastine +<br>Fluticasone<br>(N = 52)<br>No. of Patients (%) | Total<br>(N = 151)<br>No. of Patients (%) |
|---|---|---|---|---|
| SELECTIVE SEROTONIN REUPTAKE INHIBITORS | | | | |
| Any Preferred Term | 2 (4.1) | 4 (8.0) | 2 (3.8) | 8 (5.3) |
| ESCITALOPRAM OXALATE | 0 (0.0) | 4 (8.0) | 0 (0.0) | 4 (2.6) |
| FLUOXETINE HYDROCHLORIDE | 0 (0.0) | 0 (0.0) | 1 (1.9) | 1 (0.7) |
| PAROXETINE HYDROCHLORIDE | 1 (2.0) | 0 (0.0) | 0 (0.0) | 1 (0.7) |
| SERTRALINE HYDROCHLORIDE | 1 (2.0) | 0 (0.0) | 1 (1.9) | 2 (1.3) |
| SELENIUM | | | | |
| Any Preferred Term | 1 (2.0) | 0 (0.0) | 0 (0.0) | 1 (0.7) |
| SELENIUM | 1 (2.0) | 0 (0.0) | 0 (0.0) | 1 (0.7) |
| SYMPATHOMIMETICS | | | | |
| Any Preferred Term | 2 (4.1) | 3 (6.0) | 2 (3.8) | 7 (4.6) |
| ADVIL /01717101/ | 0 (0.0) | 0 (0.0) | 1 (1.9) | 1 (0.7) |

-continued

| | Azelastine (N = 49) No. of Patients (%) | Fluticasone (N = 50) No. of Patients (%) | Azelastine + Fluticasone (N = 52) No. of Patients (%) | Total (N = 151) No. of Patients (%) |
|---|---|---|---|---|
| PSEUDOEPHEDRINE | 1 (2.0) | 1 (2.0) | 0 (0.0) | 2 (1.3) |
| PSEUDOEPHEDRINE HYDROCHLORIDE | 1 (2.0) | 2 (4.0) | 0 (0.0) | 3 (2.0) |
| PSEUDOEPHEDRINE, COMBINATIONS | 0 (0.0) | 0 (0.0) | 1 (1.9) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428                                                                                               Program: MEDS.SAS 14.3.6 Concomitant Medications
Intent-to-Treat Population
(Page 17 of 19)

| Anatomical Therapeutic Class Preferred Term | Azelastine (N = 49) No. of Patients (%) | Fluticasone (N = 50) No. of Patients (%) | Azelastine + Fluticasone (N = 52) No. of Patients (%) | Total (N = 151) No. of Patients (%) |
|---|---|---|---|---|
| SYMPATHOMIMETICS USED AS DECONGESTANTS | | | | |
| Any Preferred Term | 0 (0.0) | 0 (0.0) | 1 (1.9) | 1 (0.7) |
| TETRYZOLINE HYDROCHLORIDE | 0 (0.0) | 0 (0.0) | 1 (1.9) | 1 (0.7) |
| SYMPATHOMIMETICS, PLAIN | | | | |
| Any Preferred Term | 0 (0.0) | 0 (0.0) | 1 (1.9) | 1 (0.7) |
| OXYMETAZOLINE HYDROCHLORIDE | 0 (0.0) | 0 (0.0) | 1 (1.9) | 1 (0.7) |
| TESTOSTERONE-5-ALPHA REDUCTASE INHIBITORS | | | | |
| Any Preferred Term | 2 (4.1) | 0 (0.0) | 0 (0.0) | 2 (1.3) |
| FINASTERIDE | 2 (4.1) | 0 (0.0) | 0 (0.0) | 2 (1.3) |
| THIAZIDES, PLAIN | | | | |
| Any Preferred Term | 1 (2.0) | 0 (0.0) | 0 (0.0) | 1 (0.7) |
| HYDROCHLOROTHIAZIDE | 1 (2.0) | 0 (0.0) | 0 (0.0) | 1 (0.7) |
| THYROID HORMONES | | | | |
| Any Preferred Term | 3 (6.1) | 1 (2.0) | 2 (3.8) | 6 (4.0) |
| LEVOTHYROXINE SODIUM | 2 (4.1) | 0 (0.0) | 2 (3.8) | 4 (2.6) |

Note:
Concomitant medications were coded using the WHO Drug dictionary. A patient who took multiple medications is counted only once in each row.
Reference: 16.2.5.2
MedPoints Pharmaceuticals
MP 428                                                                                               Program: MEDS.SAS 14.3.6 Concomitant Medications
Intent-to-Treat Population
(Page 18 of 19)

| Anatomical Therapeutic Class Preferred Term | Azelastine (N = 49) No. of Patients (%) | Fluticasone (N = 50) No. of Patients (%) | Azelastine + Fluticasone (N = 52) No. of Patients (%) | Total (N = 151) No. of Patients (%) |
|---|---|---|---|---|
| THYROID HORMONES | | | | |
| NOVOTHYRAL | 1 (2.0) | 0 (0.0) | 0 (0.0) | 1 (0.7) |
| THYROID | 0 (0.0) | 1 (2.0) | 0 (0.0) | 1 (0.7) |
| TONICS | | | | |
| Any Preferred Term | 1 (2.0) | 0 (0.0) | 0 (0.0) | 1 (0.7) |
| ROYAL JELLY | 1 (2.0) | 0 (0.0) | 0 (0.0) | 1 (0.7) |
| UNSPECIFIED HERBAL | | | | |
| Any Preferred Term | 2 (4.1) | 1 (2.0) | 0 (0.0) | 3 (2.0) |
| GINKGO BILOBA | 1 (2.0) | 0 (0.0) | 0 (0.0) | 1 (0.7) |
| GLYCINE MAX EXTRACT | 0 (0.0) | 1 (2.0) | 0 (0.0) | 1 (0.7) |
| LINUM USITATISSIMUM SEED OIL | 2 (4.1) | 0 (0.0) | 0 (0.0) | 2 (1.3) |
| OENOTHERA BIENNIS OIL | 1 (2.0) | 0 (0.0) | 0 (0.0) | 1 (0.7) |
| URINARY ANTISPASMODICS | | | | |
| Any Preferred Term | 0 (0.0) | 1 (2.0) | 0 (0.0) | 1 (0.7) |
| TOLTERODINE L-TARTRATE | 0 (0.0) | 1 (2.0) | 0 (0.0) | 1 (0.7) |

Note:
Concomitant medications were coded using the WHO Drug dictionary. A patient who took multiple medications is counted only once in each row.
Reference: 16.2.5.2
MedPoints Pharmaceuticals
MP 428                                                                                               Program: MEDS.SAS 14.3.6 Concomitant Medications
Intent-to-Treat Population
(Page 19 of 19)

| Anatomical Therapeutic Class Preferred Term | Azelastine (N = 49) No. of Patients (%) | Fluticasone (N = 50) No. of Patients (%) | Azelastine + Fluticasone (N = 52) No. of Patients (%) | Total (N = 151) No. of Patients (%) |
|---|---|---|---|---|
| VITAMIN B-COMPLEX, PLAIN | | | | |
| Any Preferred Term | 0 (0.0) | 1 (2.0) | 0 (0.0) | 1 (0.7) |
| B-COMPLEX | 0 (0.0) | 1 (2.0) | 0 (0.0) | 1 (0.7) |

| | | | | |
|---|---|---|---|---|
| -continued | | | | |
| VITAMIN B12 (CYANOCOBALAMIN AND ANALOGUES) | | | | |
| Any Preferred Term | 2 (4.1) | 0 (0.0) | 0 (0.0) | 2 (1.3) |
| CYANOCOBALAMIN | 1 (2.0) | 0 (0.0) | 0 (0.0) | 1 (0.7) |
| CYANOCOBALAMIN-TANNIN COMPLEX | 1 (2.0) | 0 (0.0) | 0 (0.0) | 1 (0.7) |

Note:
Concomitant medications were coded using the WHO Drug dictionary. A patient who took multiple medications is counted only once in each row.
Reference: 16.2.5.2

The present invention has been described with reference to certain embodiments thereof. However, the scope of the invention is not limited to the embodiments described or exemplified. Workers of ordinary skill in the relevant arts will readily appreciate that other embodiments and examples can be practiced without departing from the scope of the present invention. All such variations are considered to be part of, and therefore encompassed by, the present invention.

All publications, patents and patent applications mentioned or referenced in this specification are herein incorporated by reference to the same extent as if each individual publication, patent or patent application was specifically and individually indicated to be incorporated by reference.

What is claimed is:

1. A composition of matter comprising:
   (a) a single unit dosage of a pharmaceutical composition; and
   (b) a unit dosage container comprising:
      (i) a squeezable chamber holding said single unit dosage and having an opening; and
      (ii) a closure mechanism removably attached to said opening of said squeezable chamber,
   wherein said unit dosage container is made of high density polyethylene (HDPE),
   wherein said single unit dosage of said pharmaceutical composition has a volume of less than about 0.6 ml,
   wherein said squeezable chamber has a volume of less than or equal to about 1.0 ml,
   wherein when said closure mechanism is removed, said unit dosage is retained in said squeezable chamber when said unit dosage container is inverted, and
   wherein when said squeezable chamber is squeezed, said squeezable chamber is deformed, the pressure within said container is increased, and said single unit dosage exits said opening in droplet form.

2. The composition of matter of claim 1, wherein said volume of said single unit dosage of the pharmaceutical composition is in a range of from about 0.1 ml to about 0.5 ml.

3. The composition of matter of claim 1, wherein said squeezable chamber has a volume of about 0.5 ml to about 1.0 ml.

4. The composition of matter of claim 1, further comprising:
   an extension attached to said squeezable chamber, said extension having opposed first and second surfaces, wherein identification can be located on at least one of said first and second surfaces.

5. The composition of matter of claim 4, wherein said identification is engraved on said extension.

6. The composition of matter of claim 4, wherein said identification indicates the contents of the unit dosage container.

7. The composition of matter of claim 4, wherein said identification is in writing.

8. The composition of matter of claim 4, wherein said identification indicates an expiration date of said pharmaceutical composition.

9. The composition of matter of claim 1, wherein said pharmaceutical composition comprises an active pharmaceutical ingredient selected from the group consisting of one or more antihistamines, one or more steroids, one or more leukotriene antagonists, one or more prostaglandin D2 receptor antagonists, one or more decongestants, one or more expectorants, one or more anti-fungal agents, triamcinolone or one or more triamcinolone derivatives, one or more non-steroidal immunophilin-dependent immunosuppressants (NsIDIs), one or more anti-inflammatory agents, one or more noon-steroidal anti-inflammatory agents (NSAIDs), one or more COX-2 inhibitors, one or more anti-infective agents, one or more mucolytic agents, one or more anticholinergic agents, one or more mast cell stabilizers, one or more non-antibiotic anti-microbial agents, one or more anti-viral agents, one or more antiseptics, one or more neurokinin antagonists, platelet activating factor (PAF) and one or more 5-lipoxygenase (5-LO) inhibitors.

10. The composition of matter of claim 9, wherein said pharmaceutical composition comprises one or more antihistamines.

11. The composition of matter of claim 10, wherein said one or more antihistamines are selected from the group consisting of azelastine, acrivastine, cyclizine, carebastine, cyproheptadine, carbinoxamine, doxylamine, dimethindene, ebastine, epinastine, efletirizine, ketotifen, levocabastine, mizolastine, mequitazine, mianserin, noberastine, meclizine, norastemizole, olopatadine, picumast, tripelenamine, temelastine, trimeprazine, triprolidine, bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, terfenadine, loratadine, cetirizine, levocetirizine, fexofenadine, descarboethoxyloratadine, desloratadine, dimenhydrinate and hydroxyzine, and pharmaceutically acceptable salts, esters and derivatives thereof.

12. The composition of matter of claim 10, wherein said pharmaceutical composition comprises azelastine or a pharmaceutically acceptable salt thereof.

13. The composition of matter of claim 12, wherein said pharmaceutical composition comprises azelastine hydrochloride.

14. The composition of matter of claim 9, wherein said one or more steroids are selected from the group consisting of fluoromethalone, fluticasone, mometasone, triamcinolone, betamethasone, flunisolide, budesonide, beclomethasone, rimexolone, loteprednol, beloxil, prednisone and dexamethasone, and pharmaceutically acceptable conjugates, salts, esters, variants or derivatives thereof.

15. The composition of matter of claim 14, wherein said steroid is fluticasone or a pharmaceutically acceptable conjugate, salt, ester, variant or derivative thereof.

16. The composition of matter of claim 15, wherein said steroid is selected from the group consisting of fluticasone propionate fluticasone dipropionate, fluticasone furoate, fluticasone maleate and fluticasone valerate.

17. The composition of matter of claim 9, wherein said one or more leukotriene antagonists are selected from the group consisting of albuterol sulfate, aminophylline, amoxicillin, ampicillin, astemizole, attenuated tubercle *bacillus*, azithromycin, bacampicillin, beclomethasone dipropionate, budesonide, bupropion hydrochloride, cefaclor, cefadroxil, cefixime, cefprozil, cefuroxime axetil, cephalexin, ciprofloxacin hydrochloride, clarithromycin, clindamycin, cloxacillin, doxycycline, erythromycin, ethambutol, fenoterol hydrobromide, fluconazole, flunisolide, fluticasone propionate, formoterol fumarate, gatifloxacin, influenza virus vaccine, ipratropium bromide, isoniazid, isoproterenol hydrochloride, itraconazole, ketoconazole, ketotifen, levofloxacin, minocycline, montelukast, moxifloxacin, nedocromil sodium, nicotine, nystatin, ofloxacin, orciprenaline, oseltamivir, oseltamivir sulfate, oxtriphylline, penicillin, pirbuterol acetate, pivampicillin, pneumococcal conjugate vaccine, pneumococcal polysaccharide vaccine, prednisone, pyrazinamide, rifampin, salbutamol, salmeterol xinafoate, sodium cromoglycate, terbutaline sulfate, terfenadine, theophylline, triamcinolone acetonide, zafirlukast and zanamivir.

18. The composition of matter of claim 9, wherein said pharmaceutical composition comprises one or more prostaglandin D2 receptor antagonists.

19. The composition of matter of claim 9, wherein said one or more decongestants are selected from the group consisting of pseudoephedrine, phenylephedrine, phenylephrine, phenylpropanolamine, oxymetazoline, propylhexedrine, xylometazoline, epinephrine, ephedrine, desoxyephedrine, naphazoline, and tetrahydrozoline.

20. The composition of matter of claim 9, wherein said one or more expectorants are selected from the group consisting of guaifenesin, sodium cromoglycate, codeine phosphate and isoproterenol hydrochloride.

21. The composition of matter of claim 9, wherein said one or more anti-fungal agents are selected from the group consisting of amphotericin B, nystatin, fluconazole, ketoconazole, terbinafine, itraconazole, imidazole, triazole, ciclopirox, clotrimazole, and miconazole.

22. The composition of matter of claim 9, wherein said pharmaceutical composition comprises a triamcinolone or one or more triamcinolone derivatives.

23. The composition of matter of claim 9, wherein said one or more non-steroidal anti-inflammatory agents are selected from the group consisting of ibuprofen, diclofenac, aceclofenac, naproxen, etodolac, flurbiprofen, fenoprofen, ketoprofen, suprofen, fenbufen, fluprofen, tolmetin sodium, oxaprozin, zomepirac, sulindac indomethacin, piroxicam, mefenamic acid, nabumetone, meclofenamate sodium, diflunisal, flufenisal, piroxicam, ketorolac, sudoxicam and isoxicam.

24. The composition of matter of claim 9, wherein said one or more non-steroidal immunophilin-dependent immunosuppressants (NsIDIs) are selected from the group consisting of cyclosporine, tacrolimus, ascomycin, pimecrolimus, rapamycin, everolimus, and other agents that inhibit calcineurin.

25. The composition of matter of claim 9, wherein said one or more COX-2 inhibitors are selected from the group consisting of rofecoxib, celecoxib, valdecoxib, lumiracoxib, meloxicam, and nimesulide.

26. The composition of matter of claim 9, wherein said one or more anti-infective agents are selected from the group consisting of penicillin, beta lactam antibiotics, cephalosporins, macrolides, ketolides, sulfonamides, quinolones, aminoglycosides, cefuroxime, vancomycin, amoxicillin, gentamicin and linezolid.

27. The composition of matter of claim 9, wherein said one or more mucolytic agents are selected from the group consisting of acetylcysteine and dornase alpha.

28. The composition of matter of claim 9, wherein said pharmaceutical composition comprises one or more anticholinergic agents selected from the group consisting of mivacurium, atracurium, fazadinium, rocuronium, vecuronium, doxacurium, metocurine, pancuronium, pipecuronium, gallamine, hexafluoronium, suxamethonium, succinylcholine, decamethonium, atropine, scopolamine, hyoscyamine, benzatropine, trihexyphenidyl, biperiden, glycopyrrolate, ipratropium, pirenzepine, telenzepine, tiotropium, darifenacin, vedaclidine, tropicamide, cyclopentolate, dicycloverine, tolterodine, oxybutynin, homatropine, orphenadrine, diphenhydramine, hemicholinium-3, vesamicol, pralidoxime, obidoxime, oxitropium, alcuronium, dimethyltubocurarine, tubocurarine and ipratropium.

29. The composition of matter of claim 9, wherein said one or more mast cell stabilizers are selected from the group consisting of cromolyn and nedcromil sodium.

30. The composition of matter of claim 9, wherein said one or more non-antibiotic anti-microbial agents is taurolidine.

31. The composition of matter of claim 9, wherein said pharmaceutical composition comprises one or more anti-viral agents selected from the group consisting of abacavir, acyclovir, adefovir, amantadine, amprenavir, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, integrase inhibitor, lamivudine, lopinavir, loviride, maraviroc, moroxydine, nelfinavir, nevirapine, nexavir, oseltamivir, peginterferon alfa-2a, penciclovir, peramivir, pleconaril, podophyllotoxin, raltegravir, ribavirin, rimantadine, ritonavir, saquinavir, stavudine, tenofovir, tipranavir, trifluridine, trizivir, tromantadine, truvada, valaciclovir, valganciclovir, vicriviroc, vidarabine, viramidine, zalcitabine, zanamivir and zidovudine.

32. The composition of matter of claim 9, wherein said one or more antiseptics are selected from the group consisting of iodine, chlorhexidine acetate, sodium hypochlorite and calcium hydroxide.

33. The composition of matter of claim 9, wherein said one or more neurokinin antagonists are selected from the group consisting of oximes, hydrazones, piperidines, piperazines, aryl alkyl amines, hydrazones, nitroalkanes, amides, isoxazolines, quinolines, isoquinolines, azanorbornanes, naphthyridines and benzodiazepines.

34. The composition of matter of claim 9, wherein said one or more 5-lipoxygenase inhibitors are selected from the group consisting of zileuton, docebenone, piripost and tenidap.

35. The composition of matter of claim 9, wherein said pharmaceutical composition further comprises one or more additional active pharmaceutical ingredients.

36. The composition of matter of claim 35, wherein said one or more additional active pharmaceutical ingredients is selected from the group consisting of (a) one or more antihistamines; (b) one or more steroids; (c) one or more leukotriene antagonists; (d) one or more decongestants; and (e) one or more non-steroidal anti-inflammatory agents.

37. A composition of matter comprising:
  (a) a plurality of unit dosage containers, each of said unit dosage containers comprising a single unit dosage of a pharmaceutical composition, wherein each unit dosage container comprises:

(b) a squeezable chamber holding said single unit dosage and having an opening wherein the pressure within said container is increased and said single unit dosage exits said opening in droplet form when said squeezable chamber is squeezed,
wherein said squeezeable chamber is deformed when squeezed, and
wherein said, unit dosage is retained in said squeezable chamber when said unit dosage container is inverted; and
(c) a closure mechanism removably attached to said opening of said squeezable chamber,
wherein said unit dose container is made of high density polyethylene (HDPE), and wherein said single unit dosage of said pharmaceutical composition has a volume of less than about 0.6 ml and wherein said squeezable chamber has a volume of less than or equal to about 1.0 ml.

38. The composition of matter of claim 37, wherein said volume of said single unit dosage of said pharmaceutical composition is in a range from about 0.1 ml to about 0.5 ml.

39. The composition of matter of claim 37, wherein said squeezable chamber has a volume of about 0.5 ml to about 1.0 ml.

40. An assembly comprising the composition of matter of claim 37, wherein at least two of said unit dosage containers are removably attached to each other.

41. A container comprising the composition of matter of claim 37.

42. The container of claim 41, further comprising instructions for use of the unit dosage containers.

43. A unit dosage form comprising a unit dosage container made of high density polyethylene, said unit dosage container comprising a squeezable chamber holding a single unit dosage and having an opening,
wherein the pressure within said container is increased and said unit dosage exits said opening in droplet form when said squeezable chamber is squeezed,
wherein said unit dosage is retained in said squeezable chamber when said unit dosage container is inverted,
said unit dosage container having a volume of less than about 0.6 ml,
said squeezable chamber having a volume of less than about 1.0 ml, and
said unit dosage form containing one or more antihistamines or pharmaceutically acceptable salts thereof.

44. The unit dosage form of claim 43, wherein said antihistamine comprises azelastine or a pharmaceutically acceptable salt thereof.

45. The unit dosage form of claim 44, wherein said unit dosage form comprises azelastine hydrochloride.

46. The unit dosage form of claim 43, further comprising one more pharmaceutically acceptable carriers or diluents.

47. The unit dosage form of claim 43, further comprising one or more additional active pharmaceutical ingredients.

48. The unit dosage form of claim 47, wherein said one or more additional active pharmaceutical ingredients is selected from the group consisting of one or more antihistamines, one or more steroids, one or more leukotriene antagonists, one or more prostaglandin D2 receptor antagonists, one or more decongestants, one or more expectorants, one or more anti-fungal agents, triamcinolone, one or more non-steroidal immunophilin-dependent immunosuppressants, one or more anti-inflammatory agents, one or more non-steroidal anti-inflammatory agents (NSAIDs), one or more COX-2 inhibitors, one or more anti-infective agents, one or more mucolytic agents, one or more anticholinergic agents, one or more mast cell stabilizers, one or more non-antibiotic anti-microbial agents, one or more anti-viral agents, one or more antiseptics, one or more neurokinin antagonists, platelet activating factor and one or more 5-lipoxygenase (5-LO) inhibitors.

49. The unit dosage form of claim 48, wherein said one or more steroids are selected from the group consisting of fluorometholone, fluticasone, mometasone, triamcinolone, betamethasone, flunisolide, budesonide, beclomethasone, rimexolone, loteprednol, beloxil, prednisone and dexamethasone, and pharmaceutically acceptable conjugates, salts, esters, variants or derivatives thereof.

50. The unit dosage form of claim 49, wherein said steroid is fluticasone or a pharmaceutically acceptable conjugate, salt, ester, variant or derivative thereof.

51. The unit dosage form of claim 49, wherein said steroid is selected from the group consisting of fluticasone propionate, fluticasone dipropionate, fluticasone furoate, fluticasone maleate and fluticasone valerate.

52. The unit dosage form of claim 48, wherein said one or more leukotriene antagonists are selected from the group consisting of albuterol sulfate, aminophylline, amoxicillin, ampicillin, astemizole, attenuated tubercle *bacillus*, azithromycin, bacampicillin, beclomethasone dipropionate, budesonide, bupropion hydrochloride, cefaclor, cefadroxil, cefixime, cefprozil, cefuroxime axetil, cephalexin, ciprofloxacin hydrochloride, clarithromycin, clindamycin, cloxacillin, doxycycline, erythromycin, ethambutol, fenoterol hydrobromide, fluconazole, flunisolide, fluticasone propionate, formoterol fumarate, gatifloxacin, influenza virus vaccine, ipratropium bromide, isoniazid, isoproterenol hydrochloride, itraconazole, ketoconazole, ketotifen, levofloxacin, minocycline, montelukast, moxifloxacin, nedocromil sodium, nicotine, nystatin, ofloxacin, orciprenaline, oseltamivir, oseltamivir sulfate, oxtriphylline, penicillin, pirbuterol acetate, pivampicillin, pneumococcal conjugate vaccine, pneumococcal polysaccharide vaccine, prednisone, pyrazinamide, rifampin, salbutamol, salmeterol xinafoate, sodium cromoglycate, terbutaline sulfate, terfenadine, theophylline, triamcinolone acetonide, zafirlukast and zanamivir.

53. The unit dosage form of claim 48, wherein said pharmaceutical composition comprises one or more prostaglandin D2 receptor antagonists.

54. The unit dosage form of claim 48, wherein said one or more decongestants are selected from the group consisting of pseudoephedrine, phenylephedrine, phenylephrine, phenylpropanolamine, oxymetazoline, propylhexedrine, xylometazoline, epinephrine, ephedrine, desoxyephedrine, naphazoline, and tetrahydrozoline.

55. The unit dosage form of claim 48, wherein said one or more expectorants are selected from the group consisting of guaifenesin, sodium cromoglycate, codeine phosphate and isoproterenol hydrochloride.

56. The unit dosage form of claim 48, wherein said one or more anti-fungal agents are selected from the group consisting of amphotericin B, nystatin, fluconazole, ketoconazole, terbinafine, itraconazole, imidazole, triazole, ciclopirox, clotrimazole, and miconazole.

57. The unit dosage form of claim 48, wherein said pharmaceutical composition comprises a triamcinolone or one or more triamcinolone derivatives.

58. The unit dosage form of claim 48, wherein said one or more non-steroidal anti-inflammatory agents are selected from the group consisting of ibuprofen, diclofenac, aceclofenac, naproxen, etodolac, flurbiprofen, fenoprofen, ketoprofen, suprofen, fenbufen, fluprofen, tolmetin sodium, oxaprozin, zomepirac, sulindac indomethacin, piroxicam, mefenamic acid, nabumetone, meclofenamate sodium, diflunisal, flufenisal, piroxicam, ketorolac, sudoxicam and isoxicam.

59. The unit dosage form of claim 48, wherein said one or more non-steroidal immunophilin-dependent immunosuppressants (NsIDIs) are selected from the group consisting of cyclosporine, tacrolimus, ascomycin, pimecrolimus, rapamycin, everolimus, and other agents that inhibit calcineurin.

60. The unit dosage form of claim 48, wherein said one or more COX-2 inhibitors are selected from the group consisting of rofecoxib, celecoxib, valdecoxib, lumiracoxib, meloxicam, and nimesulide.

61. The unit dosage form of claim 48, wherein said one or more anti-infective agents are selected from the group consisting of penicillin, beta lactam antibiotics, cephalosporins, macrolides, ketolides, sulfonamides, quinolones, aminoglycosides, cefuroxime, vancomycin, amoxicillin, gentamicin and linezolid.

62. The unit dosage form of claim 48, wherein said one or more mucolytic agents are selected from the group consisting of acetylcysteine and dornase alpha.

63. The unit dosage form of claim 48, wherein said pharmaceutical composition comprises one or more anticholinergic agents selected from the group consisting of mivacurium, atracurium, fazadinium, rocuronium, vecuronium, doxacurium, metocurine, pancuronium, pipecuronium, gallamine, hexafluoronium, suxamethonium, succinylcholine, decamethonium, atropine, scopolamine, hyoscyamine, benzatropine, trihexyphenidyl, biperiden, glycopyrrolate, ipratropium, pirenzepine, telenzepine, tiotropium, darifenacin, vedaclidine, tropicamide, cyclopentolate, dicycloverine, tolterodine, oxybutynin, homatropine, orphenadrine, diphenhydramine, hemicholinium-3, vesamicol, pralidoxime, obidoxime, oxitropium, alcuronium, dimethyltubocurarine, tubocurarine and ipratropium.

64. The unit dosage form of claim 48, wherein said one or more mast cell stabilizers are selected from the group consisting of cromolyn and nedcromil sodium.

65. The unit dosage form of claim 48, wherein said one or more non-antibiotic anti-microbial agents is taurolidine.

66. The unit dosage form of claim 48, wherein said pharmaceutical composition comprises one or more anti-viral agents are selected from the group consisting of abacavir, acyclovir, adefovir, amantadine, amprenavir, arbidol, atazanavir, atripla, boceprevir, cidofovir, combivir, darunavir delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, integrase inhibitor, lamivudine, lopinavir, loviride, maraviroc, moroxydine, nelfinavir, nevirapine nexavir, oseltamivir, peginterferon alfa-2a, penciclovir, peramivir, pleconaril, podophyllotoxin, raltegravir, ribavirin, rimantadine, ritonavir, saquinavir, stavudine, tenofovir, tipranavir, trifluridine, trizivir, tromantadine, truvada, valaciclovir, valganciclovir, vicriviroc, vidarabine, viramidine, zalcitabine, zanamivir and zidovudine.

67. The unit dosage form of claim 48, wherein said one or more antiseptics are selected from the group consisting of iodine, chlorhexidine acetate, sodium hypochlorite and calcium hydroxide.

68. The unit dosage form of claim 48, wherein said one or more neurokinin antagonists are selected from the group consisting of oximes, hydrazones, piperidines, piperazines, aryl alkyl amines, hydrazones, nitroalkanes, amides, isoxazolines, quinolines, isoquinolines, azanorbornanes, naphthyridines and benzodiazepines.

69. The unit dosage form of claim 48, wherein said one or more 5-lipoxygenase inhibitors are selected from the group consisting of zileuton, docebenone, piripost and tenidap.

70. A unit dosage form comprising a unit dosage container made of high density polyethylene, said unit dosage container comprising a squeezable chamber holding a single unit dosage and having an opening,
    wherein the pressure within said container is increased and said unit dosage exits said opening in droplet form when said squeezable chamber is squeezed,
    wherein said unit dosage is retained in said squeezable chamber when said unit dosage container is inverted,
    said unit dosage container having a volume of less than about 0.6 ml, said squeezable chamber having a volume of less than about 1.0 ml containing about 0.1% to about 0.15% azelastine HCl, about 0.05% to about 0.15% sucralose and about 1% to about 10% sorbitol.

71. A unit dosage form comprising a unit dosage container made of high density polyethylene, said unit dosage container comprising a squeezable chamber holding a single unit dosage and having an opening,
    wherein the pressure within said container is increased and said unit dosage exits said opening in droplet form when said squeezable chamber is squeezed,
    wherein said unit dosage is retained in said squeezable chamber when said unit dosage container is inverted,
    said unit dosage container having a volume of less than about 0.6 ml, and
    said squeezable chamber having a volume of less than about 1.0 ml containing about 0.15% azelastine HCl, about 0.15% sucralose and about 5% to about 10% sorbitol.

72. A method for treating a physical disorder or a symptom thereof, said method comprising:
    (a) providing a unit dosage form of a pharmaceutical formulation comprising a unit dosage container made of high density polyethylene containing a pharmaceutical composition in a volume of less than about 0.6 ml,
    wherein said unit dosage container comprises a squeezable chamber holding said pharmaceutical composition and having an opening,
    wherein the pressure within said container is increased and said pharmaceutical composition exits said opening in droplet form when said squeezable chamber is squeezed,
    wherein said unit dosage is retained in said squeezable chamber when said unit dosage container is inverted,
    said squeezable chamber having a volume of less than about 1.0 ml, and
    said pharmaceutical composition comprising one or more antihistamines or pharmaceutically acceptable salts thereof; and
    (b) administering the pharmaceutical composition in said unit dosage form to a subject in need thereof.

73. The method of claim 72, wherein said pharmaceutical composition is administered to the eye or ocular mucosa of the subject.

74. The method of claim 72, wherein said pharmaceutical composition is administered to the nasal passage or nasal mucosa of the subject.

75. The method of claim 72, wherein said pharmaceutical composition is administered to the ear.

76. The method of claim 72, wherein said physical disorder is an allergic condition selected from the group consisting of allergic conjunctivitis and allergic rhinitis.

77. The method of claim 72, wherein said physical disorder is allergic conjunctivitis, and wherein the unit dosage form is administered to the eye of the subject.

78. The method of claim 72, wherein said antihistamine is azelastine hydrochloride.

79. The method of claim 72, further comprising one more pharmaceutically acceptable carriers or diluents.

80. The method of claim 72, further comprising one or more additional active pharmaceutical ingredients.

81. The method of claim 80, wherein said one or more additional active pharmaceutical ingredients is selected from the group consisting of one or more antihistamines, one or more steroids, one or more leukotriene antagonists, one or more prostaglandin D2 receptor antagonists, one or more decongestants, one or more expectorants, one or more anti-fungal agents, triamcinolone, one or more non-steroidal immunophilin-dependent immunosuppressants, one or more anti-inflammatory agents, one or more non-steroidal anti-inflammatory agents (NSAIDs), one or more COX-2 inhibitors, one or more anti-infective agents, one or more mucolytic agents, one or more anticholinergic agents, one or more mast cell stabilizers, one or more non-antibiotic anti-microbial agents, one or more anti-viral agents, one or more antiseptics, one or more neurokinin antagonists, platelet activating factor and one or more 5-lipoxygenase (5-LO) inhibitors.

82. The method of claim 81, wherein said one or more steroids are selected from the group consisting of fluorometalone, fluticasone, mometasone, triamcinolone, betamethasone, flunisolide, budesonide, beclomethasone, rimexolone, loteprednol, beloxil, prednisone and dexamethasone, and pharmaceutically acceptable conjugates, salts, esters, variants or derivatives thereof.

83. The method of claim 82, wherein said steroid is fluticasone or a pharmaceutically acceptable conjugate, salt, ester, variant or derivative thereof.

84. The method of claim 82, wherein said steroid is selected from the group consisting of fluticasone propionate, fluticasone dipropionate, fluticasone furoate, fluticasone maleate and fluticasone valerate.

85. The method of claim 81, wherein said one or more leukotriene antagonists are selected from the group consisting of albuterol sulfate, aminophylline, astemizole, azithromycin, dipropionate, bupropion hydrochloride, cefaclor, cefadroxil, cefixime, cefprozil, cefuroxime axetil, cephalexin, clarithromycin, clindamycin, cloxacillin, ethambutol, fenoterol hydrobromide, formoterol fumarate, gatifloxacin, ipratropium bromide, isoniazid, isoproterenol hydrochloride, ketotifen, levofloxacin, montelukast, moxifloxacin, nedocromil sodium, nystatin, ofloxacin, orciprenaline, oseltamivir, oseltamivir sulfate, oxtriphylline, pirbuterol acetate, pyrazinamide, rifampin, salbutamol, salmeterol xinafoate, terbutaline sulfate, terfenadine, theophylline, zafirlukast and zanamivir.

86. The method of claim 81, wherein said pharmaceutical composition comprises one or more prostaglandin D2 receptor antagonists.

87. The method of claim 81, wherein said one or more decongestants are selected from the group consisting of pseudoephedrine, phenylephedrine, phenylephrine, phenylpropanolamine, oxymetazoline, propylhexedrine, xylometazoline, epinephrine, ephedrine, desoxyephedrine, naphazoline, and tetrahydrozoline.

88. The method of claim 81, wherein said one or more expectorants are selected from the group consisting of guaifenesin, sodium cromoglycate, codeine phosphate and isoproterenol hydrochloride.

89. The method of claim 81, wherein said one or more anti-fungal agents are selected from the group consisting of amphotericin B, nystatin, fluconazole, ketoconazole, terbinafine, itraconazole, imidazole, triazole, ciclopirox, clotrimazole, and miconazole.

90. The method of claim 81, wherein said pharmaceutical composition comprises a triamcinolone or one or more triamcinolone derivatives.

91. The method of claim 81, wherein said one or more non-steroidal anti-inflammatory agents are selected from the group consisting of ibuprofen, diclofenac, aceclofenac, naproxen, etodolac, flurbiprofen, fenoprofen, ketoprofen, suprofen, fenbufen, fluprofen, tolmetin sodium, oxaprozin, zomepirac, sulindac indomethacin, piroxicam, mefenamic acid, nabumetone, meclofenamate sodium, diflunisal, flufenisal, piroxicam, ketorolac, sudoxicam and isoxicam.

92. The method of claim 81, wherein said one or more non-steroidal immunophilin-dependent immunosuppressants (NsIDIs) are selected from the group consisting of cyclosporine, tacrolimus, ascomycin, pimecrolimus, rapamycin, everolimus, and other agents that inhibit calcineurin.

93. The method of claim 81, wherein said one or more COX-2 inhibitors are selected from the group consisting of rofecoxib, celecoxib, valdecoxib, lumiracoxib, meloxicam, and nimesulide.

94. The method of claim 81, wherein said one or more anti-infective agents are selected from the group consisting of penicillin, beta lactam antibiotics, cephalosporins, macrolides, ketolides, sulfonamides, quinolones, aminoglycosides, cefuroxime, vancomycin, amoxicillin, gentamicin and linezolid.

95. The method of claim 81, wherein said one or more mucolytic agents are selected from the group consisting of acetylcysteine and dornase alpha.

96. The method of claim 81, wherein said pharmaceutical composition comprises one or more anticholinergic agents selected from the group consisting of mivacurium, atracurium, fazadinium, rocuronium, vecuronium, doxacurium, metocurine, pancuronium, pipecuronium, gallamine, hexafluoronium, suxamethonium, succinylcholine, decamethonium, atropine, scopolamine, hyoscyamine, benzatropine, trihexyphenidyl, biperiden, glycopyrrolate, ipratropium, pirenzepine, telenzepine, tiotropium, darifenacin, vedaclidine, tropicamide, cyclopentolate, dicycloverine, tolterodine, oxybutynin, homatropine, orphenadrine, diphenhydramine, hemicholinium-3, vesamicol, pralidoxime, obidoxime, oxitropium, alcuronium, dimethyltubocurarine, tubocurarine and ipratropium.

97. The method of claim 81, wherein said one or more mast cell stabilizers are selected from the group consisting of cromolyn and nedcromil sodium.

98. The method of claim 81, wherein said one or more non-antibiotic anti-microbial agents is taurolidine.

99. The method of claim 81, wherein said pharmaceutical composition comprises one or more anti-viral agents are selected from the group consisting of abacavir, acyclovir, adefovir, amantadine, amprenavir, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, integrase inhibitor, lamivudine, lopinavir, loviride, maraviroc, moroxydine, nelfinavir, nevirapine nexavir, oseltamivir, peginterferon alfa-2a, penciclovir, peramivir, pleconaril, podophyllotoxin, raltegravir, ribavirin, rimantadine, ritonavir, saquinavir, stavudine, tenofovir, tipranavir, trifluridine, trizivir, tromantadine, truvada, valaciclovir, valganciclovir, vicriviroc, vidarabine, viramidine, zalcitabine, zanamivir and zidovudine.

100. The method of claim 81, wherein said one or more antiseptics are selected from the group consisting of iodine, chlorhexidine acetate, sodium hypochlorite and calcium hydroxide.

101. The method of claim 81, wherein said one or more neurokinin antagonists are selected from the group consisting of oximes, hydrazones, piperidines, piperazines, aryl alkyl amines, hydrazones, nitroalkanes, amides, isoxazolines, quinolines, isoquinolines, azanorbornanes, naphthyridines and benzodiazepines.

102. The method of claim 81, wherein said one or more 5-lipoxygenase inhibitors are selected from the group consisting of zileuton, docebenone, piripost and tenidap.

103. A method of treating or preventing a physical disorder or condition in a patient comprising administering a unit dosage form comprising azelastine or a pharmaceutically acceptable salt thereof to a subject in need thereof, wherein said physical disorder or condition is selected from the group consisting of postoperative ocular inflammation, acute anterior uveitis, dermatitis/keratitis, allergic blepharitis and keratitis, said method comprising:
 (a) providing a unit dosage form of a pharmaceutical formulation comprising a unit dosage container made of high density polyethylene containing a pharmaceutical composition in a volume of less than about 0.6 ml,
 wherein said unit dosage container comprises a squeezable chamber holding said pharmaceutical composition and having an opening,
 wherein the pressure within said container is increased and said pharmaceutical composition exits said opening in droplet form when said squeezable chamber is squeezed,
 wherein said unit dosage is retained in said squeezable chamber when said unit dosage container is inverted,
 said squeezable chamber having a volume of less than about 1.0 ml, and said pharmaceutical composition comprising one or more antihistamines or pharmaceutically acceptable salts thereof; and
 (b) administering the pharmaceutical composition in said unit dosage form to a subject in need thereof.

104. A high density polyethylene (HDPE) unit dosage container containing a formulation for nasal or ocular administration,
 wherein said unit dosage container comprises a squeezable chamber holding said formulation and having an opening,
 wherein the pressure within said container is increased and said formulation exits said opening in droplet form when said squeezable chamber is squeezed, and
 wherein said unit dosage is retained in said squeezable chamber when said unit dosage container is inverted,
 wherein said formulation consists essentially of a therapeutically effective amount of one or more antihistamines, one or more pharmaceutically acceptable carriers or diluents, sucralose and/or sorbitol, wherein said unit dosage container has a volume of less than about 1.0 ml.

105. The unit dose container of claim 104, wherein said one or more antihistamines is azelastine hydrochloride.

106. The unit dose container of claim 104, further comprising one more pharmaceutically acceptable carriers or diluents.

107. The unit dose container of claim 104, further comprising one or more additional active pharmaceutical ingredients.

108. The unit dosage container of claim 107, wherein said one or more additional active pharmaceutical ingredients is selected from the group consisting of one or more antihistamines, one or more steroids, one or more leukotriene antagonists, one or more prostaglandin D2 receptor antagonists, one or more decongestants, one or more expectorants, one or more anti-fungal agents, triamcinolone, one or more non-steroidal immunophilin-dependent immunosuppressants, one or more anti-inflammatory agents, one or more non-steroidal anti-inflammatory agents (NSAIDs), one or more COX-2 inhibitors, one or more anti-infective agents, one or more mucolytic agents, one or more anticholinergic agents, one or more mast cell stabilizers, one or more non-antibiotic anti-microbial agents, one or more anti-viral agents, one or more antiseptics, one or more neurokinin antagonists, platelet activating factor and one or more 5-lipoxygenase (5-LO) inhibitors.

109. The unit dosage container of claim 108, wherein said one or more steroids are selected from the group consisting of fluoromethalone, fluticasone, mometasone, triamcinolone, betamethasone, flunisolide, budesonide, beclomethasone, rimexolone, loteprednol, beloxil, prednisone and dexamethasone, and pharmaceutically acceptable conjugates, salts, esters, variants or derivatives thereof.

110. The unit dosage container of claim 109, wherein said steroid is fluticasone or a pharmaceutically acceptable conjugate, salt, ester, variant or derivative thereof.

111. The unit dosage container of claim 109, wherein said steroid is selected from the group consisting of fluticasone propionate, fluticasone dipropionate, fluticasone furoate, fluticasone maleate and fluticasone valerate.

112. The unit dosage container of claim 108, wherein said one or more leukotriene antagonists are selected from the group consisting of albuterol sulfate, aminophylline, amoxicillin, ampicillin, astemizole, attenuated tubercle bacillus, azithromycin, bacampicillin, beclomethasone dipropionate, budesonide, bupropion hydrochloride, cefaclor, cefadroxil, cefixime, cefprozil, cefuroxime axetil, cephalexin, ciprofloxacin hydrochloride, clarithromycin, clindamycin, cloxacillin, doxycycline, erythromycin, ethambutol, fenoterol hydrobromide, fluconazole, flunisolide, fluticasone propionate, formoterol fumarate, gatifloxacin, influenza virus vaccine, ipratropium bromide, isoniazid, isoproterenol hydrochloride, itraconazole, ketoconazole, ketotifen, levofloxacin, minocycline, montelukast, moxifloxacin, nedocromil sodium, nicotine, nystatin, ofloxacin, orciprenaline, oseltamivir, oseltamivir sulfate, oxtriphylline, penicillin, pirbuterol acetate, pivampicillin, pneumococcal conjugate vaccine, pneumococcal polysaccharide vaccine, prednisone, pyrazinamide, rifampin, salbutamol, salmeterol xinafoate, sodium cromoglycate, terbutaline sulfate, terfenadine, theophylline, triamcinolone acetonide, zafirlukast and zanamivir.

113. The unit dosage container of claim 108, wherein said pharmaceutical composition comprises one or more prostaglandin D2 receptor antagonists.

114. The unit dosage container of claim 108, wherein said one or more decongestants are selected from the group consisting of pseudoephedrine, phenylephedrine, phenylephrine, phenylpropanolamine, oxymetazoline, propylhexedrine, xylometazoline, epinephrine, ephedrine, desoxyephedrine, naphazoline, and tetrahydrozoline.

115. The unit dosage container of claim 108, wherein said one or more expectorants are selected from the group consisting of guaifenesin, sodium cromoglycate, codeine phosphate and isoproterenol hydrochloride.

116. The unit dosage container of claim 108, wherein said one or more anti-fungal agents are selected from the group consisting of amphotericin B, nystatin, fluconazole, ketoconazole, terbinafine, itraconazole, imidazole, triazole, ciclopirox, clotrimazole, and miconazole.

117. The unit dosage container of claim 108, wherein said pharmaceutical composition comprises a triamcinolone or one or more triamcinolone derivatives.

118. The unit dosage container of claim 108, wherein said one or more non-steroidal anti-inflammatory agents are selected from the group consisting of ibuprofen, diclofenac, aceclofenac, naproxen, etodolac, flurbiprofen, fenoprofen, ketoprofen, suprofen, fenbufen, fluprofen, tolmetin sodium, oxaprozin, zomepirac, sulindac indomethacin, piroxicam, mefenamic acid, nabumetone, meclofenamate sodium, diflunisal, flufenisal, piroxicam, ketorolac, sudoxicam and isoxicam.

119. The unit dosage container of claim 108, wherein said one or more non-steroidal immunophilin-dependent immunosuppressants (NsIDIs) are selected from the group consisting of cyclosporine, tacrolimus, ascomycin, pimecrolimus, rapamycin, everolimus, and other agents that inhibit calcineurin.

120. The unit dosage container of claim 108, wherein said one or more COX-2 inhibitors are selected from the group consisting of rofecoxib, celecoxib, valdecoxib, lumiracoxib, meloxicam, and nimesulide.

121. The unit dosage container of claim 108, wherein said one or more anti-infective agents are selected from the group consisting of penicillin, beta lactam antibiotics, cephalosporins, macrolides, ketolides, sulfonamides, quinolones, aminoglycosides, cefuroxime, vancomycin, amoxicillin, gentamicin and linezolid.

122. The unit dosage container of claim 108, wherein said one or more mucolytic agents are selected from the group consisting of acetylcysteine and dornase alpha.

123. The unit dosage container of claim 108, wherein said pharmaceutical composition comprises one or more anticholinergic agents selected from the group consisting of mivacurium, atracurium, fazadinium, rocuronium, vecuronium, doxacurium, metocurine, pancuronium, pipecuronium, gallamine, hexafluoronium, suxamethonium, succinylcholine, decamethonium, atropine, scopolamine, hyoscyamine, benzatropine, trihexyphenidyl, biperiden, glycopyrrolate, ipratropium, pirenzepine, telenzepine, tiotropium, darifenacin, vedaclidine, tropicamide, cyclopentolate, dicycloverine, tolterodine, oxybutynin, homatropine, orphenadrine, diphenhydramine, hemicholinium-3, vesamicol, pralidoxime, obidoxime, oxitropium, alcuronium, dimethyltubocurarine, tubocurarine and ipratropium.

124. The unit dosage container of claim 108, wherein said one or more mast cell stabilizers are selected from the group consisting of cromolyn and nedcromil sodium.

125. The unit dosage container of claim 108, wherein said one or more non-antibiotic anti-microbial agents is taurolidine.

126. The unit dosage container of claim 108, wherein said pharmaceutical composition comprises one or more anti-viral agents selected from the group consisting of abacavir, acyclovir, adefovir, amantadine, amprenavir, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, integrase inhibitor, lamivudine, lopinavir, loviride, maraviroc, moroxydine, nelfinavir, nevirapine nexavir, oseltamivir, peginterferon alfa-2a, penciclovir, peramivir, pleconaril, podophyllotoxin, raltegravir, ribavirin, rimantadine, ritonavir, saquinavir, stavudine, tenofovir, tipranavir, trifluridine, trizivir, tromantadine, truvada, valaciclovir, valganciclovir, vicriviroc, vidarabine, viramidine, zalcitabine, zanamivir and zidovudine.

127. The unit dosage container of claim 108, wherein said one or more antiseptics are selected from the group consisting of iodine, chlorhexidine acetate, sodium hypochlorite and calcium hydroxide.

128. The unit dosage container of claim 108, wherein said one or more neurokinin antagonists are selected from the group consisting of oximes, hydrazones, piperidines, piperazines, aryl alkyl amines, hydrazones, nitroalkanes, amides, isoxazolines, quinolines, isoquinolines, azanorbornanes, naphthyridines and benzodiazepines.

129. The unit dosage container of claim 108, wherein said one or more 5-lipoxygenase inhibitors are selected from the group consisting of zileuton, docebenone, piripost and tenidap.

130. The composition of matter of claim 1, wherein the wall thickness of said squeezable chamber is from about 0.2 mm to about 7 mm.

131. The unit dosage form of claim 37, wherein the wall thickness of said squeezable chamber is from about 0.2 mm to about 7 mm.

132. The unit dosage form of claim 43, wherein the wall thickness of said squeezable chamber is from about 0.2 mm to about 7 mm.

133. The unit dosage form of claim 70, wherein the wall thickness of said squeezable chamber is from about 0.2 mm to about 7 mm.

134. The unit dosage form of claim 71, wherein the wall thickness of said squeezable chamber is from about 0.2 mm to about 7 mm.

135. The unit dosage container of claim 104, wherein the wall thickness of said squeezable chamber is from about 0.2 mm to about 7 mm.

136. The composition of matter of claim 1, wherein when said squeezable chamber is squeezed, a droplet of about 0.01 to about 0.05 ml forms.

137. The unit dosage form of claim 37, wherein when said squeezable chamber is squeezed, a droplet of about 0.01 to about 0.05 ml forms.

138. The unit dosage form of claim 43, wherein when said squeezable chamber is squeezed, a droplet of about 0.01 to about 0.05 ml forms.

139. The unit dosage form of claim 70, wherein when said squeezable chamber is squeezed, a droplet of about 0.01 to about 0.05 ml forms.

140. The unit dosage form of claim 71, wherein when said squeezable chamber is squeezed, a droplet of about 0.01 to about 0.05 ml forms.

141. The unit dosage container of claim 104, wherein when said squeezable chamber is squeezed, a droplet of about 0.01 to about 0.05 ml forms.

* * * * *

UNITED STATES PATENT AND TRADEMARK OFFICE
CERTIFICATE OF CORRECTION

PATENT NO.        : 8,758,816 B2
APPLICATION NO.   : 12/569548
DATED             : June 24, 2014
INVENTOR(S)       : Fuge et al.

Page 1 of 2

It is certified that error appears in the above-identified patent and that said Letters Patent is hereby corrected as shown below:

In the Claims

Column 226
Line 27, claim 31, please replace "amprenavir, atazanavir" with --amprenavir, arbidol, atazanavir--.

Column 226
Lines 31-32, claim 31, please replace "immunovir" with --imunovir--.

Column 226
Line 48, claim 33, please replace "amines, hydrazones, nitroalkanes" with --amines, nitroalkanes--.

Column 227
Line 8, claim 37, please replace "wherein said," with --wherein said--.

Column 229
Line 43, claim 66, please replace "agents are" with --agents--.

Column 229
Line 45, claim 66, please replace "darunavir" with --darunavir,--.

Column 229
Line 49, claim 66, please replace "immunovir" with --imunovir--.

Column 229
Line 65, claim 68, please replace "amines, hydrazones, nitroalkanes" with --amines, nitroalkanes--.

Column 232
Line 55, claim 99, please replace "agents are selected" with --agents selected--.

Signed and Sealed this
Twenty-eighth Day of October, 2014

Michelle K. Lee
*Deputy Director of the United States Patent and Trademark Office*

CERTIFICATE OF CORRECTION (continued)
U.S. Pat. No. 8,758,816 B2

Column 232

Line 62, claim 99, please replace "immunovir" with --imunovir--.

Column 233

Line 11, claim 101, please replace "amines, hydrazones, nitroalkanes" with --amines, nitroalkanes--.

Column 236

Line 2, claim 126, please replace "immunovir" with --imunovir--.

Column 236

Line 18, claim 128, please replace "amines, hydrazones, nitroalkanes" with --amines, nitroalkanes--.